US012441706B2

(12) United States Patent
Lu et al.

(10) Patent No.: US 12,441,706 B2
(45) Date of Patent: Oct. 14, 2025

(54) PROTEIN DEGRADATION AGENT COMPOUND PREPARATION METHOD AND APPLICATION

(71) Applicants: SHANGHAI JEMINCARE PHARMACEUTICALS CO., LTD., Shanghai (CN); JIANGXI JEMINCARE GROUP CO., LTD., Nanchang (CN)

(72) Inventors: Hongfu Lu, Shanghai (CN); Weiqiang Xing, Shanghai (CN); Baojian Qi, Shanghai (CN); Jianbiao Peng, Shanghai (CN); Haibing Guo, Shanghai (CN)

(73) Assignees: SHANGHAI JEMINCARE PHARMACEUTICALS CO., LTD., Shanghai (CN); JIANGXI JEMINCARE GROUP CO., LTD., Nanchang (CN)

( * ) Notice: Subject to any disclaimer, the term of this patent is extended or adjusted under 35 U.S.C. 154(b) by 523 days.

(21) Appl. No.: 17/788,154

(22) PCT Filed: Dec. 23, 2020

(86) PCT No.: PCT/CN2020/138572

§ 371 (c)(1),
(2) Date: Jun. 22, 2022

(87) PCT Pub. No.: WO2021/129653

PCT Pub. Date: Jul. 1, 2021

(65) Prior Publication Data

US 2023/0111119 A1 Apr. 13, 2023

(30) Foreign Application Priority Data

Dec. 23, 2019 (CN) ......................... 201911342649.0
Mar. 20, 2020 (CN) ......................... 202010200682.6
Jun. 3, 2020 (CN) ......................... 202010496353.0
Dec. 16, 2020 (CN) ......................... 202011486334.6

(51) Int. Cl.

| | |
|---|---|
| ***C07D 401/14*** | (2006.01) |
| ***A61P 15/00*** | (2006.01) |
| ***A61P 25/28*** | (2006.01) |
| ***A61P 35/00*** | (2006.01) |

(52) U.S. Cl.

CPC ............ *C07D 401/14* (2013.01); *A61P 15/00* (2018.01); *A61P 25/28* (2018.01); *A61P 35/00* (2018.01); *C07B 2200/07* (2013.01)

(58) Field of Classification Search

CPC ........ C07D 401/14; A61P 25/28; A61P 15/00; A61P 35/00; C07B 2200/07

See application file for complete search history.

(56) References Cited

U.S. PATENT DOCUMENTS

| | | | |
|---|---|---|---|
| 9,814,698 | B2 | 11/2017 | Narayanan et al. |
| 11,767,312 | B2 | 9/2023 | Lu et al. |
| 2003/0203902 | A1 | 10/2003 | Lehmann et al. |
| 2015/0291562 | A1 | 10/2015 | Crew et al. |
| 2016/0058872 | A1 | 3/2016 | Crew et al. |
| 2016/0214972 | A1 | 7/2016 | Jin et al. |
| 2018/0099940 | A1 | 4/2018 | Crew et al. |
| 2018/0134684 | A1 | 5/2018 | Bradner et al. |
| 2018/0215731 | A1 | 8/2018 | Crew et al. |
| 2018/0228907 | A1 | 8/2018 | Crew et al. |
| 2019/0262458 | A1 | 8/2019 | Gray et al. |
| 2019/0263823 | A1 | 8/2019 | Bradner et al. |

FOREIGN PATENT DOCUMENTS

| | | | |
|---|---|---|---|
| CN | 110194762 | A | 3/2019 |
| CN | 110506039 | A | 11/2019 |
| CN | 112390852 | A | 2/2021 |
| CN | 112457366 | A | 3/2021 |
| CN | 112457367 | A | 3/2021 |
| CN | 112574278 | A | 3/2021 |

(Continued)

OTHER PUBLICATIONS

Ran et al, Recent Developments in Androgen Receptor Antagonists, Arch. Pharm. Chem. Life Sci., 348:757-775 (2015).

Haiban WEI et al, The Application and Progress of Chimeric Molecules (DHT-PROTAC) in Prostate Cancer, Progress in Modern Biomedicine, 14(3):590-592 (2014). Machine Translation in English.

Wei Li et al, Patent Overview of Phthalazinone-Type PARP Inhibitors Structural Modification Based on Patented Technologies in China, Guangzhou Chemical Industry, 47(9):34-40 (May 2019). Machine Translation in English.

Wei Li et al, Patent Overview of Phthalazinone-Type PARP Inhibitors Structural Modification Based on Patented Technologies in China, Guangzhou Chemical Industry, 47(9):34-40 (May 2019).

(Continued)

*Primary Examiner* — Joseph K McKane
*Assistant Examiner* — Quincy McKoy
(74) *Attorney, Agent, or Firm* — Armstrong Teasdale LLP

(57) ABSTRACT

Provided are a protein degradation agent compound preparation method and application; specifically, provided are the compound represented by formula (I) and a pharmacologically acceptable salt thereof, and an application of said compound in the degradation of androgen receptor (AR).

(I)

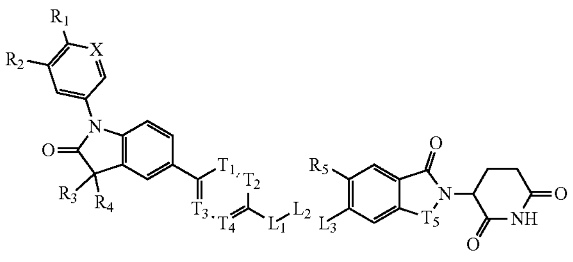

31 Claims, 1 Drawing Sheet

(56) References Cited

FOREIGN PATENT DOCUMENTS

| | | | | | |
|---|---|---|---|---|---|
| CN | 113582974 | A | | 11/2021 | |
| WO | WO-2016/197032 | A1 | | 12/2013 | |
| WO | 2018/098275 | A1 | | 5/2018 | |
| WO | WO-2018098280 | A1 | * | 5/2018 | ............ A61K 45/06 |
| WO | WO-2021/249534 | A1 | | 12/2021 | |

OTHER PUBLICATIONS

Haiban Wei et al, The Application and Progress of Chimeric Molecules (DHT-PROTAC) in Prostate Cancer, Progress in Modern Biomedicine, 14(3):590-592 (2014).
Xin Han et al., Discovery of ARD-69 as a Highly Potent Proteolysis Targeting Chimera (PROTAC) Degrader of Androgen Receptor (AR) for the Treatment of Prostate Cancer, J. Med. Chem., 62:941-964, (Jan. 10, 2019).
Jiantao Hu et al., Discovery of ERD-308 as a Highly Potent Proteolysis Targeting Chimera (PROTAC) Degrader of Estrogen Receptor (ER), J. Med. Chem., 62:1420-1442, (Jan. 18, 2019).
Guo et al, Design of oxobenzimidazoles and oxindoles as novel androgen receptor antagonists, Bioorganic & Medicinal Chemistry Letters, vol. 22, pp. 2572-2578 (2012).
Jing Liu et al, PROTACs: A novel strategy for cancer therapy, Seminars in Cancer Biology, vol. 67, pp. 171-179 (Feb. 11, 2020).
Nobuyuki Ito et al, A medium-term rat liver bioassay for rapid in vivo detection of carcinogenic potential of chemicals, Cancer Sci, 94(1):3-8 (Jan. 2003).
Minna Helin-Tanninen et al, Oral Solids, Y. Bouwman-Boer et al (eds.) Practical Pharmaceutics: An International Guidelien for the Preparation, Care and Use of Medicinal Products, KNMP and Springer International Publishing Switzerland, Chapter 4, pp. 51-75 (2015).
Li Wei et al, Patent Overview of Phtalazinone-type PARP Inhibitors Structural Modification Based on Patented Technologies in China, Guangzhou Chemical Industry, 47(9):34-40 (May 2019).
Ishoey, M et. al., "Translation Termination Factor GSPT1 1s a Phenotypically Relevant Off-Target of Heterobifunctional Phthalimide Degraders", ACS Chem. Biol., vol. 13, pp. 553-560, Jan. 22, 2018.
Panga, S et. al., "Design, Synthesis, Characterization, and In Vitro Evaluation of Isatin-Pomalidomide Hybrids for Cytotoxicity against Multiple Myeloma", J. Heterocyclic Chem., vol. 55, pp. 2919-2928, Oct. 19, 2018.
Mar. 23, 2021 International Search Report issued in International Patent Application No. PCT/CN2020/138572.
Mar. 23, 2021 Written Opinion of the International Searching Authority issued in International Patent Application No. PCT/CN2020/138572.
Nov. 27, 2021 Taiwan Office Action issued in Taiwan Patent Application No. 109145818.
Mette Ishoey et al, The translation termination factor GSPT1 is a phenotypically relevant off-target of heterobifunctional phthalimide degraders, ACS Chem. Biol., 13(3):553-560 (2018).
Shyam Panga et al, Design, Synthesis, Characterization, and In Vitro Evaluation of Isatin-Pomalidomide Hybrids for Cytotoxicity against Multiple Myeloma Cell Lines, J. Heterocyclic Chem., 55(12):2919-2928 (2018).
Dyson et al. (1964) "Chemistry of Synthetic Drugs", Publishing house Mir Moscow, pp. 12-19.
Harkevich, D.A. (2010) "Pharmacology", GEOTAR-Media, pp. 73-74.

* cited by examiner

PROTEIN DEGRADATION AGENT COMPOUND PREPARATION METHOD AND APPLICATION

The present application is the National Stage Application of PCT/CN2020/138572, filed on Dec. 23, 2020, which claims the right of the following priorities for: CN201911342649.0, application date: Dec. 23, 2019, CN202010200682.6, application date: Mar. 20, 2020; CN202010496353.0, application date: Jun. 3, 2020; CN202011486334.6, application date: Dec. 16, 2020, all of which are incorporated by reference for all purposes as if fully set forth herein.

TECHNICAL FIELD

The present disclosure relates to a compound represented by formula (I) or a pharmacologically acceptable salt thereof, and use of the compound in the degradation of androgen receptor (AR).

BACKGROUND

Prostate cancer (PCa) is one of the most common cancers worldwide and the second leading cause of cancer deaths in adult men worldwide. Prostate cancer has no significant symptoms in the early stage and grows relatively slowly. In the advanced stage, symptoms such as frequent urination, dysuria, hematuria, and urodynia may occur, and may metastasize to other parts. Most patients are diagnosed with advanced cancer. In the United States, the incidence rate of prostate cancer had surpassed that of lung cancer and become the first cancer threatening men's health. In 2016, there were 120,000 new prostate cancer patients in China. It is estimated that by 2030, the number of new prostate cancer patients in China will reach 237,000, with a compound annual growth rate of 5%. It also means that in the next 10 years, the incidence of prostate cancer in China will enter a peak period and become the first killer of male cancer. Due to the low early diagnosis rate, the mortality rate of prostate cancer patients in China is much higher than that in developed countries. In the United States, the survival rate of patients with the disease for 5 years is more than 98%, while the survival rate of the same patients in China is only 50%.

Prostate cancer is an androgen-dependent tumor, and androgens stimulate prostate cancer cell growth and disease progression. Endocrine therapy is one of the conventional treatment methods. For example, the standard of treatment for advanced PCa is androgen deprivation therapy (ADT), such as surgical castration (bilateral orchiectomy)/drug castration (such as injection of Zoladex). ADT therapy has a remarkable effect in the early stage of treatment, but with the progress of the disease, androgen receptor (AR) mutates, and the mutated AR is more sensitive to low levels of androgen, thus driving the disease to progress to castration-resistant prostate cancer (CRPC). Almost all patients with advanced prostate cancer will eventually progress to CRPC after receiving endocrine therapy. Furthermore, up to 30% of prostate cancer patients will turn into metastatic castration-resistant prostate cancer (mCRPC) within 10 years of initial treatment. At present, the patients diagnosed with early focal prostate cancer are usually curable, but the patients diagnosed with asymptomatic or mild metastatic castration-resistant prostate cancer (mCRPC) have no cure options clinically.

At present, the approved oral drugs for the treatment of metastatic castration-resistant prostate cancer mainly include abiraterone and enzalutamine. Among them, abiraterone is a novel inhibitor of androgen biosynthesis, which could block androgen synthesis in testis, adrenal gland or in the environment of tumor cell. While enzalutamine is an androgen receptor inhibitor, which can competitively inhibit the binding of androgen to the receptor. When enzalutamine binds to AR, it could also further inhibit the nuclear transport of AR, thus blocking the interaction between AR and DNA.

Despite being castration-refractory, CRPC relies on the AR signaling axis for continued growth. The mutation of AR decreases the antagonistic activity of small molecules targeting AR, and even turns into AR agonist, which shows drug resistance clinically. Therefore, selective androgen receptor degraders (SARD) can not only inhibit androgen receptor and block the process of androgen receptor signal transmission, but also degrade the receptor itself, bringing more benefits.

The disclosure mainly relies on protein degradation targeting chimera (PROTAC) technology to obtain a class of selective AR degraders (SARD). PROTAC technology mainly relies on the intracellular ubiquitin-proteasome system. This system is the "cleaner" in the cell, and the main function of the ubiquitination system is to ubiquitinate the denatured, mutated or harmful proteins in the cell. Ubiquitinated proteins are degraded by the proteasome system inside the cell. The design idea of PROTAC is that one end of the molecule is AR interaction fragment, and the other end is ubiquitin-proteasome interaction fragment, and the two ends are connected into a chimeric molecule by intermediate connection. PROTAC interacts with the target protein (AR) and the proteasome system at the same time, so that the proteasome and AR proteins are spatially close to each other, and then the AR is degraded by ubiquitination.

The small-molecule PROTAC technology was reported in 2008. Currently, only a small-molecule drug ARV-110 (currently unknown in structure) based on AR degradation of Arvinas is in the first phase of clinical research and development. PROTAC technology belongs to the frontier field. In recent years, a large number of literature reports have shown that PROTAC plays a role in combination with degradation targets and ubiquitination systems at the same time. Its mechanism of action is far more complicated than that of traditional small molecule drugs: the mode of action of such molecules involves three-body binding kinetics, and is affected by PROTAC's own catalyst characteristics (and potential hook effect issues). Therefore, the molecular design ideas of PROTAC are completely different from those of small molecules, and there is no obvious regularity. Common drug-chemical strategies, such as the equivalent replacement of effective fragments, are not necessarily applicable in the design of such molecules.

Patent CN110506039A designs a series of compounds based on PROTAC technology, wherein embodiment 158 is disclosed. Such PROTAC molecules generally have the defects of large molecular weight and poor solubility, which limit the increase of drug dosage. Therefore, it is of great significance to improve the metabolic stability of the compound in vivo and improve the drug activity (animal efficacy) at the same dosage.

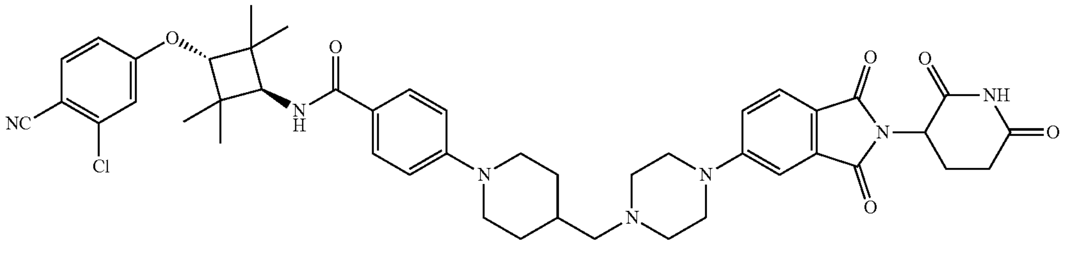

CN110506039A
Embodiment 158

At present, there is still a need to develop PROTAC molecules with novel structures for AR degradation in this filed.

CONTENT OF THE PRESENT INVENTION

In one aspect of the present disclosure, the present disclosure provides a compound represented by formula (I), an optical isomer thereof or a pharmacologically acceptable salt thereof,

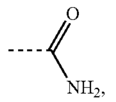

$C_{1-6}$ alkyl, $C_{3-6}$ cycloalkyl, $C_{1-6}$ alkyl-C(═O)—, $C_{1-6}$ alkoxy, $C_{1-6}$ alkylthio and $C_{1-6}$ alkylamino, the $C_{1-6}$ alkyl, (I)

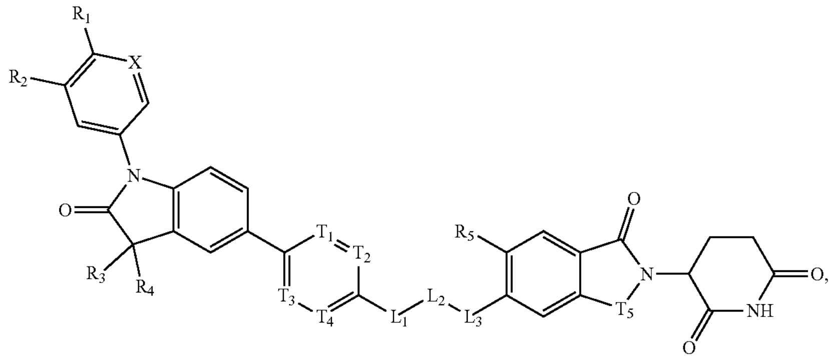

wherein X is selected from C(R) and N;

$T_1$, $T_2$, $T_3$ and $T_4$ are each independently selected from C(R) and N;

$T_5$ is selected from —(C═O)— and —$CH_2$—;

$R_1$, $R_2$, $R_3$ and $R_4$ are each independently selected from CN, halogen, $C_{1-6}$ alkyl and $C_{1-6}$ alkoxy, and the $C_{1-6}$ alkyl and $C_{1-6}$ alkoxy are optionally substituted by 1, 2 or 3 R;

$L_1$, $L_2$ and $L_3$ are each independently selected from single bond, O, S, NH, C(═O), S(═O), S(═O)$_2$, $C_{1-6}$ alkyl, —$C_{1-6}$ alkyl-O—, —$C_{1-6}$ alkyl-NH—, —O—$C_{1-6}$ alkyl-O—, —O—$C_{1-6}$ alkyl-O—$C_{1-6}$ alkyl-, —O—$C_{2-3}$ alkenyl, $C_{2-3}$ alkynyl, $C_{3-10}$ cycloalkyl, 3- to 10-membered heterocycloalkyl, phenyl, and 5- to 9-membered heteroaryl, the $C_{1-6}$ alkyl, —$C_{1-6}$ alkyl-O—, —$C_{1-3}$ alkyl-NH—, —O—$C_{1-6}$ alkyl-O—, —O—$C_{1-6}$ alkyl-O—$C_{1-6}$ alkyl-, $C_{2-3}$ alkenyl, $C_{2-3}$ alkynyl, $C_{3-10}$ cycloalkyl, 3- to 10-membered heterocycloalkyl, phenyl, and 5- to 9-membered heteroaryl are optionally substituted by 1, 2 or 3 $R_L$;

$R_L$ are each independently selected from H, halogen, OH, $NH_2$, CN, $C_{3-6}$ cycloalkyl, $C_{1-6}$ alkoxy, $C_{1-6}$ alkylthio and $C_{1-6}$ alkylamino are optionally substituted by 1, 2 or 3 R';

R' is selected from F, Cl, Br, I, OH, $NH_2$,

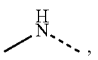 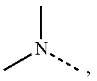

$CH_3$, $CH_2CH_3$, $CH_2F$, $CHF_2$ and $CF_3$;

R is selected from H, F, Cl, Br, I, OH and $C_{1-6}$ alkyl;

$R_5$ is selected from H, halogen and $C_{1-6}$ alkyl;

the 3- to 10-membered heterocycloalkyl or 5- to 9-membered heteroaryl contains 1, 2 or 3 heteroatoms or heteroatomic groups independently selected from —O—, —NH—, —S—, —C(═O)—, —C(═O)O—, —S(═O)—, —S(═O)$_2$— and N.

In another aspect of the present disclosure, the present disclosure also provides a compound represented by formula (II), an optical isomer thereof or a pharmacologically acceptable salt thereof, (II)

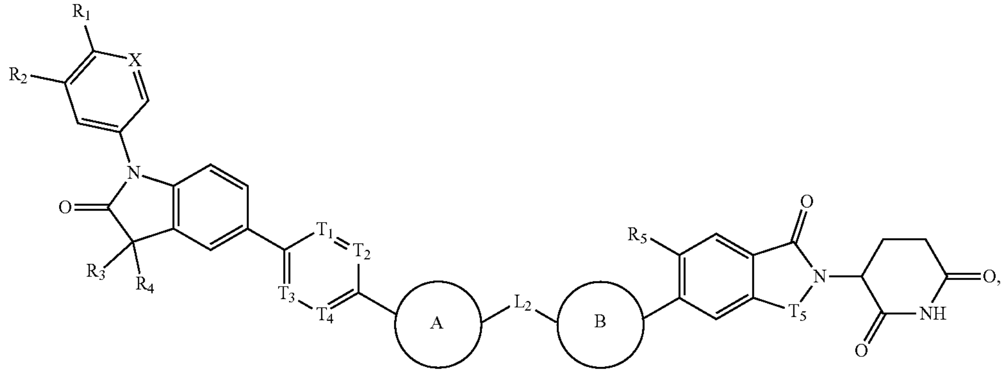

wherein, ring A and ring B are independently selected from 3- to 8-membered heterocycloalkyl, 5- to 6-membered heteroaryl or absent, and the 3- to 8-membered heterocycloalkyl or 5- to 6-membered heteroaryl is optionally substituted by 1, 2 or 3 R;

$R_1$, $R_2$, $R_3$ and $R_4$ are each independently selected from CN, halogen, $C_{1-6}$ alkyl and $C_{1-6}$ alkoxy, and the $C_{1-6}$ alkyl and $C_{1-6}$ alkoxy are optionally substituted by 1, 2 or 3 R;

X is selected from C(R) and N;

$T_1$, $T_2$, $T_3$ and $T_4$ are each independently selected from C(R) and N;

$T_5$ is selected from —(C═O)— and —$CH_2$—;

$L_2$ is selected from single bond, O, S, NH, C(═O), S(═O), S(═O)$_2$, $C_{1-6}$ alkyl, —$C_{1-6}$ alkyl-O—, —$C_{1-3}$ alkyl-NH—, —O—$C_{1-6}$ alkyl-O—, —O—$C_{1-6}$ alkyl-O—$C_{1-6}$ alkyl-, —O—$C_{2-3}$ alkenyl, $C_{2-3}$ alkynyl, $C_{3-10}$ cycloalkyl, 3- to 10-membered heterocycloalkyl, phenyl, and 5- to 9-membered heteroaryl, the $C_{1-6}$ alkyl, —$C_{1-6}$ alkyl-O—, —$C_{1-3}$ alkyl-NH—, —O—$C_{1-6}$ alkyl-O—, —O—$C_{1-6}$ alkyl-O—$C_{1-6}$ alkyl-, $C_{2-3}$ alkenyl, $C_{2-3}$ alkynyl, $C_{3-10}$ cycloalkyl, 3- to 10-membered heterocycloalkyl, phenyl, and 5- to 9-membered heteroaryl are optionally substituted by 1, 2 or 3 $R_L$;

$R_L$ are each independently selected from H, halogen, OH, $NH_2$, CN,

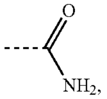

$C_{1-6}$ alkyl, $C_{3-6}$ cycloalkyl, $C_{1-6}$ alkyl-C(═O)—, $C_{1-6}$ alkoxy, $C_{1-6}$ alkylthio and $C_{1-6}$ alkylamino, the $C_{1-6}$ alkyl, $C_{3-6}$ cycloalkyl, $C_{1-6}$ alkoxy, $C_{1-6}$ alkylthio and $C_{1-6}$ alkylamino are optionally substituted by 1, 2 or 3 R';

R' is selected from F, Cl, Br, I, OH, $NH_2$,

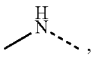,
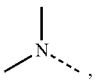, $CH_3$, $CH_2CH_3$, $CH_2F$, $CHF_2$ and $CF_3$;

R is selected from H, F, Cl, Br, I, OH and $C_{1-6}$ alkyl;

$R_5$ is selected from H, halogen and $C_{1-6}$ alkyl;

the 3- to 8-membered heterocycloalkyl, 3- to 10-membered heterocycloalkyl, 5- to 6-membered heteroaryl or 5- to 9-membered heteroaryl contains 1, 2 or 3 heteroatoms or heteroatomic groups independently selected from —O—, —NH—, —S—, —C(═O)—, —C(═O)O—, —S(═O)—, —S(═O)$_2$— and N.

In some embodiments of the present disclosure, the moiety

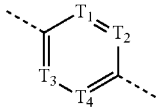

is selected from

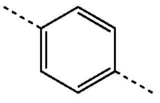,
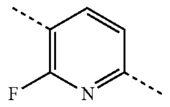,
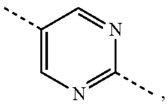,
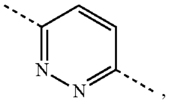,
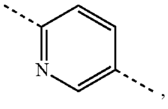,
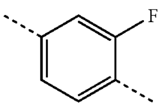
and
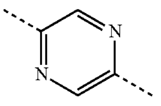, the other variables are as defined in the present disclosure.

In some embodiments of the present disclosure, the R is selected from H, halogen, OH, methyl, ethyl, n-propyl and isopropyl, the other variables are as defined in the present disclosure.

In some embodiments of the present disclosure, the $R_1$ and $R_2$ are each independently selected from CN, halogen, $CH_3O$— and —$CF_3$, the other variables are as defined in the present disclosure.

In some embodiments of the present disclosure, the $R_3$ and $R_4$ are selected from methyl, ethyl, n-propyl and isopropyl, the other variables are as defined in the present disclosure.

In some embodiments of the present disclosure, the moiety

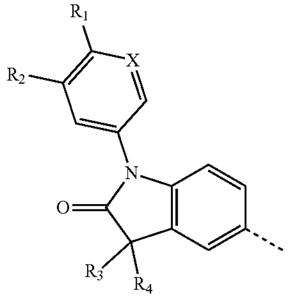

is selected from

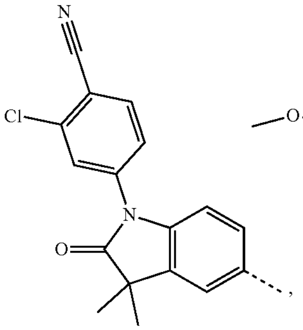
,
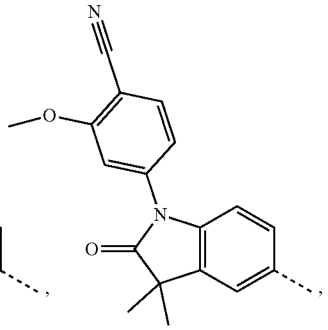
,
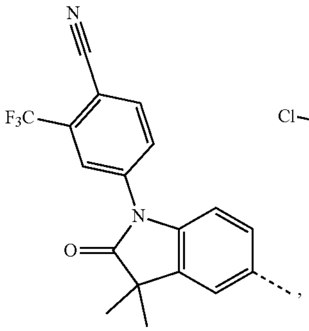
,
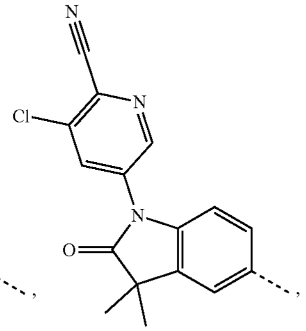
,
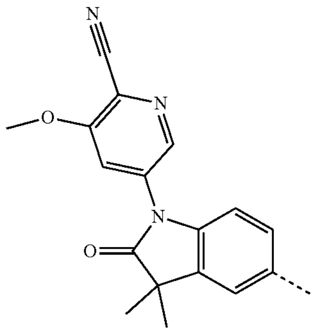

and

-continued

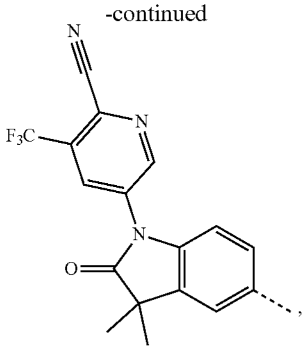
, the other variables are as defined in the present disclosure.

In some embodiments of the present disclosure, the $L_1$, $L_2$ and $L_3$ are each independently selected from single bond, O, S, NH, C(═O), S(═O), $S(═O)_2$, $C_{1-3}$ alkyl, —$C_{1-4}$ alkyl-O—, —$C_{1-3}$ alkyl-NH—, —O—$C_{1-4}$ alkyl-O—, —O—$C_{1-3}$ alkyl-O—$C_{1-3}$ alkyl-, —O—$C_{2-3}$ alkenyl, $C_{2-3}$ alkynyl, $C_{3-8}$ cycloalkyl, 3- to 8-membered heterocycloalkyl, phenyl, and 5- to 6-membered heteroaryl, the $C_{1-3}$ alkyl, —$C_{1-4}$ alkyl-O—, —O—$C_{1-4}$ alkyl-O—, —$C_{1-3}$ alkyl-NH—, —O—$C_{1-3}$ alkyl-O—$C_{1-3}$ alkyl-, $C_{2-3}$ alkenyl, $C_{2-3}$ alkynyl, $C_{3-8}$ cycloalkyl, 3- to 8-membered heterocycloalkyl, phenyl, and 5- to 6-membered heteroaryl are optionally substituted by 1, 2 or 3 $R_L$, the other variables are as defined in the present disclosure.

In some embodiments of the present disclosure, the $R_L$ is each independently selected from H, halogen, OH, $NH_2$, CN,

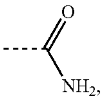
, $C_{1-3}$ alkyl, $C_{3-6}$ cycloalkyl, $C_{1-3}$ alkyl-C(═O)—, $C_{1-3}$ alkoxy, $C_{1-3}$ alkylthio and $C_{1-3}$ alkylamino, the $C_{1-3}$ alkyl, $C_{3-6}$ cycloalkyl, $C_{1-3}$ alkoxy, $C_{1-3}$ alkylthio and $C_{1-3}$ alkylamino are optionally substituted by 1, 2 or 3 R', the other variables are as defined in the present disclosure.

In some embodiments of the present disclosure, the $L_1$, $L_2$ and $L_3$ are each independently selected from single bond, O, S, NH, C(═O), S(═O), $S(═O)_2$, $CH_2$, —$CH(CH_3)$—, $CH_2CH_2$—, —$CH_2CH_2CH_2$—,

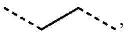
,
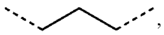
,
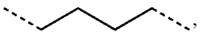
,
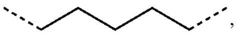
,
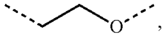
,
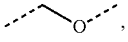
,
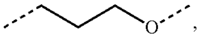
,
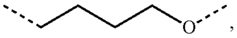
,
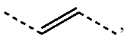
,
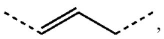
,
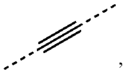
,
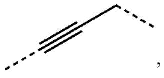
,
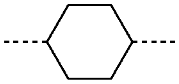
,
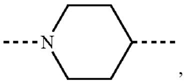
,
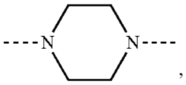
,
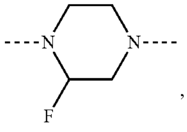
,
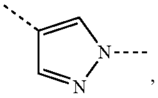
, -continued

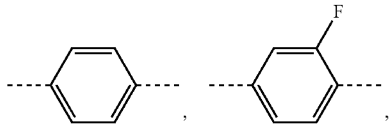
,

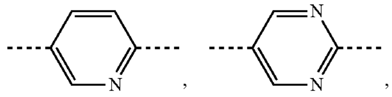
,

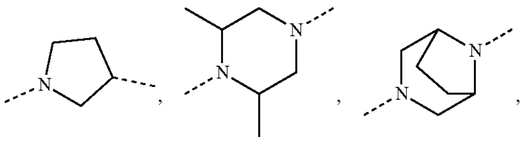
,

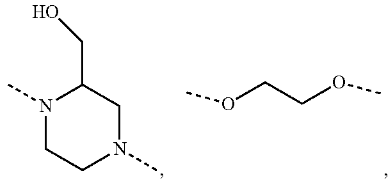
,

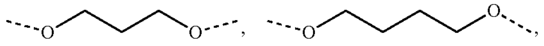
,

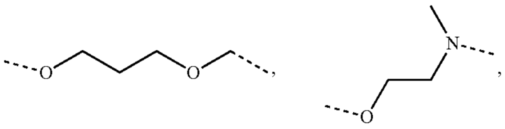
,

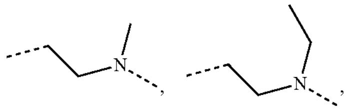
,

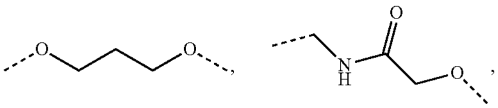
,

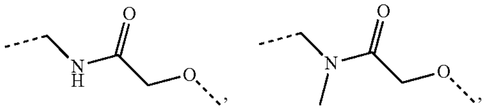
,

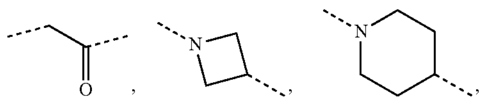
,

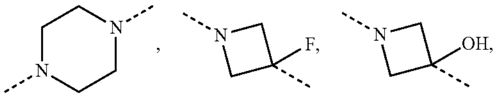
,

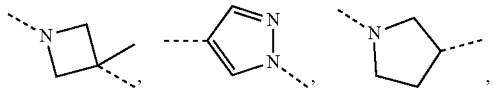
,

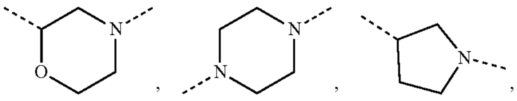
,

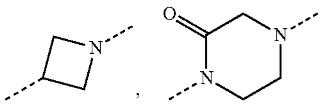
and

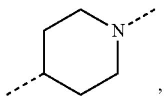
, the other variables are as defined in the present disclosure.

In some embodiments of the present disclosure, the $L_2$ is selected from O, —$C_{1-3}$ alkyl-, —O—$C_{1-4}$ alkyl-, —$C_{1-3}$ alkyl-NH—, —O—$C_{1-4}$ alkyl-O—, —O—$C_{1-3}$ alkyl-O—$C_{1-3}$ alkyl-,

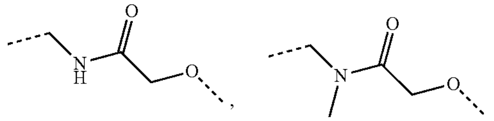
and

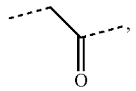

the $C_{1-3}$ alkyl, —O—$C_{1-4}$ alkyl-, —$C_{1-3}$ alkyl-NH—, —O—$C_{1-4}$ alkyl-O— or —O—$C_{1-3}$ alkyl-O—$C_{1-3}$ alkyl- are optionally substituted by 1, 2 or 3 $R_L$, the other variables are as defined in the present disclosure.

In some embodiments of the present disclosure, the $L_2$ is selected from —O—, —$CH_2$—, —$CH_2CH_2$—, —$CH_2CH_2CH_2$—, —$CH(CH_3)$—,

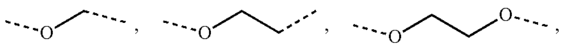
,

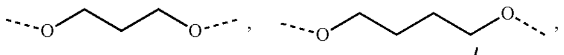
,

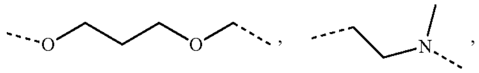
,

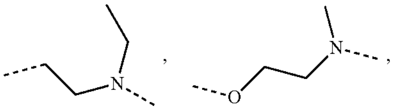
,

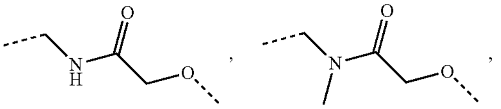
,

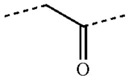
and

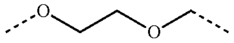
, the other variables are as defined in the present disclosure.

In some embodiments of the present disclosure, the moiety

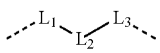

is selected from

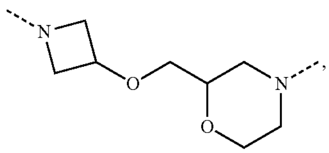

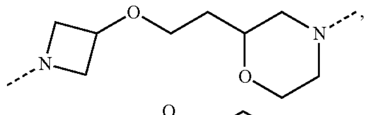

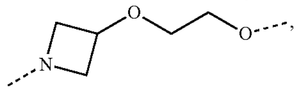

-continued
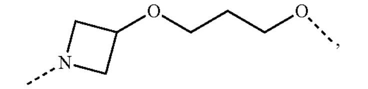
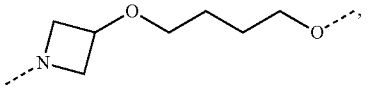
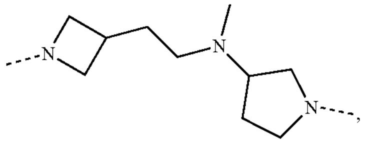
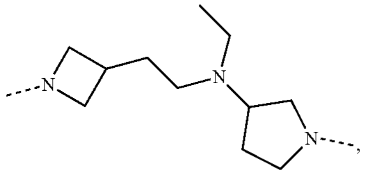
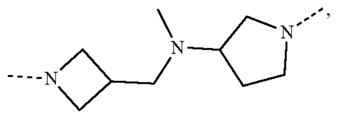
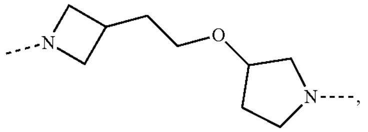
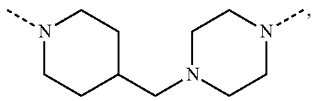
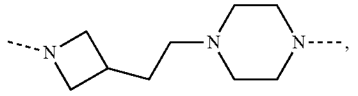
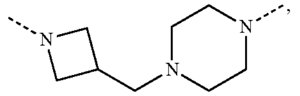
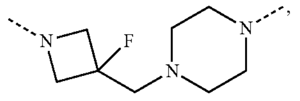
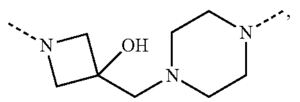
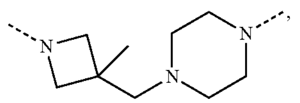
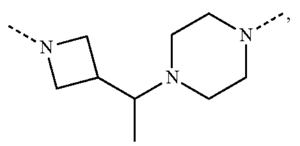
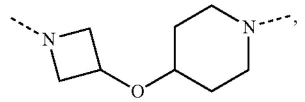
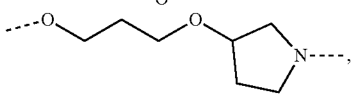
-continued
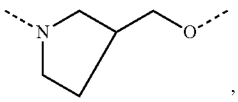
,
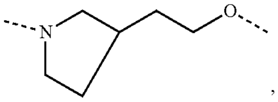
,
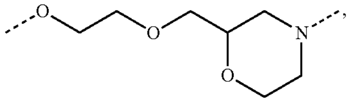
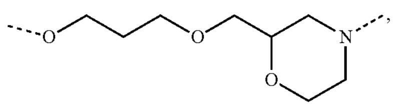
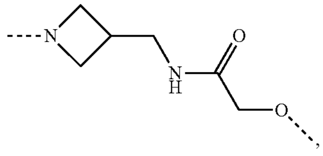
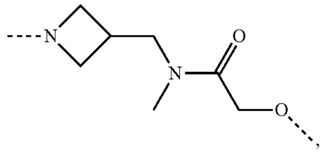
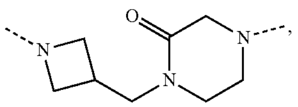
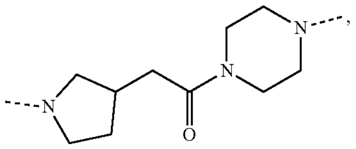
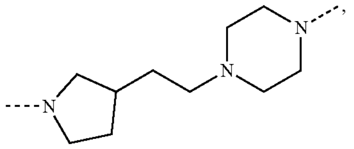
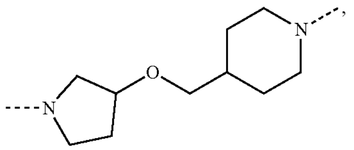
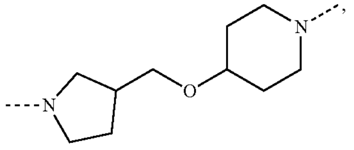
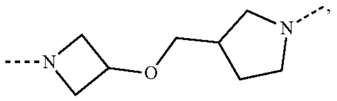
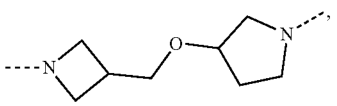
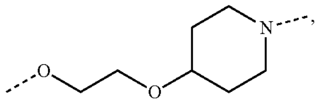

-continued
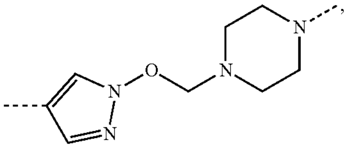
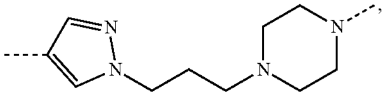
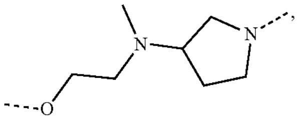
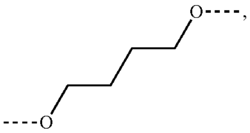
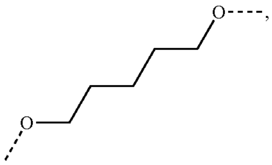
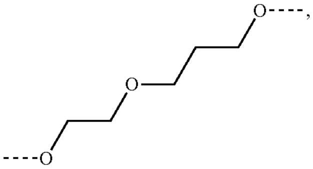
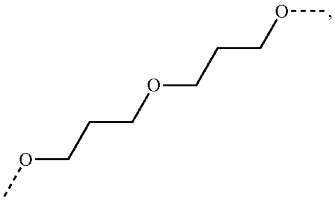
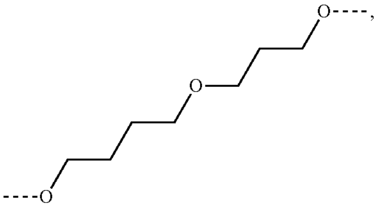
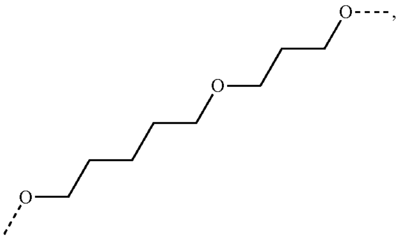
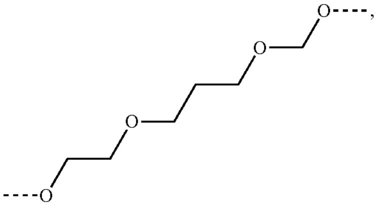
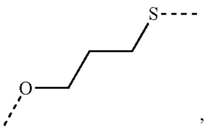
,
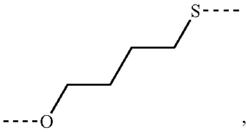
,
-continued
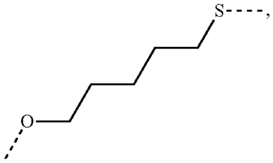
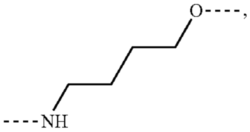
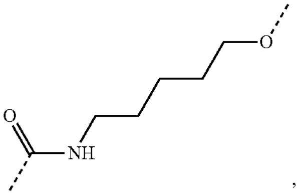
,
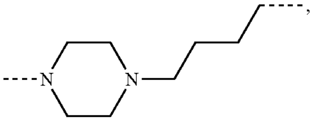
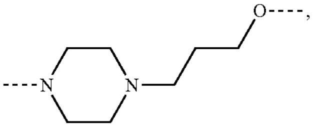
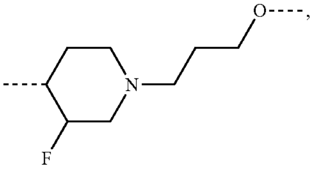
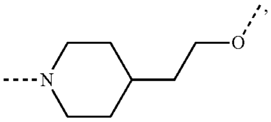
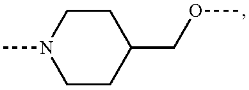
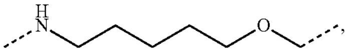
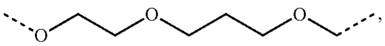
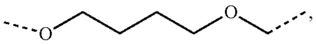
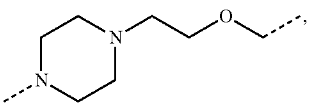
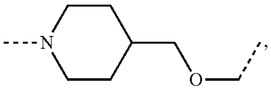
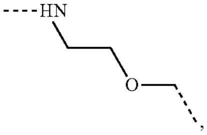
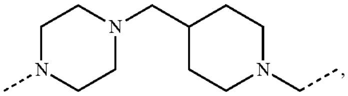

-continued

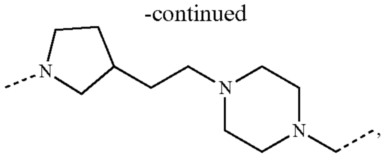

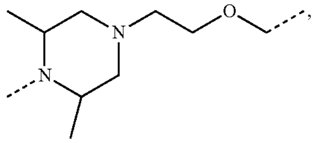

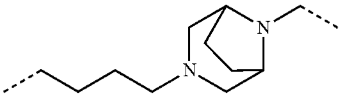

and

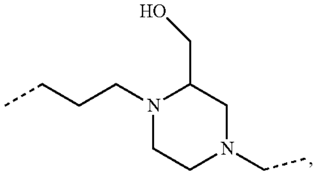

the other variables are as defined in the present disclosure.

In some embodiments of the present disclosure, the ring A and ring B are independently selected from 4- to 6-membered heterocycloalkyl and 5- to 6-membered heteroaryl, and the 4- to 6-membered heterocycloalkyl or 5- to 6-membered heteroaryl is optionally substituted by 1, 2 or 3 R, the other variables are as defined in the present disclosure.

In some embodiments of the present disclosure, the ring A is selected from azetidinyl, piperidinyl, piperazinyl, pyrazolyl and tetrahydropyrrolyl, the azetidinyl, piperidinyl, piperazinyl, pyrazolyl and tetrahydropyrrolyl are optionally substituted by 1, 2 or 3 R, the other variables are as defined in the present disclosure.

In some embodiments of the present disclosure, the ring A is selected from

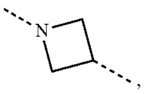

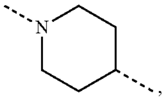

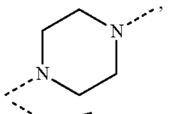

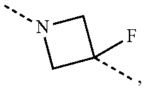

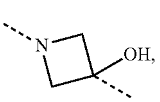

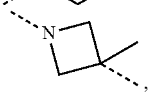

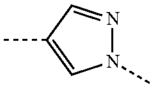

and

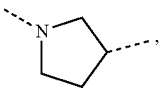

the other variables are as defined in the present disclosure.

In some embodiments of the present disclosure, the ring B is selected from morpholinyl, piperazinyl, tetrahydropyrrolyl, piperidinyl, azetidinyl and piperazine-2-ketonyl, and the morpholinyl, piperazinyl, tetrahydropyrrolyl, piperidinyl, azetidinyl and piperazine-2-ketonyl is optionally substituted by 1, 2 or 3 R, the other variables are as defined in the present disclosure.

In some embodiments of the present disclosure, the ring B is selected from

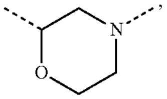

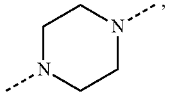

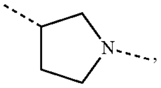

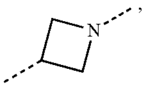

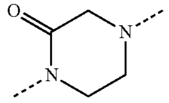

and

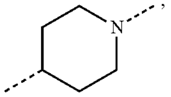

the other variables are as defined in the present disclosure.

In some embodiments of the present disclosure, the moiety

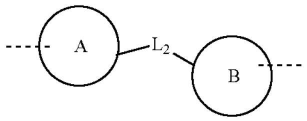

is selected from

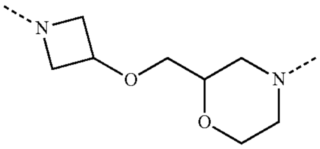

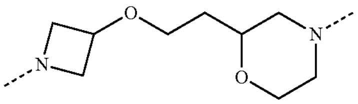

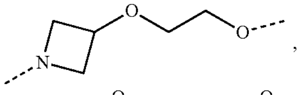

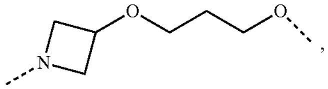

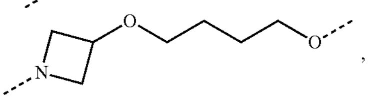

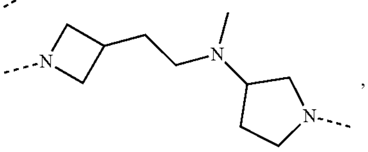

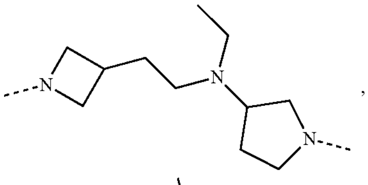

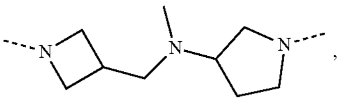

-continued
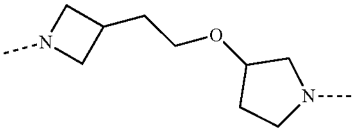
,
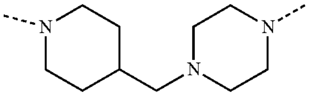
,
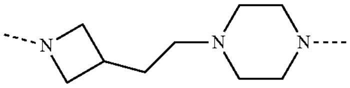
,
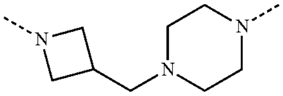
,
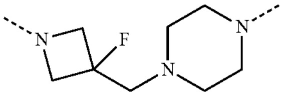
,
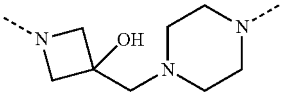
,
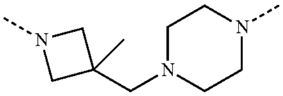
,
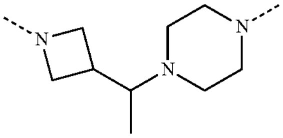
,
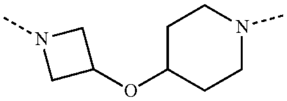
,
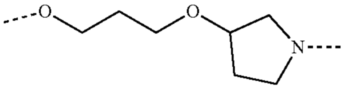
,
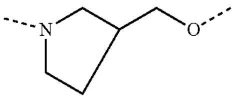
,
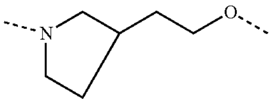
,
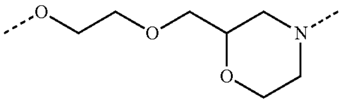
,
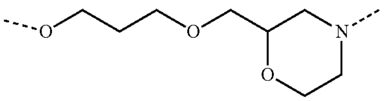
,
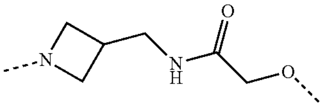
,
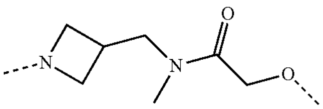
,
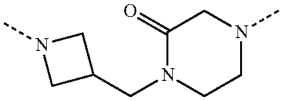
,
-continued
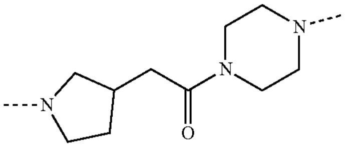
,
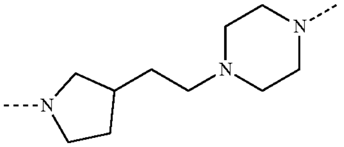
,
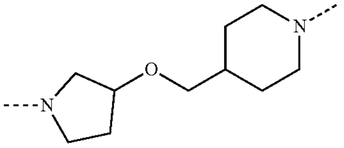
,
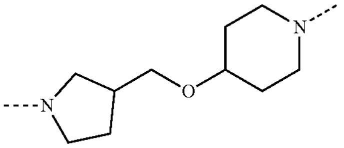
,
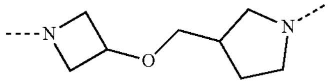
,
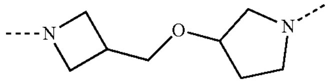
,
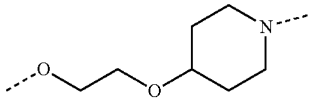
,
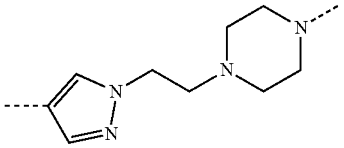
,
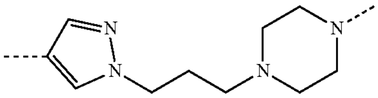
and
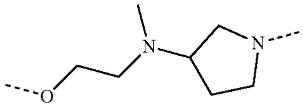
,
the other variables are as defined in the present disclosure.
In some embodiments of the present disclosure, the moiety
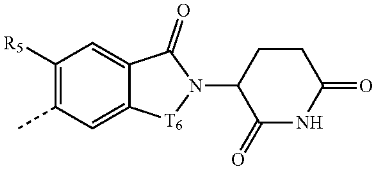

is selected from
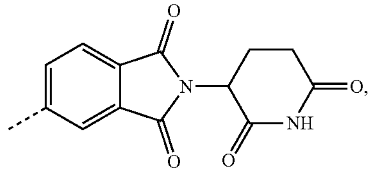
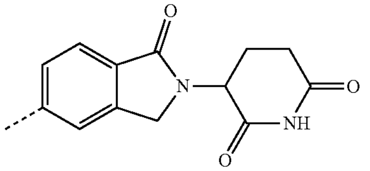
and
-continued
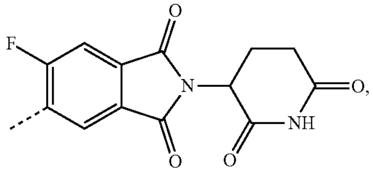
the other variables are as defined in the present disclosure.
In another aspect of the present disclosure, the present disclosure also provides a compound represented by the following formula, an optical isomer thereof or a pharmacologically acceptable salt thereof, which is selected from
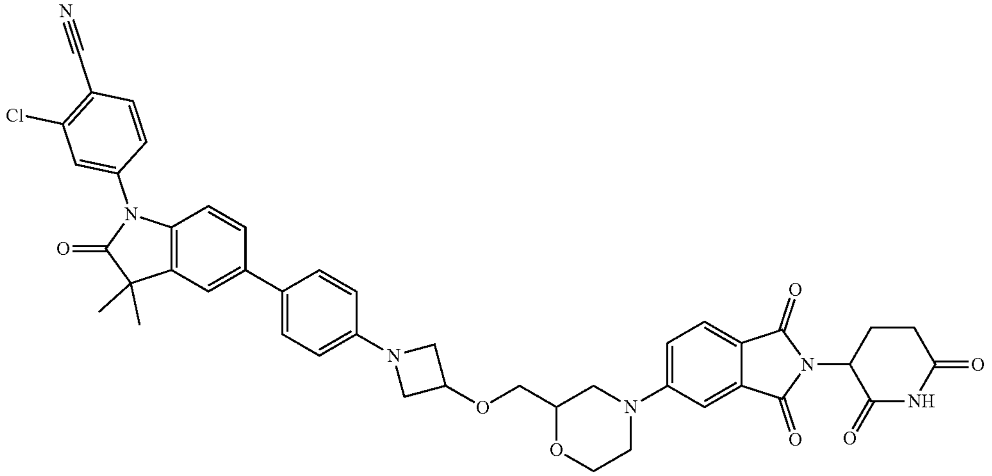
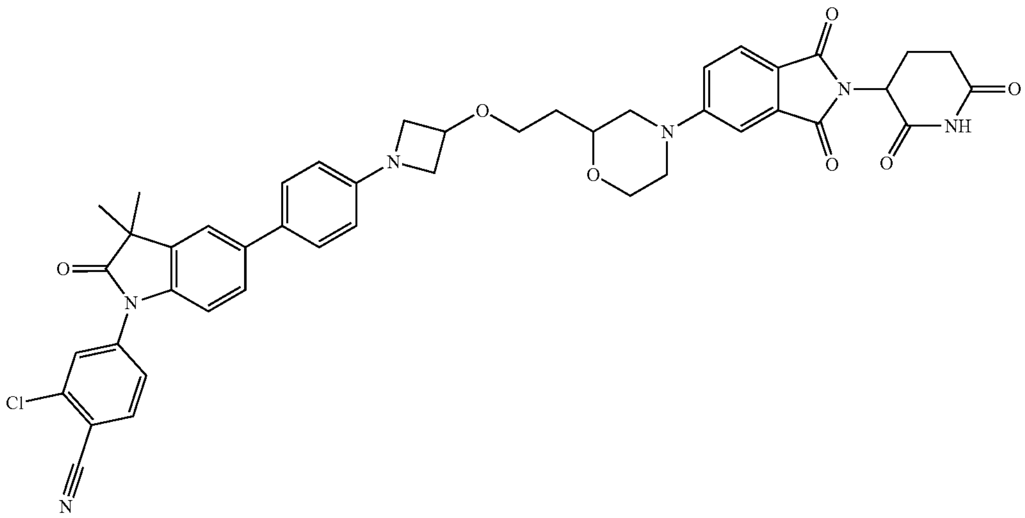

-continued
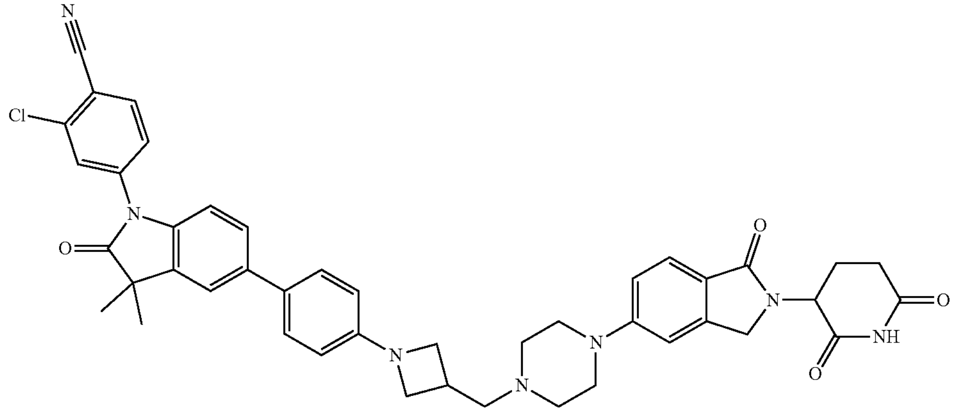
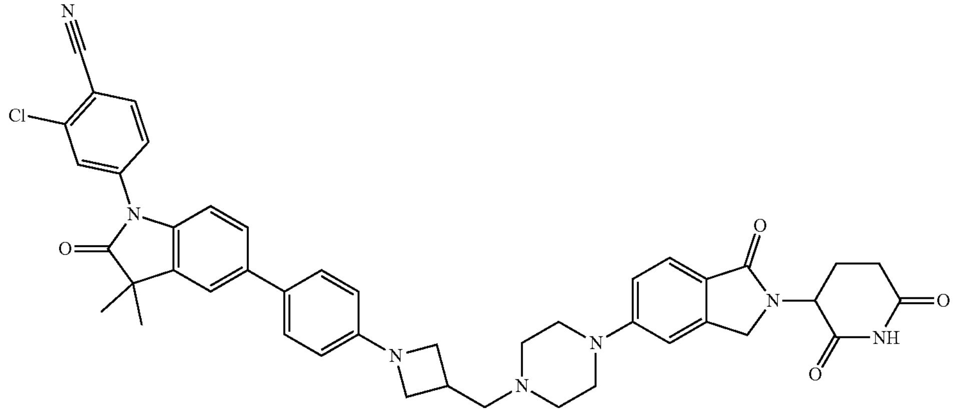
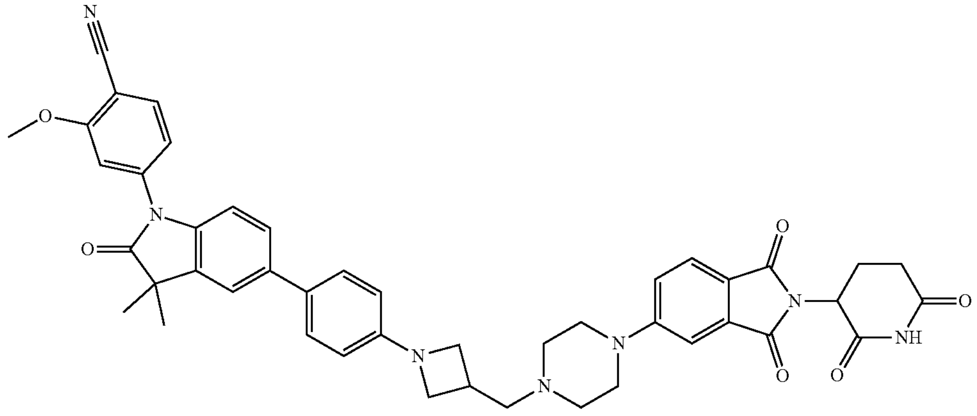
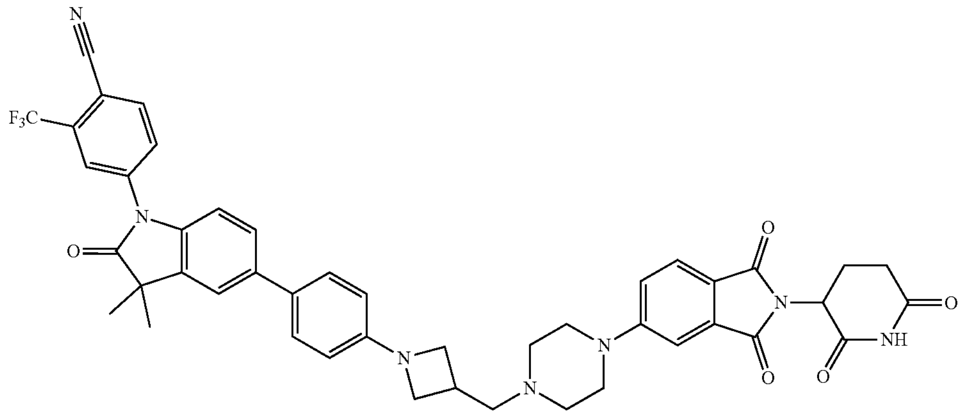

-continued
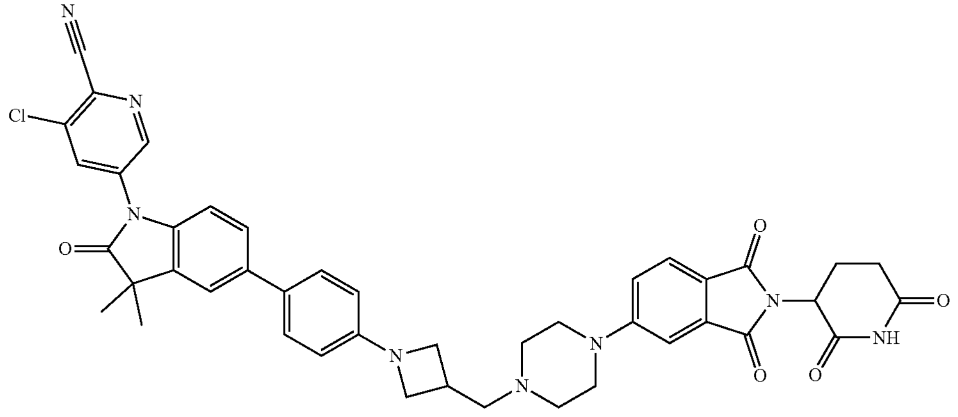
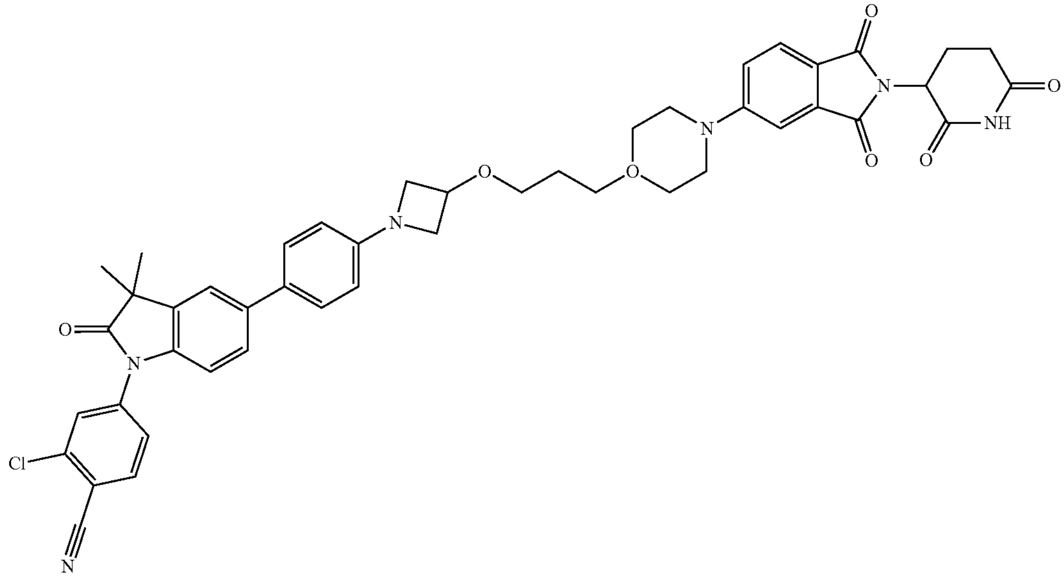
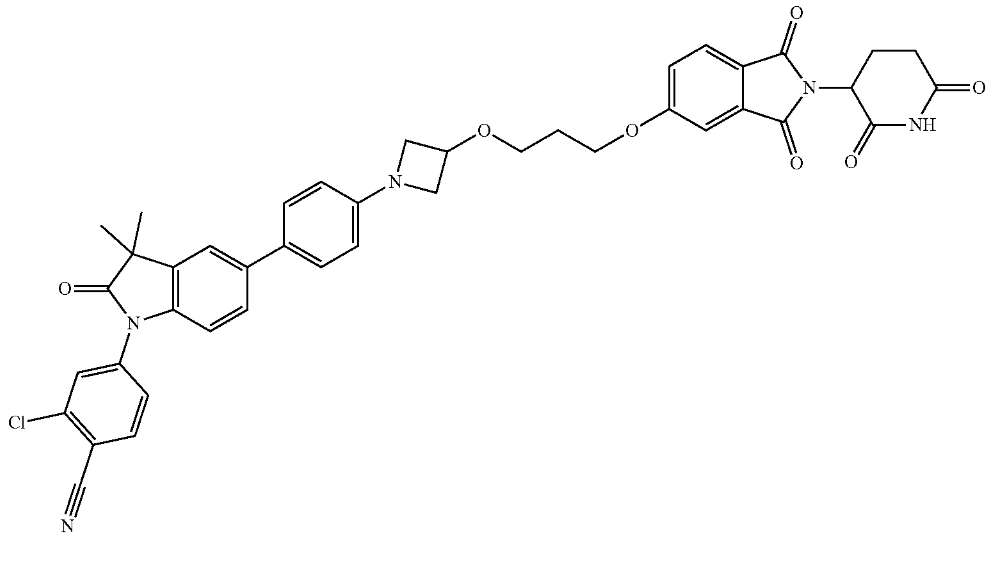

-continued
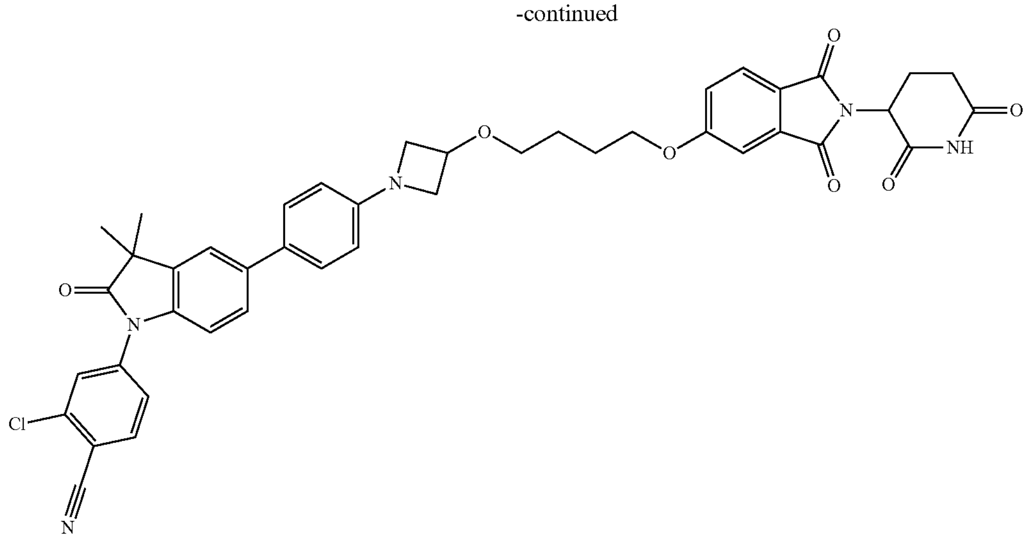
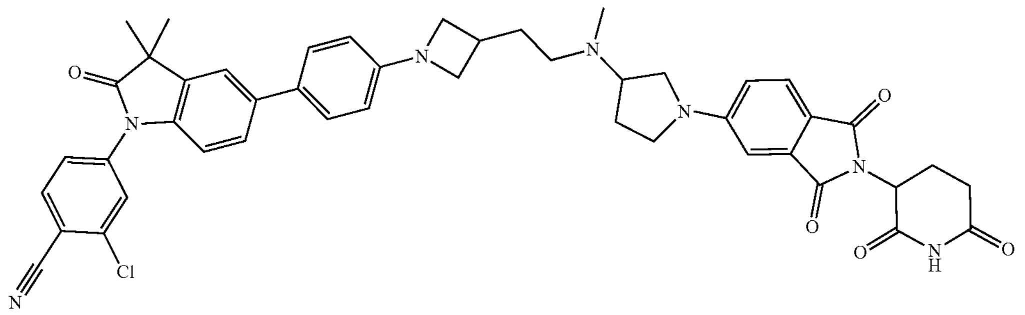
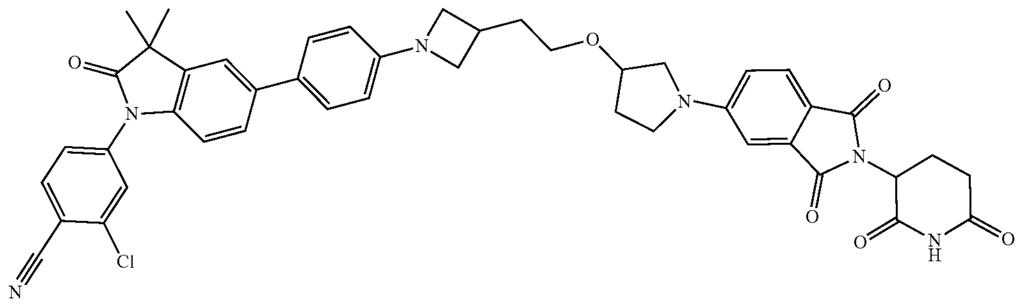
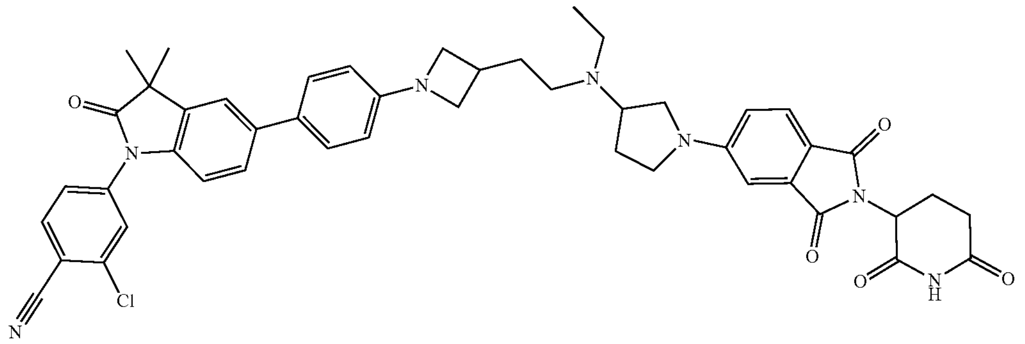 [SMILES: CCN(CCC1CN(c2ccc(-c3ccc4c(c3)C(C)(C)C(=O)N4c3ccc(C#N)c(Cl)c3)cc2)C1)C1CCN(c2ccc3c(c2)C(=O)N(C2CCC(=O)NC2=O)C3=O)C1]

-continued
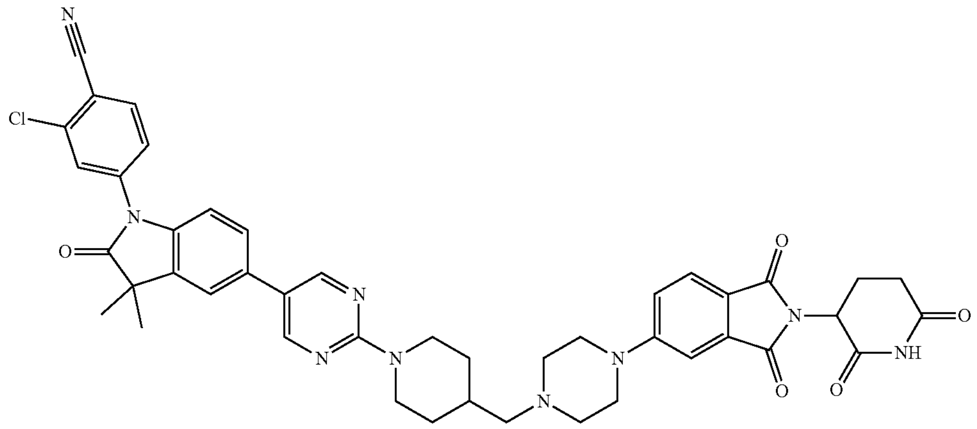
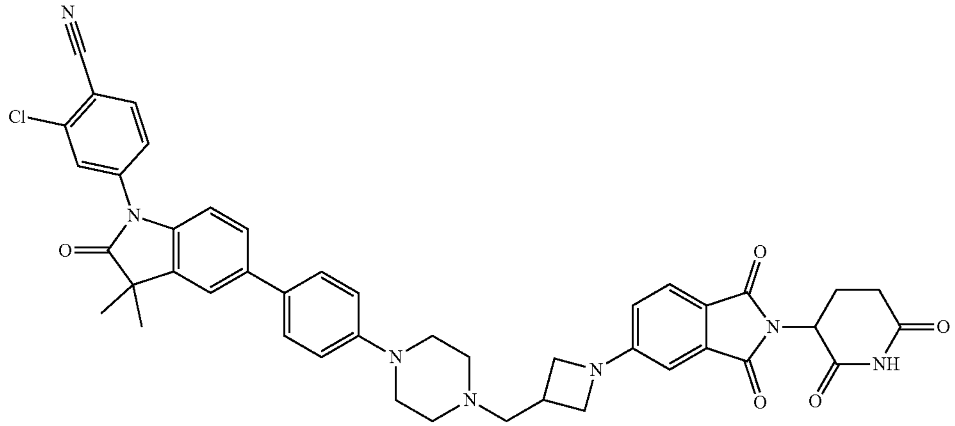
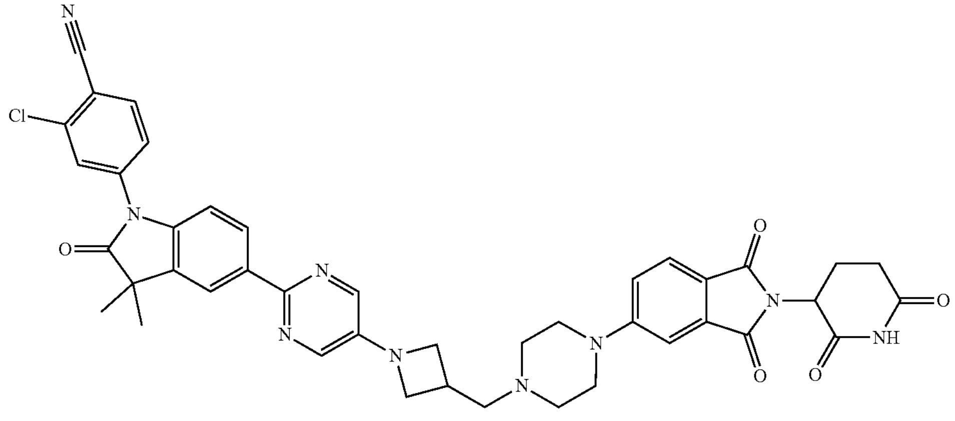

-continued
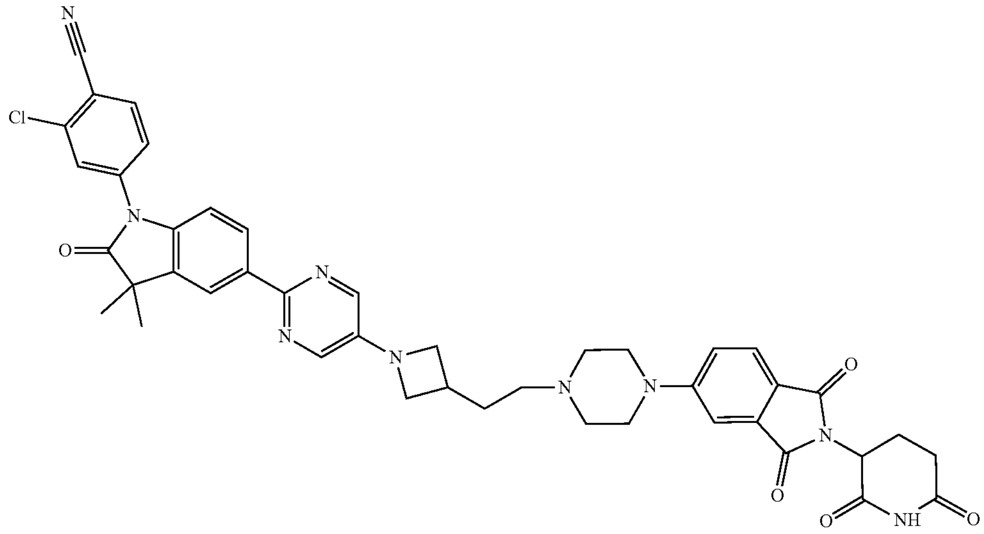
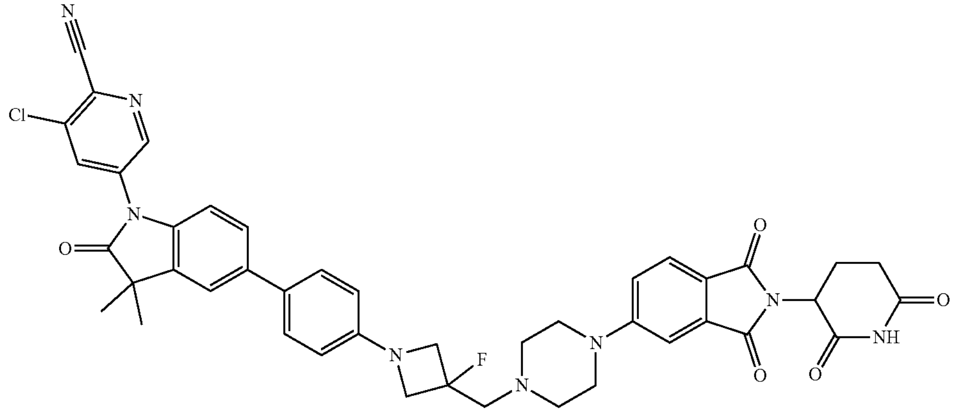
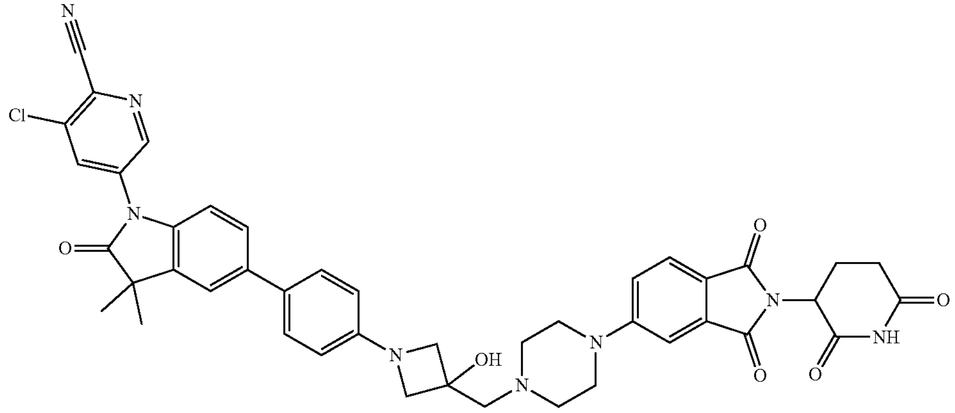

-continued
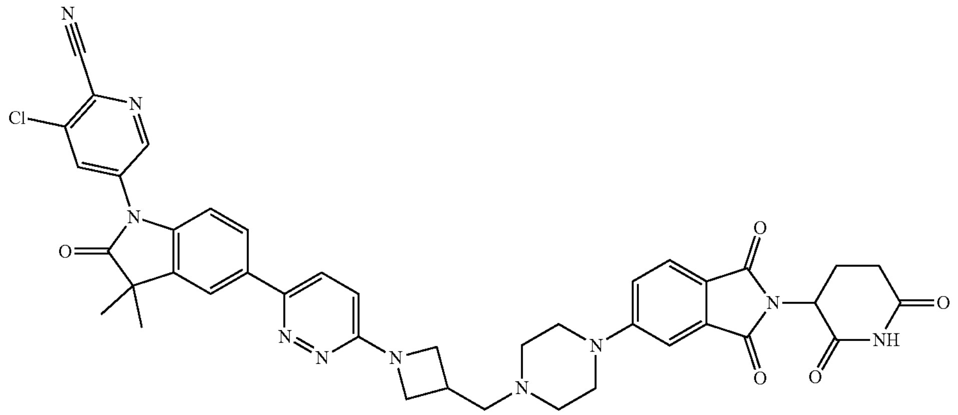
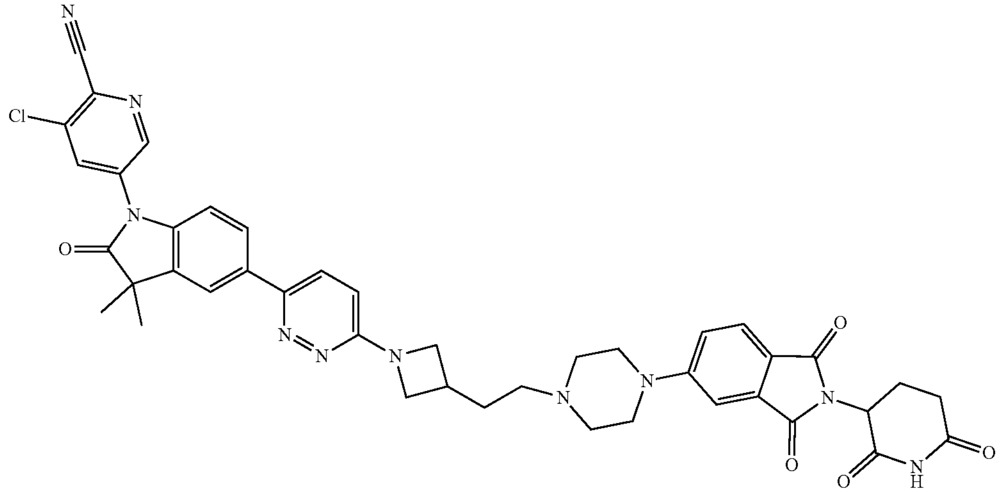
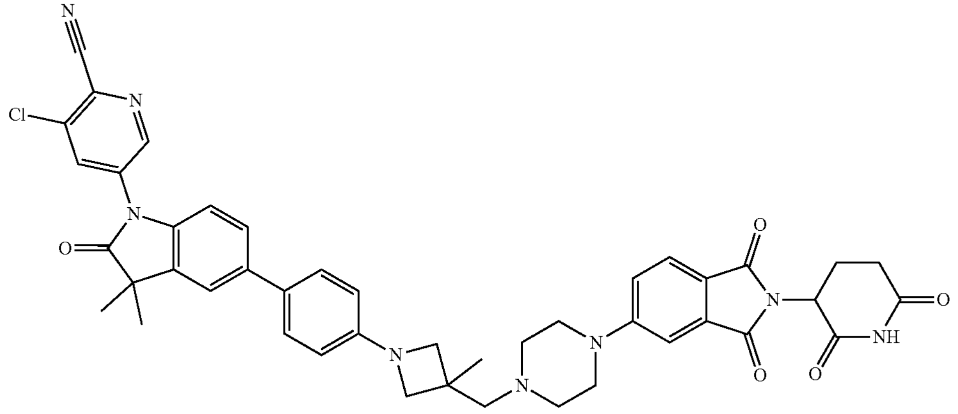

-continued
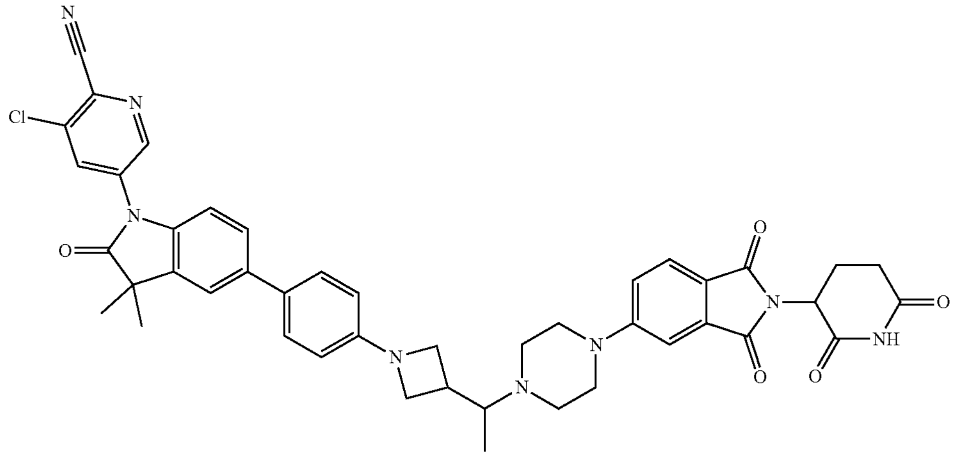
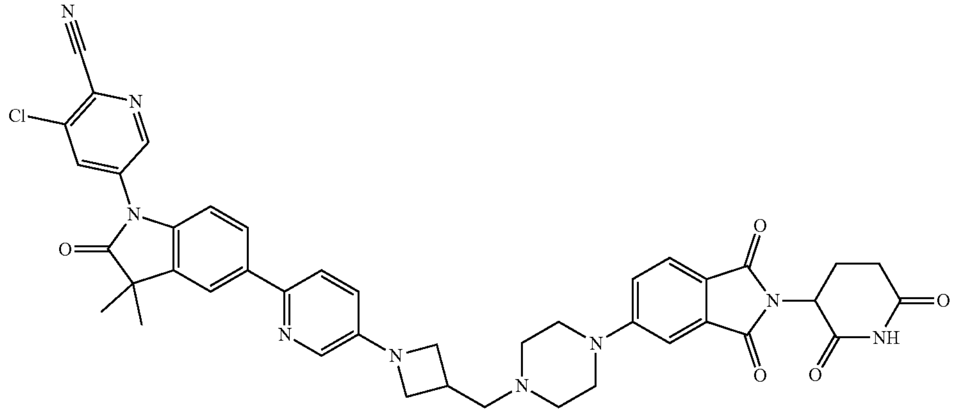
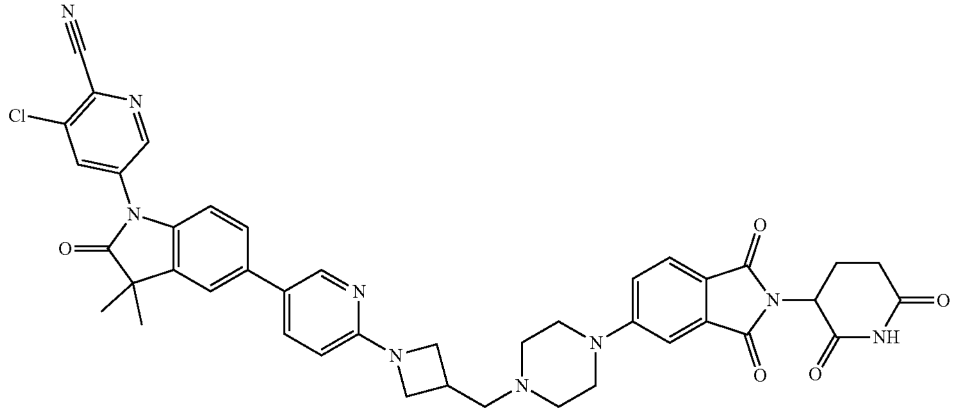
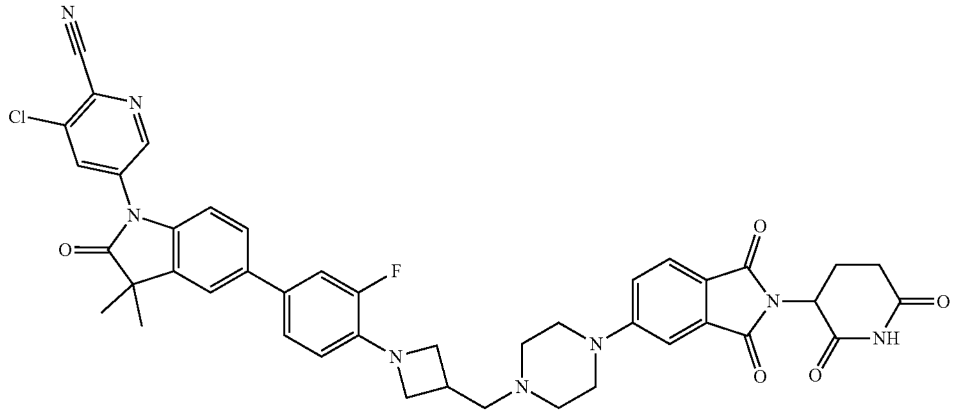

-continued
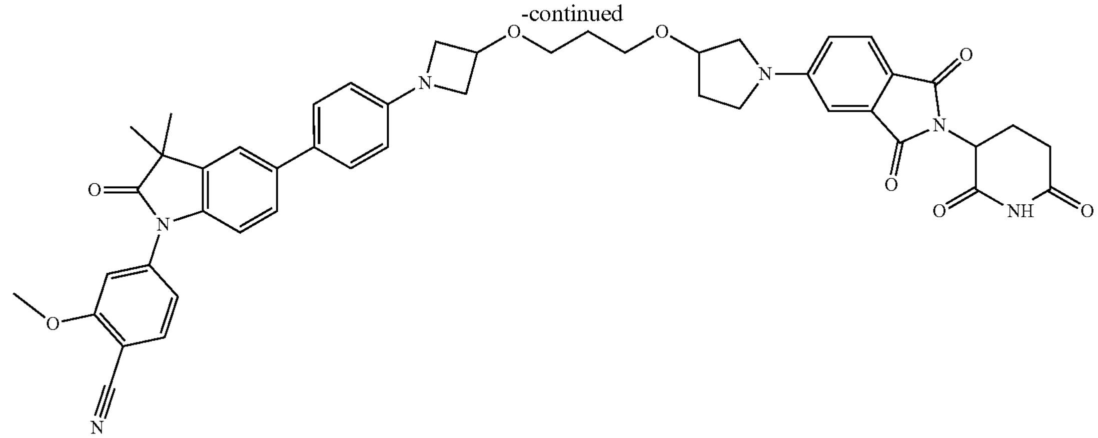
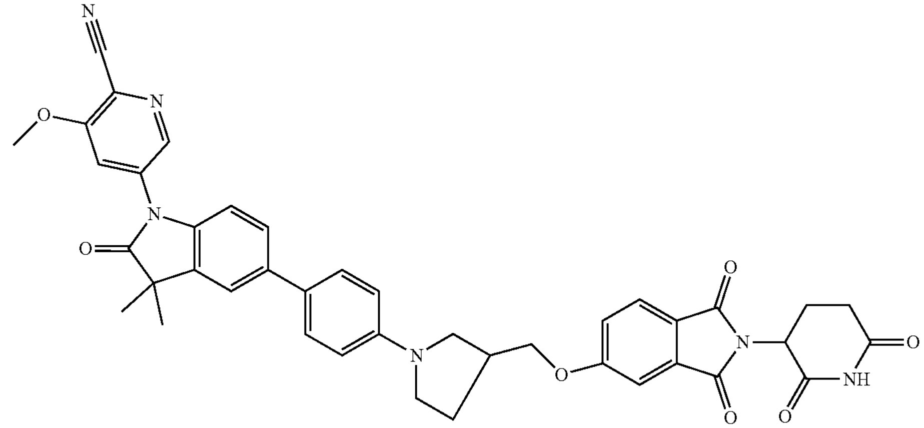
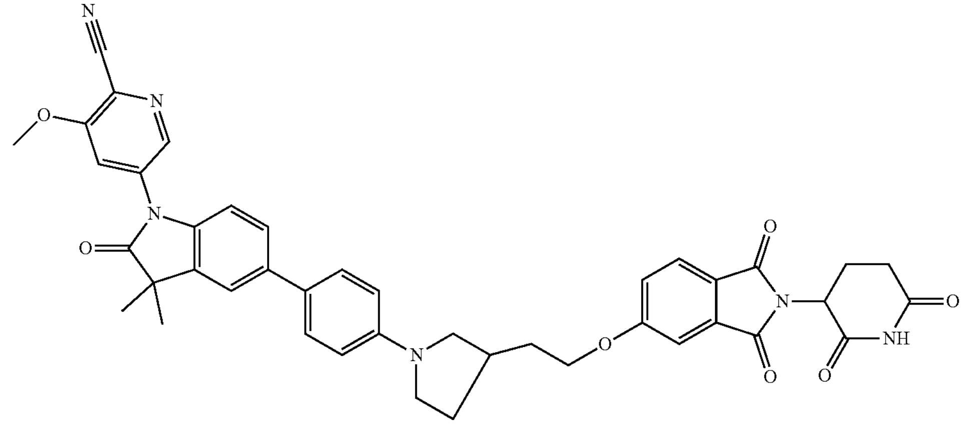
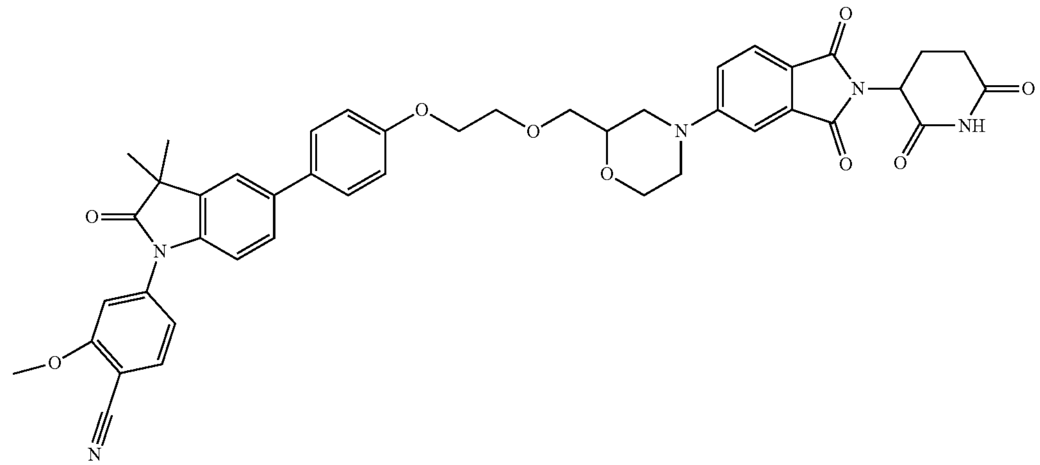

-continued
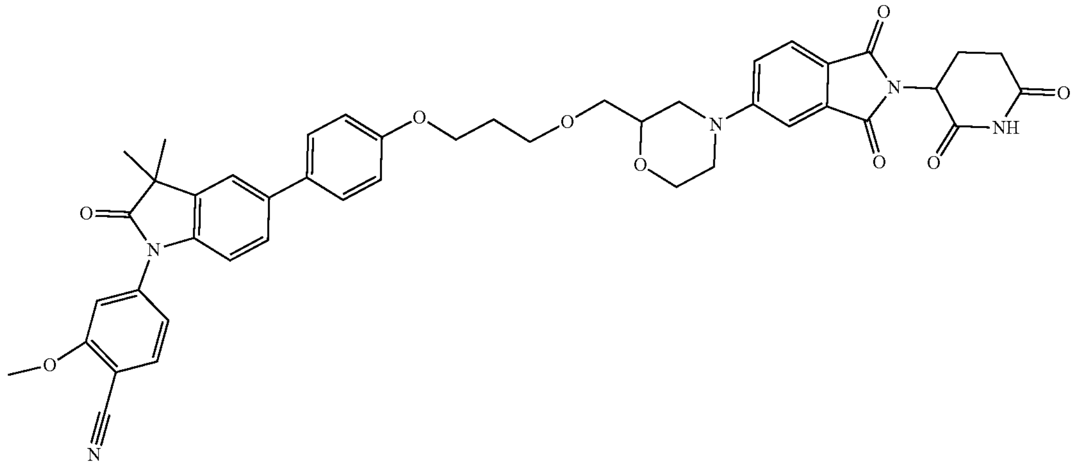
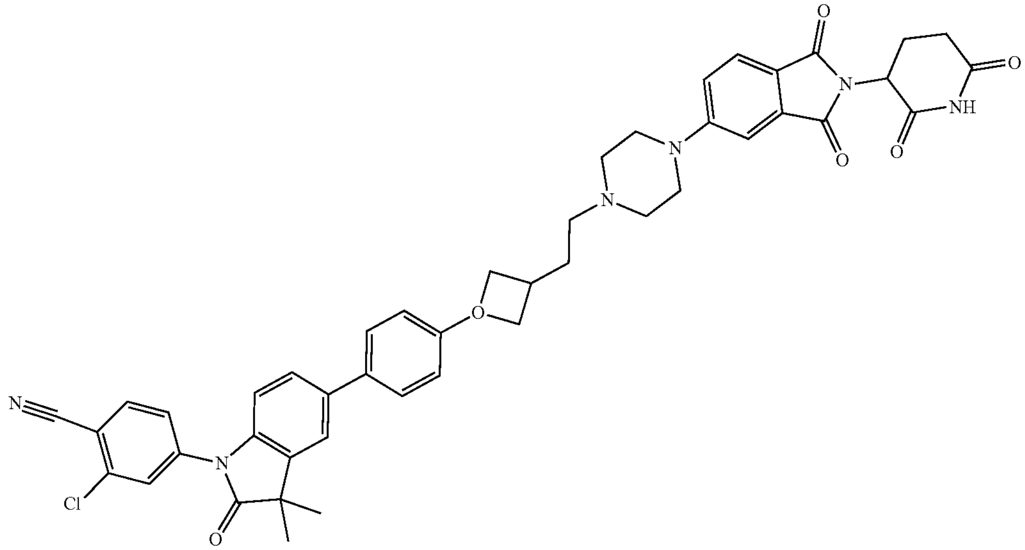
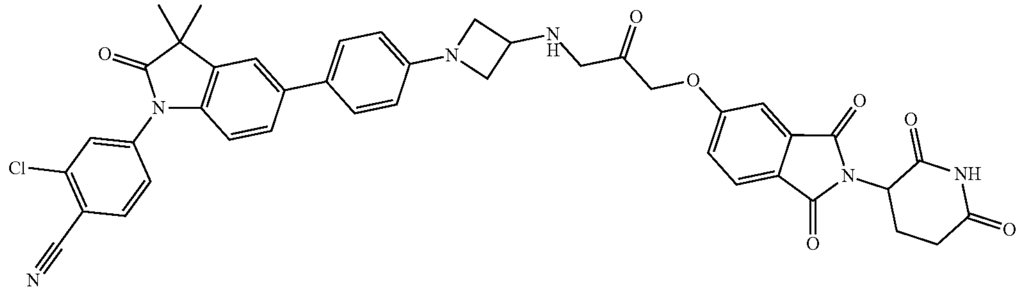
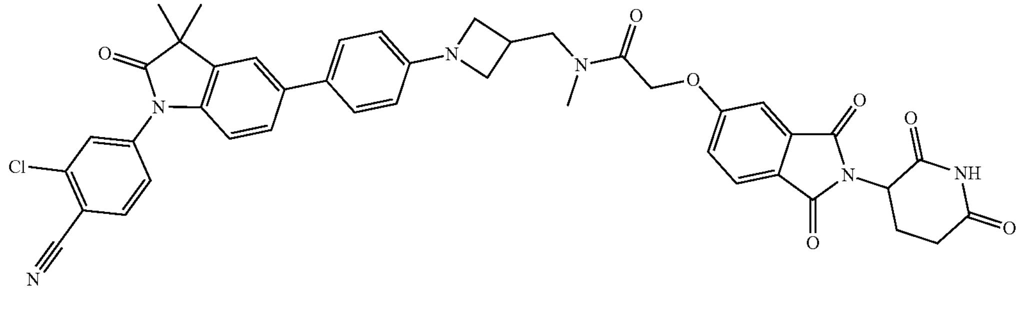

-continued
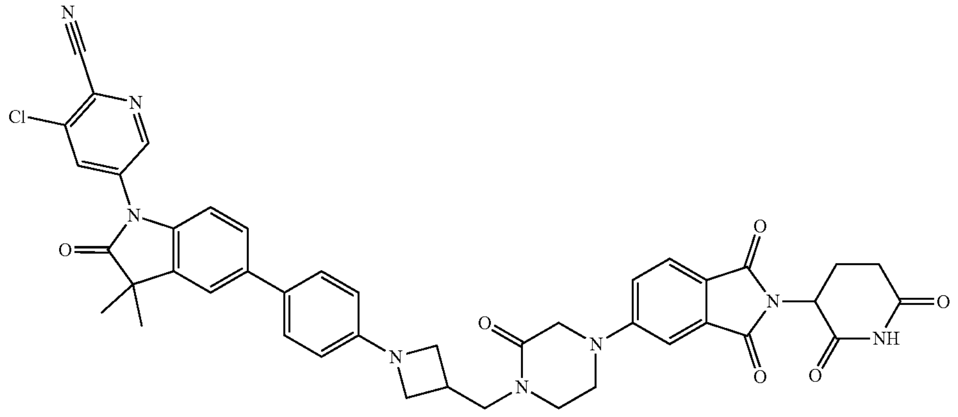
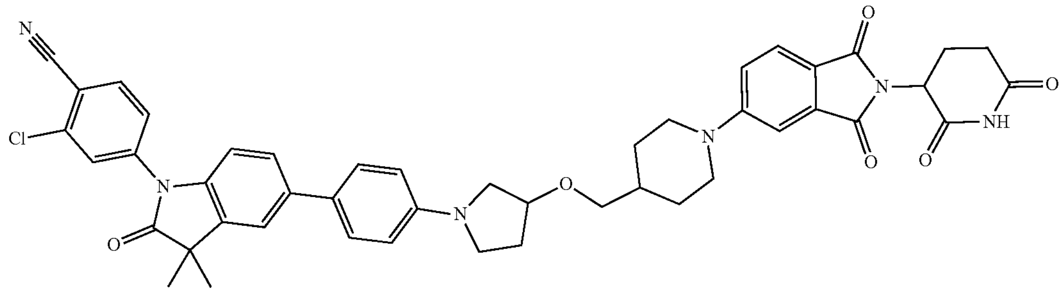
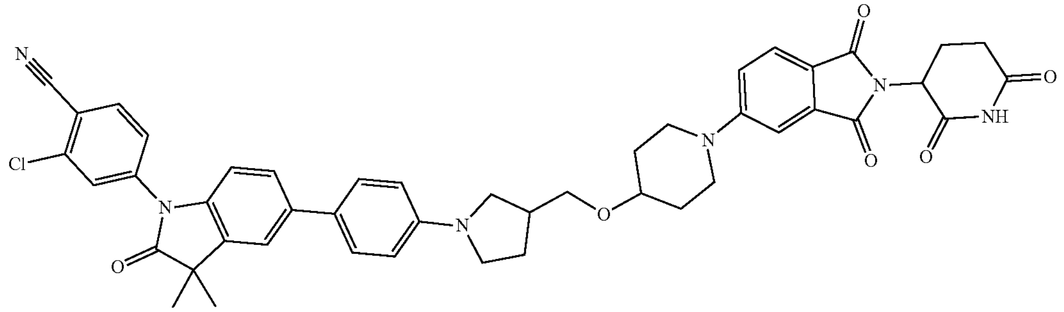
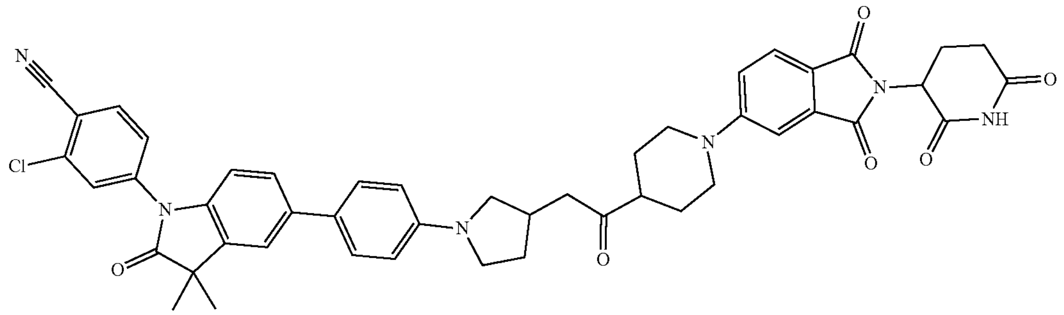
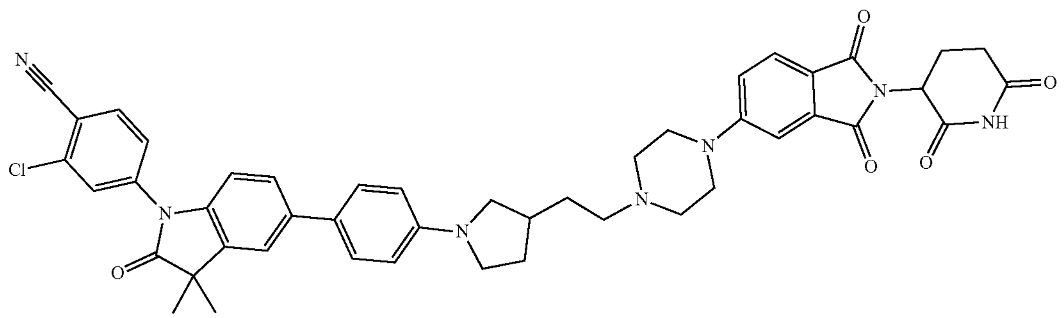

-continued
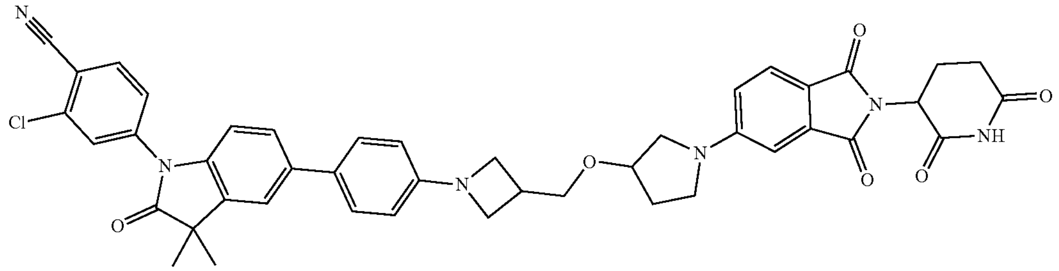
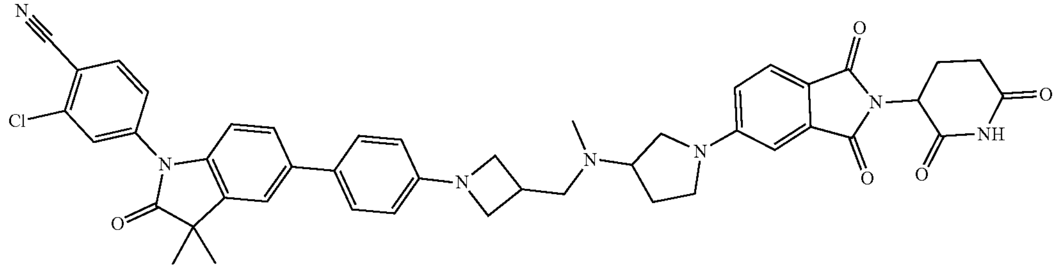
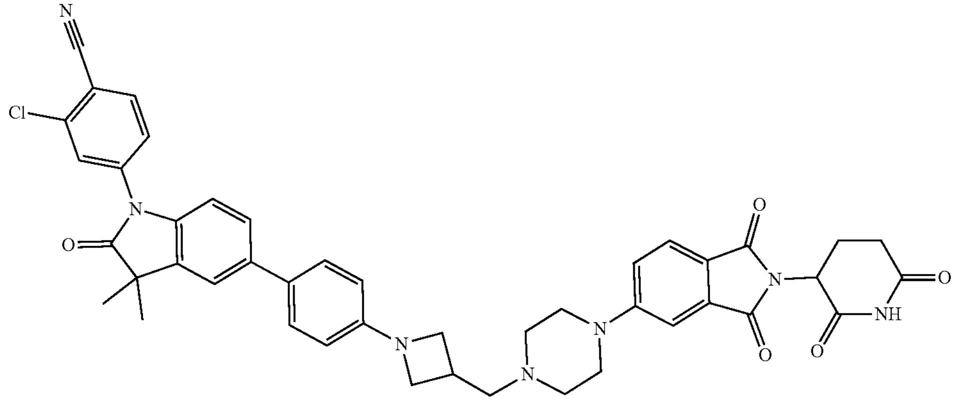
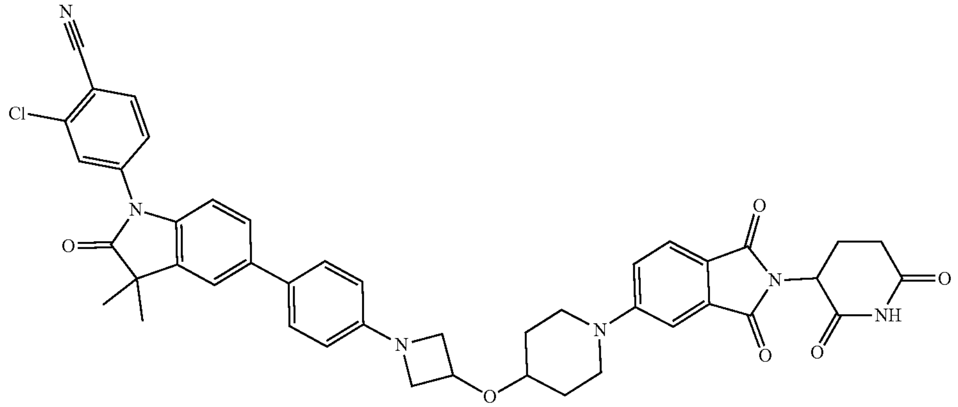
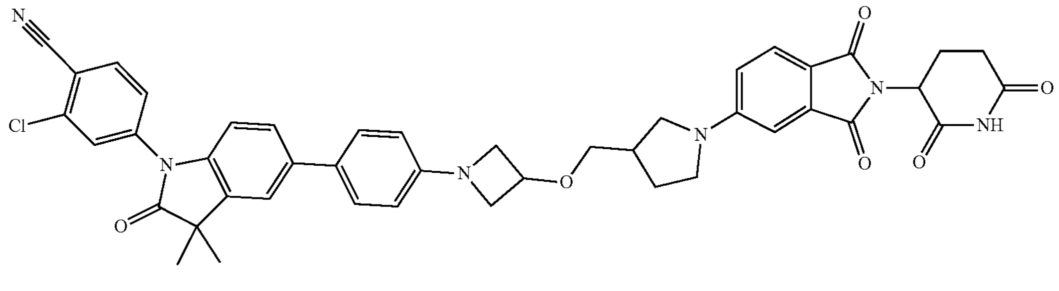

-continued
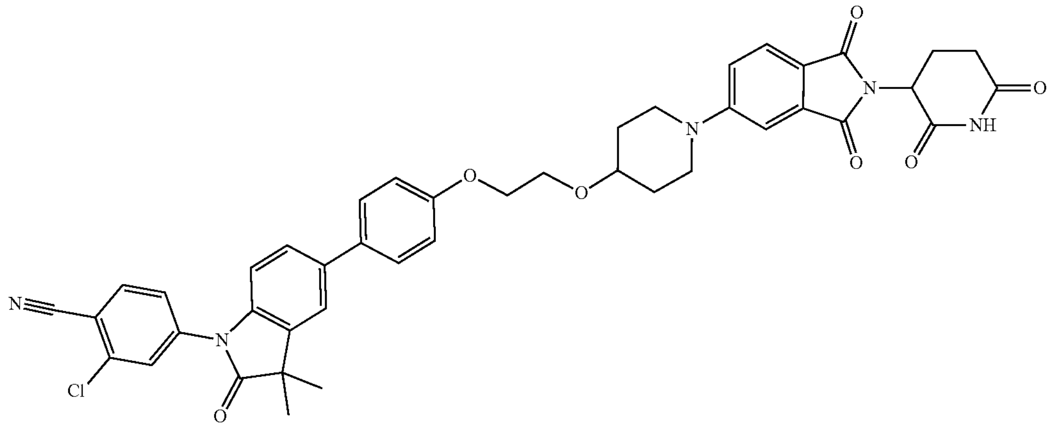
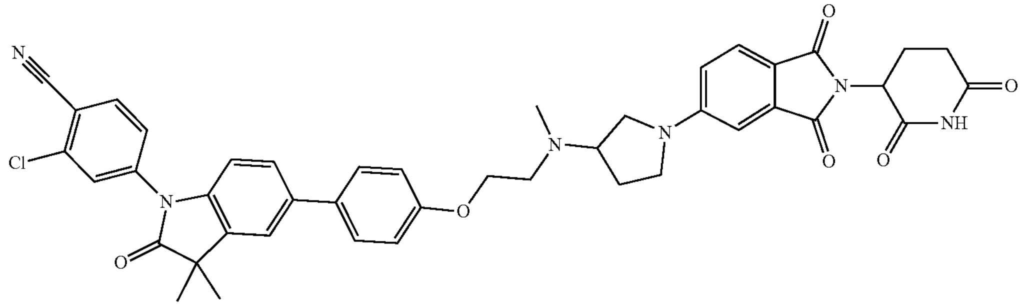
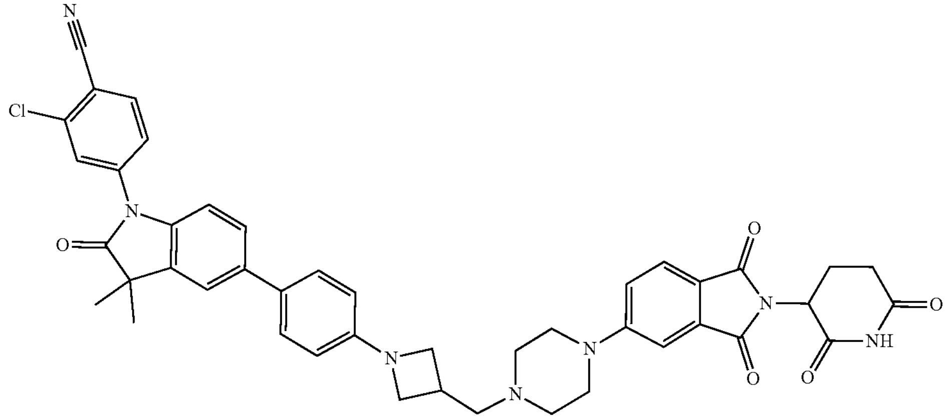
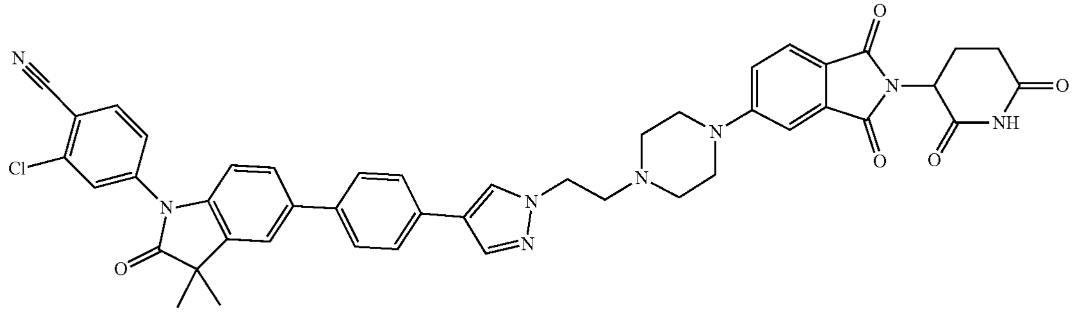

-continued

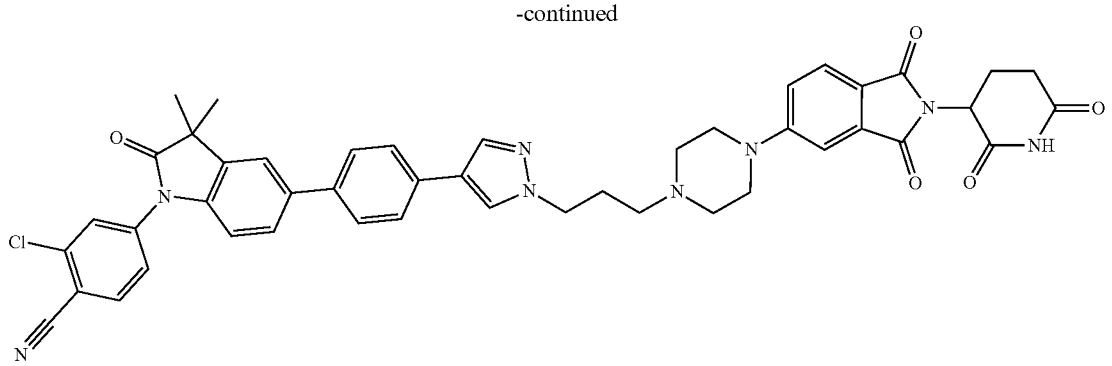

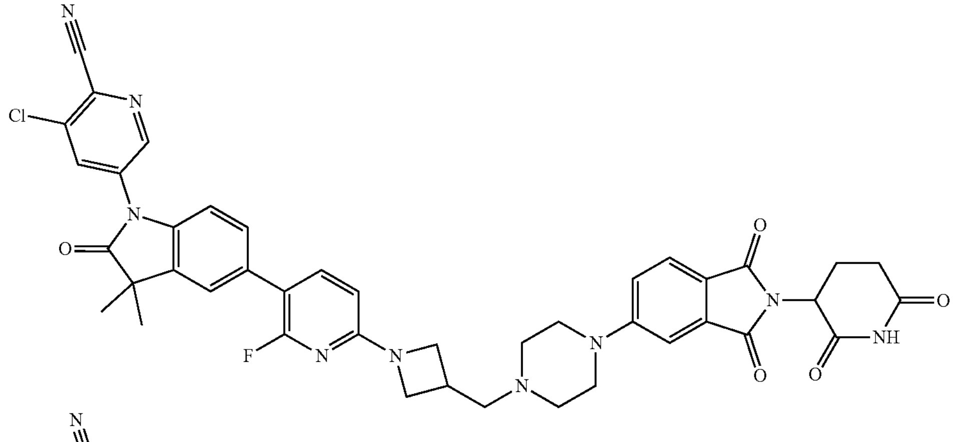

and

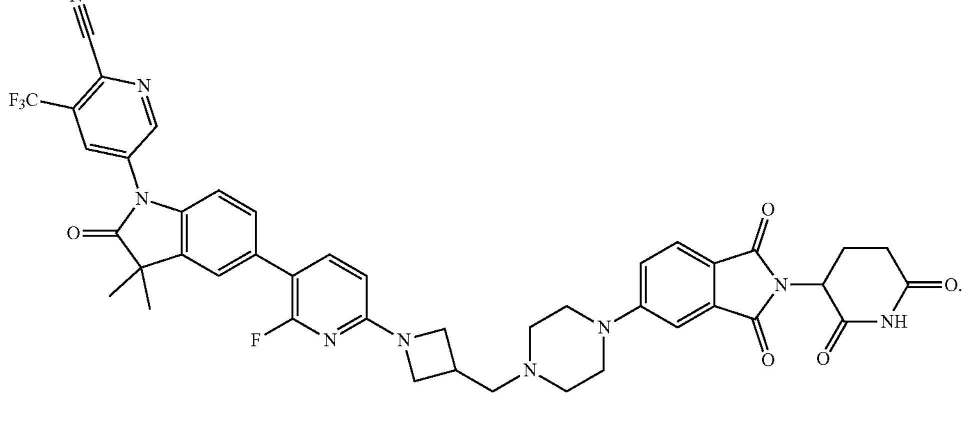

In another aspect of the present disclosure, the present disclosure also provides use of the compound, the optical isomer thereof or the pharmacologically acceptable salt thereof in the manufacture of a medicament for preventing and/or treating cancer or Kennedy's disease.

In some embodiments of the present disclosure, the cancer is AR-related cancer, such as prostate cancer and breast cancer.

In another aspect of the present disclosure, the present disclosure also provides a method of treating cancer (e.g., prostate cancer, breast cancer, etc.) or Kennedy's disease. The method comprises administering the compound, the optical isomer thereof, or the pharmacologically acceptable salt thereof to a patient in need thereof.

Definition and Description

Unless otherwise stated, the following terms and phrases used in the present disclosure are intended to have the following meanings. A specific term or phrase should not be regarded indefinite or unclear in the absence of a particular definition, but should be understood according to the common meaning. When a trade name appears herein, it is intended to refer to its corresponding commercial product or active ingredient thereof.

The term "pharmacologically acceptable" is used herein in terms of those compounds, materials, compositions, and/or dosage forms, which are suitable for use in contact with human and animal tissues within the scope of reliable medical judgment, without excessive toxicity, irritation, allergic response or other problems or complications, and commensurate with a reasonable benefit/risk ratio.

The term "pharmacologically acceptable salt" refers to a salt of the compound of the present disclosure that is prepared by reacting the compound having a particular substituent of the present disclosure with a relatively non-toxic acid or base. When the compound of the present disclosure contains a relatively acidic functional group, a base addition salt can be obtained by contacting the neutral form of such a compound with a sufficient amount of a base in a pure solution or a suitable inert solvent. The pharmacologically acceptable base addition salts include salts of sodium, potassium, calcium, ammonium, organic amine or magnesium, or similar salts. When the compound of the present disclosure contains a relatively basic functional group, an acid addition salt can be obtained by contacting the neutral form of the compound with a sufficient amount of an acid in a pure solution or a suitable inert solvent.

Examples of the pharmacologically acceptable acid addition salts include salts derived from inorganic acids, such as hydrochloric acid, hydrobromic acid, nitric acid, carbonic acid, bicarbonate radical, phosphoric acid, monohydrogen phosphate, dihydrogen phosphate, sulfuric acid, hydrogen sulfate, hydroiodic acid, phosphorous acid, and the like; and salts derived from organic acids, such as acetic acid, propionic acid, isobutyric acid, trifluoroacetic acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acids (such as arginine, etc.), and salts of organic acids such as glucuronic acid and the like. Certain specific compounds of the present disclosure contain both basic and acidic functional groups that allow the compound to be converted into either base or acid addition salts.

The pharmacologically acceptable salts of the present disclosure can be prepared from the parent compound having an acidic or basic group by conventional chemical methods. Generally, such salts are prepared by reacting the free acid or base form of the compound with a stoichiometric amount of an appropriate base or acid in water or an organic solvent or a mixture thereof.

The compound of the present disclosure may exist in specific geometric or stereoisomeric forms. The present disclosure contemplates all such compounds, including cis and trans isomers, (−)- and (+)-enantiomers, (R)- and (S)-enantiomers, diastereoisomers, (D)-isomers, (L)-isomers, and racemic mixtures and other mixtures thereof, such as enantiomers or diastereomer enriched mixtures, all of which are encompassed within the scope of the present disclosure. Additional asymmetric carbon atoms may be present in substituents such as alkyl. All these isomers and their mixtures are encompassed within the scope of the present disclosure.

The compounds of the present disclosure may exist in particular forms. Unless otherwise specified, the term "tautomer" or "tautomeric form" means that at room temperature, different functional isomers are in dynamic equilibrium and can be transformed into each other rapidly. If tautomers are possibly (such as in solution), the chemical equilibrium of the tautomers can be achieved. For example, a proton tautomer (also known as a prototropic tautomer) includes interconversion through proton migration, such as keto-enol isomerization and imine-enamine isomerization. A valence tautomer includes interconversion by recombination of some bonding electrons. A specific example of the keto-enol tautomerization is the interconversion between two tautomers of pentane-2,4-dione and 4-hydroxypent-3-en-2-one.

The compound of the present disclosure may contain an unnatural proportion of atomic isotope at one or more one of the atom(s) that constitute the compound. For example, the compound may be radiolabeled with a radioactive isotope, such as tritium ($^3H$), iodine-125 ($^{125}I$) or C-14 ($^{14}C$). For another example, hydrogen can be substituted by deuterium to form a deuterated drug, and the bond formed by deuterium and carbon is firmer than that of ordinary hydrogen and carbon, compared with non-deuterated drugs, deuterated drugs have the advantages of reduced toxic side effects, increased drug stability, enhanced efficacy, and prolonged biological half-life of drugs, and the like. All isotopic variations of the compounds of the present disclosure, whether radioactive or not, are encompassed within the scope of the present disclosure. The term "optional" or "optionally" means that the subsequently described event or circumstance may, but does not necessarily, occur, and the description includes instances where the event or circumstance occurs and instances where it does not.

The term "substituted" means that one or more hydrogen atom(s) on a specific atom are substituted by the substituent, including deuterium and hydrogen variables, as long as the valence of the specific atom is normal and the substituted compound is stable. The term "optionally substituted" means that an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 1, 2 or 3 R', the group can be optionally substituted with 1, 2 or 3 R' wherein the definition of R' at each occurrence is independent. Moreover, a combination of the substituent and/or the variant thereof is allowed only if the combination results in a stable compound.

When one of the variables is selected from a single bond, it means that the two groups linked by the single bond are connected directly, for example, when $L_1$ in

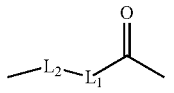

represents a single bond, it means that the structure is actually

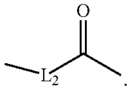

When it is not specified by which atom the listed substituent is linked to the group to be substituted, the substituent can be linked via any atom of the group. For example, pyridyl as a substituent can be linked to the group to be substituted via any carbon atom on the pyridine ring.

When the linking direction of the linking group listed is specified, the direction for linking is arbitrary, for example, when the linking group L contained in

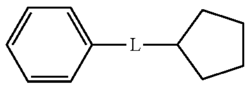

is —$CH_2O$—, then —$CH_2O$— can link phenyl and cyclopentyl to form

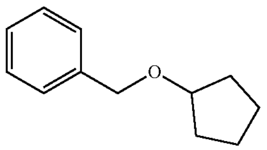 [SMILES: c1ccc(COC2CCCC2)cc1]

in the direction same as left-to-right reading order, and form

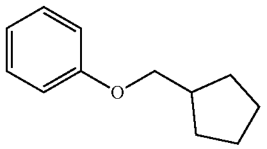 [SMILES: c1ccc(OCC2CCCC2)cc1]

in the direction contrary to left-to-right reading order. A combination of the linking groups, substituents and/or variables thereof are allowed only if the combination can result in a stable compound.

Unless otherwise specified, the number of atoms on a ring is generally defined as the number of ring members, e.g., "3- to 6-membered ring" refers to a "ring" on which 3 to 6 atoms are arranged in a circle.

Unless otherwise specified, the term "$C_{1-6}$ alkyl" refers to a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl, and the like. It can be monovalent (such as $CH_3$), bivalent ($—CH_2—$) or multivalent

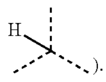

).

Examples of $C_{1-6}$ alkyl include, but are not limited to $CH_3$,

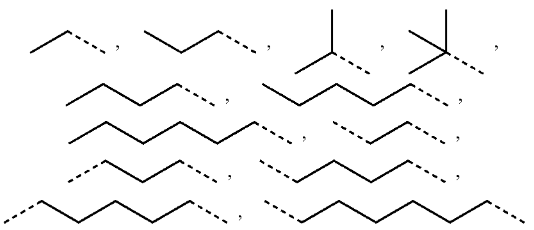

and the like.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl and the like. It can be monovalent (such as $CH_3$), divalent (such as $—CH_2—$) or multivalent (such as

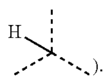

).

Examples of $C_{1-3}$ alkyl include, but are not limited to $CH_3$,

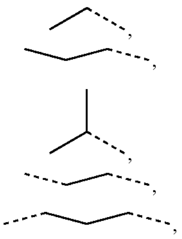

and the like.

Unless otherwise specified, "$C_{2-3}$ alkenyl" refers to a linear or branched hydrocarbon group containing 2 to 3 carbon atoms containing at least one carbon-carbon double bond, which may be located anywhere in the group. The $C_{2-3}$ alkenyl includes $C_3$, and $C_2$ alkenyl. It can be monovalent, divalent or multivalent. Examples of $C_{2-3}$ alkenyl include, but are not limited to

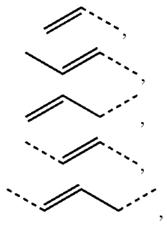

and the like.

Unless otherwise specified, "$C_{2-3}$ alkynyl" refers to a linear or branched hydrocarbon group containing 2 to 3 carbon atoms containing at least one carbon-carbon triple bond, which may be located anywhere in the group. It can be monovalent, bivalent or multivalent. The $C_{2-3}$ alkynyl includes $C_3$, and $C_2$ alkynyl, and the like. Examples of $C_{2-3}$ alkynyl include, but are not limited to

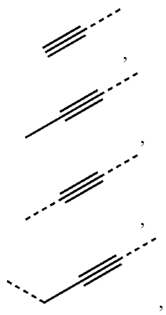

and the like.

Unless otherwise specified, the term "$C_{1-6}$ alkoxy" refers to those alkyl groups that each contains 1 to 6 carbon atoms and is linked to the rest part of the molecule through an oxygen atom. The $C_{1-6}$ alkoxy includes $C_{1-4}$, $C_{1-3}$, $C_{1-2}$, $C_{2-6}$, $C_{2-4}$, $C_6$, $C_5$, $C_4$ and $C_3$ alkoxy, and the like. Examples of $C_{1-6}$ alkoxy include, but are not limited to, methoxy, ethoxy, propoxy (including n-propoxy and isopropoxy), butoxy (including n-butoxy, isobutoxy, s-butoxy and t-butoxy), pentyloxy (including n-pentyloxy, isopentyloxy and neopentyloxy), hexyloxy, and the like.

Unless otherwise specified, the term "$C_{1-3}$ alkoxy" refers to those alkyl groups that each contains 1 to 3 carbon atoms and is linked to the rest part of the molecule through an oxygen atom. The $C_{1-3}$ alkoxy includes $C_{1-3}$, $C_{1-2}$, $C_{2-3}$, $C_1$, $C_2$ and $C_3$ alkoxy, and the like. Examples of $C_{1-3}$ alkoxy include, but are not limited to methoxy, ethoxy, propoxy (including n-propoxy and isopropoxy), and the like.

Unless otherwise specified, the term "$C_{1-6}$ alkylamino" refers to those alkyl groups that each contains 1 to 6 carbon atoms and is linked to the rest part of the molecule through an amino group. The $C_{1-6}$ alkylamino includes $C_{1-4}$, $C_{1-3}$, $C_{1-2}$, $C_{2-6}$, $C_{2-4}$, $C_6$, $C_5$, $C_4$, $C_3$ and $C_2$ alkylamino, and the like. Examples of $C_{1-6}$ alkylamino include, but are not limited to $-NHCH_3$, $-N(CH_3)_2$, $-NHCH_2CH_3$, $-N(CH_3)CH_2CH_3$, $-N(CH_2CH_3)(CH_2CH_3)$, $-NHCH_2CH_2CH_3$, $-NHCH_2(CH_3)_2$, $-NHCH_2CH_2CH_2CH_3$, and the like.

Unless otherwise specified, the term "$C_{1-3}$ alkylamino" refers to those alkyl groups that each contains 1 to 3 carbon atoms and is linked to the rest part of the molecule through an amino atom. The $C_{1-3}$ alkylamino includes $C_{1-3}$, $C_{1-2}$, $C_{2-3}$, $C_1$, $C_2$ and $C_3$ alkylamino, and the like. Examples of $C_{1-3}$ alkylamino include, but are not limited to $-NHCH_3$, $-N(CH_3)_2$, $-NHCH_2CH_3$, $-N(CH_3)CH_2CH_3$, $-NHCH_2CH_2CH_3$, $-NHCH_2(CH_3)_2$, and the like.

Unless otherwise specified, the term "$C_{1-6}$ alkylthio" refers to those alkyl groups that each contains 1 to 6 carbon atoms and is linked to the rest part of the molecule through a sulfur atom. The $C_{1-6}$ alkylthio includes $C_{1-4}$, $C_{1-3}$, $C_{1-2}$, $C_{2-6}$, $C_{2-4}$, $C_6$, $C_5$, $C_4$, $C_3$ and $C_2$ alkylthio, and the like. Examples of $C_{1-6}$ alkylthio include, but are not limited to $-SCH_3$, $-SCH_2CH_3$, $-SCH_2CH_2CH_3$, $-SCH_2(CH_3)_2$, and the like.

Unless otherwise specified, the term "$C_{1-3}$ alkylthio" refers to those alkyl groups that each contains 1 to 3 carbon atoms, and is linked to the rest part of the molecule through a sulfur atom. The $C_{1-3}$ alkylthio includes $C_{1-3}$, $C_{1-2}$, $C_{2-3}$, $C_1$, $C_2$ and $C_3$ alkylthio, and the like. Examples of $C_{1-3}$ alkylamino include, but are not limited to $-SCH_3$, $-SCH_2CH_3$, $-SCH_2CH_2CH_3$, $-SCH_2(CH_3)_2$, and the like.

Unless otherwise specified, "$C_{3-9}$ cycloalkyl" refers to a saturated cyclic hydrocarbon group consisting of 3 to 9 carbon atoms, including monocyclic and bicyclic ring systems, the $C_{3-9}$ cycloalkyl includes $C_{3-8}$, $C_{3-7}$, $C_{3-6}$, $C_{3-5}$ and $C_{5-6}$ cycloalkyl, and the like. It may be monovalent, divalent or multivalent. Examples of $C_{3-9}$ cycloalkyl include, but are not limited to, cyclopropyl, cyclobutyl, cyclopentyl, cyclohexyl, cycloheptane, and the like.

Unless otherwise specified, "$C_{3-6}$ cycloalkyl" refers to a saturated cyclic hydrocarbon group consisting of 3 to 6 carbon atoms, including monocyclic and bicyclic ring systems, the $C_{3-6}$ cycloalkyl includes $C_{3-5}$, $C_{4-5}$ and $C_{5-6}$, and the like. It may be monovalent, divalent or multivalent. Examples of $C_{3-6}$ alkynyl include, but are not limited to, cyclopropyl, cyclobutyl, cyclopentyl, cyclohexyl, and the like.

Unless otherwise specified, the term "3- to 12-membered heterocycloalkyl" by itself or in combination with other terms respectively refers to a saturated cyclic group consisting of 3 to 12 ring atoms, of which 1, 2, 3, or 4 ring atoms are heteroatoms independently selected from O, S, and N with the remaining being carbon atoms, where the nitrogen atom is optionally quaternized, and the nitrogen and sulfur heteroatoms are optionally oxidized (i.e., NO and $S(O)_p$, p is 1 or 2). It includes monocyclic, bicyclic and tricyclic systems, wherein bicyclic and tricyclic systems include spiro, fused and bridged rings. Moreover, with respect to the "3- to 12-membered heterocycloalkyl", a heteroatom may occupy the position where the heterocycloalkyl is linked to the rest part of the molecule. The 3- to 12-membered heterocycloalkyl includes 3- to 10-membered, 3- to 9-membered, 3- to 8-membered, 3- to 6-membered, 3- to 5-membered, 4- to 6-membered, 5- to 6-membered, 4-membered, 5-membered and 6-membered heterocycloalkyl, and the like. Examples of 3- to 12-membered heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl and tetrahydrothien-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, homopiperidinyl or dioxepanyl,

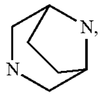

and the like.

Unless otherwise specified, the term "3- to 9-membered heterocycloalkyl" by itself or in combination with other terms respectively refers to a saturated cyclic group consisting of 3 to 9 ring atoms, of which 1, 2, 3 or 4 ring atoms are heteroatoms independently selected from O, S, and N with the remaining being carbon atoms, where the nitrogen atom is optionally quaternized, and the nitrogen and sulfur heteroatoms are optionally oxidized (i.e., NO and $S(O)_p$, p is 1 or 2). It includes monocyclic and bicyclic systems, wherein bicyclic system includes spiro, fused and bridged rings. Moreover, with respect to the "3- to 9-membered heterocycloalkyl", a heteroatom may occupy the position where the heterocycloalkyl is linked to the rest part of the molecule. The 3- to 9-membered heterocycloalkyl includes 3- to 6-membered, 4- to 7-membered, 4-membered, 5-membered, 6-membered, 7-membered, 8-membered and 9-membered heterocycloalkyl, and the like. Examples of 3- to 9-membered heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl and tetrahydrothien-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl or homopiperidinyl, and the like.

Unless otherwise specified, the term "3- to 6-membered heterocycloalkyl" by itself or in combination with other terms respectively refers to a saturated cyclic group consisting of 3 to 6 ring atoms, of which 1, 2, 3 or 4 ring atoms are heteroatoms independently selected from O, S, and N with the remaining being carbon atoms, where the nitrogen atom is optionally quaternized, and the nitrogen and sulfur heteroatoms are optionally oxidized (i.e., NO and $S(O)_p$, p is 1 or 2). It includes monocyclic and bicyclic systems, wherein bicyclic system includes spiro, fused and bridged rings. Moreover, with respect to the "3-6 membered heterocycloalkyl", a heteroatom may occupy the position where the heterocycloalkyl is linked to the rest part of the molecule. The 3- to 6-membered heterocycloalkyl includes 4- to 6-membered, 5- to 6-membered, 4-membered, 5-membered and 6-membered heterocycloalkyl, and the like. Examples of 3- to 6-membered heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl and tetrahydrothien-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl or homopiperidinyl, and the like.

Unless otherwise specified, the term "$C_{6-10}$ aromatic ring" and "$C_{6-10}$ aryl" are used interchangeably, and the term "$C_{6-10}$ aromatic ring" or "$C_{6-10}$ aryl" refers to a cyclic hydrocarbon group having a conjugated π-electron system composed of 6 to 10 carbon atoms, which can be a monocyclic, fused bicyclic or fused tricyclic system, where each ring is aromatic. It may be monovalent, divalent or polyvalent, and the $C_{6-10}$ aryl includes $C_{6-9}$, $C_9$, $C_{10}$ and $C_6$ aryl groups, and the like. Examples of $C_{6-10}$ aryl include, but are not limited to, phenyl, naphthyl (including 1-naphthyl and 2-naphthyl, etc.).

Unless otherwise specified, the terms "5- to 12-membered heteroaromatic ring" and "5- to 12-membered heteroaryl" can be used interchangeably in the present disclosure, and the term "5- to 12-membered heteroaryl" refers to a ring consisting of 5 to 12 rings and having a conjugated π-electron system, wherein 1, 2, 3 or 4 ring atoms are heteroatoms independently selected from O, S and N, and the others are carbon atoms. It can be a monocyclic, fused bicyclic or fused tricyclic system, wherein each ring is aromatic. The nitrogen atoms are optionally quaternized and the nitrogen and sulfur heteroatoms are optionally oxidized (i.e. NO and $S(O)_p$, p is 1 or 2). The 5- to 12-membered heteroaryl can be linked to the rest part of the molecule via a heteroatom or a carbon atom. The 5- to 12-membered heteroaryl includes 5-to 10-membered, 5- to 9-membered, 5- to 8-membered, 5- to 7-membered, 5- to 6-membered, 5-membered and 6-membered heteroaryl, and the like. Examples of the 5- to 12-membered heteroaryl include, but are not limited to, pyrrolyl (including N-pyrrolyl, 2-pyrrolyl and 3-pyrrolyl, etc.), pyrazolyl (including 2-pyrazolyl and 3-pyrrolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (including 1H-1,2,3-triazolyl, 2H-1,2,3-triazolyl, 1H-1,2,4-triazolyl and 4H-1,2,4-triazolyl, etc.), tetrazolyl, isoxazolyl(3-isoxazolyl, 4-isoxazolyl and 5-isoxazolyl, etc.), thiazolyl (including 2-thiazolyl, 4-thiazolyl and 5-thiazolyl, etc.), furanyl (including 2-furanyl and 3-furanyl, etc.), thienyl (including 2-thienyl and 3-thienyl, etc.), pyridyl (including 2-pyridyl, 3-pyridyl and 4-pyridyl, etc.), pyrazinyl, pyrimidinyl (including 2-pyrimidinyl and 4-pyrimidinyl, etc.), benzothiazolyl (including 5-benzothiazolyl, etc.), purinyl, benzimidazolyl (including 2-benzimidazolyl, etc.), benzoxazolyl, indolyl (including 5-indolyl, etc.), isoquinolinyl (including 1-isoquinolinyl, etc.) and 5-isoquinolinyl, etc.), quinoxalinyl (including 2-quinoxalinyl and 5-quinoxalinyl, etc.) or quinolinyl (including 3-quinolinyl and 6-quinolinyl, etc.).

Unless otherwise specified, the terms "5- to 6-membered heteroaromatic ring" and "5-to 6-membered heteroaryl" are used interchangeably in the present disclosure, the term "5- to 6-membered heteroaryl" refers to a monocyclic group consisting of 5 to 6 ring and having a conjugated π-electron system, where 1, 2, 3 or 4 ring atoms are heteroatoms independently selected from O, S and N, and the others are carbon atoms. The nitrogen atoms are optionally quaternized and the nitrogen and sulfur heteroatoms are optionally oxidized (i.e. NO and $S(O)_p$, p is 1 or 2). The 5- to 6-membered heteroaryl can be linked to the rest part of the molecule via a heteroatom or a carbon atom. The 5- to 6-membered heteroaryl includes 5-membered and 6-membered heteroaryl, and the like. Examples of the 5- to 6-membered heteroaryl include, but are not limited to, pyrrolyl (including N-pyrrolyl, 2-pyrrolyl and 3-pyrrolyl, etc.), pyrazolyl (including 2-pyrazolyl and 3-pyrrolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (including 1H-1,2,3-triazolyl, 2H-1,2,3-triazolyl, 1H-1,2,4-triazolyl and 4H-1,2,4-triazolyl, etc.), tetrazolyl, isoxazolyl(3-isoxazolyl, 4-isoxazolyl and 5-isoxazolyl, etc.), thiazolyl (including 2-thiazolyl, 4-thiazolyl and 5-thiazolyl, etc.), furanyl (including 2-furanyl and 3-furanyl, etc.), thienyl (including 2-thienyl and 3-thienyl, etc.), pyridyl (including 2-pyridyl, 3-pyridyl and 4-pyridyl, etc.), pyrazinyl or pyrimidinyl (including 2-pyrimidinyl and 4-pyrimidinyl, etc.).

Unless otherwise specified, the terms "5- to 6-membered heteroaromatic ring" and "5-to 6-membered heteroaryl" are used interchangeably in the present disclosure, the term "5- to 6-membered heteroaryl" refers to a monocyclic group consisting of 5 to 6 ring and having a conjugated π-electron system, where 1, 2, 3 or 4 ring atoms are heteroatoms independently selected from O, S and N, and the others are carbon atoms. The nitrogen atoms are optionally quaternized and nitrogen and sulfur heteroatoms are optionally oxidized (i.e. NO and $S(O)_p$, p is 1 or 2). The 5-10 membered heteroaryl can be linked to the rest part of the molecule through a heteroatom or a carbon atom. The 5- to 10-membered heteroaryl includes 5-membered, 6-membered, 7-membered, 8-membered, 9-membered and 10-membered heteroaryl, and the like.

Examples of the 5- to 10-membered heteroaryl include, but are not limited to, pyrrolyl (including N-pyrrolyl, 2-pyrrolyl and 3-pyrrolyl, etc.), pyrazolyl (including 2-pyrazolyl and 3-pyrrolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (including 1H-1,2,3-triazolyl, 2H-1,2,3-triazolyl, 1H-1,2,4-triazolyl and 4H-1,2,4-triazolyl, etc.), tetrazolyl, isoxazolyl(3-isoxazolyl, 4-isoxazolyl and 5-isoxazolyl, etc.), thiazolyl (including 2-thiazolyl, 4-thiazolyl and 5-thiazolyl, etc.), furanyl (including 2-furanyl and 3-furanyl, etc.), thienyl (including 2-thienyl and 3-thienyl, etc.), pyridyl (including 2-pyridyl, 3-pyridyl and 4-pyridyl, etc.), pyrazinyl or pyrimidinyl (including 2-pyrimidinyl and 4-pyrimidinyl, etc.).

Unless otherwise specified, $C_{n-n+m}$ or $C_{n-Cn+m}$ includes any one of the specific cases of n to n+m carbon atoms, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range within n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, and the like. Similarly, n-membered to n+m-membered means that the number of atoms on the ring is from n to n+m. For example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring, and any range within n to n+m is also included. For example, 3- to 12-membered ring includes 3- to 6-membered ring, 3- to 9-membered ring, 5-to 6-membered ring, 5- to 7-membered ring, 5- to 10-membered ring, 6- to 7-membered ring, 6- to 8-membered ring, and 6- to 10-membered ring, and the like.

The term "leaving group" refers to a functional group or atom which can be substituted by another functional group or atom through a substitution reaction (such as affinity substitution reaction). For example, representative leaving groups include trifluoromethanesulfonate; chlorine, bromine, and iodine; sulfonate group, such as methanesulfonate, tosylate, p-bromobenzenesulfonate, p-toluenesulfonate etc.; acyloxy, such as acetoxy, trifluoroacetoxy, etc.

The term "protecting group" includes, but is not limited to "amino protecting group", "hydroxyl protecting group" or "mercapto protecting group". The term "amino protecting group" refers to a protecting group suitable for preventing side reactions occurring at the nitrogen of an amino group. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl, such as benzyl (Bn), triphenyl methyl (Tr), 1,1-bis-(4'-methoxyphenyl)methyl; silyl, such as trimethylsilyl (TMS) and tert-butyldimethylsilyl (TBS) and the like. The term "hydroxy protecting group" refers to a protecting group suitable for preventing side reactions of a hydroxyl. Representative hydroxyl protecting groups include, but are not limited to: alkyl, such as methyl, ethyl, and tert-butyl; acyl, such as alkanoyl (e.g., acetyl); arylmethyl, such as benzyl (Bn), p-methoxybenzyl (PMB), 9-fluorenylmethyl (Fm), and diphenylmethyl (benzhydryl, DPM); silyl, such as trimethylsilyl (TMS) and tert-butyl dimethyl silyl (TBS) and the like.

The compounds of the present disclosure can be prepared by a variety of synthetic methods well known to those skilled in the art, including the specific embodiments listed below, the embodiments formed by their combination with other chemical synthesis methods, and equivalent alternatives well known to those skilled in the art, preferred implementations include but are not limited to the embodiments of the present disclosure.

The solvents used in the present disclosure are commercially available.

The compounds of the present disclosure are named according to the conventional nomenclature principles in the art or using ChemDraw® software, and the commercially available compounds use the supplier's catalog names.

DETAILED DESCRIPTION OF THE EMBODIMENTS

Figure 1:
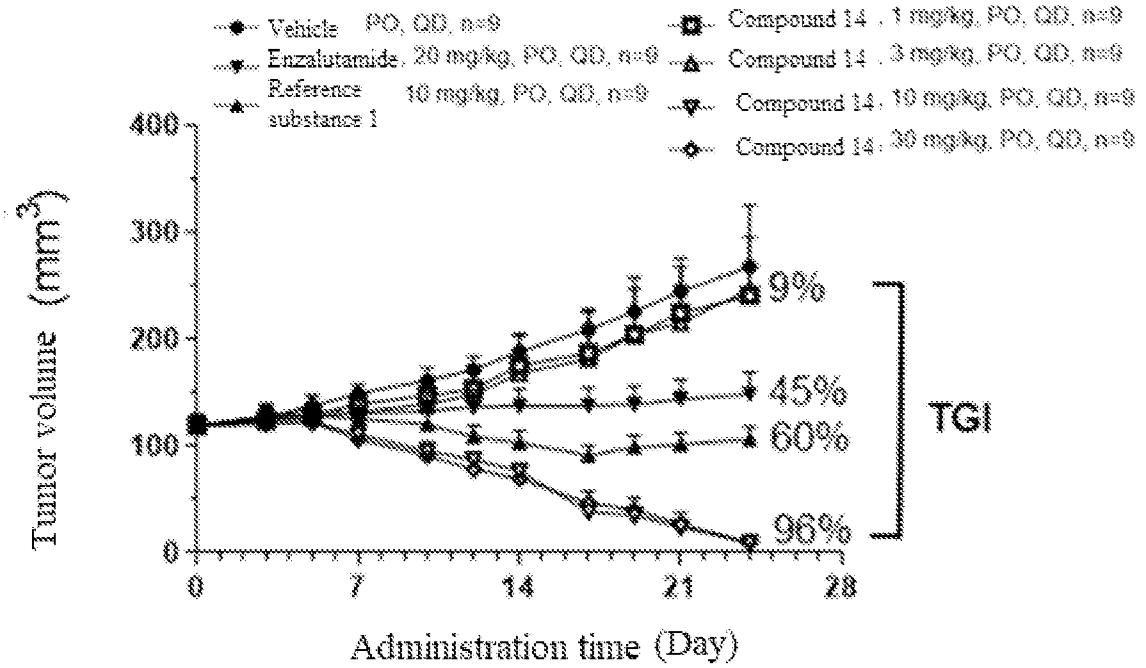
FIG. 1 shows the effect of compound 14 on the growth of tumor volume in human prostate cancer VCaP cell subcutaneous xenograft tumor CB17 SCID mouse model.

The present disclosure is described in detail with the embodiments below, but it does not mean that there are any adverse restrictions to the present disclosure. The present disclosure has been described in detail herein, wherein specific embodiments thereof are also disclosed, and it will be apparent to those skilled in the art that various variations and improvements can be made to specific embodiments of the present disclosure without departing from the spirit and scope of the present disclosure.

Preparation of Intermediates

Reference Embodiment 1: Preparation of Intermediate I-1

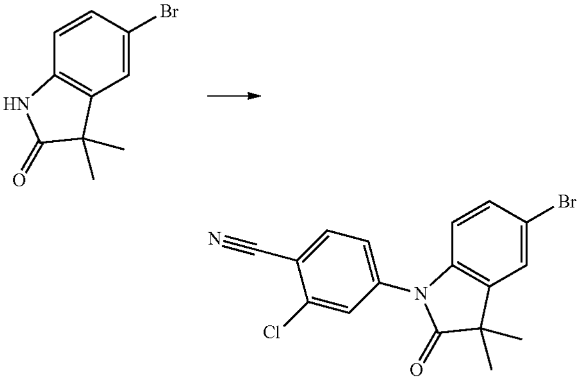

I-1

5-Bromo-3,3-dimethyl-1H-indol-2-one (3.50 g, 14.60 mmol) and potassium tert-butoxide (2.46 g, 21.90 mmol) were dissolved in dimethyl sulfoxide (50 mL) at room temperature. After the mixture was stirred and reacted for 30 minutes, 2-chloro-4-fluorobenzonitrile (2.72 g, 17.50 mmol) was added to the reaction solution, and the reaction solution was stirred at 20° C. for 20 hours. Water (100 mL) and ethyl acetate (50 mL) were added to the reaction system, the organic phase was separated, and the aqueous phase was extracted with ethyl acetate (50 mL×2). The organic phases were combined, washed with saturated brine (10 mL), dried with anhydrous sodium sulfate and filtered. The filtrate was concentrated under reduced pressure, and the residue was purified by silica gel chromatography to obtain intermediate I-1.

LC-MS (ESI) $[M+H]^+$ 375.1;

$^1$H NMR (400 MHz, DMSO-$d_6$) δ 8.18 (d, J=8.4 Hz, 1H), 7.96 (d, J=1.9 Hz, 1H), 7.76 (d, J=2.0 Hz, 1H), 7.70 (dd, J=8.4, 1.9 Hz, 1H), 7.44 (dd, J=8.4, 2.1 Hz, 1H), 6.93 (d, J=8.4 Hz, 1H), 1.42 (s, 6H).

Reference Embodiment 2: Preparation of Intermediate I-2

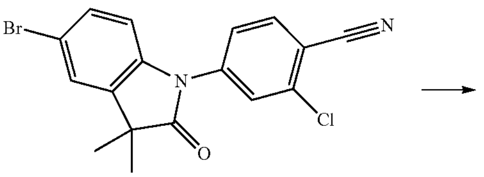

I-1

-continued

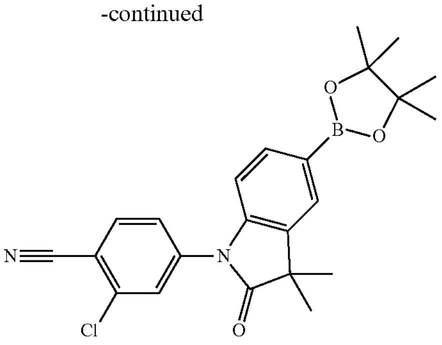

I-2

At room temperature, intermediate I-1 (1.00 g, 2.67 mmol), bis(pinacolato)diboron (1.08 g, 4.01 mmol), [1,1'-bis(diphenylphosphino)ferrocene]dichloropalladium(II) (195 mg, 0.27 mmol) and potassium acetate (785 mg, 8.01 mmol) were dissolved in dioxane (40 mL), the reaction solution was replaced with nitrogen for three times and then heated to 90° C. and stirred for two hours. The reaction solution was evaporated under reduced pressure, and the residue was separated and purified by silica gel chromatography to obtain intermediate I-2.

LC-MS (ESI) $[M+H]^+$ 423.3.

Reference Embodiment 3: Preparation of Intermediate I-3

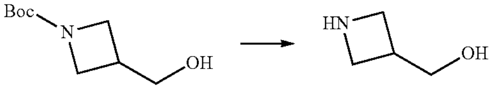

I-3

At 25° C., 3-hydroxymethyl-N-boc-azetidine (1.00 g, 5.34 mmol) was dissolved in hydrochloric acid/dioxane (10 mL) and reacted at room temperature for 5 hours. The reaction solution was evaporated under reduced pressure to obtain crude product of the intermediate I-3, and the crude product was then used directly for the next reaction without purification.

Reference Embodiment 4: Preparation of Intermediate I-4

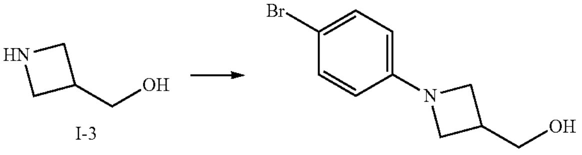

I-3

I-4

At 25° C., intermediate I-3 (800.00 mg) was dissolved in dimethyl sulfoxide (20 mL), then potassium carbonate (2.21 g, 16.02 mmol), p-bromoiodobenzene (1.81 g, 6.41 mmol), L-proline (123.19 mg, 1.07 mmol) and cuprous iodide (203.78 mg, 1.07 mmol) were sequentially added. The reaction solution was stirred at 90° C. for 16 hours under the protection of nitrogen. After the reaction solution was cooled to room temperature, the reaction solution was added to water (50 mL), and extracted with ethyl acetate (50 mL×3). The organic phases were combined, washed with saturated brine (50 mL), dried with anhydrous sodium sulfate, filtered and spin-dried. The filtrate was concentrated under reduced pressure to obtain a residue, and the residue was purified by silica gel chromatography to obtain intermediate I-4.

LC-MS (ESI) $[M+H]^+$: 242.0.

Reference Embodiment 5: Preparation of Intermediate I-5

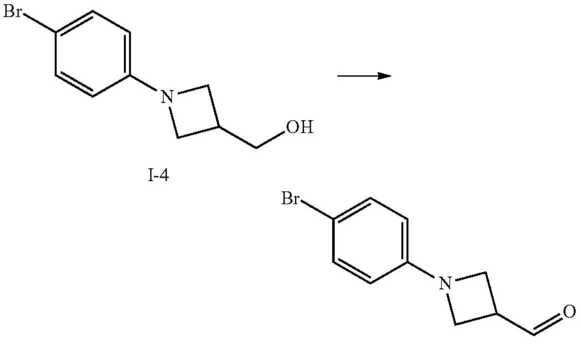

I-4

I-5

Oxalyl chloride (420.11 mg, 3.31 mmol) was dissolved in dichloromethane (10 mL), and the mixture was cooled to −60° C., dimethyl sulfoxide (532.07 mg, 6.81 mmol) was slowly added, and the reaction solution was stirred at −60° C. for 0.5 hours. Then a dichloromethane (5 mL) solution of intermediate I-4 (500.00 mg, 2.07 mmol) was added. After the reaction solution was stirred at −60° C. for 1 hour, triethylamine (1.05 g, 10.35 mmol) was added, and the reaction solution was further stirred at −60° C. for 0.5 hours. After the reaction solution was raised to room temperature and stirred for 0.5 hours, water (20 mL) was added, then extracted with dichloromethane (20 mL×3). The organic phases were combined, washed with saturated brine (20 mL), dried with anhydrous sodium sulfate and filtered. The filtrate was concentrated under reduced pressure to obtain a residue, and the residue was purified by silica gel chromatography to obtain intermediate I-5.

LC-MS (ESI) $[M+H]^+$: 240.0.

Reference Embodiment 6: Preparation of Intermediate I-6

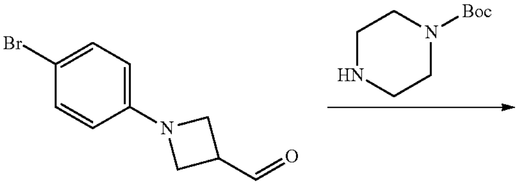

I-5

-continued

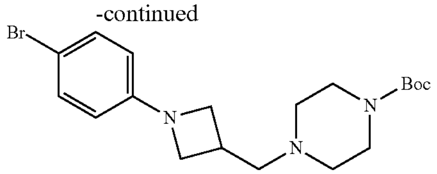

I-6

At 25° C., intermediate I-5 (200.00 mg, 0.83 mmol) was dissolved in dichloromethane (10 mL), 1-Boc-piperazine (232.72 mg, 1.25 mmol), sodium triacetoxyborohydride (353.09 mg, 1.67 mmol) and acetic acid (5.00 mg, 0.083 mmol) were sequentially added, and the reaction solution was stirred at room temperature for 16 hours. Water (10 mL) was added to the reaction system, and the reaction system was extracted with dichloromethane (10 mL×3). The organic phases were combined, washed with saturated brine (10 mL), dried with anhydrous sodium sulfate and filtered. The filtrate was concentrated under reduced pressure to obtain a residue, and the residue was purified by silica gel chromatography to obtain intermediate I-6.

LC-MS (ESI) $[M+H]^+$: 410.2.

Reference Embodiment 7: Preparation of Intermediate I-7

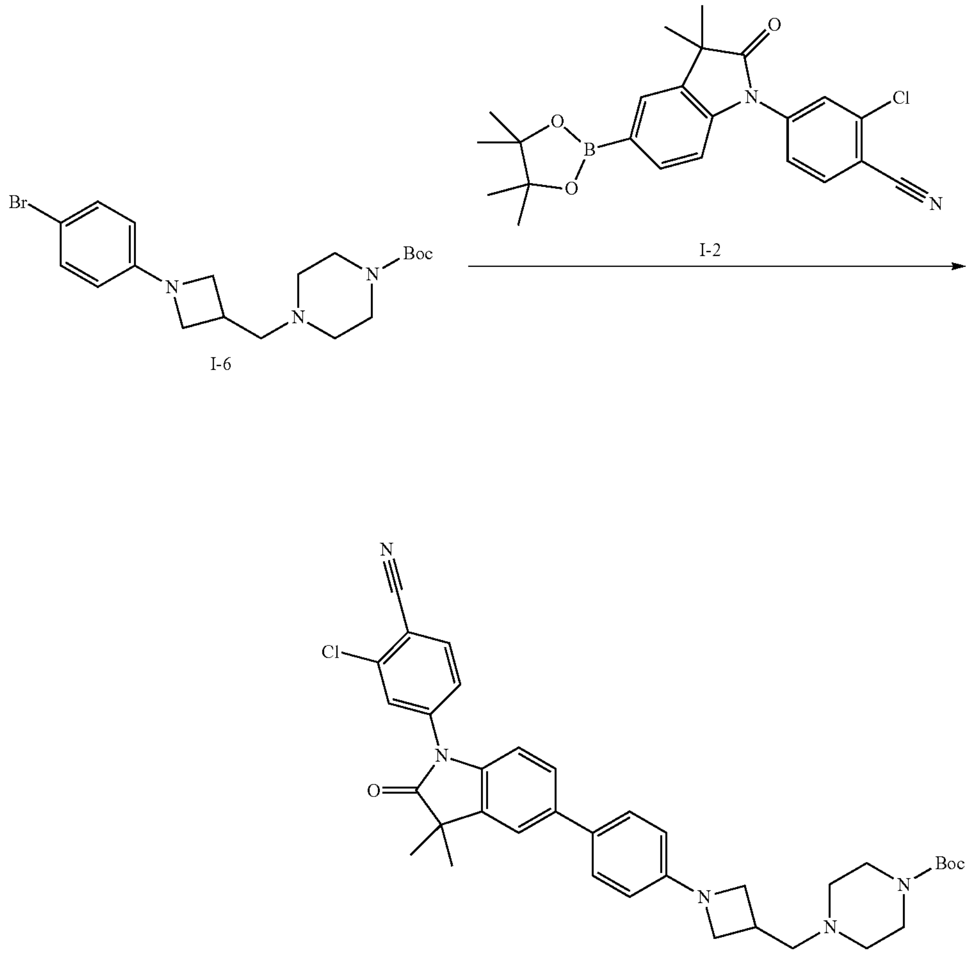

I-6

I-2

I-7

Intermediate I-6 (200.00 mg, 0.48 mmol) was dissolved in a mixed solution of dioxane/water (8 mL/2 mL), then potassium carbonate (194.93 mg, 1.41 mmol), intermediate I-2 (239.52 mg, 0.56 mmol) and [1,1'-bis(diphenylphosphino)ferrocene]dichloropalladium(II) (68.78 mg, 0.094 mmol) were sequentially added. The reaction solution was stirred at 80° C. for 16 hours under the protection of nitrogen. The reaction solution was cooled to room temperature, added with water (10 mL), and extracted with ethyl acetate (10 mL×3). The organic phases were combined, washed with saturated brine (10 mL), dried with anhydrous sodium sulfate and filtered. The filtrate was concentrated under reduced pressure to obtain a residue, and the residue was purified by silica gel chromatography to obtain intermediate I-7.

LC-MS (ESI) $[M+H]^+$: 626.4.

Reference Embodiment 8: Preparation of Intermediate I-8

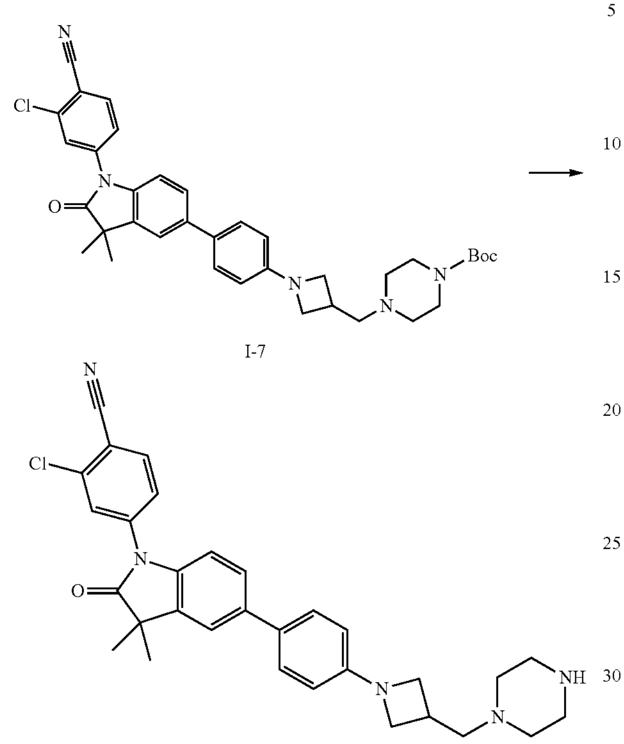

I-7

I-8

Intermediate I-7 (200.00 mg, 0.32 mmol) was dissolved in dichloromethane (4 mL), then trifluoroacetic acid (2 mL) was added, and the reaction solution was stirred at room temperature for 3 hours. The reaction solution was concentrated under reduced pressure to obtain a residue, and the residue was purified by silica gel chromatography to obtain intermediate I-8.

LC-MS (ESI) $[M+H]^+$: 526.3.

Reference Embodiment 9: Preparation of Intermediate I-9

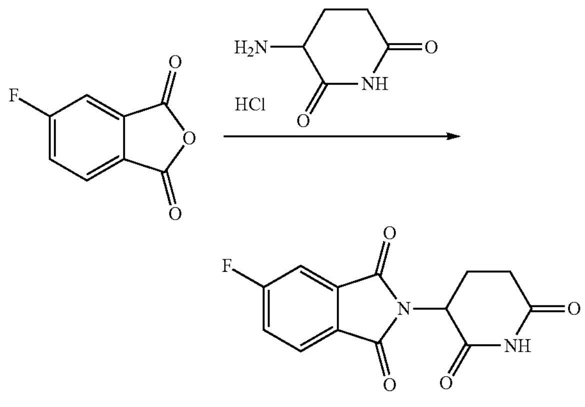

I-9

3-Aminopiperidine-2,6-dione hydrochloride (991 mg, 6.02 mmol) and sodium acetate (988 mg, 12.04 mmol) were added to an acetic acid (10 mL) solution of 4-fluorophthalic anhydride (1.0 g, 6.02 mmol) at room temperature. The reaction mixture was reacted at 120° C. for 16 hours. The reaction solution was cooled to room temperature and concentrated under reduced pressure to remove most of the acetic acid solvent. The residue was poured into water (25 mL), stirred for 10 minutes, and filtered. The filter cake was washed with water (20 mL×2) and dried in vacuo to obtain intermediate I-9.

$^1H$ NMR (400 MHz, DMSO-$d_6$) δ 11.14 (s, 1H), 8.01 (dd, J=8.3, 4.5 Hz, 1H), 7.85 (dd, J=7.5, 2.3 Hz, 1H), 7.76-7.69 (m, 1H), 5.16 (dd, J=12.8, 5.4 Hz, 1H), 2.95-2.83 (m, 1H), 2.65-2.51 (m, 2H), 2.11-2.02 (m, 1H).

Reference Embodiment 10: Preparation of Intermediate I-10

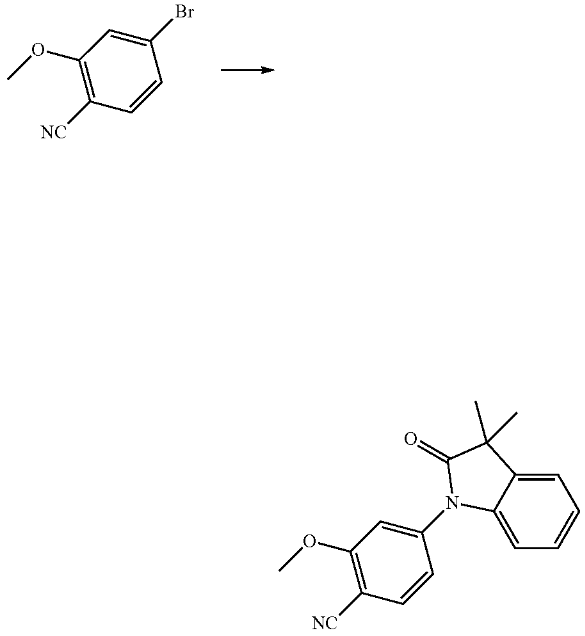

I-10

2-Methoxy-4-bromobenzonitrile (6.20 g, 29.20 mmol), 3,3-dimethyl-1-hydro-indol-2-one (4.71 g, 29.20 mmol), (1R,2R)-N,N'-dimethyl-1,2-cyclohexanediamine (1.66 g, 11.70 mmol), cuprous iodide (1.11 g, 5.84 mmol) and potassium carbonate (8.07 g, 58.40 mmol) were added to N-methylpyrrolidone (100 mL). The reaction system was stirred at 140° C. under argon atmosphere overnight. After the reaction mixture was cooled to room temperature, the reaction mixture was poured into water (50 mL), extracted with ethyl acetate (100 mL×2) and the organic phases were combined. The organic phases were washed with saturated brine (200 mL), dried with anhydrous sodium sulfate and filtered. The filtrate was concentrated under reduced pressure to remove the organic solvent, and the crude product was separated and purified by silica gel chromatography to obtain intermediate I-10.

LCMS (ESI) $[M+H]^+$: 293.1.

Reference Embodiment 11: Preparation of Intermediate I-11

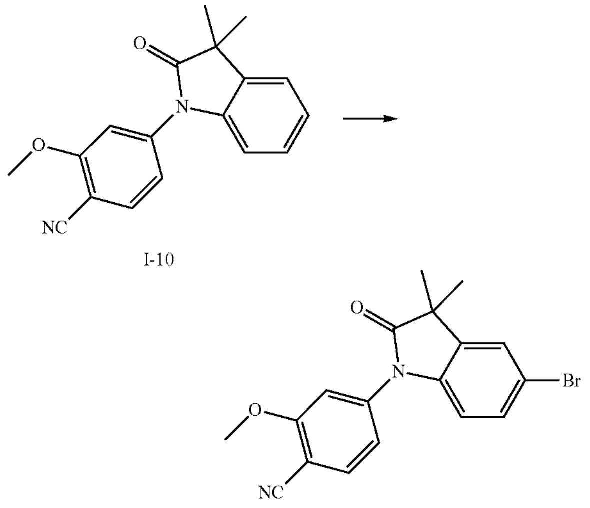

I-10

I-11

Intermediate I-10 (530 mg, 1.81 mmol) and sodium acetate (148 mg, 1.81 mmol) were dissolved in acetic acid (8 mL) and added to an acetic acid (2 mL) solution of liquid bromine (347 mg, 2.17 mmol) with stirring at room temperature. The reaction mixture was stirred and reacted at room temperature overnight. The reaction mixture was poured into water (100 mL), extracted with ethyl acetate (20 mL×2) and the organic phases were combined. The organic phases were washed with saturated sodium bicarbonate solution (50 mL×2), saturated brine (50 mL), dried with anhydrous sodium sulfate and filtered. The filtrate was concentrated under reduced pressure to remove the organic solvent to obtain intermediate I-11.

LC-MS (ESI) $[M+H]^+$: 371.2.

$^1H$ NMR (400 MHz, $CDCl_3$) δ 7.69 (d, J=8.7 Hz, 1H), 7.41 (d, J=2.0 Hz, 1H), 7.36 (dd, J=8.4, 2.0 Hz, 1H), 7.12-7.05 (m, 2H), 6.84 (d, J=8.4 Hz, 1H), 3.96 (s, 3H), 1.49 (s, 6H).

Reference Embodiment 12: Preparation of Intermediate I-12

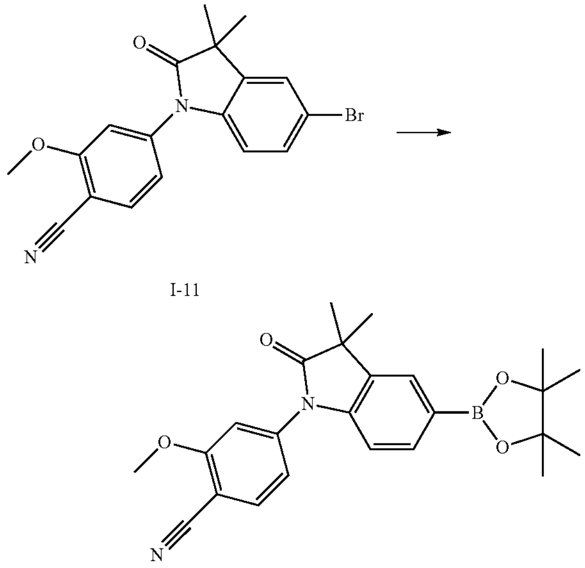

I-11

I-12

At 25° C., intermediate I-11 (500 mg, 1.35 mmol) was dissolved in dioxane (10 mL), then bis(pinacolato)diboron (448 mg, 1.75 mmol), [1,1'-bis(diphenylphosphino)ferrocene]dichloropalladium(II) (95 mg, 0.13 mmol) and potassium acetate (264 mg, 2.7 mmol) were sequentially added thereto. The mixture was stirred at 80° C. overnight under the protection of nitrogen. After the reaction was completed, the reaction solution was poured into water (20 mL), and extracted with ethyl acetate (20 mL×3). The organic phases were combined, and washed with saturated brine (30 mL), dried with anhydrous sodium sulfate and filtered. The filtrate was concentrated under reduced pressure to remove the organic solvent to obtain a crude product. The crude product was separated and purified by silica gel chromatography to obtain intermediate I-12.

$^1H$ NMR (400 MHz, MeOH-$d_4$) δ 7.82 (d, J=8.00 Hz, 1H), 7.76 (s, 1H), 7.70 (dd, J=1.13, 7.88 Hz, 1H), 7.33 (d, J=1.50 Hz, 1H), 7.16-7.23 (m, 1H), 7.00 (d, J=8.00 Hz, 1H), 4.01 (s, 3H), 1.50 (s, 6H), 1.23-1.29 (m, 12H).

Reference Embodiment 13: Preparation of Intermediate I-13

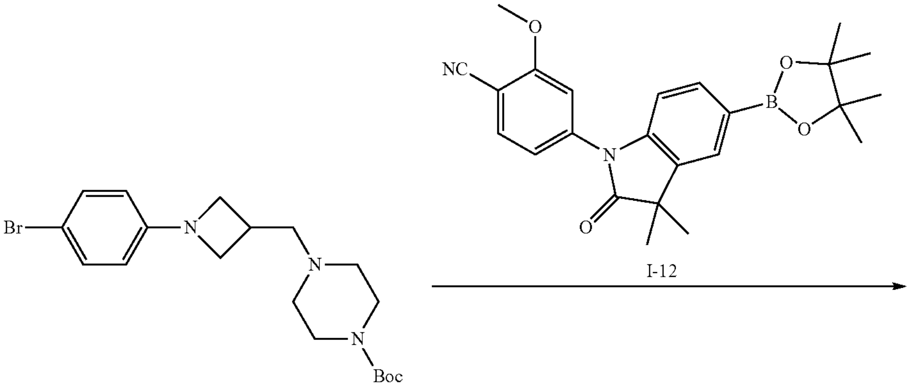

I-12

I-6

-continued

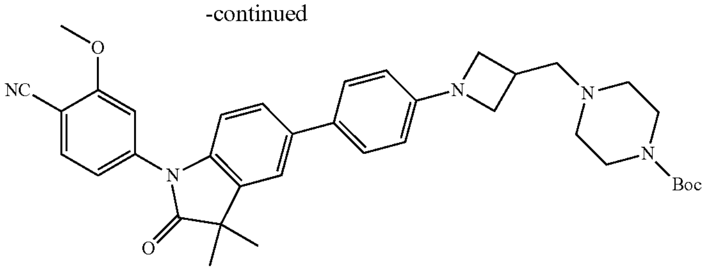

I-13

Intermediate I-6 (150 mg, 0.366 mmol), intermediate I-12 (152 mg, 0.363 mmol) and potassium phosphate (232 mg, 1.09 mmol) were dissolved in a mixed solution of tetrahydrofuran/water (5 mL/5 mL). Under the protection of argon, [2'-(amino)[1,1'-biphenyl]-2-yl][[2',6'-bis(1-methylethoxy) [1,1'-biphenyl]-2-yl]dicyclohexylphosphine]chloropalladium (28 mg, 0.036 mmol) was added under stirring. The reaction mixture was stirred at 70° C. for 8 hours under the protection of argon. The reaction solution was diluted with water (10 mL) and extracted with ethyl acetate (20 mL×3). The organic phases were combined and washed with saturated brine (30 mL×2), dried with anhydrous sodium sulfate, and filtered. The filtrate was concentrated under reduced pressure to remove the organic solvent to obtain a residue. The residue was separated and purified by silica gel chromatography to obtain intermediate I-13.

LC-MS (ESI) $[M+H]^+$ 622.5.

Reference Embodiment 14: Preparation of Intermediate I-14

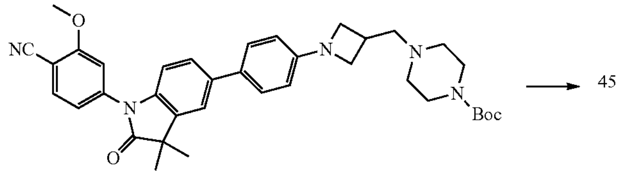

I-13

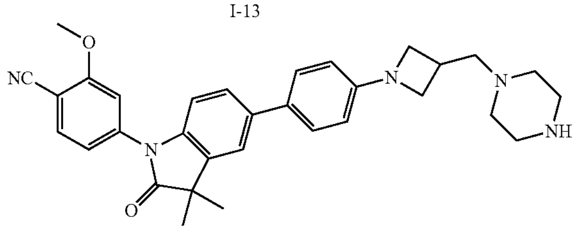

I-14

Intermediate I-13 (166 mg, 0.267 mmol) was dissolved in dichloromethane (5 mL), then trifluoroacetic acid (1 mL) was added. The reaction mixture was stirred and reacted at room temperature for 16 hours. The reaction solution was concentrated to obtain crude product of the intermediate I-14, and the crude product was then used directly for the next reaction without purification.

Reference Embodiment 15: Preparation of Intermediate I-15

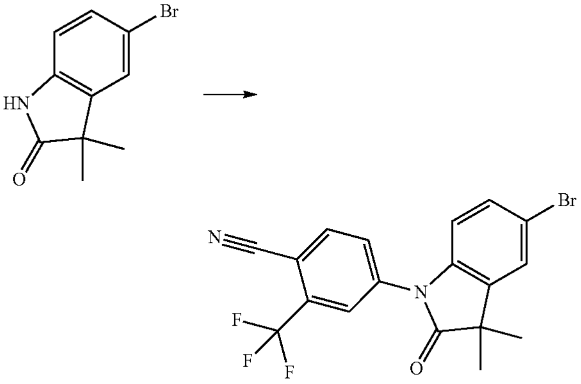

I-15

5-Bromo-3,3-dimethyl-1H-indol-2-one (5.76 g, 24.00 mmol) and 4-fluoro-2-(trifluoromethyl)phenylacetonitrile (6.81 g, 36.00 mmol) were dissolved in dimethyl sulfoxide (60 mL), potassium tert-butoxide (4.04 g, 36.00 mmol) was added at room temperature, and the reaction solution was stirred at 20° C. for 5 hours. The reaction system was added with water (30 mL), and extracted with ethyl acetate (30 mL×3). The organic phases were combined, washed with saturated brine (30 mL), dried with anhydrous sodium sulfate and filtered. The filtrate was concentrated under reduced pressure, and the residue was separated and purified by silica gel chromatography to obtain intermediate I-15.

$^1H$ NMR (400 MHz, DMSO-$d_6$) δ 8.37 (d, J=8.3 Hz, 1H), 8.18 (d, J=1.6 Hz, 1H), 8.05 (dd, J=8.3, 1.8 Hz, 1H), 7.77 (d, J=2.0 Hz, 1H), 7.45 (dd, J=8.4, 2.1 Hz, 1H), 6.97 (d, J=8.4 Hz, 1H), 1.44 (s, 6H).

Reference Embodiment 16: Preparation of Intermediate I-16

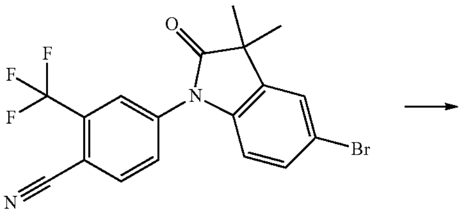

I-15

-continued

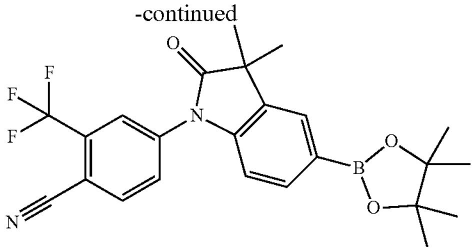

I-16

At 25° C., intermediate I-15 (200 mg, 0.48 mmol) was dissolved in dioxane (10 mL), then bis(pinacolato)diboron (185 mg, 0.73 mmol), potassium acetate (95 mg, 0.13 mmol) and [1,1'-bis(diphenylphosphino)ferrocene]dichloropalladium(II) (35 mg, 0.048 mmol) were sequentially added. The reaction mixture was stirred at 80° C. for 12 hours under the protection of nitrogen. The reaction solution was cooled to room temperature, concentrated under reduced pressure to remove the organic solvent to obtain a crude product. The crude product was separated and purified by silica gel chromatography to obtain intermediate I-16.

LCMS(ESI) [M+H]$^+$ 457.18.

Reference Embodiment 17: Preparation of Intermediate I-17

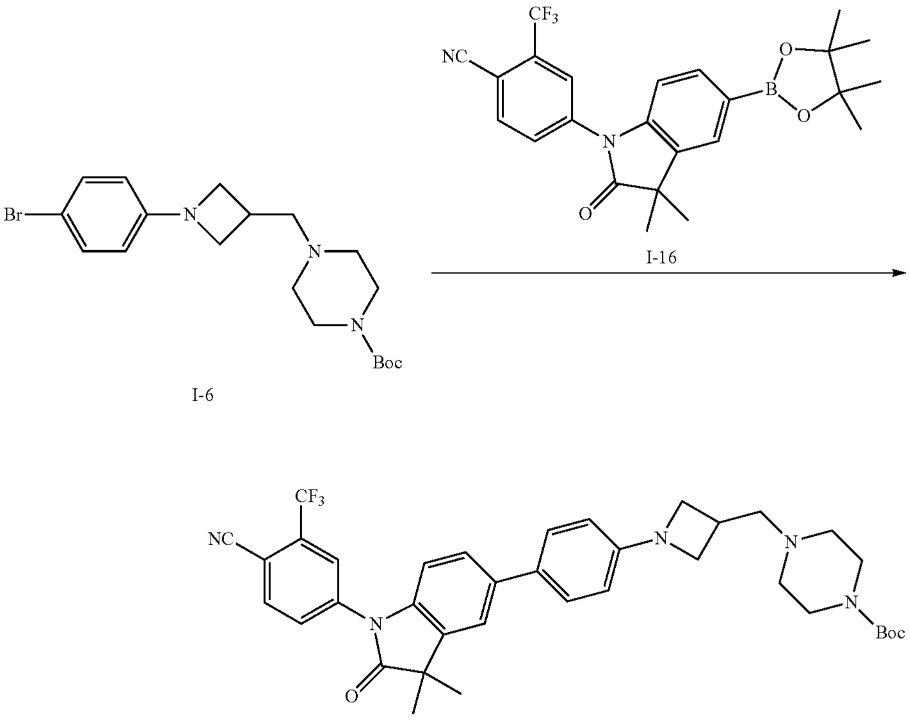

I-6 I-16 I-17

Intermediate I-6 (150 mg, 0.36 mmol), intermediate I-16 (250 mg, 0.55 mmol) and potassium phosphate (235 mg, 1.11 mmol) were dissolved in a mixed solution of tetrahydrofuran and water (8 mL/2 mL). Under the protection of argon, [2'-(amino)[1,1'-biphenyl]-2-yl][[2',6'-bis(1-methylethoxy)[1,1'-biphenyl]-2-yl]dicyclohexylphosphine]chloropalladium (29 mg, 0.037 mmol) was added under stirring. The reaction mixture was stirred at 60° C. for 5 hours under the protection of argon. The reaction solution was diluted with water (10 mL) and extracted with ethyl acetate (20 mL×3). The organic phases were combined and washed with saturated brine (30 mL×2), dried with anhydrous sodium sulfate, then filtered and the filtrate was concentrated under reduced pressure to remove the organic solvent to obtain a residue of intermediate I-17. The residue was separated and purified by silica gel chromatography to obtain intermediate I-17.

LC-MS (ESI) [M+H]$^+$ 660.4.

Reference Embodiment 18: Preparation of Intermediate I-18

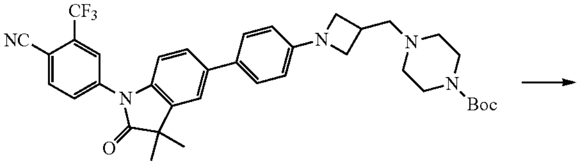

I-17

-continued

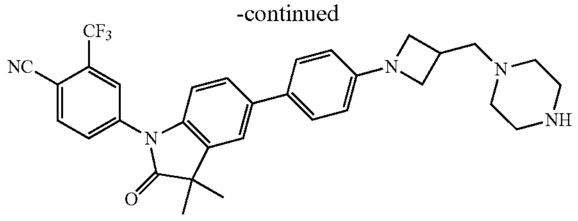

I-18

Intermediate I-17 (160 mg, 0.24 mmol) was dissolved in dichloromethane (5 mL), then trifluoroacetic acid (1 mL) was added. The reaction mixture was stirred and reacted at room temperature for 6 hours. The reaction solution was concentrated to obtain crude product of the intermediate I-18, and the crude product was then used directly for the next reaction without purification.

LC-MS (ESI) $[M+H]^+$ 560.4.

Reference Embodiment 19: Preparation of Intermediate I-19

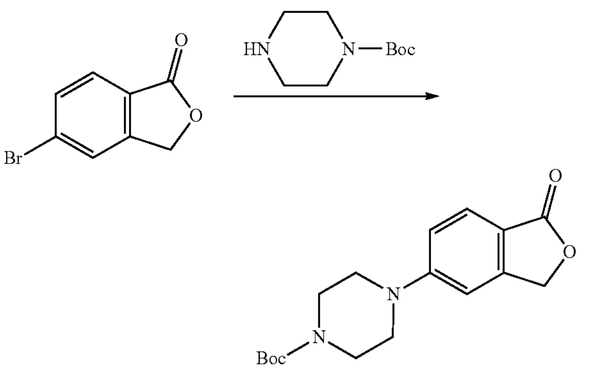

I-19

5-Bromophthalide (3.00 g, 14.08 mmol) was dissolved in 1,4-dioxane (50 mL), then 1-Boc-piperazine (2.62 g, 14.08 mmol), 4,5-bis(diphenylphosphino)-9,9-dimethylxanthene (816 mg, 1.41 mmol), tris(dibenzylideneacetone)dipalladium (1.29 g, 1.41 mmol) and potassium phosphate (5.97 g, 28.16 mmol) were sequentially added. The reaction mixture was stirred at 100° C. for 10 hours under the protection of argon. The reaction solution was cooled to room temperature, filtered, concentrated under reduced pressure to obtain a residue, and the residue was separated and purified by silica gel chromatography to obtain intermediate I-19.

LC-MS (ESI) $[M+H]^+$ 319.3.

Reference Embodiment 20: Preparation of Intermediate I-20

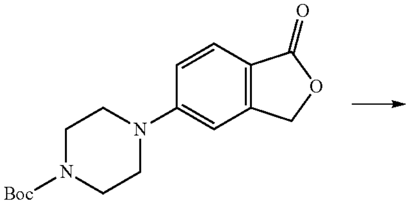

I-19

-continued

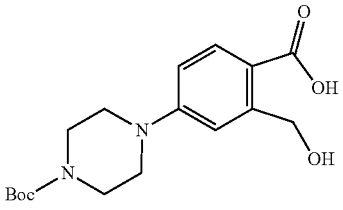

I-20

Intermediate I-19 (1.00 g, 3.14 mmol) was dissolved in methanol/water/tetrahydrofuran (30 mL, 1:1:1) and sodium hydroxide (502 mg, 12.56 mmol) was added. The reaction mixture was stirred for 1 hour. The pH of the reaction solution was adjusted to below 5 with HCl aqueous solution (1M) and extracted with ethyl acetate (50 mL×3). The organic phases were combined and washed with saturated brine (50 mL×2), dried with anhydrous sodium sulfate. The mixture was filtered, the filtrate was concentrated under reduced pressure to obtain a residue, and the residue was separated and purified by silica gel chromatography to obtain intermediate I-20.

LC-MS (ESI) $[M+H]^+$: 337.0.

Reference Embodiment 21: Preparation of Intermediate I-21

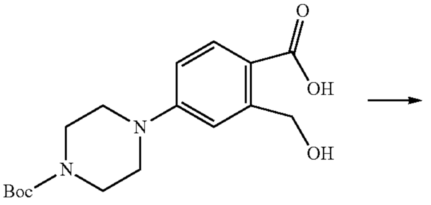

I-20

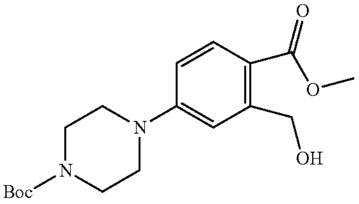

I-21

Intermediate I-20 (600 mg, 1.78 mmol) was dissolved in methanol/ethyl acetate (20 mL, 1:1) and (trimethylsilyl) diazomethane (611 mg, 5.35 mmol) was added. The reaction mixture was stirred at −10° C. for 0.25 hours. After the reaction solution was concentrated under reduced pressure, the residue was diluted with water (30 mL), and extracted with ethyl acetate (30 mL×3). The organic phases were combined and washed with saturated brine (50 mL×2), dried with anhydrous sodium sulfate. The mixture was filtered, the filtrate was concentrated under reduced pressure to remove the organic solvent to obtain crude product of intermediate I-21. The crude product was then used directly for the next reaction without purification.

LC-MS (ESI) $[M+H]^+$: 351.2.

Reference Embodiment 22: Preparation of Intermediate I-22

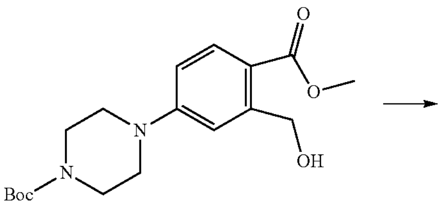

I-21

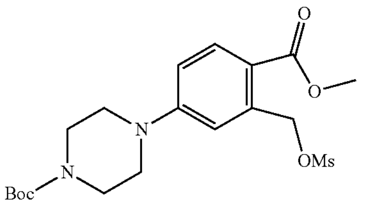

I-22

Intermediate I-21 (400 mg) was dissolved in dichloromethane (20 mL) and methanesulfonyl chloride (170 mg, 1.48 mmol) and triethylamine (346 mg, 3.42 mmol) were added. The reaction mixture was stirred at 0° C. for 2 hours. After the reaction solution was concentrated under reduced pressure to obtain a residue, the residue was added to water (30 mL), and extracted with ethyl acetate (30 mL×3). The organic phases were combined and washed with saturated brine (50 mL×2), dried with anhydrous sodium sulfate. The mixture was filtered, the filtrate was concentrated under reduced pressure to remove the organic solvent to obtain crude product of intermediate I-22. The crude product was then used directly for the next reaction without purification.

LC-MS (ESI) $[M+H]^+$: 429.0.

Reference Embodiment 23: Preparation of Intermediate I-23

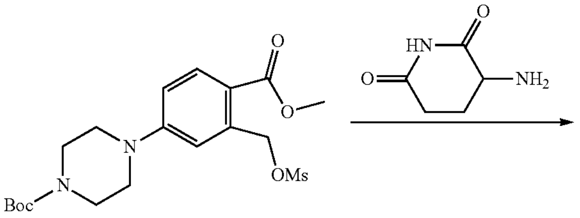

I-22

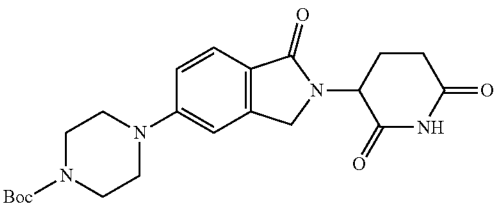

I-23

Intermediate I-22 (350 mg) was dissolved in acetonitrile (20 mL) and 3-amino-2,6-piperidinedione (157 mg, 1.23 mmol) and N,N-diisopropylethylamine (318 mg, 2.46 mmol) were added. The reaction mixture was stirred and reacted at 80° C. for 16 hours. The reaction solution was cooled to room temperature, then filtered, the filtrate was concentrated under reduced pressure to remove the organic solvent to obtain a residue, and the residue was separated and purified by silica gel chromatography to obtain intermediate I-23.

LC-MS (ESI) $[M+H]^+$ 429.1.

Reference Embodiment 24: Preparation of Intermediate I-24

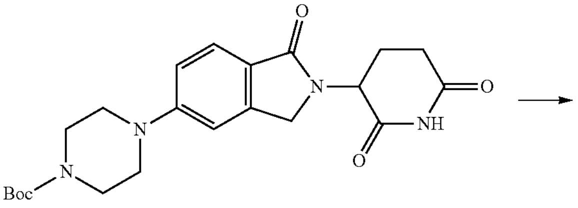

I-23

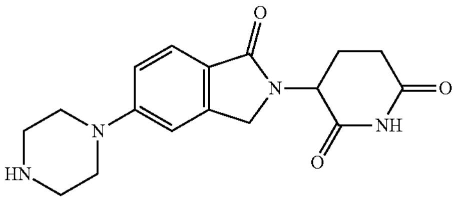

I-24

Intermediate I-23 (200 mg, 0.467 mmol) was dissolved in dichloromethane (20 mL), then trifluoroacetic acid (160 mg, 1.40 mmol) was added. The reaction mixture was stirred for 1 hour. The reaction solution was concentrated under reduced pressure to obtain a residue. The residue was separated and purified by silica gel chromatography to obtain intermediate I-24.

LC-MS (ESI) $[M+H]^+$ 329.2.

Reference Embodiment 25: Preparation of Intermediate I-25

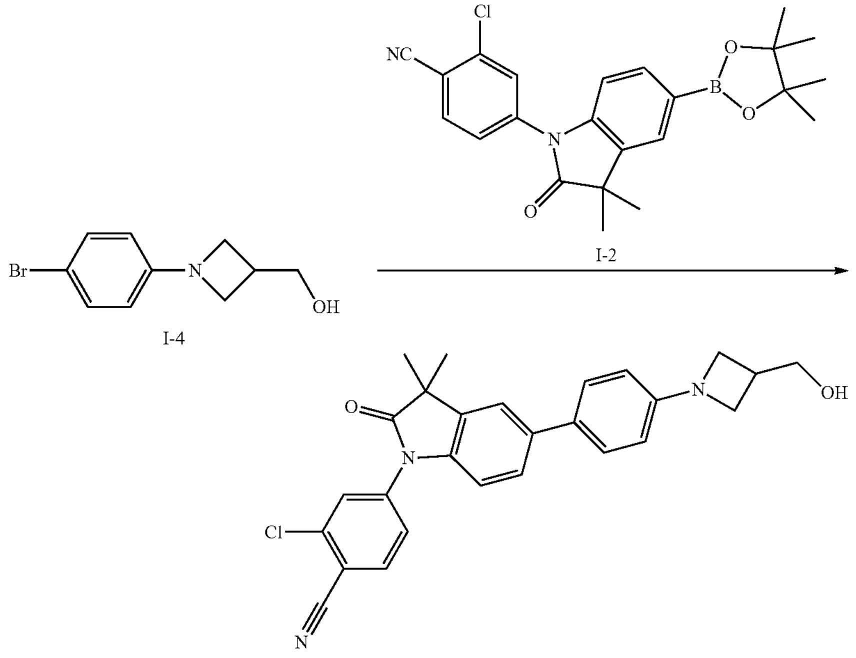

I-25

Intermediate I-4 (1.00 g, 4.13 mmol), intermediate I-2 (2.09 g, 4.96 mmol) and potassium phosphate (2.63 g, 12.4 mmol) were dissolved in a mixed solution of dioxane (100 mL) and water (20 mL). Under the protection of argon, [1,1'-bis(diphenylphosphino)ferrocene]dichloropalladium (II) (302 mg, 0.41 mmol) was added under stirring. The reaction mixture was stirred at 100° C. for 16 hours. The reaction solution was cooled to room temperature, concentrated under reduced pressure to remove the organic solvent to obtain a crude product. The crude product was separated and purified by silica gel chromatography to obtain intermediate I-25.

LC-MS (ESI) $[M+H]^+$ 458.3.

Reference Embodiment 26: Preparation of Intermediate I-26

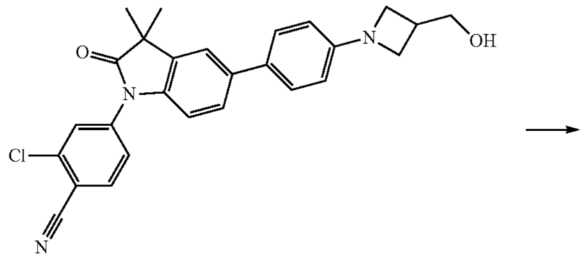

I-25

-continued

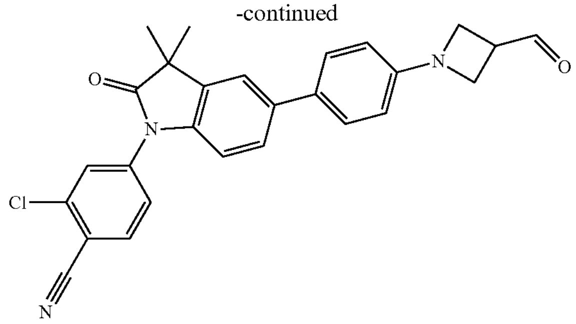

I-26

Intermediate I-25 (300 mg, 0.655 mmol) was dissolved in ethyl acetate (30 mL), then 2-iodoylbenzoic acid (1.47 g, 5.24 mmol) was added thereto. The reaction mixture was stirred and reacted at 100° C. for 3 hours. The reaction solution was filtered, and the filtrate was concentrated to obtain crude product of the intermediate I-26, and the crude product was then used directly for the next reaction without purification.

LC-MS (ESI) $[M+H]^+$ 456.0.

Reference Embodiment 27: Preparation of Intermediate I-27

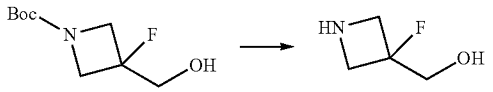

I-27 tert-Butyl 3-fluoro-3-(hydroxymethyl)azetidine-1-carboxylate (50 mg, 1.70 mmol) was dissolved in dichloromethane (5 mL) and then trifluoroacetic acid (3 mL) was added. The reaction solution was stirred at room temperature overnight under the protection of nitrogen. The reaction solution was concentrated to obtain crude product of the intermediate I-27, and the crude product was then used directly for the next reaction without purification.

Reference Embodiment 28: Preparation of Intermediate I-28

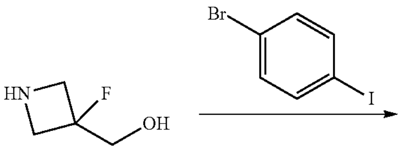

I-27

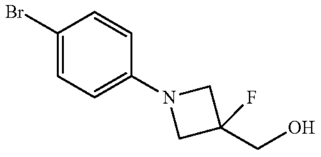

I-28

Intermediate I-27 (179 mg, 1.70 mmol), p-bromoiodobenzene (482 mg, 1.70 mmol), L-proline (78 mg, 0.68 mmol) were dissolved in N,N-dimethylformamide (10 mL), potassium carbonate (1.18 g, 8.54 mmol) and cuprous iodide (65 mg, 0.34 mmol) were added. The reaction solution was stirred at 80° C. overnight under the protection of nitrogen. The reaction solution was cooled to room temperature and diluted with ethyl acetate (60 mL). The organic phase was washed with water (30 mL) and saturated brine (30 mL), dried with anhydrous sodium sulfate and filtered. The filtrate was concentrated to obtain a residue, and the residue was separated and purified by silica gel chromatography to obtain intermediate I-28.

LC-MS (ESI) $[M+H]^+$: 260.0.

Reference Embodiment 29: Preparation of Intermediate I-29

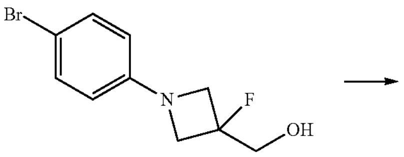

I-28

-continued

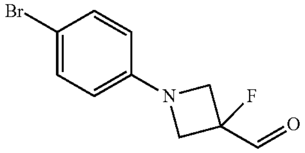

I-29

Intermediate I-28 (200 mg, 0.77 mmol) was dissolved in dichloromethane (6 mL), then Dess-Martin periodinane (388 mg, 0.92 mmol) was added. The reaction solution was stirred at room temperature overnight under the protection of nitrogen. The reaction solution was filtered and the filtrate was concentrated under reduced pressure to obtain a residue. The residue was separated and purified by silica gel chromatography to obtain intermediate I-29.

Reference Embodiment 30: Preparation of Intermediate I-30

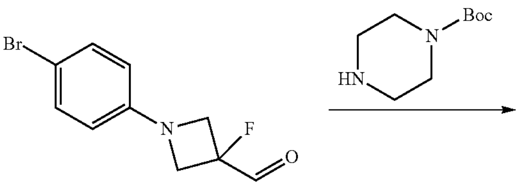

I-29

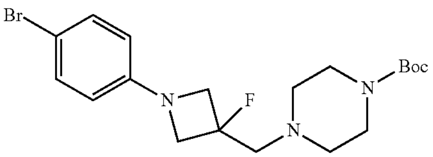

I-30

Intermediate I-29 (200 mg), N-Boc piperazine (218 mg, 1.17 mmol) was dissolved in 1,2-dichloroethane (6 mL), acetic acid (20 mg) and sodium triacetoxyborohydride (331 mg, 1.56 mmol) were added. The reaction solution was stirred at room temperature overnight under the protection of nitrogen. The reaction solution was concentrated to obtain a residue, and the residue was separated and purified by silica gel chromatography to obtain intermediate 1-30.

LC-MS (ESI) $[M+H]^+$: 428.0.

Reference Embodiment 31: Preparation of Intermediate I-31

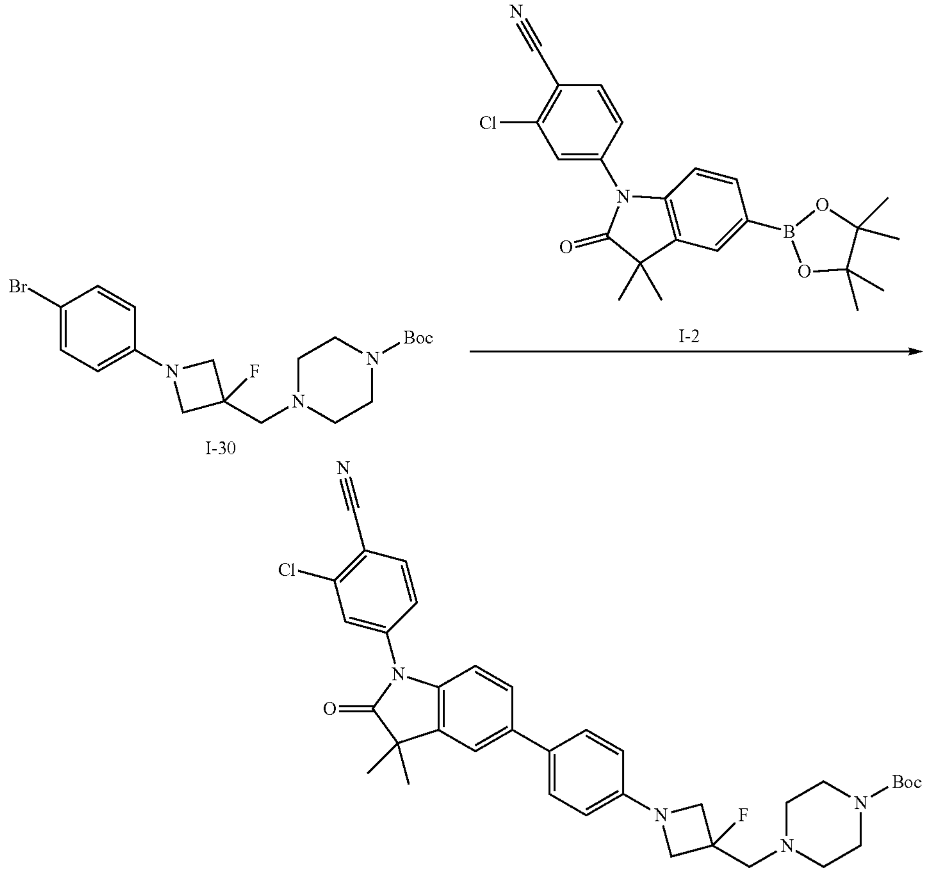

I-30

I-2

I-31

Intermediate 1-30 (50 mg, 0.12 mmol), intermediate 1-2 (59 mg, 0.14 mmol) and potassium carbonate (40 mg, 0.29 mmol) were dissolved in a mixed solution of dioxane/water (volume 4 mL: 1 mL), [1,1'-bis(diphenylphosphino)ferrocene]dichloropalladium(II) (8 mg, 0.011 mmol) was added. The reaction solution was stirred at 85° C. overnight under the protection of nitrogen. The reaction solution was cooled to room temperature, concentrated under reduced pressure to obtain a residue. The residue was separated and purified by silica gel chromatography to obtain intermediate I-31.

Reference Embodiment 32: Preparation of Intermediate I-32

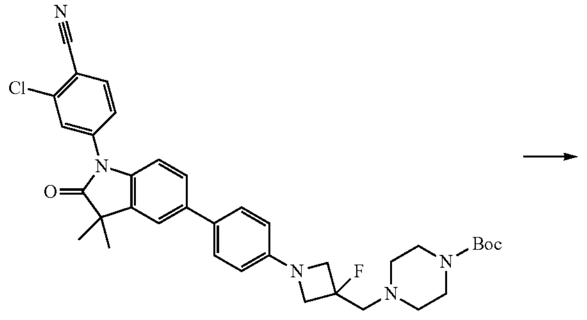

I-31

-continued

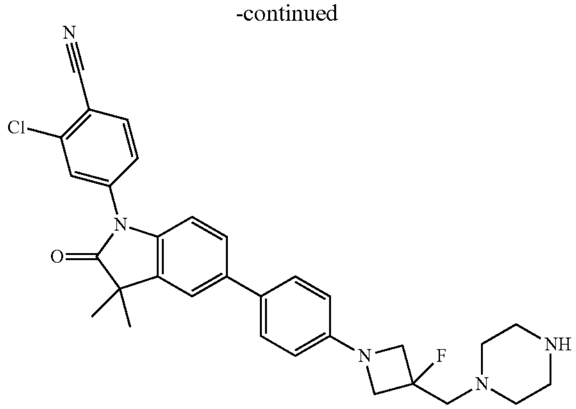

I-32

Intermediate I-31 (45 mg, 0.070 mmol) was dissolved in dichloromethane (4 mL), then trifluoroacetic acid (2 mL) was added. The reaction solution was stirred at room temperature overnight under the protection of nitrogen. The reaction solution was concentrated to obtain crude product of the intermediate I-32, and the crude product was then used directly for the next reaction without purification.

LC-MS (ESI) $[M+H]^+$: 544.3.

Reference Embodiment 33: Preparation of Intermediate I-33

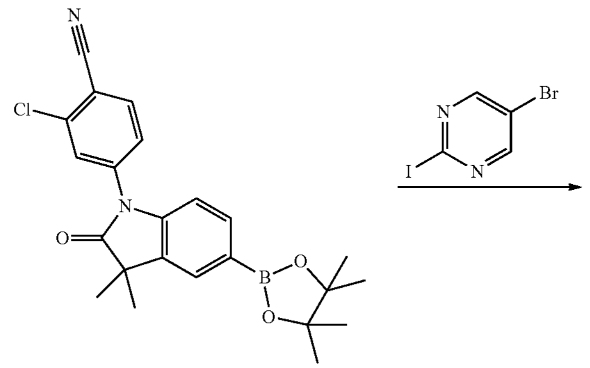

I-2

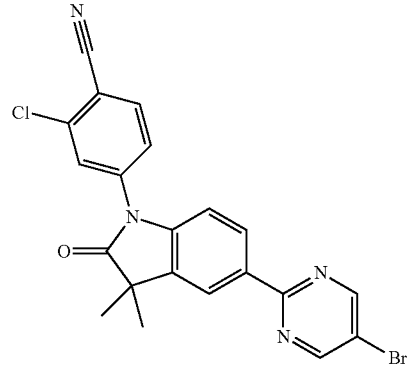

I-33

At 25° C., intermediate I-2 (150.00 mg, 0.35 mmol) was dissolved in dioxane (8 mL) and water (2 mL), then potassium carbonate (147.13 mg, 1.06 mmol), 5-bromo-2-iodopyrimidine (122.50 mg, 0.43 mmol), [1,1'-bis(diphenylphosphino)ferrocene]dichloropalladium(II) (51.95 mg, 0.071 mmol) were sequentially added. The reaction solution was stirred at 80° C. for 16 hours under the protection of nitrogen. The reaction solution was cooled to room temperature, diluted with water (10 mL), and extracted with ethyl acetate (10 mL×3). The organic phases were combined, washed with saturated brine (10 mL), dried with anhydrous sodium sulfate, filtered, and concentrated to obtain the residue. The residue was separated and purified by silica gel chromatography to obtain intermediate I-33.

LC-MS (ESI) $[M+H]^+$: 453.0.

Reference Embodiment 34: Preparation of Intermediate I-34

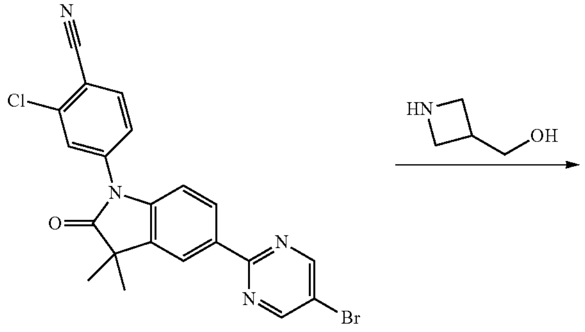

I-33

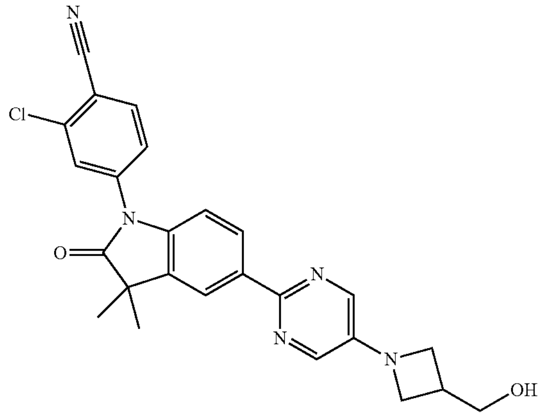

I-34

At 25° C., intermediate I-33 (140.00 mg, 0.31 mmol) was dissolved in dimethyl sulfoxide (5 mL), then potassium carbonate (128.54 mg, 0.93 mmol), 3-hydroxymethyl-azetidine (32.26 mg, 0.37 mmol), L-proline (7.18 mg, 0.062 mmol) and cuprous iodide (11.81 mg, 0.062 mmol) were sequentially added, and the system was replaced with nitrogen for three times, and reacted at 90° C. for 16 hours under a nitrogen balloon atmosphere. The reaction solution was added to water (10 mL), and extracted with ethyl acetate (10 mL×3). The organic phases were combined, washed with saturated brine (10 mL), dried with anhydrous sodium sulfate, filtered, and concentrated to obtain a residue. The residue was separated and purified by silica gel chromatography to obtain intermediate I-34.

LC-MS (ESI) $[M+H]^+$: 460.2.

Reference Embodiment 35: Preparation of Intermediate I-35

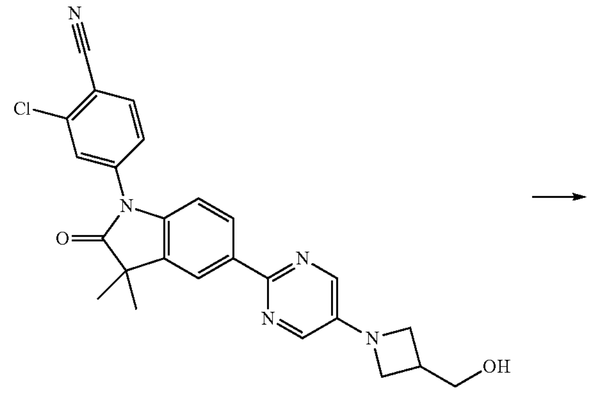

I-34

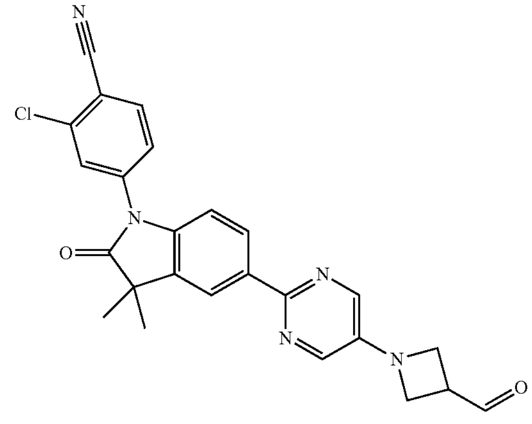

I-35

At 25° C., oxalyl chloride (22.85 mg, 0.18 mmol) was dissolved in dichloromethane (10 mL), and the mixture was cooled to −60° C., dimethyl sulfoxide (28.36 mg, 0.36 mmol) was slowly added, and the reaction solution was stirred at −60° C. for 0.5 hours. Then a dichloromethane (5 mL) solution of intermediate I-34 (50.00 mg, 0.11 mmol) was added, and further stirred at −60° C. for 0.5 hours. Triethylamine (55.65 mg, 0.55 mmol) was added, and the reaction solution was further stirred at −60° C. for 1 hour. The reaction solution was raised to room temperature, diluted with water (10 mL), and extracted with dichloromethane (10 mL×3). The organic phases were combined, washed with saturated brine (10 mL), dried with anhydrous sodium sulfate, filtered, and concentrated to obtain a residue. The residue was separated and purified by silica gel chromatography to obtain intermediate I-35.

LC-MS (ESI) $[M+H]^+$: 458.2.

Reference Embodiment 36: Preparation of Intermediate I-36

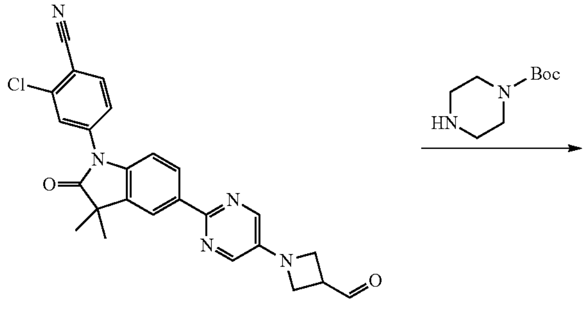

I-35

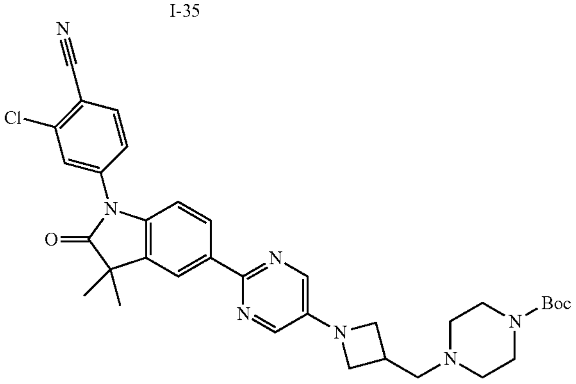

I-36

At 25° C., intermediate I-35 (45.00 mg, 0.098 mmol) was dissolved in dichloromethane (5 mL), 1-Boc-piperazine (27.94 mg, 0.15 mmol), sodium triacetoxyborohydride (42.39 mg, 0.20 mmol) and acetic acid (0.60 mg, 0.0098 mmol) were sequentially added, and the reaction solution was reacted at room temperature for 3 hours. Water (10 mL) was added to the reaction solution, and the reaction solution was extracted with dichloromethane (10 mL×3). The organic phases were combined, washed with saturated brine (10 mL), dried with anhydrous sodium sulfate, filtered, and concentrated to obtain a residue. The residue was separated and purified by silica gel chromatography to obtain intermediate I-36.

LC-MS (ESI) $[M+H]^+$: 628.4.

Reference Embodiment 37: Preparation of Intermediate I-37

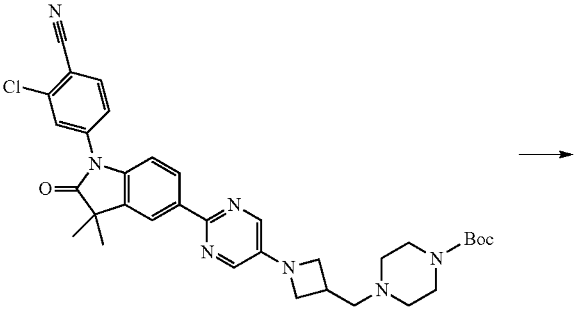

I-36

-continued

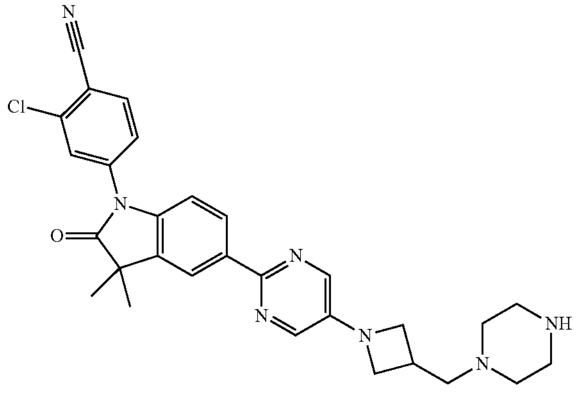

I-37

At 25° C., intermediate I-36 (25.00 mg, 0.040 mmol) was dissolved in dichloromethane (2 mL), and trifluoroacetic acid (1 mL) was added. The reaction mixture was reacted at room temperature for 3 hours. The reaction solution was concentrated to obtain crude product of the intermediate I-37, and the crude product was then used directly for the next reaction without purification.

LC-MS (ESI) $[M+H]^+$: 528.3.

Reference Embodiment 38: Preparation of Intermediate I-38

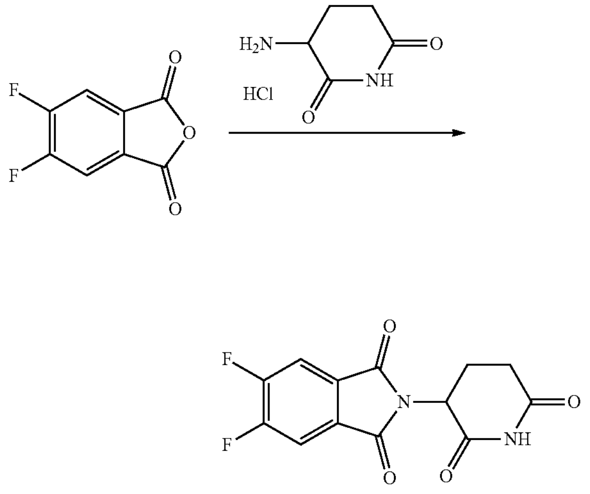

I-38

4,5-Difluorophthalic anhydride (1.00 g, 5.43 mmol) was dissolved in glacial acetic acid (20.0 mL) and sodium acetate (894 mg, 10.9 mmol) and 3-amino-2,6-piperidinedione hydrochloride (894 mg, 5.43 mmol) were added sequentially under stirring. The reaction mixture was stirred and reacted at 120° C. for 16 hours under the protection of argon. The reaction solution was cooled to room temperature, poured into water (100 mL), and a large amount of solid was precipitated, filtered, the filter cake was washed with water (10.0 mL×2), and the filter cake was dried to obtain intermediate I-38.

Reference Embodiment 39: Preparation of Intermediate I-39

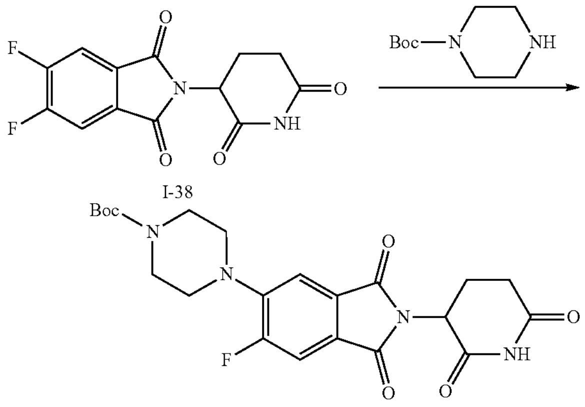

I-38

I-39

Intermediate I-38 (1.40 g, 4.76 mmol) was dissolved in anhydrous dimethyl sulfoxide (20.0 mL), diisopropylethylamine (1.23 g, 9.52 mmol) and 1-tert-butoxycarbonyl piperazine (887 mg, 4.76 mmol) were sequentially added. The reaction mixture was stirred and reacted at 110° C. for 16 hours under the protection of argon. The reaction solution was cooled to room temperature, poured into water (100 mL), and extracted with ethyl acetate (50.0 mL×3). The organic phases were combined and washed with saturated brine (50.0 mL×2), dried with anhydrous sodium sulfate. The mixture was filtered, the filtrate was concentrated under reduced pressure to remove the organic solvent to obtain a residue, and the residue was separated and purified by silica gel chromatography to obtain intermediate I-39.

LC-MS (ESI) $[M+H-56]^+$: 405.2.

Reference Embodiment 40: Preparation of Intermediate I-40

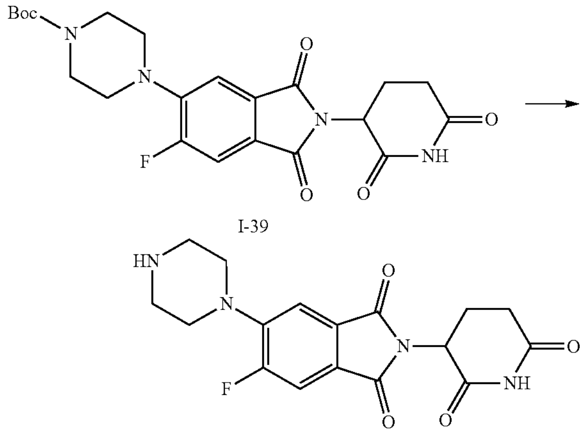

I-39

I-40

Intermediate 1-39 (600 mg, 1.30 mmol) was dissolved in a solution of dioxane hydrochloride (25.0 mL). The reaction mixture was stirred and reacted at room temperature for 1 hour under the protection of argon. The mixture was concentrated under reduced pressure to remove the organic solvent, the residue was added to water (100 mL), and the pH of the system was adjusted to 8.0 with saturated aqueous sodium bicarbonate solution. The mixture was extracted with dichloromethane (50.0 mL×3), the organic phases were combined and washed with saturated brine (50.0 mL×2), dried with anhydrous sodium sulfate. The reaction solution was filtered, and the filtrate was concentrated under reduced pressure to obtain crude product of the intermediate I-40, and the crude product was then used directly for the next reaction without purification.

LC-MS (ESI) $[M+H]^+$ 361.2.

Reference Embodiment 41: Preparation of Intermediate I-41

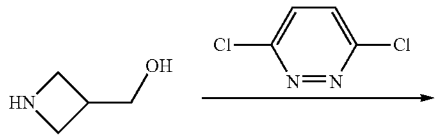

I-3

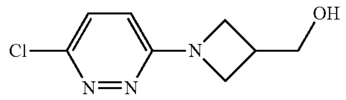

I-41

Intermediate I-3 (230.00 mg), 3,6-dichloropyridazine (589.93 mg, 3.960 mmol) and potassium carbonate (1.09 g, 7.920 mmol) were suspended in N,N-dimethylformamide (15.0 mL) at room temperature. The reaction mixture was stirred in an oil bath at 80° C. for 3 hours. The reaction solution was cooled to room temperature naturally, diluted with water (20.0 mL), and extracted with ethyl acetate (20.0 mL×3). The organic phase was dried with anhydrous sodium sulfate, filtered, the filtrate was concentrated to obtain a residue, and the residue was separated and purified by silica gel chromatography to obtain intermediate I-41.

Reference Embodiment 42: Preparation of Intermediate I-42

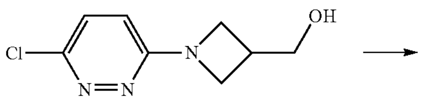

I-41

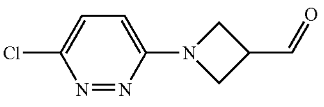

I-42

At −78° C., oxalyl chloride (305.16 mg, 2.400 mmol) was dissolved in dichloromethane (10.0 mL), and dimethyl sulfoxide (250.47 mg, 3.210 mmol) was slowly added dropwise, and the reaction solution was stirred at −78° C. for 0.5 hours. Intermediate I-41 (160.00 mg, 0.801 mmol) was dissolved in dichloromethane (5.0 mL) and added dropwise to the reaction system, and continued stirring at −78° C. for 1 hour. Triethylamine (486.61 mg, 4.810 mmol) was added dropwise to the reaction system, and the mixture was stirred for 0.5 hours and then naturally raised to room temperature. Water (30 mL) was added to dilute, and the reaction solution was extracted with dichloromethane (20 mL×3). The organic phase was dried with anhydrous sodium sulfate, filtered, the filtrate was concentrated to obtain a residue, and the residue was separated and purified by silica gel chromatography to obtain intermediate I-42.

LC-MS (ESI) $[M+H]^+$: 197.8.

Reference Embodiment 43: Preparation of Intermediate I-43

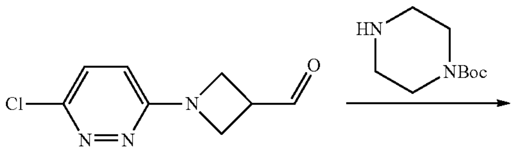

I-42

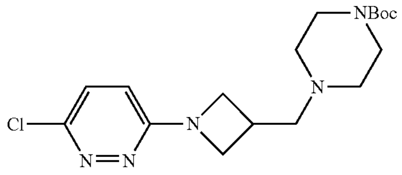

I-43

Intermediate I-42 (150.00 mg, 0.76 mmol) and N-Boc piperazine (155.51 mg, 0.83 mmol) was dissolved in 1,2-dichloroethane (15.0 mL), then sodium triacetoxyborohydride (377.61 mg, 1.60 mmol) were added thereto. The reaction solution was stirred for 3 hours. Water (30 mL) was added, and the reaction solution was extracted with dichloromethane (30 mL×3). The organic phase was dried with anhydrous sodium sulfate, filtered, the filtrate was concentrated to obtain a residue, and the residue was separated and purified by silica gel chromatography to obtain intermediate I-43.

LC-MS (ESI) $[M+H]^+$: 368.3.

Reference Embodiment 44: Preparation of Intermediate I-44

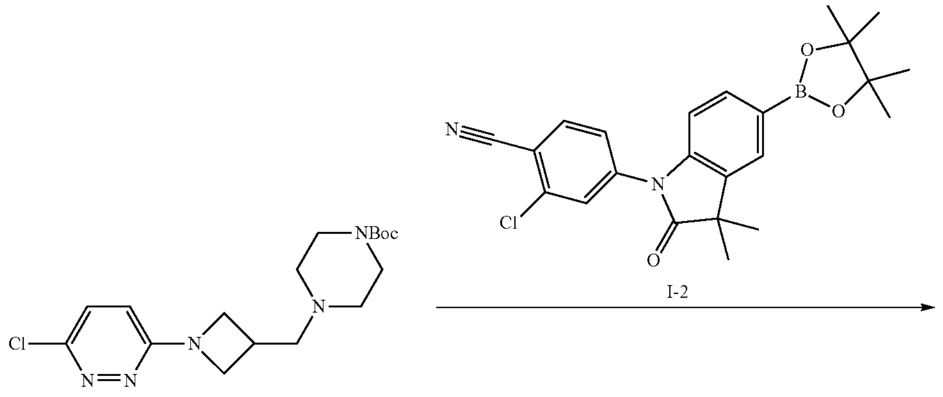

I-2

I-43

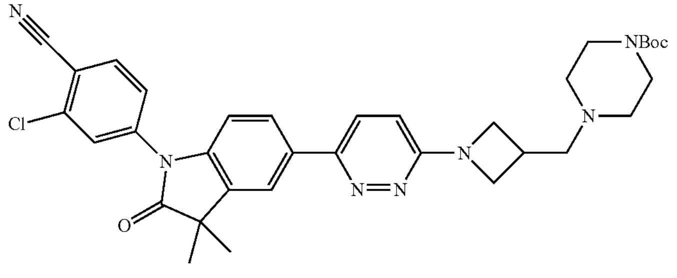

I-44

Under nitrogen protection, intermediate I-43 (50.00 mg, 0.136 mmol), I-2 (68.94 mg, 0.163 mmol), [1,1"-bis(diphenylphosphino)ferrocene]dichloropalladium(II) (9.93 mg, 0.014 mmol), potassium carbonate (46.96 mg, 0.340 mmol) were suspended in 1,4-dioxane/water (4.0 mL/1.0 mL). The reaction mixture was stirred in an oil bath at 80° C. for 3 hours. After cooling to room temperature, the insoluble substance was removed by suction filtration, and the filtrate was concentrated to obtain a residue. The residue was separated and purified by silica gel chromatography to obtain intermediate I-44.

LC-MS (ESI) $[M+H]^+$: 628.4.

Reference Embodiment 45: Preparation of Intermediate I-45

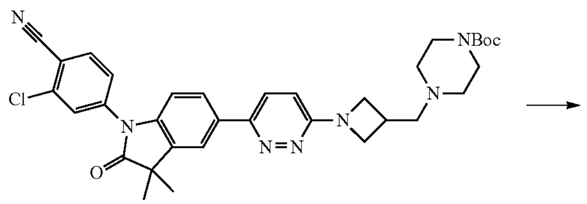

I-44

-continued

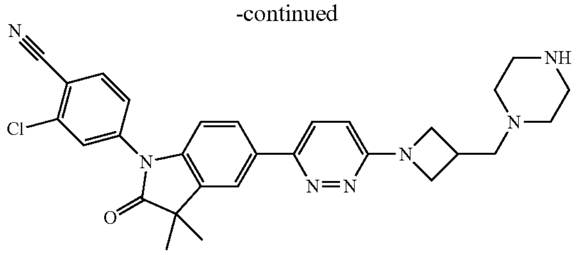

I-45

At room temperature, intermediate I-44 (60.00 mg, 0.096 mmol) was dissolved in dichloromethane (2.0 mL), then trifluoroacetic acid (1.0 mL) was added. The reaction solution was stirred at room temperature for 1 hour, and the reaction solution was concentrated to obtain crude product of the intermediate I-45, and the crude product was then used directly for the next reaction without purification.

LC-MS (ESI) $[M+H]^+$: 528.3.

Reference Embodiment 46: Preparation of Intermediate I-46

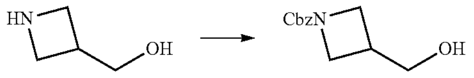

I-3 I-46

Intermediate I-3 (694.00 mg) was dissolved in dichloromethane (10 mL) at room temperature, then triethylamine (2.42 g, 23.90 mmol) and benzyl chloroformate (1.36 g, 7.97 mmol) were sequentially added, and the reaction solution was stirred overnight at room temperature. The reaction solution was poured into water (50 mL) and extracted with dichloromethane (20 mL×3). The organic phases were combined, dried with anhydrous sodium sulfate and filtered. The filtrate was concentrated to obtain a residue. The residue was separated and purified by silica gel chromatography to obtain intermediate I-46.

Reference Embodiment 47: Preparation of Intermediate I-47

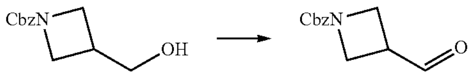

I-46 I-47

Oxalyl chloride (773.60 mg, 6.10 mmol) was dissolved in dichloromethane (5 mL), and anhydrous dimethyl sulfoxide (2.16 g, 27.71 mmol) was added under the protection of nitrogen at −60° C. and the reaction solution was stirred for 0.5 hours. Then a dichloromethane (5 mL) solution of intermediate I-46 (1.23 g, 5.54 mmol) was added, and the reaction was stirred at −60° C. for 0.5 hours. Triethylamine (2.80 g, 27.71 mmol) was added, the reaction temperature was slowly raised to room temperature after dropwise addition, the reaction solution was poured into water (50 mL), extracted with ethyl acetate (20 mL×3), dried with anhydrous sodium sulfate, and filtered. The filtrate was concentrated to obtain crude product of the intermediate I-47, and the crude product was then used directly for the next reaction without purification.

Reference Embodiment 48: Preparation of Intermediate I-48

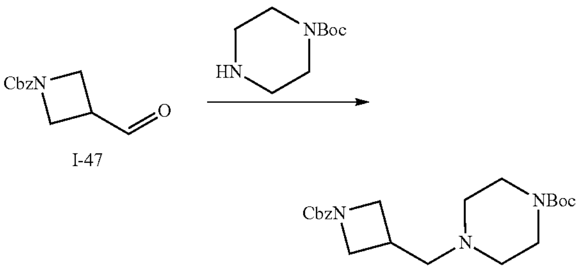

I-47

I-48

Intermediate I-47 (1.25 g), N-Boc piperazine (1.58 g, 8.55 mmol) was dissolved in dichloroethane (15 mL), acetic acid (684.77 mg, 11.40 mmol) and sodium triacetoxyborohydride (1.81 g, 8.55 mmol) were added at room temperature. The reaction solution was stirred overnight at room temperature, and the reaction solution was poured into a saturated sodium bicarbonate solution (30 mL) and extracted with ethyl acetate (20 mL×3). The organic layers were combined, dried with anhydrous sodium sulfate and filtered. The filtrate was concentrated to obtain a residue. The residue was separated and purified by silica gel chromatography to obtain intermediate I-48.

Reference Embodiment 49: Preparation of Intermediate I-49

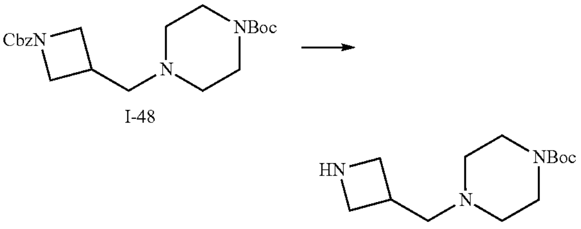

I-48

I-49

At room temperature, intermediate I-48 (1.70 g, 4.36 mmol) was dissolved in methanol (20 mL), then palladium carbon (500 mg, 10% by mass) was added. The reaction solution was stirred at room temperature overnight under hydrogen atmosphere. The reaction solution was filtered, and the filtrate was concentrated to obtain crude product of the intermediate I-49, and the crude product was then used directly for the next reaction without purification.

Reference Embodiment 50: Preparation of Intermediate I-50

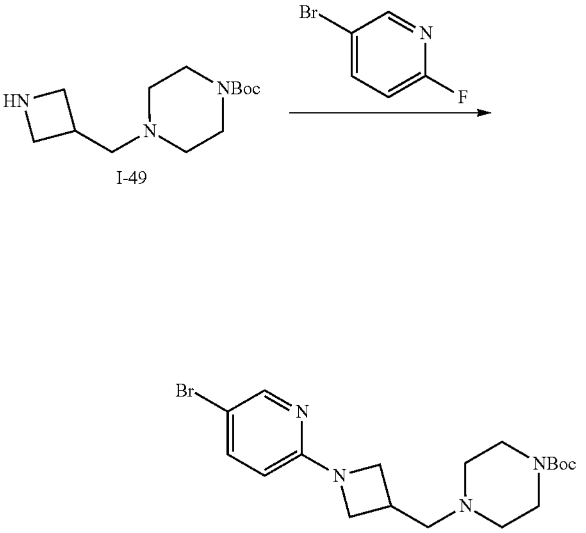

I-49

I-50

Intermediate I-49 (100.00 mg) and 2-fluoro-5-bromopyridine (103.38 mg, 0.59 mmol) were dissolved in N,N-dimethylformamide (5 mL) at room temperature and potassium carbonate was added (162.36 mg, 1.17 mmol). The reaction solution was heated and stirred at 80° C. overnight under the protection of nitrogen. The reaction solution was cooled to room temperature, poured into water (50 mL), then extracted with ethyl acetate (20 mL×3). The organic phases were combined, dried with anhydrous sodium sulfate and filtered. The filtrate was concentrated to obtain a residue, and the residue was separated and purified by silica gel chromatography to obtain intermediate I-50.

Reference Embodiment 51: Preparation of Intermediate I-51

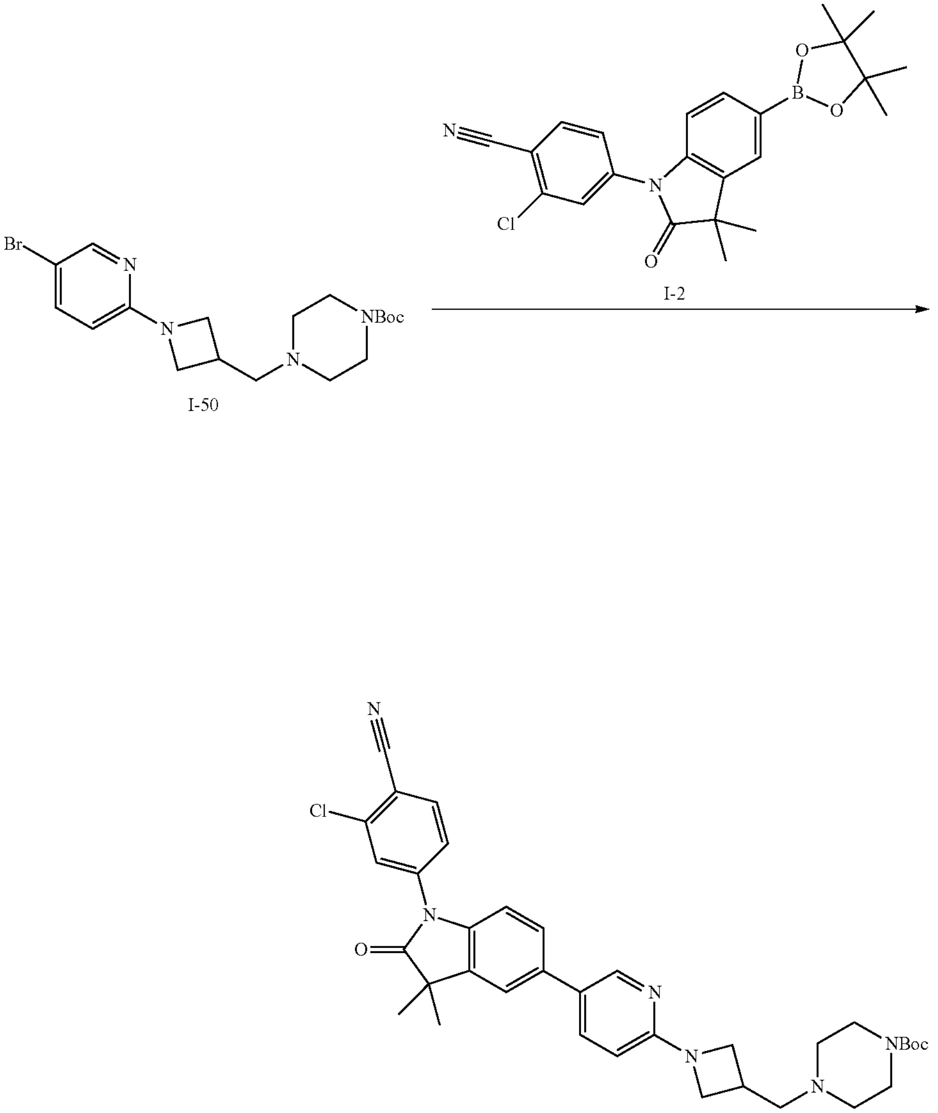

I-51

Intermediates I-50 (110.00 mg, 0.27 mmol), I-2 (112.76 mg, 0.27 mmol) were dissolved in dioxane and water (5 mL/2 mL) at room temperature and 1,1'-bis(diphenylphosphino)ferrocenedichloropalladium(II) (19.74 mg, 0.027 mmol) and potassium carbonate (111.78 mg, 0.81 mmol) were added. The reaction solution was stirred at 80° C. for 2 hours under the protection of nitrogen. The reaction solution was cooled to room temperature, poured into water (50 mL) and extracted with ethyl acetate (20 mL×3). The organic phases were combined, dried with anhydrous sodium sulfate and filtered. The filtrate was concentrated to obtain a residue, and the residue was separated and purified by silica gel chromatography to obtain intermediate I-51.

LC-MS (ESI) $[M+H]^+$: 627.4.

Reference Embodiment 52: Preparation of Intermediate I-52

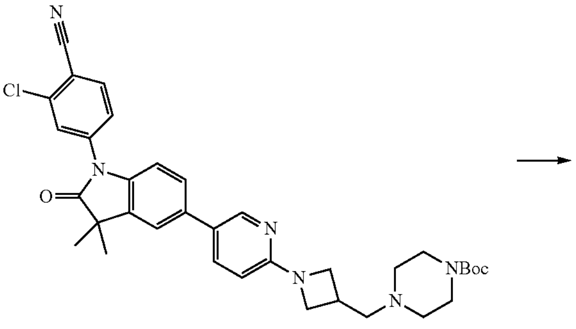

I-51

-continued

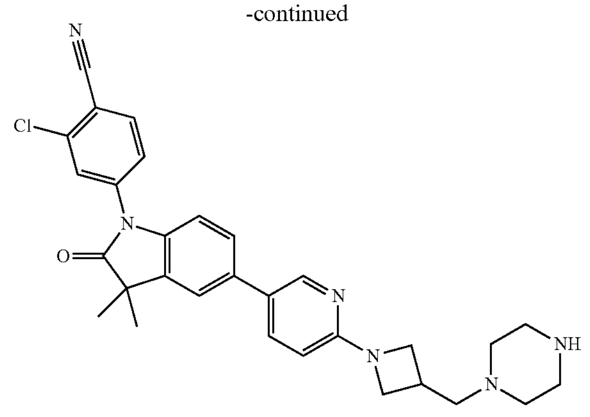

I-52

Intermediate I-51 (100 mg, 0.159 mmol) was dissolved in an ethyl acetate (3 M, 8 mL) solution of hydrogen chloride at room temperature. The reaction solution was stirred at room temperature for 2 hours, and the reaction solution was concentrated to obtain crude product of the intermediate I-52, and the crude product was then used directly for the next reaction without purification.

LCMS (ESI) $[M+H]^+$: 527.3.

Reference Embodiment 53: Preparation of Intermediate I-53

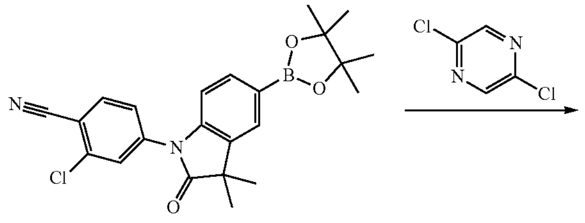

I-2

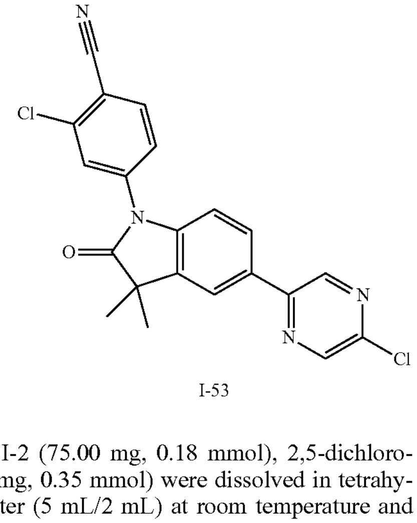

I-53

Intermediates I-2 (75.00 mg, 0.18 mmol), 2,5-dichloropyrazine (52.86 mg, 0.35 mmol) were dissolved in tetrahydrofuran and water (5 mL/2 mL) at room temperature and tetratriphenylphosphine palladium (20.50 mg, 0.018 mmol) and potassium carbonate (73.56 mg, 0.53 mmol) were added. The reaction solution was stirred at 80° C. for 2 hours under the protection of nitrogen. The reaction solution was cooled to room temperature, then poured into water (50 mL) and extracted with ethyl acetate (20 mL×3). The organic phases were dried with anhydrous sodium sulfate and filtered. The filtrate was concentrated to obtain a residue, and the residue was separated and purified by silica gel chromatography to obtain intermediate I-53.

LC-MS (ESI) $[M+H]^+$: 441.2.

Reference Embodiment 54: Preparation of Intermediate I-54

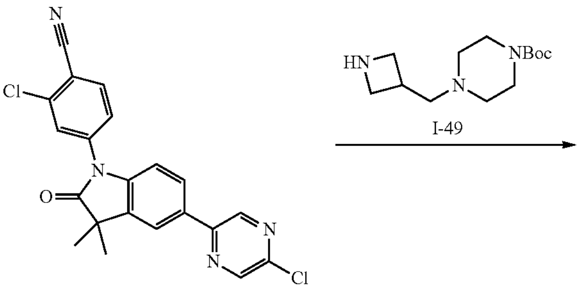

I-53

I-49

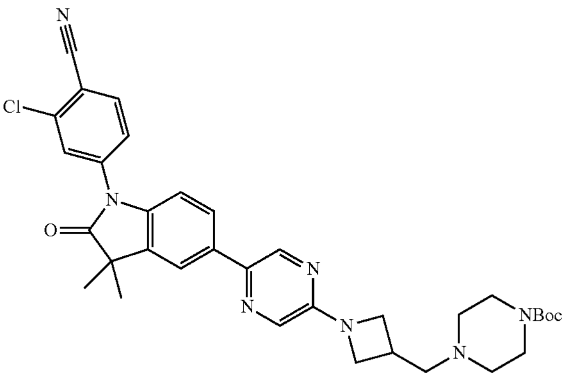

I-54

Intermediate I-53 (70.00 mg, 0.17 mmol) and I-49 (52.41 mg, 0.21 mmol) were dissolved in N,N-dimethylformamide (5 mL) at room temperature. Potassium carbonate (70.91 mg, 0.51 mmol) was added. The reaction solution was stirred at 80° C. overnight under the protection of nitrogen. The reaction solution was cooled to room temperature, poured into water (50 mL), then extracted with ethyl acetate (20 mL×3). The organic phases were combined, dried with anhydrous sodium sulfate and filtered. The filtrate was concentrated to obtain a residue, and the residue was separated and purified by silica gel chromatography to obtain intermediate I-54.

LC-MS (ESI) $[M+H]^+$: 628.4.

Reference Embodiment 55: Preparation of Intermediate I-55

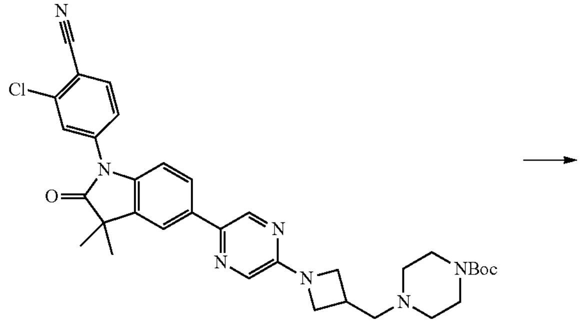

I-54

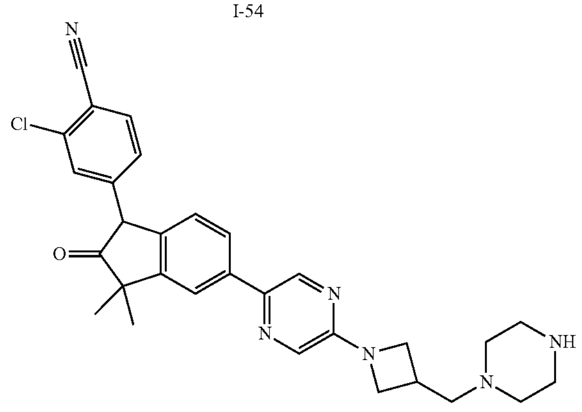

I-55

At room temperature, intermediate I-54 (60.00 mg, 0.096 mmol) was dissolved in dichloromethane (3 mL), then trifluoroacetic acid (1 mL) was added. The reaction solution was stirred at room temperature for 1 hour to obtain crude product of the intermediate I-55, and the crude product was then used directly for the next reaction without purification.

Reference Embodiment 56: Preparation of Intermediate I-56

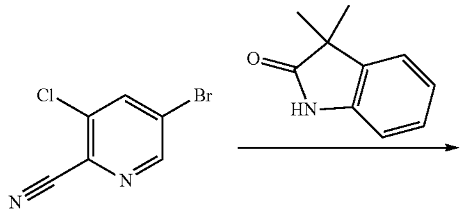

I-54

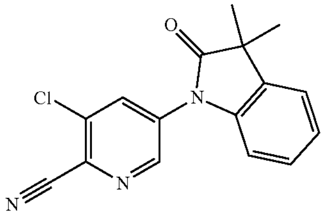

I-56

5-Bromo-3-chloropyridine-2-carbonitrile (2.00 g, 9.20 mmol) was dissolved in N-methylpyrrolidone (80.0 mL) and the intermediate 3,3-dimethylindol-2-one (1.48 g, 9.20 mol), cuprous iodide (350 mg, 1.84 mol), $N^1$,$N^2$-dimethyl-1,2-cyclohexanediamine (523 mg, 3.68 mmol) and anhydrous potassium acetate (2.71 g, 27.6 mmol) were sequentially added. The reaction mixture was stirred at 100° C. for 16 hours under the protection of argon. The reaction solution was cooled to room temperature and was separated and purified by silica gel chromatography to obtain intermediate I-56.

LC-MS (ESI) $[M+H]^+$ 298.1.

Reference Embodiment 57: Preparation of Intermediate I-57

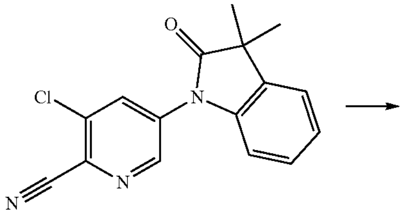

I-56

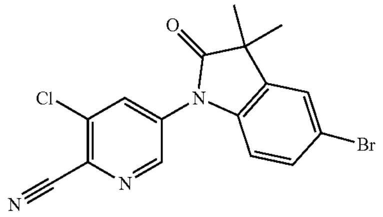

I-57

Intermediate I-56 (1.35 g, 4.53 mmol) was dissolved in acetic acid (20.0 mL), the system was cooled to 0° C., anhydrous sodium acetate (446 mg, 5.44 mmol) was added, and an acetic acid (10.0 mL) solution of bromine (796 mg, 4.98 mmol) was added dropwise. After the dropwise addition, the reaction system was under the protection of argon and stirred at room temperature for 16 hours. The pH of the system was adjusted to 8.0 with saturated aqueous sodium bicarbonate solution. The mixture was extracted with ethyl acetate (30.0 mL×3), the organic phases were combined and dried with anhydrous sodium sulfate, filtered. The filtrate was concentrated under reduced pressure to remove the organic solvent to obtain crude product of intermediate I-57. The crude product was then used directly for the next reaction without purification.

LC-MS (ESI) $[M+H]^+$ 376.0.

Reference Embodiment 58: Preparation of Intermediate I-58

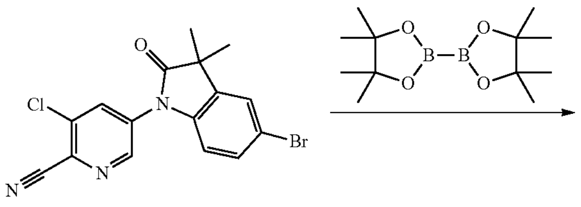

I-57

-continued

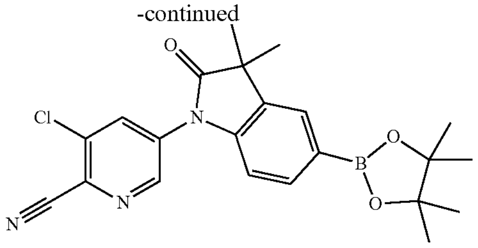

I-58

Intermediate I-57 (600 mg, 1.59 mmol) was dissolved in anhydrous dioxane (100 mL), then bis(pinacolato)diboron (485 mg, 1.91 mmol), anhydrous potassium acetate (485 mg, 1.91 mmol), 1,1'-bis(diphenylphosphino)ferrocenedichloropalladium(II) (23.3 mg, 0.032 mmol) were sequentially added thereto. The reaction system was stirred at 90° C. for 3 hours under the protection of argon. The mixture was concentrated under reduced pressure to remove the solvent to obtain a residue, and the residue was separated and purified by silica gel chromatography to obtain intermediate I-58.

LC-MS (ESI) $[M+H]^+$ 424.2.

Reference Embodiment 59: Preparation of Intermediate I-59

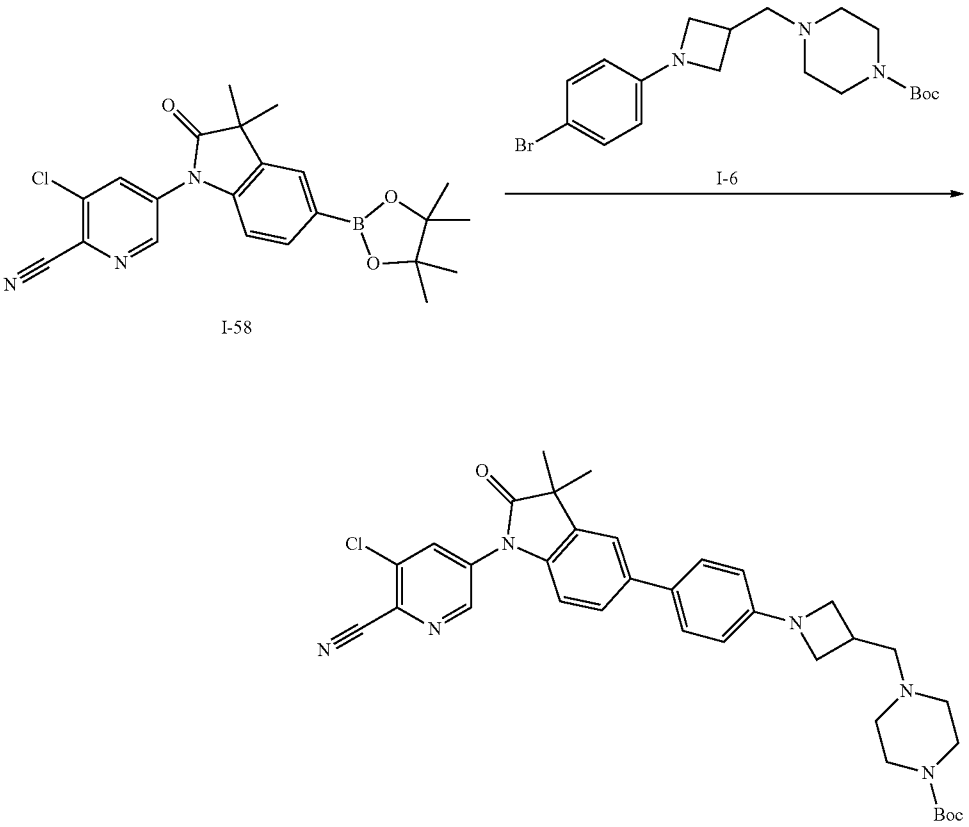

I-58

I-59

Intermediate I-6 (150 mg, 0.366 mmol) was dissolved in anhydrous dioxane and water (15 mL/5 mL), then intermediate I-58 (186 mg, 0.439 mmol), anhydrous potassium phosphate (233 mg, 1.10 mmol), 1,1'-bis(di-tert-butylphosphino)ferrocene palladium dichloride (4.77 mg, 0.00732 mmol) were sequentially added. The reaction system was stirred and reacted at 100° C. for 3 hours under the protection of argon. The mixture was concentrated under reduced pressure to remove the solvent to obtain a residue, and the residue was separated and purified by silica gel chromatography to obtain intermediate I-59.

LC-MS (ESI) $[M+H]^+$ 627.3.

Reference Embodiment 60: Preparation of Intermediate I-60

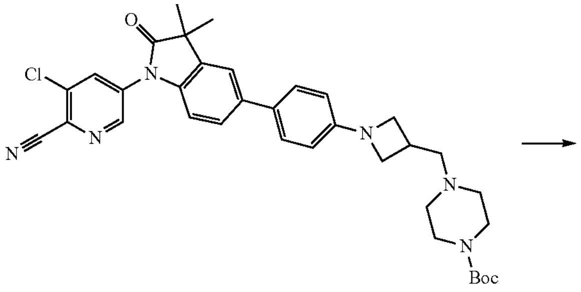

I-59

-continued

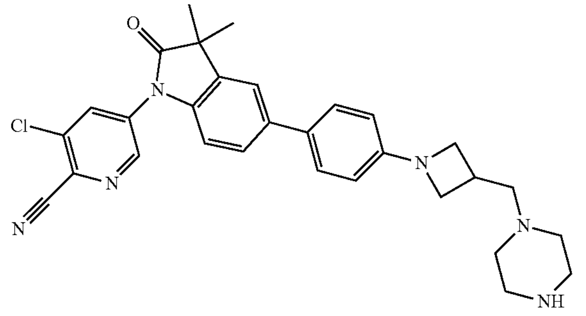

I-60

Intermediate I-59 (110 mg, 0.175 mmol) was dissolved in anhydrous dichloromethane (2.00 mL), then trifluoroacetic acid (0.60 mL) was added, the reaction system was reacted under the protection of argon, and stirred at room temperature for 1 hour. The mixture was concentrated under reduced pressure to remove the solvent to obtain a residue, and the residue was separated and purified by silica gel chromatography to obtain intermediate I-60.

LC-MS (ESI) $[M+H]^+$ 527.2.

Reference Embodiment 61: Preparation of Intermediate I-61

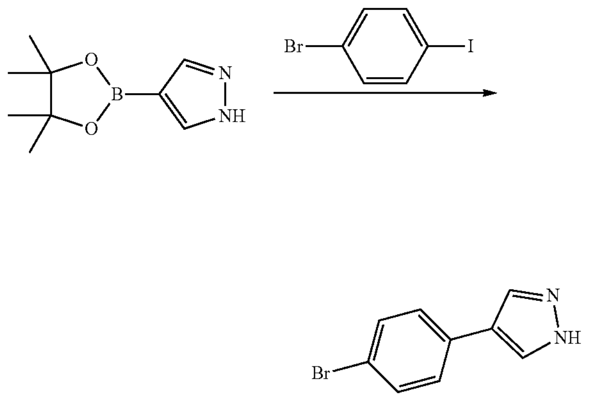

I-61

4-Pyrazoleboronic acid pinacol ester (2.00 g, 10.3 mmol), p-bromoiodobenzene (4.39 g, 15.5 mmol), potassium phosphate (4.37 g, 20.6 mmol) and [1,1'-bis(diphenylphosphino) ferrocene]dichloropalladium(II) (377 mg, 0.52 mmol) were mixed in N,N-dimethylformamide (20 mL) and water (4 mL). After the reaction mixture was replaced with argon three times at room temperature, the reaction was stirred and reacted at 90° C. for 4 hours under argon. The mixture was cooled to room temperature, poured into water (200 mL), extracted with ethyl acetate (50 mL×3), the organic phases were combined, washed with saturated brine (50 mL), dried with anhydrous sodium sulfate, filtered, and the filtrate was concentrated under reduced pressure to the residue. The residue was separated and purified by silica gel chromatography to obtain intermediate I-61.

LC-MS (ESI) $[M+H]^+$: 223.2.

Reference Embodiment 62: Preparation of Intermediate I-62

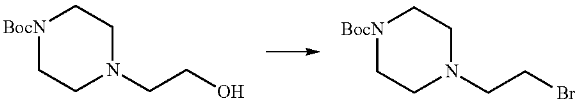

I-62

At room temperature, 4-(2-hydroxy-propyl)-piperazine-1-carboxylic acid tert-butyl ester (2 g, 8.68 mmol) and carbon tetrabromide (3.15 g, 9.50 mmol) were added into anhydrous dichloromethane (20 mL), and then a dichloromethane (8 mL) solution of triphenylphosphine (2.51 g, 9.57 mmol) was added. The reaction system was stirred at room temperature overnight under the protection of nitrogen. The reaction solution was concentrated under reduced pressure to remove the organic solvent to obtain a residue, and the residue was separated and purified by silica gel chromatography to obtain intermediate I-62.

LC-MS (ESI) $[M+H]^+$: 293.1.

$^1H$ NMR (400 MHz, $CDCl_3$) δ 3.45-3.22 (m, 6H), 2.72 (t, J=7.3 Hz, 2H), 2.50-2.25 (m, 4H), 1.61-1.43 (m, 2H), 1.39 (s, 9H).

Reference Embodiment 63: Preparation of Intermediate I-63

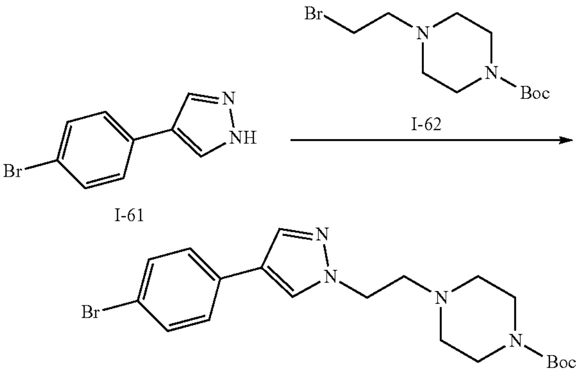

I-63

Intermediate I-61 (270 mg, 1.21 mmol) was dissolved in N,N-dimethylformamide (3 mL), and sodium hydride (72.8 mg, 1.82 mmol, 60% purity in mineral oil) was added to the mixture at 0° C., the reaction mixture was stirred and reacted at room temperature for 0.5 hours, and a solution of intermediate I-62 (355 mg, 1.21 mmol) in N,N-dimethylformamide (2 mL) was added dropwise at room temperature. The reaction mixture was stirred and reacted at room temperature overnight. The reaction solution was poured into saturated ammonium chloride solution (50 mL), extracted with ethyl acetate (15 mL×3), combined the organic phase, washed with saturated brine (30 mL), dried with anhydrous sodium sulfate, filtered. The filtrate was concentrated under reduced pressure to obtain crude product of the intermediate I-63, and the crude product was then used directly for the next reaction without purification.

LC-MS (ESI) $[M+H]^+$: 435.1.

Reference Embodiment 64: Preparation of Intermediate I-64

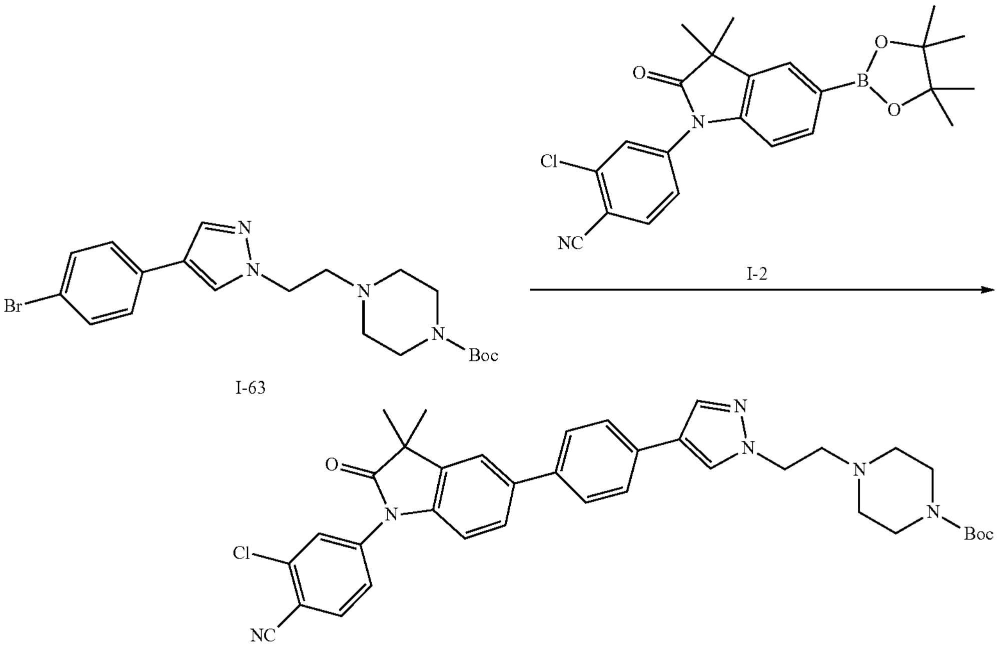

I-63

I-2

I-64

Intermediate I-63 (200 mg), intermediate I-2 (233 mg, 0.551 mmol), potassium phosphate (195 mg, 0.918 mmol) and [1,1'-bis(diphenylphosphino)ferrocene]dichloropalladium(II) (16.8 mg, 0.0230 mmol) were mixed in N,N-dimethylformamide (10 mL) and water (2 mL). After replacing argon three times at room temperature, the reaction mixture was stirred and reacted at 100° C. for 2 hours under the protection of argon. The reaction solution was cooled to room temperature, poured into water (100 mL), extracted with ethyl acetate (20 mL×3). The organic phases were combined, washed with saturated brine (30 mL), dried with anhydrous sodium sulfate, filtered, and the filtrate was concentrated under reduced pressure to obtain a residue. The residue was separated and purified by silica gel chromatography to obtain intermediate I-64.

LC-MS (ESI) $[M+H]^+$: 651.2.

Reference Embodiment 65: Preparation of Intermediate I-65

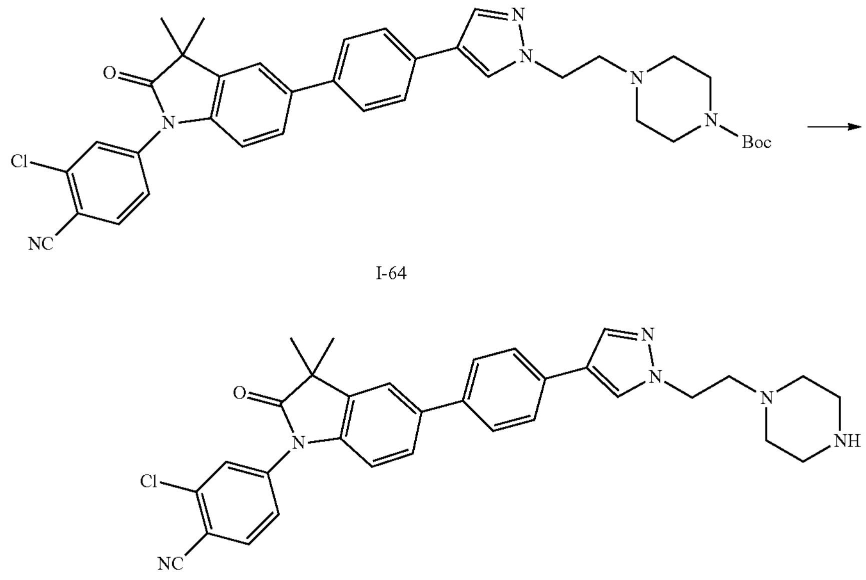

I-64

I-65

Intermediate I-64 (200 mg) was dissolved in dichloromethane (2 mL), and a solution of hydrogen chloride in dioxane (4 M, 1 mL) was added dropwise to the solution at room temperature with stirring. The reaction mixture was stirred and reacted at room temperature for 0.5 hours. The solvent was removed from the mixture under reduced pressure. The residue was separated and purified by silica gel chromatography to obtain intermediate I-65.

LC-MS (ESI) $[M+H]^+$: 551.3.

Reference Embodiment 66: Preparation of Intermediate I-66

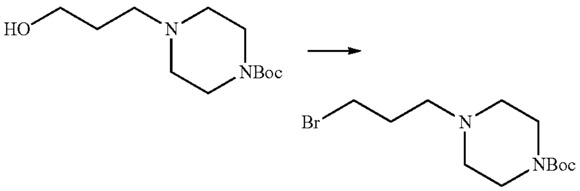

I-66

1-tert-Butoxycarbonyl-4-(3-hydroxypropane) piperazine (2.00 g, 8.19 mmol) and carbon tetrabromide (2.99 g, 9.01 mmol) were mixed in tetrahydrofuran (60 mL), after replacing with argon, a tetrahydrofuran (10 mL) solution of triphenylphosphine (2.36 g, 9.01 mmol) was added dropwise at 0° C., and the reaction mixture was stirred and reacted at room temperature under argon atmosphere overnight. The mixture was removed from the solvent under reduced pressure. The residue was separated and purified by silica gel chromatography to obtain intermediate I-66.

$^1$H NMR (400 MHz, $CDCl_3$) δ 3.47 (t, J=6.6 Hz, 2H), 3.42 (t, J=5.0 Hz, 4H), 2.48 (t, J=6.9 Hz, 2H), 2.38 (t, J=5.0 Hz, 4H), 2.02 (p, J=6.6 Hz, 2H), 1.46 (s, 9H).

Reference Embodiment 67: Preparation of Intermediate I-67

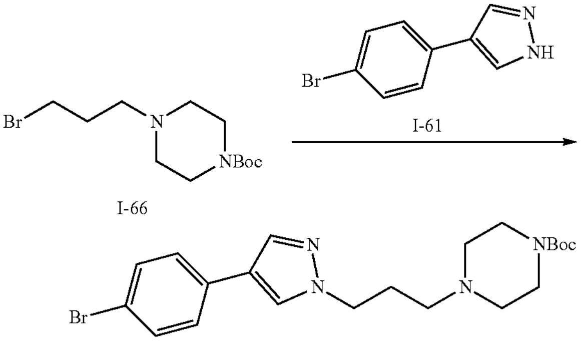

I-61

I-66

I-67

Intermediate I-61 (200 mg, 0.897 mmol) was dissolved in N,N-dimethylformamide (2 mL), and sodium hydride (54.0 mg, 1.35 mmol, 60% purity in mineral oil) was added to the mixture at 0° C. in batches, the reaction mixture was stirred and reacted at room temperature for 0.5 hours, and a solution of intermediate I-66 (276 mg, 0.897 mmol) in N,N-dimethylformamide (1 mL) was added dropwise at room temperature. The reaction mixture was stirred and reacted at room temperature for 2 hours. The reaction solution was poured into saturated ammonium chloride solution (50 mL), extracted with ethyl acetate (15 mL×3). The organic phase was combined, washed with saturated brine (30 mL), dried with anhydrous sodium sulfate, filtered. The filtrate was concentrated under reduced pressure to obtain crude product of the intermediate I-67, and the crude product was then used directly for the next reaction without purification.

LC-MS (ESI) $[M+H]^+$: 449.2.

Reference Embodiment 68: Preparation of Intermediate I-68

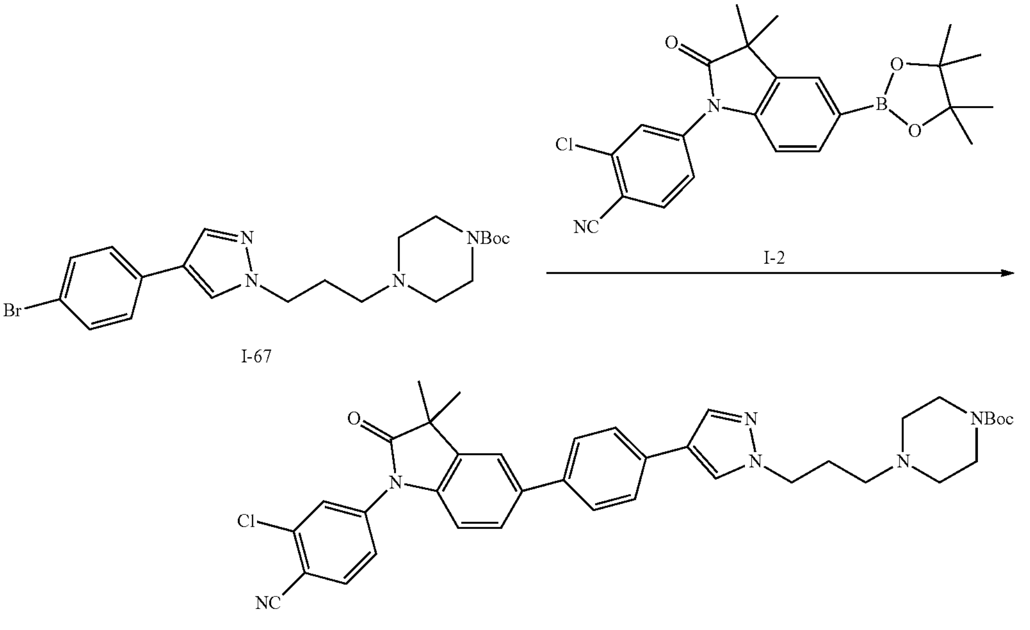

I-2

I-67

I-68

Intermediate I-67 (200 mg), intermediate I-2 (226 mg, 0.53 mmol), potassium phosphate (189 mg, 0.89 mmol) and [1,1'-bis(diphenylphosphino)ferrocene]dichloropalladium (II) (16.3 mg, 0.023 mmol) were mixed in N,N-dimethylformamide (5 mL) and water (0.5 mL). After replacing with argon three times at room temperature, the reaction mixture was stirred and reacted at 100° C. for 2 hours under the protection of argon. The reaction solution was cooled to room temperature, poured into saturated brine (50 mL), extracted with ethyl acetate (20 mL×3). The organic phase was combined, dried with anhydrous sodium sulfate, filtered, and the filtrate was concentrated under reduced pressure to obtain a residue. The residue was separated and purified by silica gel chromatography to obtain intermediate I-68.

LC-MS (ESI) $[M+H]^+$: 665.3.

Reference Embodiment 69: Preparation of Intermediate I-69

At 25° C., intermediate I-3 (3 g) was dissolved in N,N-dimethylformamide (50 mL) and potassium carbonate (6.64 g, 48.07 mmol), 2,6-difluoropyridine (2.21 g, 19.23 mmol) were sequentially added, and the reaction solution was stirred and reacted at 85° C. for 16 hours. The reaction solution was added to water (50 mL), and extracted with ethyl acetate (50 mL×3). The organic phases were combined, washed with saturated brine (50 mL), dried with anhydrous sodium sulfate, filtered, and concentrated under reduced pressure to obtain a residue. The residue was separated and purified by silica gel chromatography to obtain intermediate I-70.

LC-MS (ESI) $[M+H]^+$ 183.2.

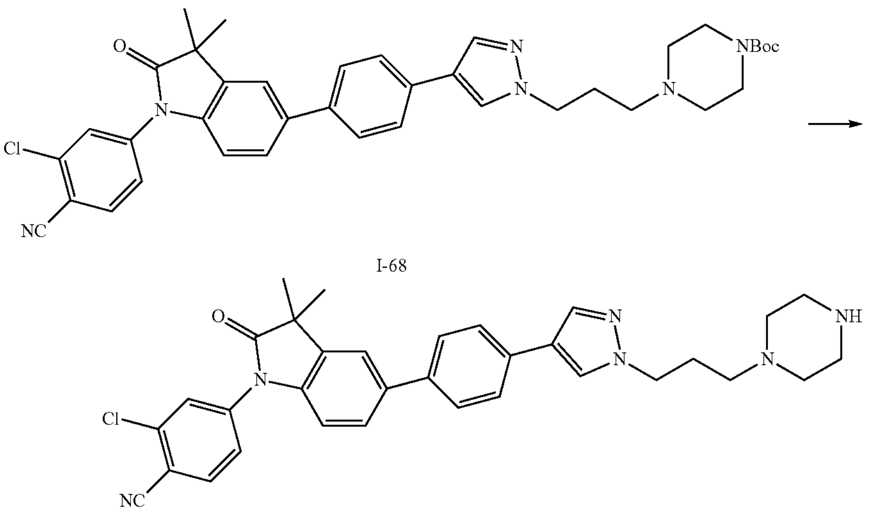

I-68

I-69

Intermediate I-68 (130 mg, 0.195 mmol) was dissolved in dichloromethane (1 mL), then a methanol solution of hydrogen chloride (3 M, 2.5 mL) was added dropwise to the solution at room temperature. The reaction mixture was stirred and reacted at room temperature for 1 hour. The solvent was removed under reduced pressure. The residue was separated and purified by silica gel chromatography to obtain intermediate I-69.

LC-MS (ESI) $[M+H]^+$: 565.3.

Reference Embodiment 70: Preparation of Intermediate I-70

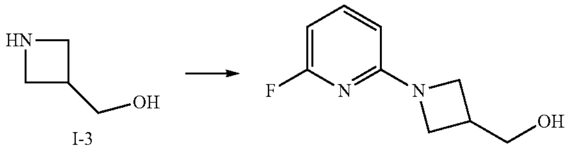

I-3

I-70

Reference Embodiment 71: Preparation of Intermediate I-71

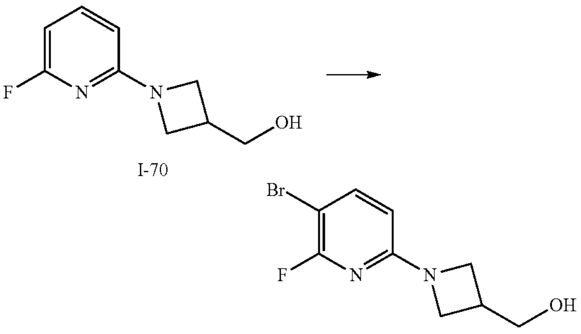

I-70

I-71

At 25° C., intermediate I-70 (1.90 g, 10.43 mmol) was dissolved in dichloromethane (50 mL), and the mixture was cooled to 0° C., N-bromosuccinimide (1.86 g, 10.43 mmol) was added, and the reaction solution was reacted at 0° C. for 10 min. Water (50 mL) was added, and the reaction solution was extracted with dichloromethane (50 mL×3). The organic phases were combined, washed with saturated brine (50 mL), dried with anhydrous sodium sulfate, filtered, and concentrated under reduced pressure to obtain a residue. The residue was separated and purified by silica gel chromatography to obtain intermediate I-71.

$^1$H NMR (400 MHz, $CDCl_3$) δ 7.58 (t, J=8.7 Hz, 1H), 6.00 (dd, J=8.5, 1.5 Hz, 1H), 4.12-4.04 (m, 2H), 3.86 (d, J=6.3 Hz, 2H), 3.81 (dd, J=8.4, 5.2 Hz, 2H), 3.02-2.84 (m, 1H), 2.77 (s, 1H).

Reference Embodiment 72: Preparation of Intermediate I-72

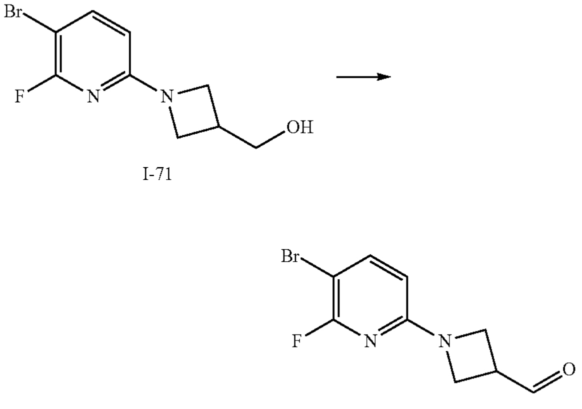

I-71

I-72

At 25° C., oxalyl chloride (855.55 mg, 6.74 mmol) was dissolved in dichloromethane (50 mL), and the mixture was cooled to −60° C., dimethyl sulfoxide (1.09 g, 13.90 mmol) was added, and the reaction solution was reacted at −60° C. for 0.5 hours. Then a dichloromethane (10 mL) solution of intermediate I-71 (1.10 g, 4.21 mmol) was added. The reaction mixture was reacted at −60° C. for 0.5 hours. Triethylamine (2.13 g, 21.07 mmol) was added, and the reaction solution was reacted at −60° C. for 0.5 hours and room temperature for 0.5 hours. Water (50 mL) was added, and the reaction solution was extracted with dichloromethane (50 mL×3). The organic phases were combined, washed with saturated brine (50 mL), dried with anhydrous sodium sulfate, filtered, and concentrated under reduced pressure to obtain a residue. The residue was separated and purified by silica gel chromatography to obtain intermediate I-72.

LC-MS (ESI) [M+H]$^+$ 259.0.

Reference Embodiment 73: Preparation of Intermediate I-73

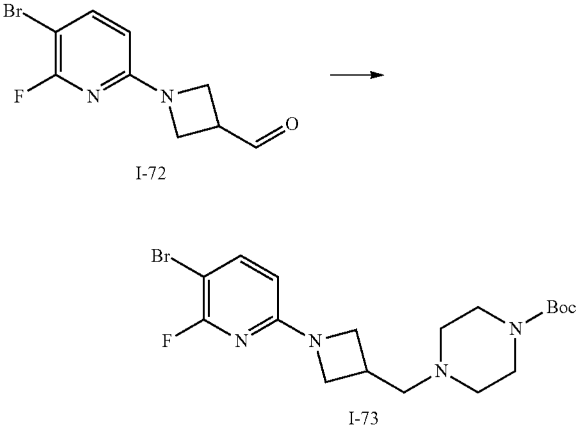

I-72

I-73

At 25° C., intermediate I-72 (1.00 g, 3.86 mmol) was dissolved in dichloromethane (20 mL), 1-boc-piperazine (1.08 g, 5.79 mmol), sodium triacetoxyborohydride (1.64 g, 7.72 mmol) and acetic acid (23.42 mg, 0.39 mmol) were sequentially added, and the reaction solution was reacted at room temperature for 3 hours. Water (20 mL) was added, and the reaction solution was extracted with dichloromethane (20 mL×3). The organic phases were combined, washed with saturated brine (20 mL), dried with anhydrous sodium sulfate, filtered, and concentrated under reduced pressure to obtain a residue. The residue was separated and purified by silica gel chromatography to obtain intermediate I-73.

LC-MS (ESI) [M+H]$^+$ 429.2.

Reference Embodiment 74: Preparation of Intermediate I-74

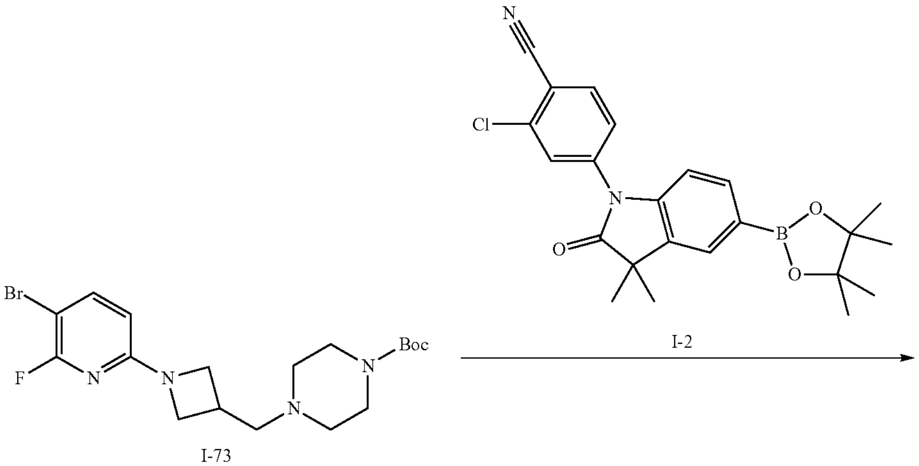

I-2

I-73

-continued

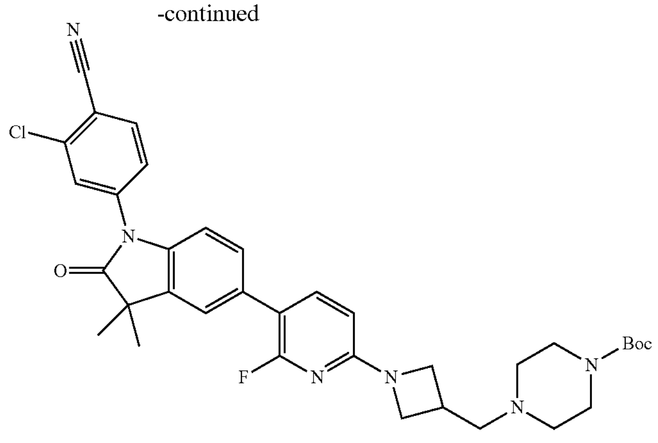

I-74

At 25° C., intermediate I-73 (150.00 mg, 0.35 mmol) was dissolved in a mixed solution of dioxane (8 mL) and water (2 mL), then potassium carbonate (144.86 mg, 1.05 mmol), intermediate 1-2 (177.23 mg, 0.42 mmol), [1,1'-bis(diphenylphosphino)ferrocene]dichloropalladium(II) (50.52 mg, 0.070 mmol) were sequentially added, the mixture was replaced with nitrogen three times, and reacted under a nitrogen balloon for 80° C. for 2 hours. The reaction solution was added to water (10 mL), and extracted with ethyl acetate (10 mL×3). The organic phases were combined, washed with saturated brine (10 mL), dried with anhydrous sodium sulfate, filtered, and concentrated under reduced pressure to obtain a residue. The residue was separated and purified by silica gel chromatography to obtain intermediate I-74.

LC-MS (ESI) $[M+H]^+$ 645.4.

Reference Embodiment 75: Preparation of Intermediate I-75

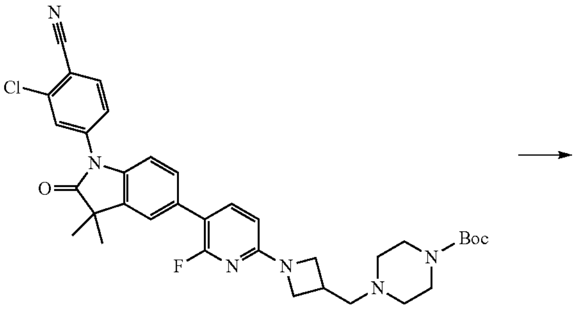

I-74

-continued

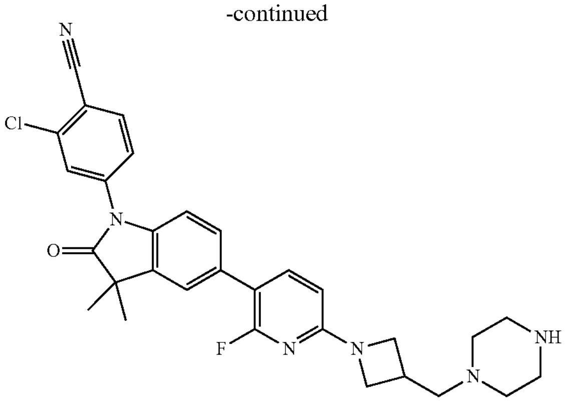

I-75

At 25° C., intermediate I-74 (120.00 mg, 0.19 mmol) was dissolved in dichloromethane (4 mL), then trifluoroacetic acid (2 mL) was added. The reaction mixture was reacted at room temperature for 3 hours. The mixture was concentrated under reduced pressure to obtain crude intermediate I-75, and the crude product was then used directly for the next reaction.

LC-MS (ESI) $[M+H]^+$ 545.3.

Reference Embodiment 76: Preparation of Intermediate I-76

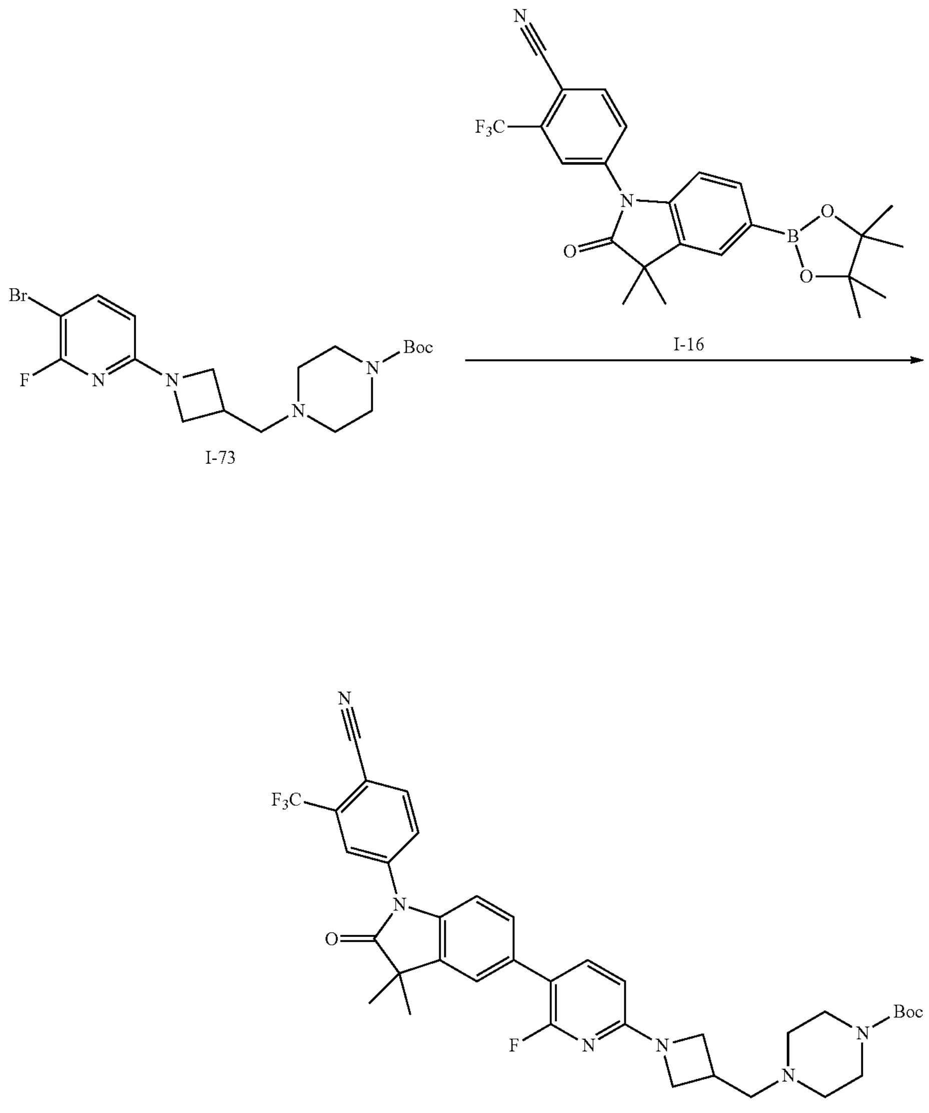

I-73

I-16

I-76

At 25° C., intermediate I-73 (100.00 mg, 0.23 mmol) was dissolved in dioxane (8 mL) and water (2 mL), then potassium carbonate (96.74 mg, 0.70 mmol), intermediate I-16 (127.53 mg, 0.28 mmol), [1,1'-bis(diphenylphosphino)ferrocene]dichloropalladium(II) (33.92 mg, 0.047 mmol) were sequentially added, the mixture was replaced with nitrogen three times, and reacted under a nitrogen balloon at 80° C. for 2 hours. Water (10 mL) was added and the mixture was extracted with ethyl acetate (10 mL×3). The organic phases were combined, washed with saturated brine (10 mL), dried with anhydrous sodium sulfate, filtered, and concentrated under reduced pressure to obtain a residue. The residue was separated and purified by silica gel chromatography to obtain intermediate I-76.

LC-MS (ESI) $[M+H]^+$ 679.4.

Reference Embodiment 77: Preparation of Intermediate I-77

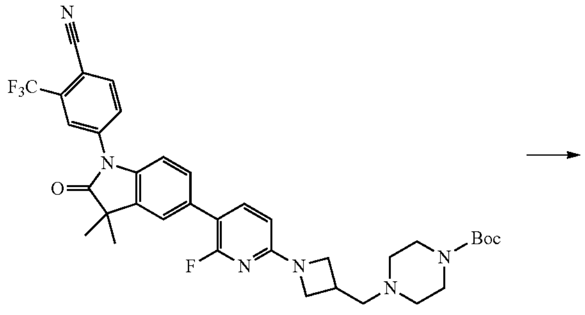

I-76

-continued

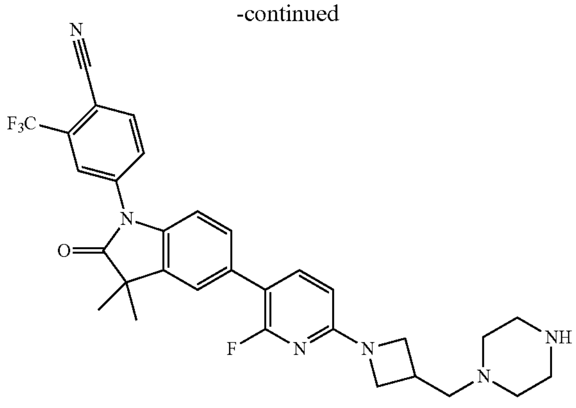

I-77

At 25° C., intermediate I-76 (110.00 mg, 0.16 mmol) was dissolved in dichloromethane (4 mL), then trifluoroacetic acid (2 mL) was added. The reaction mixture was reacted at room temperature for 3 hours. The mixture was concentrated under reduced pressure to obtain crude intermediate I-77, which was directly put into the next step reaction.

LC-MS (ESI) $[M+H]^+$ 579.3.

Preparation of Embodiments

Embodiment 1: Preparation of Compound 1

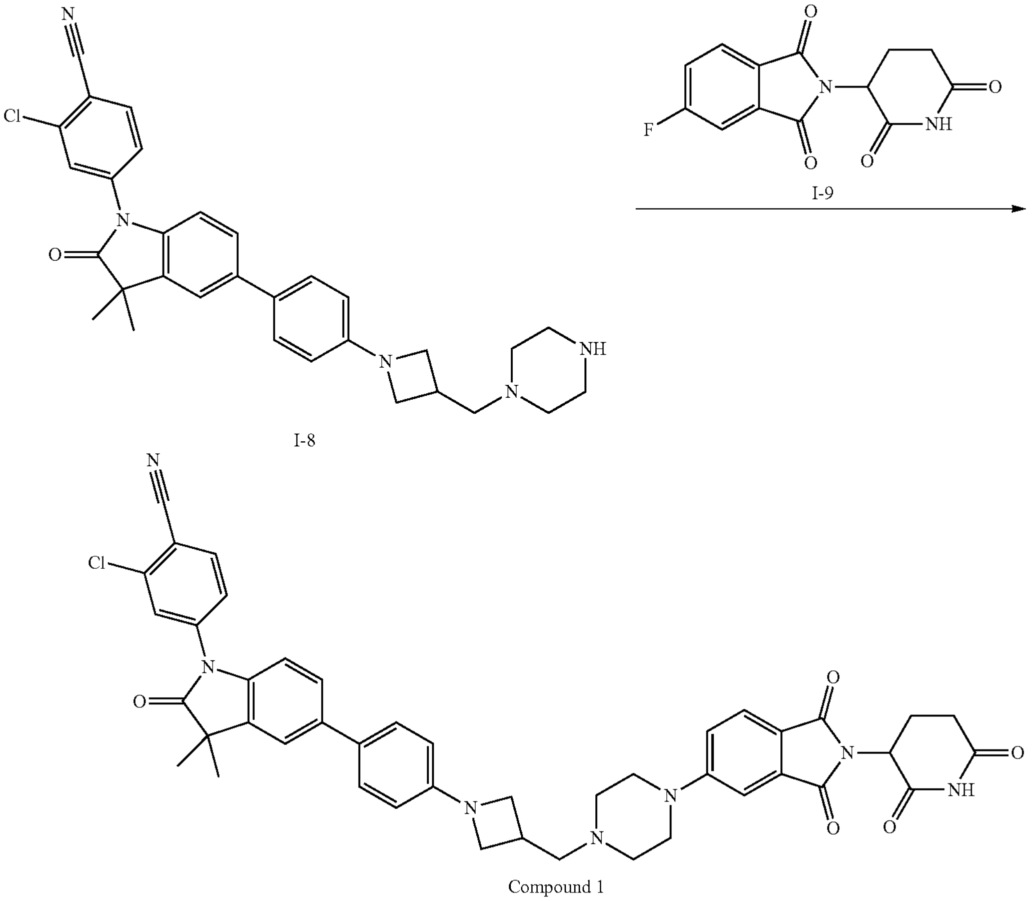

I-8

I-9

Compound 1

At 25° C., intermediate I-8 (650.00 mg, 1.24 mmol) was dissolved in dimethyl sulfoxide (8 mL) and intermediate I-9 (408.81 mg, 1.48 mmol) and N,N-diisopropylethylamine (480.81 mg, 3.72 mmol) were sequentially added, and the reaction solution was stirred at 120° C. for 16 hours. The reaction solution was cooled to room temperature, then separated and purified by chromatography to obtain target compound 1.

LC-MS (ESI) $[M+H]^+$: 782.3.

$^1H$ NMR (400 MHz, DMSO-$d_6$) δ 11.03 (s, 1H), 8.11 (d, J=8.4 Hz, 1H), 7.91 (d, J=1.9 Hz, 1H), 7.71-7.58 (m, 3H), 7.46-7.34 (m, 3H), 7.29 (d, J=2.2 Hz, 1H), 7.20 (dd, J=8.7, 2.3 Hz, 1H), 6.93 (d, J=8.3 Hz, 1H), 6.44 (d, J=8.2 Hz, 2H), 5.01 (dd, J=12.9, 5.4 Hz, 1H), 3.91 (t, J=7.4 Hz, 2H), 3.45 (t, J=6.4 Hz, 2H), 3.38 (s, 4H), 2.92 (p, J=6.8 Hz, 1H), 2.87-2.75 (m, 1H), 2.64-2.56 (m, 2H), 2.51 (t, J=11.7 Hz, 6H), 1.99-1.88 (m, 1H), 1.39 (s, 6H).

Embodiment 2: Preparation of Compound 2

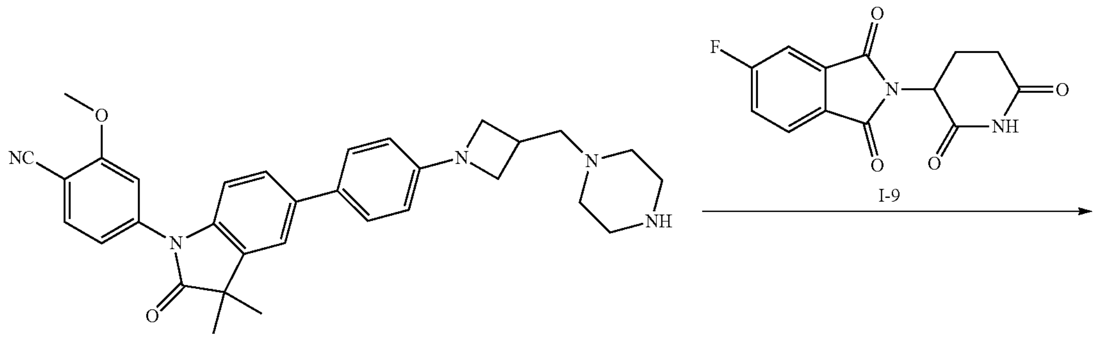

I-9

I-14

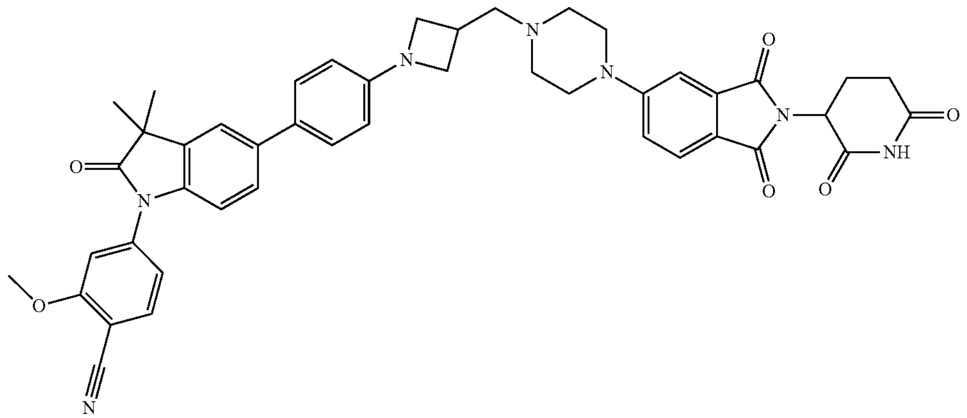

Compound 2

Intermediate I-14 (140 mg) was dissolved in DMSO (8 mL), and then intermediate I-9 (74 mg, 0.27 mmol) and diisopropylethylamine (103 mg, 0.80 mmol) were sequentially added. The reaction solution was stirred at 110° C. for 16 hours. The reaction solution was cooled to room temperature and filtered, and the filtrate was purified by preparative HPLC (containing formic acid) to obtain compound 2.

LC-MS (ESI) $[M+H]^+$: 778.4.

$^1H$ NMR (400 MHz, DMSO-$d_6$) δ 11.08 (s, 1H), 8.40(s, from formic acid), 7.92 (d, J=8.0 Hz, 1H), 7.69 (d, J=12.4 Hz, 2H), 7.49 (d, J=8.0 Hz, 2H), 7.42-7.30 (m, 3H), 7.25 (dd, J=15.0, 8.4 Hz, 2H), 6.99 (d, J=8.2 Hz, 1H), 6.50 (d, J=7.7 Hz, 2H), 5.07 (d, J=7.9 Hz, 1H), 4.20-3.80 (m, 4H), 3.56-3.42 (m, 9H), 3.03-2.80 (m, 4H), 2.69-2.59 (m, 4H), 2.05-2.01 (m, 1H), 1.46 (s, 6H).

Embodiment 3: Preparation of Compound 3

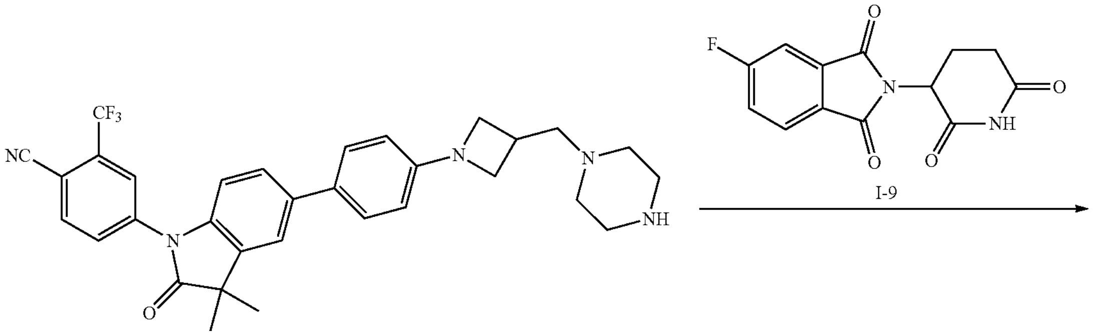

I-9

I-18

-continued

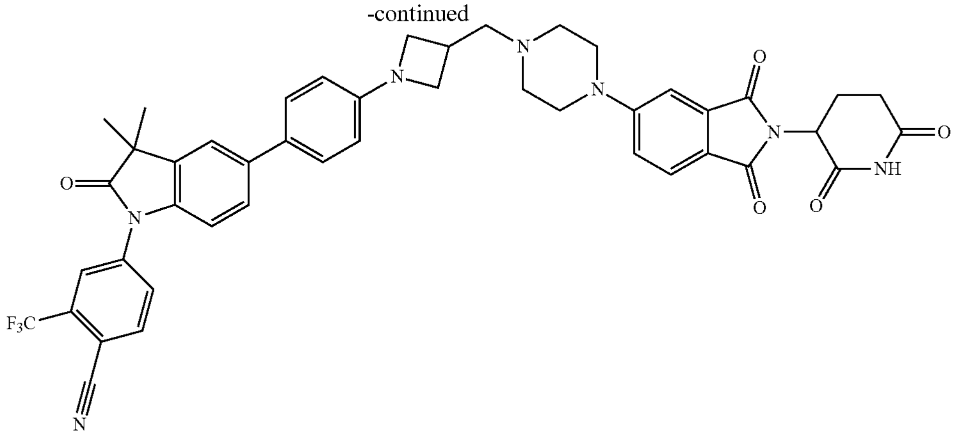

Compound 3

Intermediate I-18 (80 mg) was dissolved in N-methylpyrrolidone (10 mL), and then intermediate I-9 (50 mg, 0.181 mmol) and N,N-diisopropylethylamine (90 mg, 0.697 mmol) were sequentially added. The reaction solution was stirred at 110° C. for 16 hours. The reaction solution was cooled to room temperature and filtered, and the filtrate was purified by preparative HPLC (containing formic acid) to obtain compound 3.

LC-MS (ESI) $[M+H]^+$: 816.4.

$^1H$ NMR (400 MHz, DMSO-$d_6$) δ 11.08 (s, 1H), 8.37 (brs, 2H), 8.20 (s, 1 H), 8.09 (d, J=8.5 Hz, 1H), 7.75-7.66 (m, 2H), 7.55-7.43 (m, 3H), 7.36 (s, 1H), 7.27 (d, J=7.3 Hz, 1H), 7.05 (d, J=5.9 Hz, 1H), 6.51 (d, J=6.0 Hz, 2H), 5.08 (d, J=11.3 Hz, 1H), 3.99 (s, 2H), 3.49 (d, J=26.9 Hz, 10H), 3.05-2.82 (m, 3H), 2.70-2.60 (s, 3H), 2.05-2.01 (m, 1H), 1.48 (s, 6H). (Containing formic acid)

Embodiment 4: Preparation of Compound 4

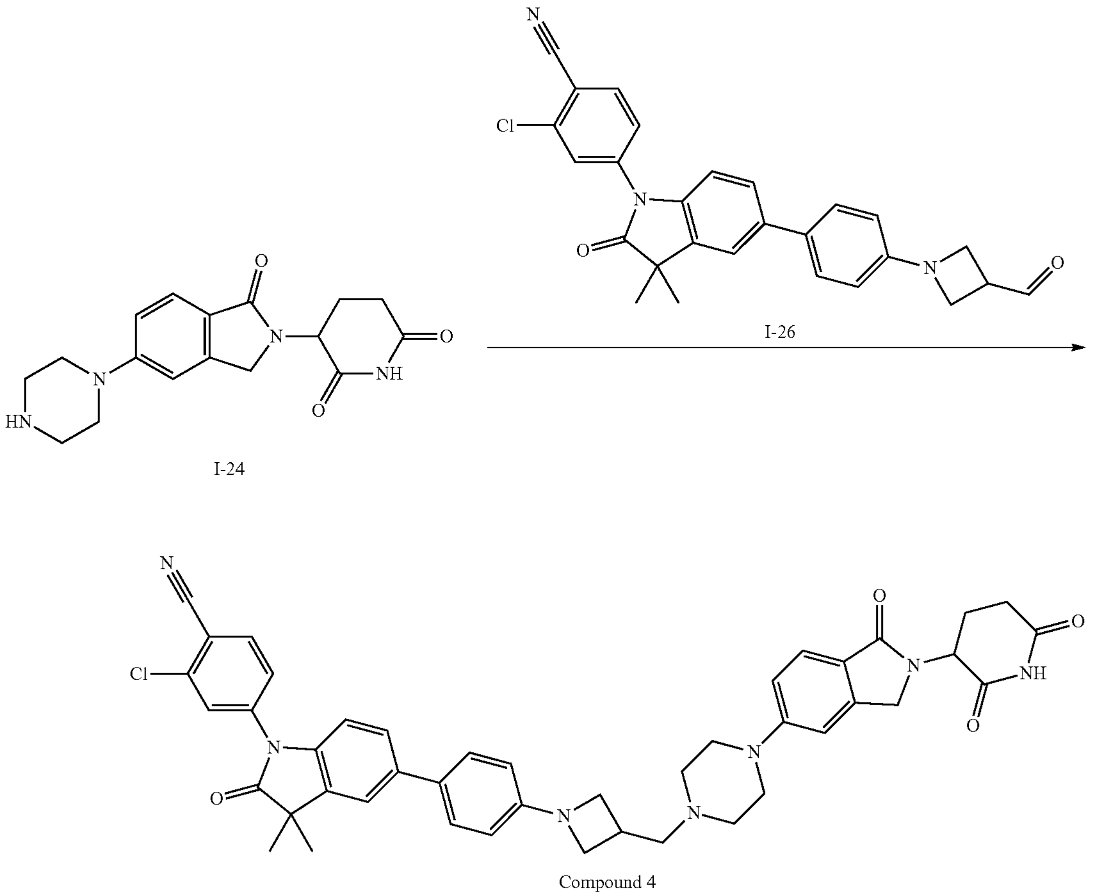

I-26

I-24

Compound 4

Intermediate I-24 (70.0 mg, 0.213 mmol) was dissolved in dichloromethane/methanol (20 mL, volume ratio 10:1), and intermediate I-26 (97.1 mg, 0.213 mmol), sodium acetate (26.0 mg, 0.317 mmol) and sodium triacetoxyborohydride (68.0 mg, 0.321 mmol) were sequentially added. The reaction mixture was stirred and reacted at room temperature for 1 hour. The reaction solution was filtered, and the filtrate was separated and purified by preparative HPLC (containing formic acid) to obtain compound 4.

LC-MS (ESI) $[M+H]^+$ 768.2.

$^1$H NMR (400 MHz, DMSO-d6) δ 10.97 (s, 1H), 8.19 (d, J=8.4 Hz, 1H), 7.98 (d, J=1.9 Hz, 1H), 7.77-7.70 (m, 2H), 7.55-7.43 (m, 4H), 7.07 (d, J=8.0 Hz, 2H), 7.00 (d, J=8.3 Hz, 1H), 6.51 (d, J=8.6 Hz, 2H), 5.05 (dd, J=13.3, 5.1 Hz, 1H), 4.27 (dd, J=51.3, 17.0 Hz, 2H), 3.98 (t, J=7.4 Hz, 2H), 3.58-3.47 (m, 4H), 3.03-2.85 (m, 3H), 2.68-2.59 (m, 3H), 2.55 (d, J=2.2 Hz, 4H), 2.44-2.29 (m, 2H), 2.03-1.94 (m, 1H), 1.46 (s, 6H).

Embodiment 5: Preparation of Compound 5

Intermediates I-32 (38 mg), I-9 (25 mg, 0.090 mmol) and diisopropylethylamine (100 μL) were dissolved in dimethyl sulfoxide (3 mL), and the reaction solution was stirred at 130° C. overnight under the protection of nitrogen. The reaction solution was cooled to room temperature, and compound 5 was obtained using preparative HPLC (containing formic acid).

LC-MS (ESI) $[M+H]^+$: 800.4.

$^1$H NMR (400 MHz, DMSO) δ: 11.09 (s, 1H), 8.18 (d, J=8.3 Hz, 1H), 7.98 (d, J=1.9 Hz, 1H), 7.77-7.64 (m, 3H), 7.59-7.43 (m, 3H), 7.35 (d, J=2.3 Hz, 1H), 7.26 (dd, J=8.7, 2.3 Hz, 1H), 7.00 (d, J=8.2 Hz, 1H), 6.61 (d, J=8.4 Hz, 2H), 5.07 (dd, J=12.9, 5.4 Hz, 1H), 4.07 (dd, J=17.8, 9.0 Hz, 2H), 3.93 (dd, J=21.3, 8.9 Hz, 2H), 3.46 (d, J=5.3 Hz, 4H), 3.02-2.81 (m, 3H), 2.68 (t, J=4.9 Hz, 4H), 2.63-2.52 (m, 2H), 2.01 (td, J=7.6, 3.6 Hz, 1H), 1.46 (s, 6H).

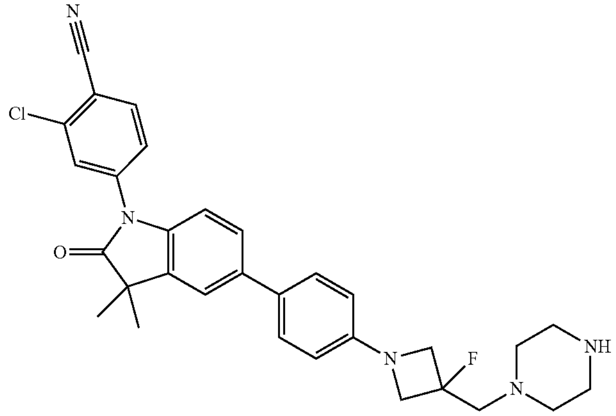

I-32

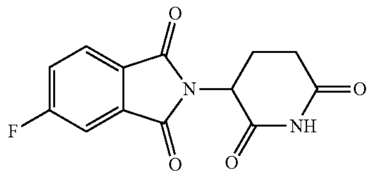

I-9

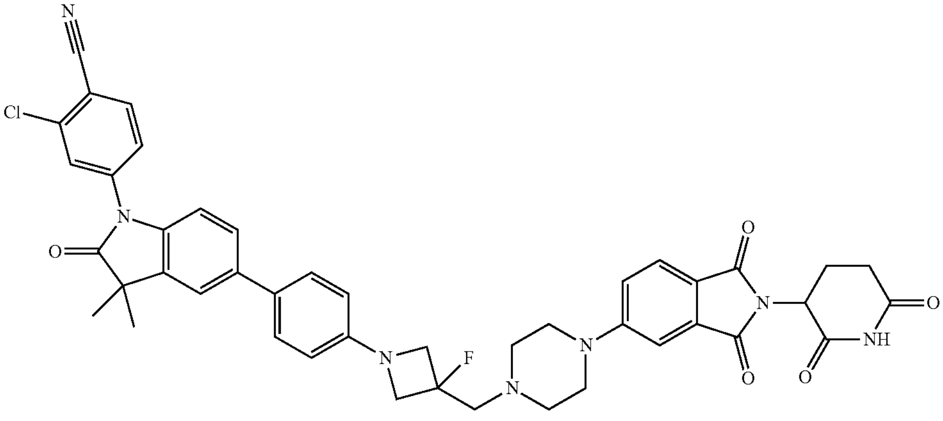

Compound 5

Embodiment 6: Preparation of Compound 6

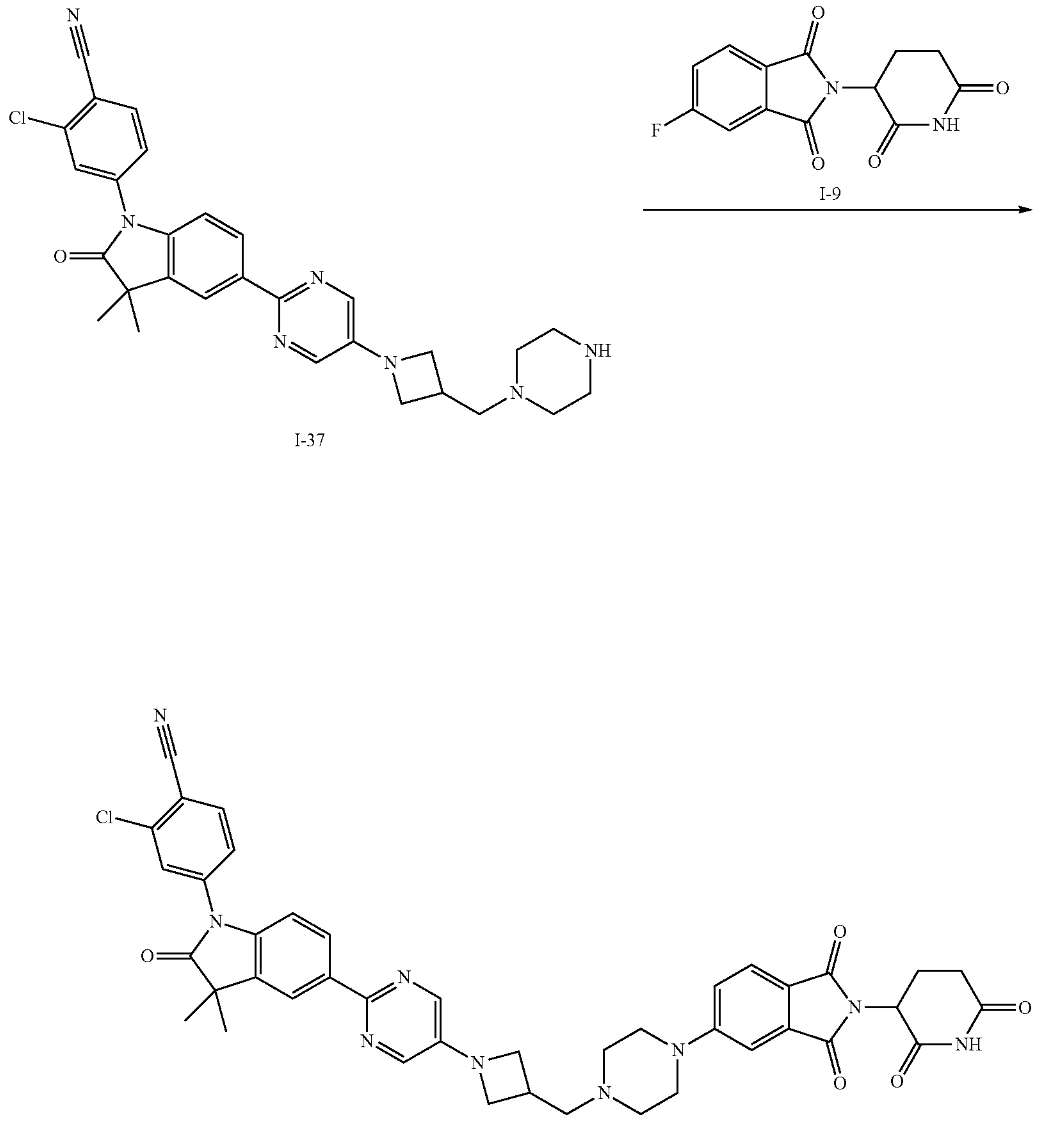

I-37

I-9

Compound 6

At 25° C., intermediate I-37 (25.00 mL) was dissolved in dimethyl sulfoxide (2 mL) and intermediate I-9 (13.26 mg, 0.048 mmol) and N,N-diisopropylethylamine (25.85 mg, 0.20 mmol) were sequentially added, and the reaction solution was stirred at 120° C. for 16 hours. The reaction solution was cooled to room temperature, and compound 6 was obtained using preparative HPLC (containing formic acid).

LC-MS (ESI) $[M+H]^+$: 784.4.

$^1H$ NMR (400 MHz, DMSO-$d_6$) δ 11.10 (s, 1H), 8.29 (d, J=1.7 Hz, 1H), 8.23-8.16 (m, 2H), 8.12 (s, 2H), 8.01 (d, J=1.9 Hz, 1H), 7.75 (dd, J=8.4, 2.0 Hz, 1H), 7.69 (d, J=8.4 Hz, 1H), 7.36 (d, J=2.4 Hz, 1H), 7.27 (dd, J=8.8, 2.3 Hz, 1H), 7.05 (d, J=8.4 Hz, 1H), 5.08 (dd, J=12.9, 5.4 Hz, 1H), 4.11 (t, J=7.7 Hz, 2H), 3.69 (dd, J=7.7, 5.5 Hz, 2H), 3.45 (t, J=4.8 Hz, 4H), 3.07 (p, J=6.6 Hz, 1H), 2.89 (ddd, J=17.3, 14.1, 5.5 Hz, 1H), 2.68 (d, J=7.4 Hz, 2H), 2.64-2.52 (m, 6H), 2.02 (dp, J=11.3, 3.9, 3.5 Hz, 1H), 1.47 (s, 6H).

Embodiment 7: Preparation of Compound 7

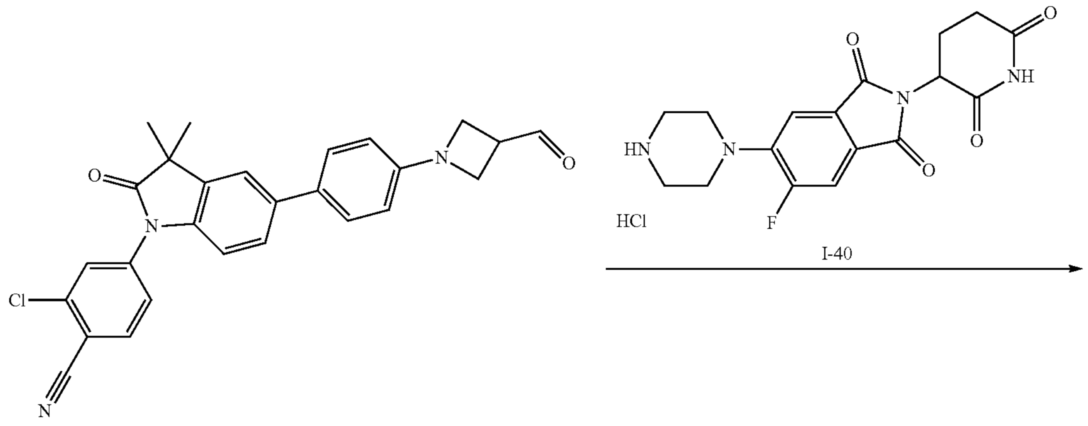

I-40

I-26

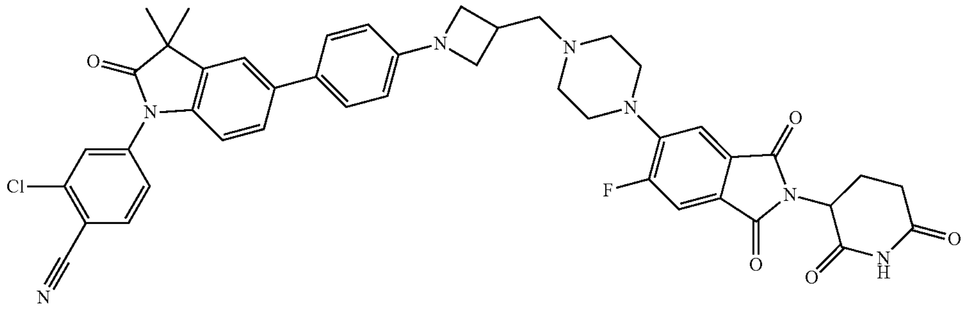

Compound 7

Intermediate I-26 (80.0 mg, 0.213 mmol) was dissolved in methanol (10 mL), and intermediate I-40 (69.4 mg, 0.175 mmol), sodium acetate (28.7 mg, 0.350 mmol) and sodium borohydride acetate (37.1 mg, 0.175 mmol) were sequentially added. The reaction solution was stirred for 3 hours at room temperature. The reaction solution was concentrated under reduced pressure to obtain a residue, which was purified by preparative HPLC (formic acid) to obtain compound 7.

LC-MS (ESI) $[M+H]^+$ 800.1.

$^1$H NMR (400 MHz, $CDCl_3$) δ 8.02 (s, 1H), 7.82 (d, J=8.4 Hz, 1H), 7.76 (d, J=1.9 Hz, 1H), 7.58 (dd, J=8.4, 2.0 Hz, 1H), 7.55-7.50 (m, 1H), 7.47-7.39 (m, 5H), 7.02 (d, J=8.2 Hz, 1H), 6.54 (d, J=8.6 Hz, 2H), 4.95 (dd, J=12.3, 5.3 Hz, 1H), 4.17 (s, 2H), 3.72 (s, 2H), 3.55 (s, 3H), 2.95-2.49 (m, 7H), 2.20-2.11 (m, 1H), 1.96-1.67 (m, 4H), 1.53 (s, 6H).

Embodiment 8: Preparation of Compound 8

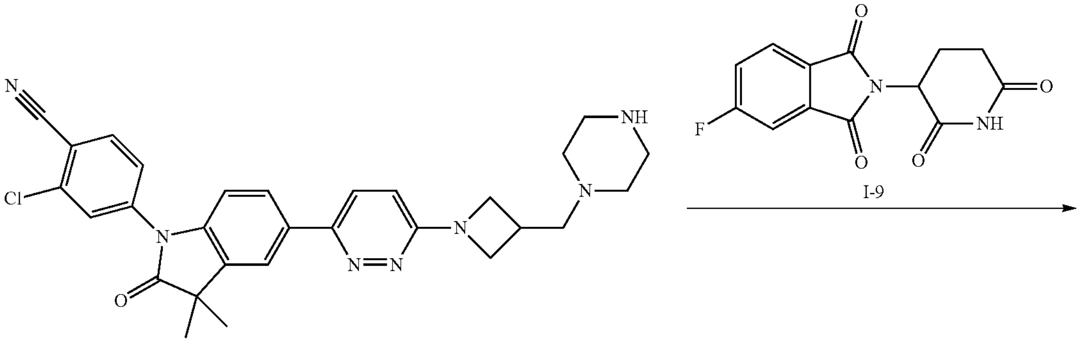

I-9

I-45

-continued

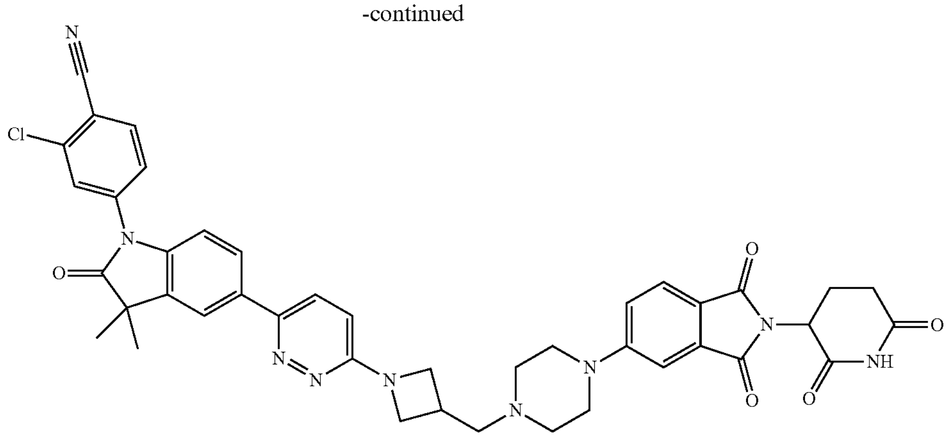

Compound 8

Intermediates I-45 (50.00 mg), I-9 (31.39 mg, 0.114 mmol) and N,N-diisopropylethylamine (122.38 mg, 0.947 mmol) were dissolved in dimethyl sulfoxide (3.0 mL) at room temperature. The reaction mixture was stirred and reacted in an oil bath at 110° C. for 16 hours. The reaction solution was naturally cooled to room temperature, then separated and purified by chromatography to obtain compound 8.

LC-MS (ESI) $[M+H]^+$: 784.4.

$^1H$ NMR (400 MHz, DMSO-$d_6$) δ 11.10 (s, 1H), 8.20 (d, J=8.0 Hz, 1H), 8.15 (d, J=1.8 Hz, 1H), 8.01 (d, J=1.9 Hz, 1H), 7.94 (t, J=9.4 Hz, 2H), 7.76 (dd, J=8.4, 2.0 Hz, 1H), 7.69 (d, J=8.5 Hz, 1H), 7.36 (d, J=2.2 Hz, 1H), 7.28 (dd, J=8.7, 2.3 Hz, 1H), 7.08 (d, J=8.3 Hz, 1H), 6.90 (d, J=9.3 Hz, 1H), 5.08 (dd, J=12.9, 5.4 Hz, 1H), 4.21 (t, J=8.1 Hz, 2H), 3.78 (dd, J=8.3, 5.5 Hz, 2H), 3.50-3.40 (m, 4H), 3.10-3.03 (m, 2H), 2.89-2.82 (m, 1H), 2.69 (d, J=7.5 Hz, 2H), 2.63-2.53 (m, 5H), 2.08-1.97 (m, 1H), 1.48 (s, 6H).

Embodiment 9: Preparation of Compound 9

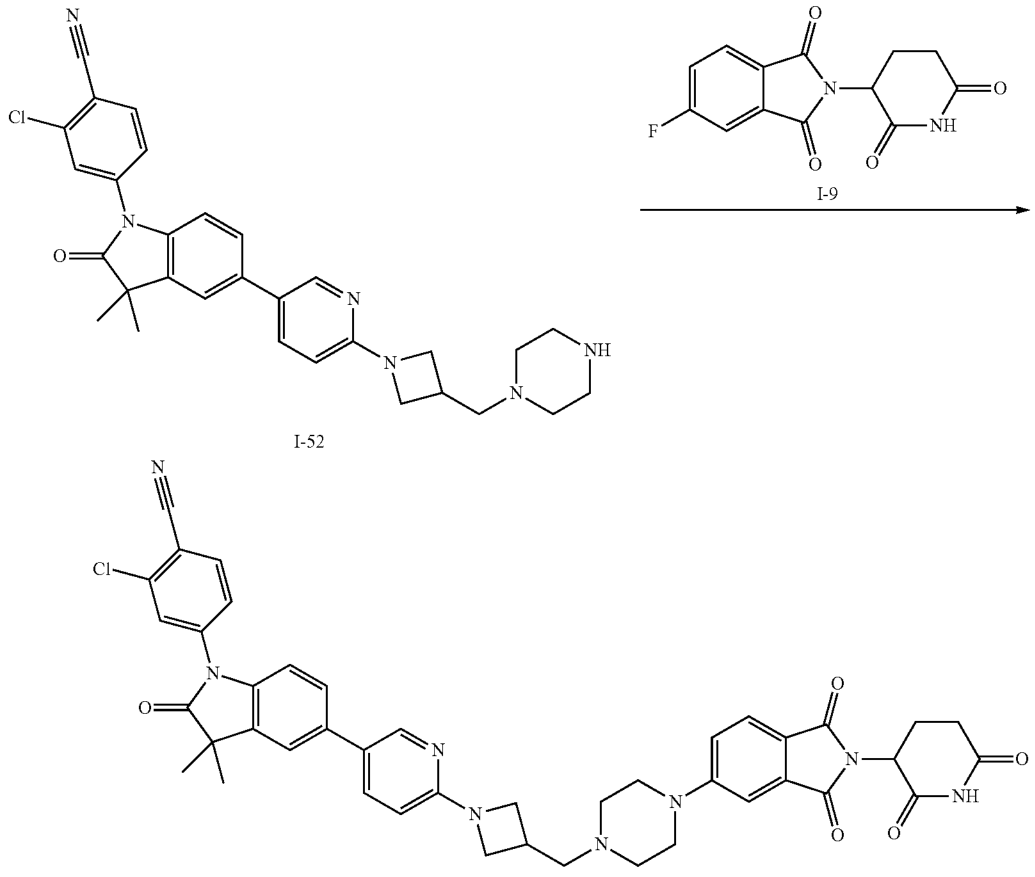

Compound 9

Intermediates I-52 (90 mg), intermediate I-9 (58.59 mg, 0.212 mmol) and N,N-diisopropylethylamine (233.72 μL, 1.41 mmol) were dissolved in dimethyl sulfoxide (2 mL), and the reaction solution was stirred at 110° C. for 16 hours. Most of the N,N-diisopropylethylamine was removed under reduced pressure, and the residue was separated by preparative-HPLC to obtain compound 9.

LCMS (ESI) $[M+H]^+$: 783.4.

$^1$H NMR (400 MHz, DMSO-$d_6$) δ 11.09 (s, 1H), 8.39 (d, J=2.13 Hz, 1H), 8.18 (d, J=8.51 Hz, 1H), 7.98 (d, J=1.75 Hz, 1H), 7.79-7.86 (m, 1H), 7.64-7.78 (m, 3H), 7.44-7.52 (m, 1H), 7.35 (s, 1H), 7.23-7.30 (m, 1H), 7.02 (d, J=8.25 Hz, 1H), 6.43-6.50 (m, 1H), 5.02-5.13 (m, 1H), 4.03-4.13 (m, 2H), 3.60-3.71 (m, 2H), 3.45 (br. s., 4H), 2.82-3.05 (m, 2H), 2.51-2.69 (m, 8H), 1.95-2.06 (m, 1H), 1.46 (s, 6H).

Embodiment 10: Preparation of Compound 10

Intermediate I-55 (50.00 mg) was dissolved in dimethyl sulfoxide (2 mL), and then N,N-diisopropylethylamine (1 mL) and intermediate I-9 (52.31 mg, 0.19 mmol) were sequentially added at room temperature. The reaction solution was stirred at 130° C. overnight under the protection of nitrogen. Most of the N,N-diisopropylethylamine was removed under reduced pressure, and the residue was separated by preparative-HPLC to obtain compound 10.

LC-MS (ESI) $[M+H]^+$: 784.4.

$^1$H NMR (400 MHz, DMSO-$d_6$) δ 11.10 (s, 1H), 8.66 (d, J=1.4 Hz, 1H), 8.19 (d, J=8.4 Hz, 1H), 8.07 (d, J=1.9 Hz, 1H), 7.97 (dd, J=21.8, 1.7 Hz, 2H), 7.86 (dd, J=8.4, 1.9 Hz, 1H), 7.79-7.63 (m, 2H), 7.42-7.16 (m, 2H), 7.04 (d, J=8.3 Hz, 1H), 5.08 (dd, J=12.9, 5.4 Hz, 1H), 4.19 (t, J=8.1 Hz, 2H), 3.88-3.67 (m, 2H), 3.45 (t, J=4.8 Hz, 4H), 3.13-3.01 (m, 1H), 2.89 (ddd, J=17.3, 13.9, 5.4 Hz, 1H), 2.68 (d, J=7.5 Hz, 2H), 2.75-2.30 (m, 6H), 2.14-1.88 (m, 1H), 1.47 (s, 6H).

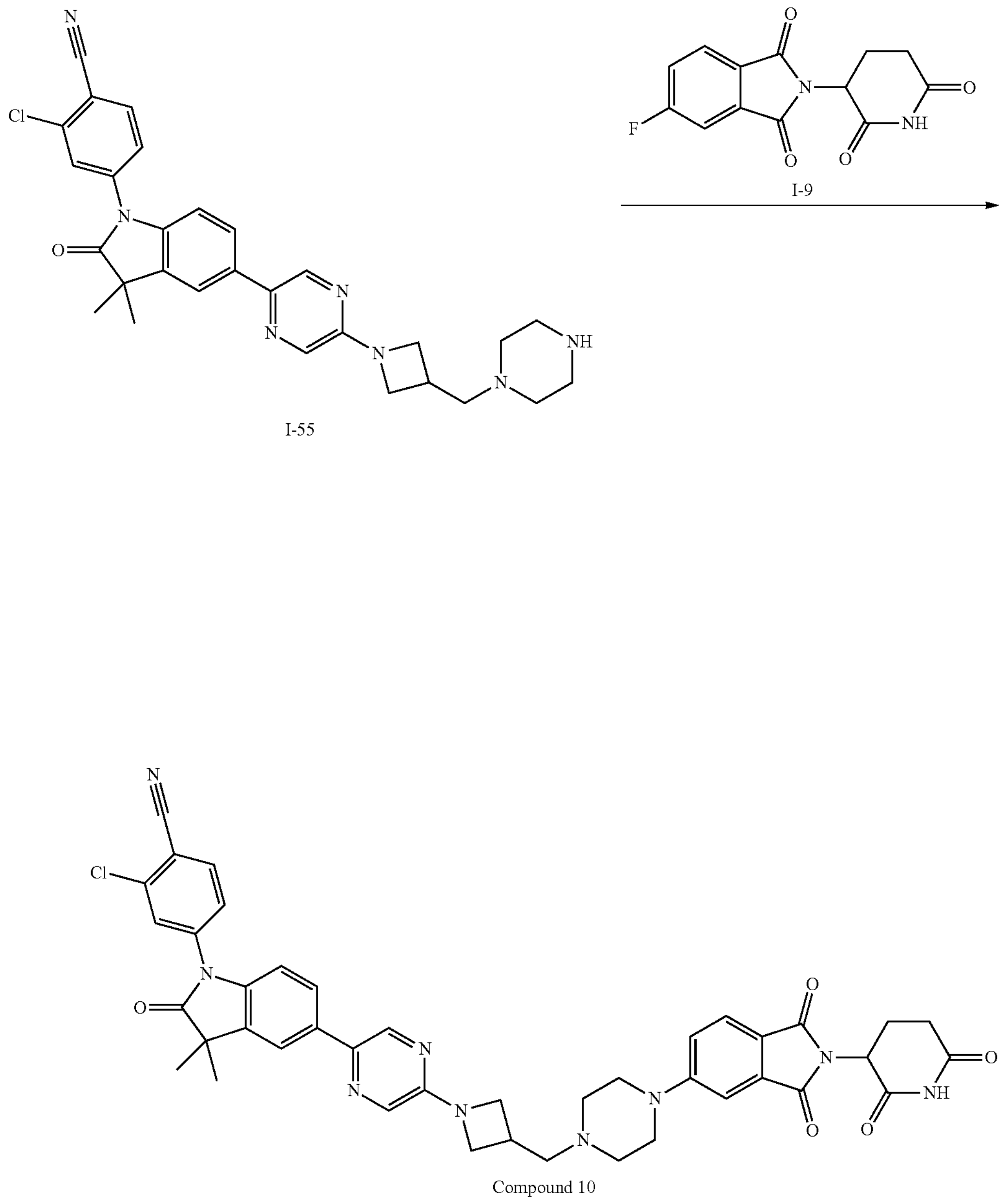

I-55

I-9

Compound 10

Embodiment 11: Preparation of Compound 11

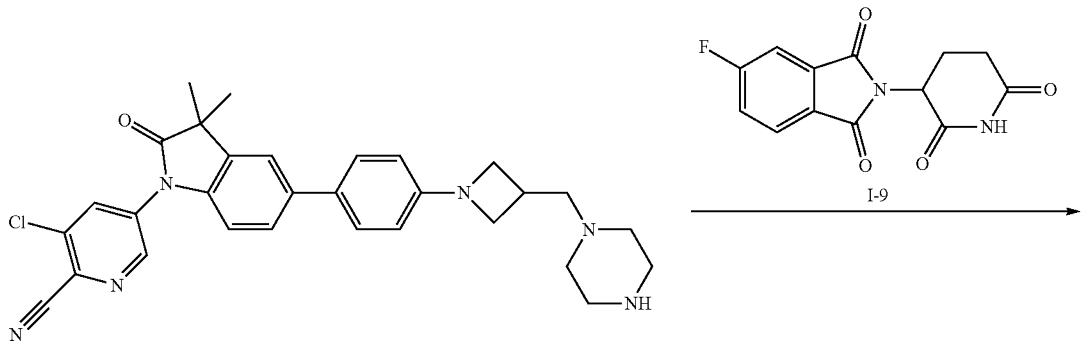

I-60

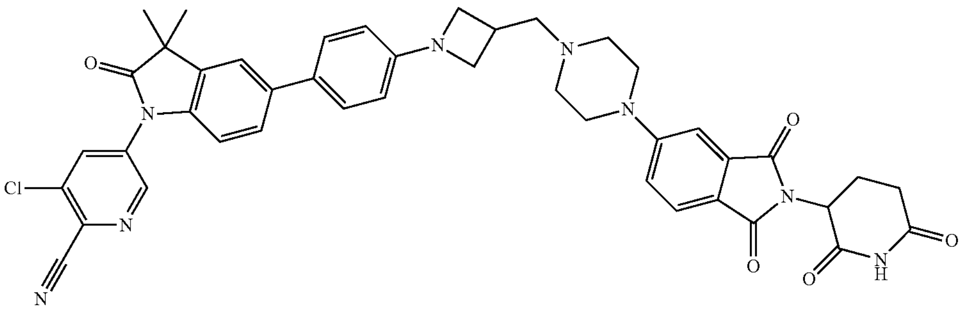

Compound 11

Intermediate I-60 (110 mg) was dissolved in DMSO (5.00 mL), and then intermediate I-9 (61.9 mg, 0.22 mmol) and diisopropylethylamine (88.9 mg, 0.69 mmol) were sequentially added. The reaction system was stirred and reacted at 110° C. for 2 hours under the protection of argon. The reaction mixture was separated and purified by preparative HPLC (containing formic acid) to obtain compound 11.

LC-MS (ESI) $[M+H]^+$: 783.3.

$^1H$ NMR (400 MHz, DMSO-$d_6$) δ 11.08 (s, 1H), 8.95 (s, 1H), 8.56 (s, 1H), 8.36 (s, 1H), 7.73 (s, 1H), 7.68 (d, J=8.6 Hz, 1H), 7.53-7.46 (m, 2H), 7.35 (s, 1H), 7.27 (d, J=8.4 Hz, 1H), 7.12 (d, J=8.1 Hz, 1H), 6.51 (d, J=8.4 Hz, 2H), 5.07 (dd, J=12.7, 5.6 Hz, 1H), 3.99 (t, J=7.2 Hz, 2H), 3.57-3.49 (m, 2H), 3.49-3.38 (m, 4H), 3.06-2.79 (m, 4H), 2.69-2.55 (m, 4H), 2.36-2.30 (m, 1H), 2.10-1.90 (m, 2H), 1.48 (s, 6H).

Embodiment 12: Preparation of Compound 12

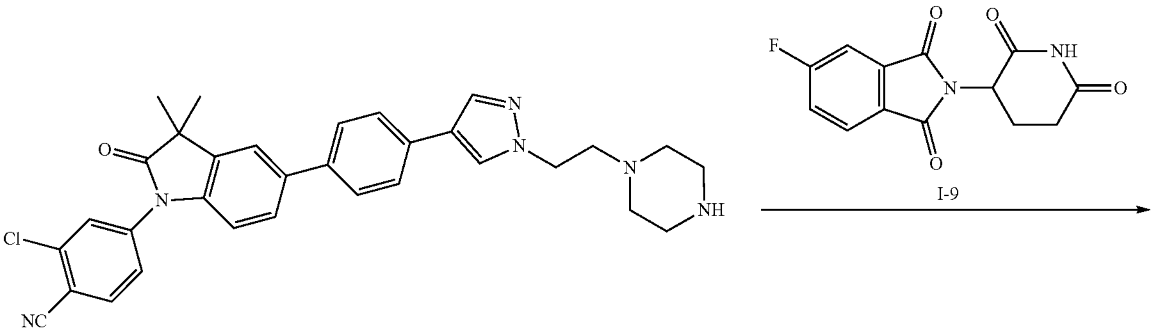

I-65

-continued

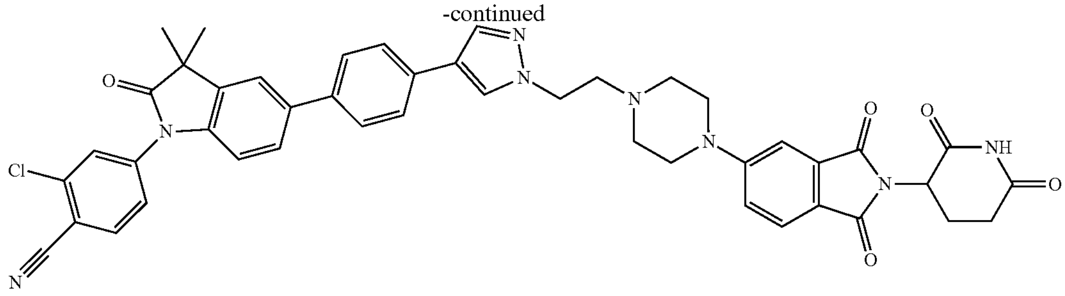

Compound 12

Intermediates I-65 (70.0 mg, 0.127 mmol), intermediate I-9 (42.0 mg, 0.152 mmol) and N,N-diisopropylethylamine (32.8 mg, 0.254 mmol) were dissolved in dimethyl sulfoxide (1.5 mL), the reaction solution was stirred and reacted at 80° C. for 4 hours. The reaction solution was cooled to 30° C. and purified by preparative HPLC (containing formic acid) to obtain compound 12.

LC-MS (ESI) $[M+H]^+$: 807.4.

$^1$H NMR (400 MHz, DMSO-$d_6$) δ 11.08 (s, 1H), 8.38 (s, 1H), 8.27 (s, 1H), 8.19 (d, J=8.4 Hz, 1H), 8.00 (s, 1H), 7.94 (s, 1H), 7.85 (s, 1H), 7.75 (d, J=8.5 Hz, 1H), 7.69-7.64 (m, 4H), 7.59 (d, J=8.4 Hz, 1H), 7.35 (s, 1H), 7.26 (d, J=8.6 Hz, 1H), 7.05 (d, J=8.2 Hz, 1H), 5.07 (dd, J=12.9, 5.4 Hz, 1H), 4.30 (t, J=6.5 Hz, 2H), 3.49-3.41 (m, 6H), 2.89-2.79 (m, 3H), 2.63-2.57 (m, 4H), 2.05-1.97 (m, 1H), 1.48 (s, 6H).

Embodiment 13: Preparation of Compound 13

Intermediates I-69 (90.0 mg, 0.159 mmol), intermediate I-9 (52.8 mg, 0.191 mmol) and N,N-diisopropylethylamine (103 mg, 0.795 mmol) were dissolved in dimethyl sulfoxide (2 mL), the reaction solution was stirred and reacted at 80° C. for 4 hours. The reaction solution was cooled to 20° C., filtered and the filtrate was subjected to preparative HPLC (containing formic acid) to obtain compound 13.

LC-MS (ESI) $[M+H]^+$: 821.2.

$^1$H NMR (400 MHz, DMSO-$d_6$) δ 11.08 (s, 1H), 8.30 (s, 1H), 8.25 (s, 1H), 8.19 (d, J=8.4 Hz, 1H), 8.00 (d, J=1.9 Hz, 1H), 7.93 (s, 1H), 7.86 (d, J=1.9 Hz, 1H), 7.75 (dd, J=8.4, 2.0 Hz, 1H), 7.68 (d, J=7.4 Hz, 4H), 7.59 (dd, J=8.3, 1.9 Hz, 1H), 7.34 (d, J=2.3 Hz, 1H), 7.26 (dd, J=8.7, 2.3 Hz, 1H), 7.05 (d, J=8.3 Hz, 1H), 5.07 (dd, J=12.9, 5.4 Hz, 1H), 4.19 (t, J=6.9 Hz, 2H), 3.45 (s, 8H), 2.93-2.83 (m, 1H), 2.62-2.52 (m, 2H), 2.34 (t, J=6.9 Hz, 2H), 2.07-1.97 (m, 3H), 1.48 (s, 6H).

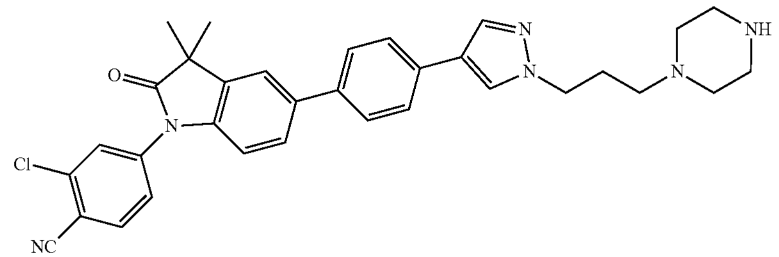

I-69

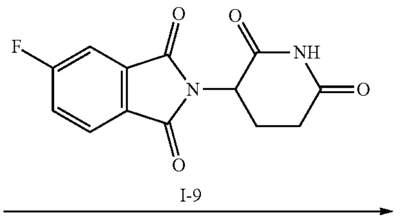

I-9

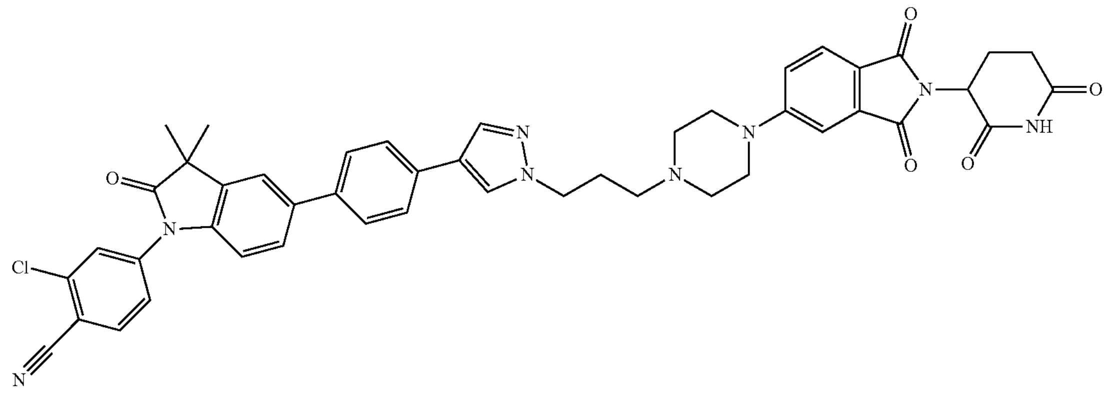

Compound 13

Embodiment 14: Preparation of Compound 14

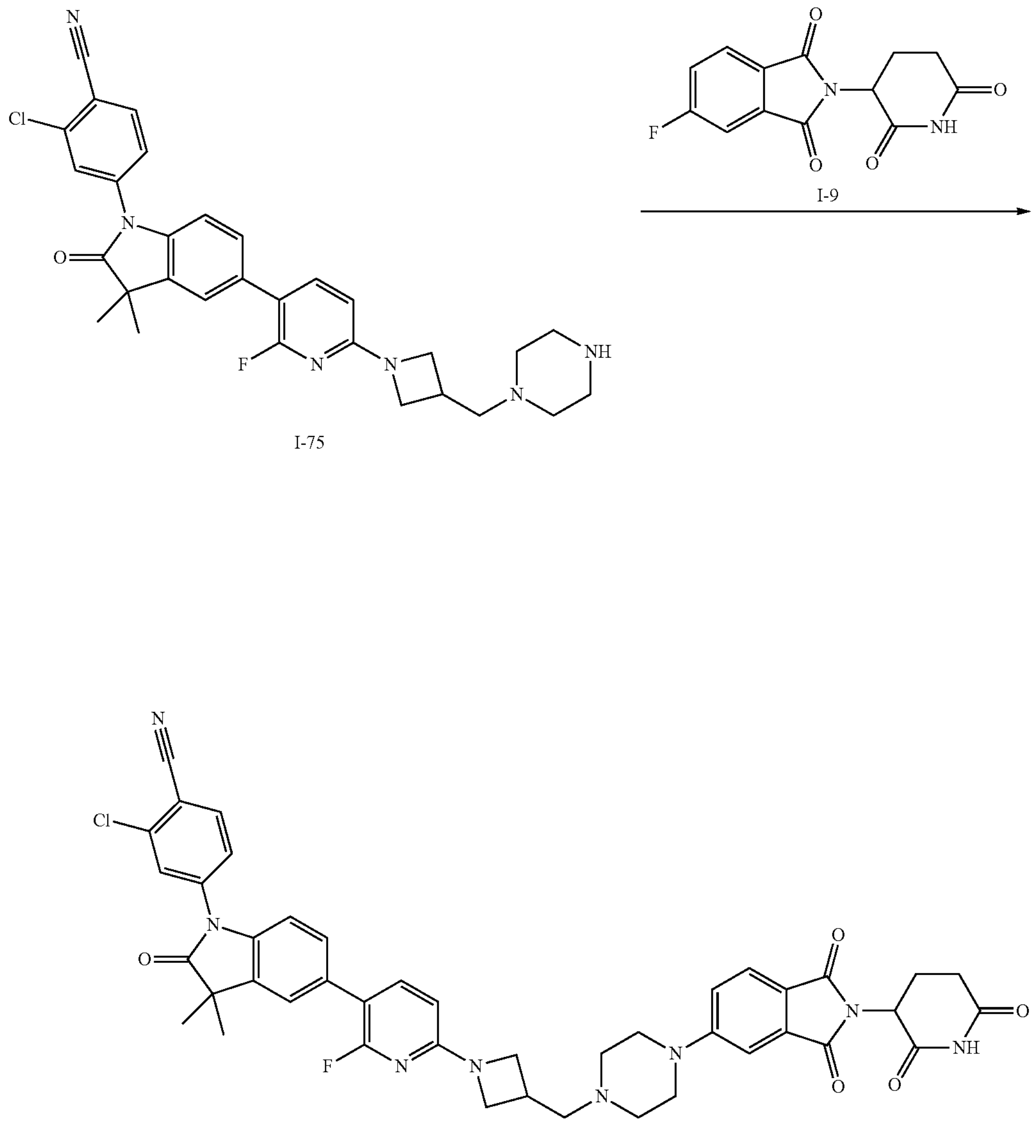

I-9

I-75

Compound

At 25° C., intermediate I-75 (125.00 mL) was dissolved in dimethyl sulfoxide (2 mL) and intermediate I-9 (63.53 mg, 0.23 mmol) and N, N-diisopropyl ethyl amine (122.79 mg, 0.95 mmol) were sequentially added, and the reaction solution was reacted at 120° C. for 16 hours. The reaction solution was cooled to 20° C. and was subjected to preparative HPLC (containing formic acid) to obtain compound 14.

LC-MS (ESI) $[M+H]^+$: 801.4.

$^1$HNMR(400 MHz, DMSO-$d_6$) δ 11.08 (s, 1H), 8.19 (d, J=8.4 Hz, 1H), 7.99 (d, J=1.9 Hz, 1H), 7.80 (dd, J=10.5, 8.2 Hz, 1H), 7.74 (dd, J=8.4, 1.9 Hz, 1H), 7.68 (d, J=8.5 Hz, 1H), 7.61 (d, J=1.6 Hz, 1H), 7.41-7.32 (m, 2H), 7.27 (dd, J=8.7, 2.3 Hz, 1H), 7.03 (d, J=8.3 Hz, 1H), 6.37 (dd, J=8.3, 1.9 Hz, 1H), 5.07 (dd, J=12.8, 5.4 Hz, 1H), 4.10 (t, J=8.1 Hz, 2H), 3.67 (dd, J=8.4, 5.5 Hz, 2H), 3.45 (t, J=4.8 Hz, 4H), 3.10-2.95 (m, 1H), 2.95-2.80 (m, 1H), 2.66 (d, J=7.4 Hz, 2H), 2.62-2.52 (m, 6H), 2.02 (ddt, J=10.8, 6.0, 3.5 Hz, 1H), 1.45 (s, 6H).

Embodiment 15. Preparation of Compound 15

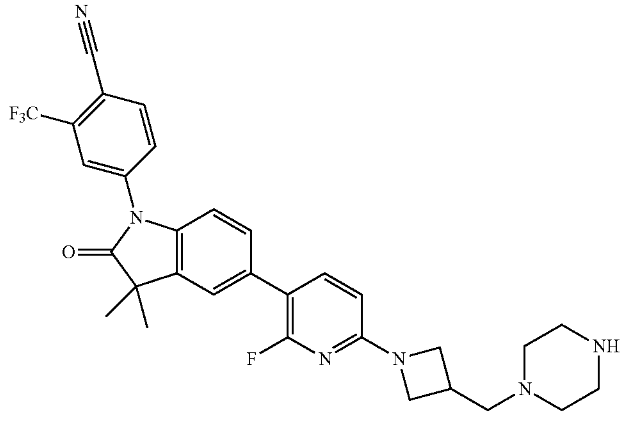

I-77

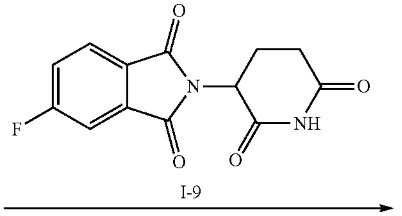

I-9

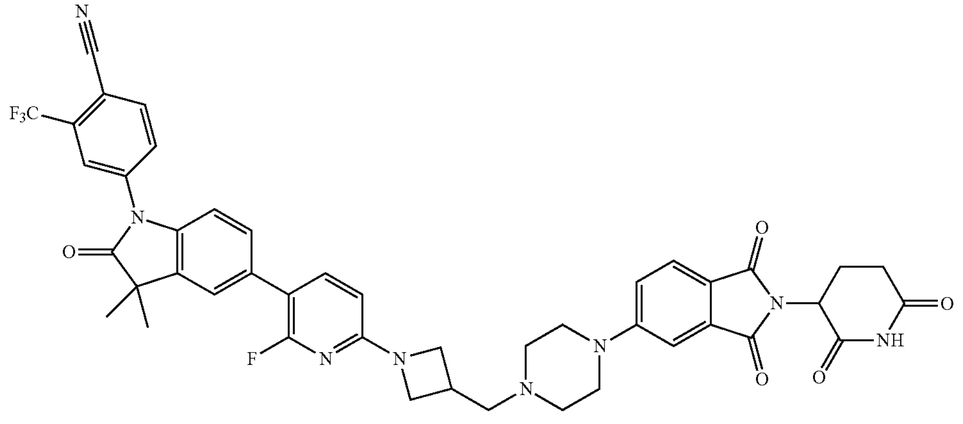

Compound

At 25° C., intermediate I-77 (110.00 mL) was dissolved in dimethyl sulfoxide (2 mL) and intermediate I-9 (52.48 mg, 0.19 mmol) and N,N-diisopropylethylamine (103.40 mg, 0.80 mmol) were sequentially added, and the reaction solution was stirred and reacted at 120° C. for 16 hours. The reaction solution was cooled to 20° C. and was subjected to preparative HPLC (containing formic acid) to obtain compound 15.

LC-MS (ESI) $[M+H]^+$: 835.4.

$^1H$ NMR (400 MHz, DMSO-$d_6$) δ 11.09 (s, 1H), 8.38 (d, J=8.3 Hz, 1H), 8.21 (d, J=1.9 Hz, 1H), 8.09 (dd, J=8.3, 2.0 Hz, 1H), 7.81 (dd, J=10.5, 8.2 Hz, 1H), 7.69 (d, J=8.5 Hz, 1H), 7.62 (d, J=1.5 Hz, 1H), 7.44-7.31 (m, 2H), 7.27 (dd, J=8.6, 2.3 Hz, 1H), 7.07 (d, J=8.3 Hz, 1H), 6.38 (dd, J=8.3, 1.9 Hz, 1H), 5.08 (dd, J=12.9, 5.4 Hz, 1H), 4.11 (t, J=8.1 Hz, 2H), 3.68 (dd, J=8.3, 5.4 Hz, 2H), 3.45 (t, J=4.9 Hz, 4H), 3.08-2.95 (m, 1H), 2.95-2.81 (m, 1H), 2.66 (d, J=7.5 Hz, 2H), 2.58-2.52 (m, 6H), 2.12-1.95 (m, 1H), 1.46 (s, 6H).

Experimental Example 1: In-Cell-Western Determination of Androgen Receptor

The determination evaluated the properties of the compounds in Lncap cells. Intracellular androgen receptor was determined by In-Cell-Western according to the determination steps described below.

In poly-D-Lysin pretreated 96-well cell culture plate (Corning 3599), LNcap cells were divided into 100 μL/well volume, and inoculated with 30,000 cells/well in LNcap cell assay medium [DMEM containing phenol red (Gibco catalog number: 11995065); fetal bovine serum FBS (Gibco catalog number: 10099141C)]. Cells were cultured for at least two days.

1. First treated cells with compound. Compounds were gradient diluted with DMSO and cell culture medium, so that DMSO contained in cell culture plates was diluted to 0.5% —polypropylene plates were used according to the following protocol: (1)(i) 200x stock plate in DMSO was prepared; (ii) 10 mM stock solution was diluted 1:4 with DMSO (10 μL stock solution+40 μL DMSO)=2000 μM, then entered into row 2; (iii) 1:4 (10 μL protac+40 μL DMSO) gradient dilution was performed from row 2 to row 9, and row 1 was reserved for 2000 M reference compound and row 10 for DMSO. (iv) A total of 8 concentrations (final concentrations on the 200x plate were 2000 μM, 400 μM and 80 μM, etc.). (2) (i) 3x stock solution was prepared in the medium. (ii) 3 μL of 200x stock solution was transferred to 197 L of culture medium (using 12-channel pipette, from line 1 to line 10), i.e. 3x stock solution plate. (iii) The stock solution plate was mixed evenly. (3) (i) The culture medium of Vcap cells was replaced with fresh culture medium, 100 μL volume culture medium. (ii) The well-mixed 3x stock solution was transferred to the cell culture plate (using a 12-channel pipette, and 50 μL of stock solution was transferred from line 1 to line 10). (iii) Cells were cultured for 24 hours.

2. The expression level of intracellular androgen receptor after compound treatment was deleted and determined according to the following method.

(1)(i) Equal volume of 8% paraformaldehyde was added to the cell culture plate for cell fixation. The fixing solution in the cell plate was discarded and washed three times with PBS. (ii) Triton solution (1:1000 dilution of the stock solution) was prepared. The solution in the cell plate was discarded, and 200 μL of Triton diluent was added into each well. (iii) 2×blocking solution (1:4 dilution of 10×blocking stock solution) was prepared. The solution in the cell plate was discarded, and 100 μL of 2×blocking solution was added into each well. (iv) Primary antibody solution (Androgen receptor Rabbbit mAb, Cell Signaling Technology catalog number: 5153; 1:1000 dilution) was prepared. The solution in the cell plate was discarded, 100 μL volume of primary antibody diluent was added to each well, and incubated at 4° C. overnight. (v) The primary antibody solution was discarded and the cell plate was washed with 1×Wash buffer. (vi) Secondary antibody solution (GOAT Antirabbit IgG (H+L), HRP, Thermo catalog number: 31460; 1:5000 dilution) was prepared, and 100 μL volume of secondary antibody dilution was added to each well for incubation. (vii) The secondary antibody solution in the cell plate was discarded and the cell plate was washed with 1×Wash buffer. (viii) TMB chromogenic solution (BD catalog number: 550534) was prepared, and 100 μL chromogenic solution was added into each well. (ix) 50 μL volume of stop solution (BD catalog number: 550534) was added to each well. (x) The absorption values at OD 450 nm and 570 nm were read though EnVision. (2) (i) Normalized analysis was performed on the number of cells in each well. The solution in the cell plate was discarded, and washed with wash buffer for three times. (ii) Janus dilution (1:3 dilution) was prepared. (iii) 50 μL volume diluent was added to each well for incubation. (iv) The solution in the plate was discarded and washed with deionized water. (v) 1M hydrochloric acid (diluted with concentrated hydrochloric acid at a ratio of 1:24) was prepared, and 200 μL diluted hydrochloric acid was added into each well to treat the cells. (vi) The absorption values at OD 595 nm were read though Flex Station. (vii) According to the obtained readings, effects of the tested compounds on androgen receptor expression were calculated. The experimental results are shown in Table 1.

TABLE 1

Evaluation of compounds on androgen receptor degrading activity in LnCaP cells

| Compound number | $DC_{50}$ (nM) | $D_{max}$ (%) |
|---|---|---|
| 1 | 90.27 | 82 |
| 3 | 87.13 | 89 |
| 4 | 108.37 | 91 |
| 7 | 72.12 | 75 |
| 11 | 74.65 | 74 |
| 12 | 78.81 | 75 |
| 13 | 73.38 | 100 |
| 14 | 66.30 | 93 |
| 15 | 3.49 | 67 |

$D_{max}$: maximum degradation of AR in LnCaP cells.

$DC_{50}$: Concentration of compound required to achieve half of the maximal degradation of AR in LnCaP cells.

Experimental Example 2: Inhibitory Effect of Test Compounds on the Proliferation of LNcap FGC Cells Tumor cell line LNcap FGC (ATCC catalog number CRL-1740) was cultured in RPMI 1640 (Gibco catalog number 11875-093) and DMEM (Gibco catalog number. 11965-092) medium containing 10% FBS (Gibco catalog number 10099-141C), respectively.

The determination method was as follows:

LNcap FGC cells were inoculated in a 384-well plate (Perkin Elmer catalog number 6007460) at a cell density of 400 cells/well in a volume of 20 μL/well and incubated overnight in a carbon dioxide incubator (Thermo). The prepared compound solutions of different concentrations were added in a volume of 5 μL/well. The corresponding vehicle control was set at the same time. After being cultured in the incubator for 6 days, the cell plate and the contents were equilibrated to room temperature, and 25 μL of Cell Titer Glor (Promega catalog number G7573) was added to each well, shook and mixed well, incubated in dark for 10-30 minutes, and the signal values were detected with Envision microplate reader (PerkinElmer).

Experimental data processing method:

The percentage inhibition rate of compound-treated wells was calculated from the vehicle control wells on the plate, and the percentage inhibition rate data corresponding to different concentrations were fitted by GraphPad prism, and the $IC_{50}$ values were calculated by 4-parameter nonlinear logic formula. The experimental results are shown in Table 2.

TABLE 2

Evaluation of Compounds for LnCaP Cell Proliferation Inhibitory Activity

| Compound number | $IC_{50}$ (nM) | $E_{max}$ (%) |
|---|---|---|
| 1 | 66.08 | 91 |
| 2 | 89.08 | 98 |
| 3 | 54.79 | 93 |
| 5 | 95.71 | 93 |
| 6 | 76.71 | 99 |
| 9 | 35.51 | 100 |
| 10 | 39.38 | 100 |
| 12 | 81.95 | 68 |
| 14 | 60.65 | 100 |

$E_{max}$: maximum degree of inhibition of LnCaP cell proliferation.

$IC_{50}$: Concentration of compound required to achieve half of the maximal inhibition of LnCaP cell proliferation.

Experimental Embodiment 3: In-Cell-Western Determination of Androgen Receptor The determination evaluated the properties of the compounds in Vcap cells. Intracellular androgen receptor was determined by In-Cell-Western according to the determination steps described below.

In poly-D-Lysin pretreated 96-well cell culture plate (Corning 3599), Vcap cells were divided into 500 μL/well volume, and inoculated with 50,000 cells/well in Vcap cell assay medium [DMEM containing phenol red (Gibco catalog number: 11995065); fetal bovine serum FBS (Gibco catalog number: 10099141C)]. Cells were cultured for at least two days.

1. First treated cells with compound. Compounds were gradient diluted with DMSO and cell culture medium, so that DMSO contained in cell culture plates was diluted to 0.5% —polypropylene plates were used according to the following protocol:

(1)(i) 200× stock plate in DMSO was prepared; (ii) 10 mM stock solution was diluted 1:4 with DMSO (10 μL stock solution+40 μL DMSO)=2000 μM, then entered into row 2; (iii) 1:4 (10 μL protac+40 μL DMSO) gradient dilution was performed in row 2 to row 9, and row 1 was reserved for 2000 μM reference compound and row 10 for DMSO. (iv) A total of 8 concentrations (final concentrations on the 200×plate were 2000 μM, 400 μM, 80 μM, etc.). (i) 3×stock solution in medium was prepared; (ii) 3 μL of 200× stock solution was transferred to 197 μL of culture medium (using 12-channel pipette, from line 1 to line 10), i.e. 3× stock solution plate. (iii) The stock solution plate was mixed evenly. (3) (i) The culture medium of Vcap cells was replaced with fresh culture medium, 100 μL volume culture medium. (ii) The well-mixed 3×stock solution was transferred to the cell culture plate (using 12-channel pipette, and 50 μL of stock solution was transferred from line 1 to line 10). (iii) Cells were cultured for 24 hours.

2. The expression level of intracellular androgen receptor after compound treatment was deleted and determined according to the following method.

(1)(i) Equal volume of 8% paraformaldehyde was added to the cell culture plate for cell fixation. The fixing solution in the cell plate was discarded and washed three times with PBS. (ii) Triton solution (1:1000 dilution of the stock solution) was prepared. The solution in the cell plate was discarded, and 200 μL of Triton diluent was added into each well. (iii) 2×blocking solution (1:4 dilution of 10×blocking stock solution) was prepared. The solution in the cell plate was discarded, and 100 μL of 2×blocking solution was added into each well. (iv) Primary antibody solution (Androgen receptor Rabbbit mAb, Cell Signaling Technology catalog number: 5153; 1:1000 dilution) was prepared. The solution in the cell plate was discarded, 100 μL volume of primary antibody diluent was added to each well, and incubated at 4° C. overnight. (v) The primary antibody solution was discarded and the cell plate was washed with 1×Wash buffer. (vi) Secondary antibody solution (GOAT Antirabbit IgG (H+L), HRP, Thermo catalog number: 31460; 1:5000 dilution) was prepared, and 100 μL volume of secondary antibody dilution was added to each well for incubation. (vii) The secondary antibody solution in the cell plate was discarded and the cell plate was washed with 1× Wash buffer. (viii) TMB chromogenic solution (BD catalog number: 550534) was prepared, and 100 μL chromogenic solution was added into each well. (ix) 50 μL volume of stop solution (BD catalog number: 550534) was added to each well. (x) The absorption values at OD 450 nm and 570 nm were read though EnVision. (2)(i) Normalized analysis was performed on the number of cells in each well. The solution in the cell plate was discarded, and washed with wash buffer for three times. (ii) Janus dilution (1:3 dilution) was prepared. (iii) 50 μL volume diluent was added to each well for incubation. (iv) The solution in the plate was discarded and washed with deionized water. (v) 1M hydrochloric acid (diluted with concentrated hydrochloric acid at a ratio of 1:24) was prepared, and 200 μL diluted hydrochloric acid was added into each well to treat the cells. (vi) The absorption values at OD 595 nm were read though Flex Station. (vii) According to the obtained readings, effects of the tested compounds on androgen receptor expression were calculated. The experimental results are shown in Table 3.

TABLE 3

Evaluation of compounds on androgen receptor degrading activity in VCaP cells

| Compound number | $DC_{50}$ (nM) | $D_{max}$ (%) |
|---|---|---|
| 1 | 35 | 68 |
| 3 | 76 | 60 |
| 9 | 121 | 56 |
| 14 | 94 | 85 |

$D_{max}$: maximum degradation of AR in VCaP cells.
$DC_{50}$: Concentration of compound required to achieve half of the maximal degradation of AR in VCaP cells.

Experimental Example 4: Inhibitory Effect of Test Compounds on the Proliferation of VCap Cells Tumor cell line VCap FGC (ATCC catalog number CRL-2876) was cultured in DMEM (Gibco catalog number 11965-092) medium containing 10% FBS (Gibco catalog number 10099-141C), respectively. During the determination, Vcap cells were replaced with DMEM medium containing 5% FBS and 0.1 nM R1881 (Sigma catalog number R0908).

The determination method was as follows:

Vcap FGC cells were inoculated in a 384-well plate (Perkin Elmer catalog number 6007460) at a cell density of 1200 cells/well in a volume of 20 μL/well and incubated overnight in a carbon dioxide incubator (Thermo). The prepared compound solutions of different concentrations were added in a volume of 5 μL/well. The corresponding vehicle control was set at the same time. After being cultured in the incubator for 6 days, the cell plate and the contents were equilibrated to room temperature, and 25 μL of Cell Titer Glor (Promega catalog number G7573) was added to each well, shake and mix well, incubated in dark for 10-30 minutes, and the signal values were detected though Envision microplate reader (PerkinElmer).

Experimental data processing method:

The percentage inhibition rate of compound-treated wells was calculated from vehicle control wells on the plate, and the percentage inhibition rate data corresponding to different concentrations were fitted by GraphPad prism, and the $IC_{50}$ values were calculated by 4-parameter nonlinear logic formula. The experimental results are shown in Table 4.

TABLE 4

Evaluation of Compounds for VCaP Cell Proliferation Inhibitory Activity

| Compound number | $IC_{50}$ (nM) | $E_{max}$ (%) |
|---|---|---|
| 6 | 81 | 94 |
| 9 | 61 | 97 |
| 10 | 50 | 98 |
| 14 | 67 | 94 |
| 15 | 82 | 92 |

$E_{max}$: maximum degree of inhibition of VCaP cell proliferation.
$IC_{50}$: Concentration of compound required to achieve half of the maximal inhibition of VCaP cell proliferation.

Experimental Example 5: In Vivo Pharmacokinetic Experiments of the Compounds of the Present Disclosure In this experimental example, in vivo pharmacokinetics in mice were evaluated by intravenous injection and oral administration.

Experimental methods and conditions: Male CD1 mice, aged 6-8 weeks, all animals were free access to food and water, and were given a single dose of the compound to be tested at 1 mg/Kg by intravenous injection (solvent 5% DMSO/15% Solutol/80% Saline), at 5 min, 15 min, 30 min, 1 hr, 2 hr, 4 hr, 8 hr, 24 hr, 48 h after drug administration, or oral gavage administration of 10 mg/kg (solvent 5% DMSO/10% Solutol/85% Saline), at 15 min, 30 min, 1 hr, 2 hr, 4 hr, 6 h, 8 hr, 24 hr, 48 h after administration, blood was collected from the orbit, no less than 50 μL for each sample, heparin sodium was used for anticoagulation, and then placed on ice after collection, and centrifuged within 1 hour to separate the plasma for testing. The plasma concentration of the drug was detected by liquid tandem mass spectrometry (LC/MS/MS), and the pharmacokinetic parameters were calculated by Phoenix WinNonlin software. Taking embodiment 158 in CN110506039A as reference substance 1, the experimental results are shown in Table 5 and Table 6.

TABLE 5

Pharmacokinetics of Oral Administration (10 mg/kg)

| Compound | $T_{1/2}$ (hr) | $C_{max}$ (ng/mL) | AUC0-$_{inf}$ (ng × hr/mL) | F (%) |
|---|---|---|---|---|
| Compound 6 | 11.2 | 2920 | 70268 | 71.3 |
| Compound 14 | 17.8 | 2647 | 71075 | 68.6 |
| Reference substance 1 | 14.4 | 1417 | 53042 | 99.0 |

TABLE 6

Pharmacokinetics of Intravenous Administration (1 mg/kg)

| Compound | $T_{1/2}$ (hr) | $AUC_{0-inf}$ (ng × hr/mL) | Cl (mL/min/kg) |
|---|---|---|---|
| Compound 6 | 11.2 | 9860 | 1.69 |
| Compound 14 | 20.4 | 10365 | 1.61 |
| Reference substance 1 | 13.4 | 5359 | 3.11 |

Experimental data show that the compounds of the present disclosure exhibit higher $C_{max}$, in vivo exposure and oral bioavailability in mice.

Experimental Example 6: In Vivo Pharmacodynamic Study of Tested Compounds on Human Prostate Cancer VCaP Cell Subcutaneous Xenograft Tumor CB17 SCID Mouse Model Experimental animal: male mice of CB17 SCID strain, aged 6-8 weeks, weighing 18-22 grams, supplier: Beijing Weitong Lihua Laboratory Animal Technology Co., Ltd. Shanghai Branch, animal certificate number: 20170011005577. Animals were reared in the experimental environment for 7 days after arrival and the experiment was started.

Experimental method: Human prostate cancer cell VCaP cells (ATCC-CRL-2876) were cultured in vitro in monolayer, and the culture conditions were DMEM medium with 20% fetal bovine serum, 100 U/mL penicillin and 100 μg/mL streptomycin, cultured in a 5% $CO_2$ incubator at 37° C. Conventional digestion with trypsin-EDTA was performed twice a week for passage. When the cell saturation was 80%-90% and the number reached the requirement, the cells were collected, counted, and inoculated. 0.2 mL ($10\times10^6$ cells+Matrigel) VCaP cells were subcutaneously inoculated into the left upper limb of each mouse, and castration was performed 33 days after cell inoculation. When the average tumor volume reached 119 $mm^3$, the drugs were administered in groups, and the doses of compound 14 were set to four groups: 1 mg/kg, 3 mg/kg, 10 mg/kg and 30 mg/kg.

Daily observation of experimental animals: the health status and death of animals were monitored every day. Routine examinations included observing the effects of tumor growth and drug treatment on the daily behavior of animals, such as behavioral activities, food and water intake (visual observation only), and weight changes (body weight measured three times a week), physical signs or other abnormal conditions.

Tumor measurements and experimental indicators: Experimental indicators were to examine whether tumor growth was inhibited, delayed or cured. Tumor diameters were measured with vernier calipers three times a week.

The calculation formula of tumor volume is: V=0.5a×b2, where a and b represented the long diameter and short diameter of the tumor, respectively. The antitumor effect of the compound was evaluated by TGI (%) or relative tumor proliferation rate T/C (%). TGI (%), reflecting the tumor growth inhibition rate. Calculation of TGI (%): TGI (%)=[1−(average tumor volume at the end of administration of a certain treatment group−average tumor volume at the beginning of administration of the treatment group)/(average tumor volume at the end of treatment in the vehicle control group−average tumor volume at the beginning of treatment in the vehicle control group)]×100%. Relative tumor proliferation rate T/C (%): the calculation formula is as follows: T/C %=TRTV/CRTV×100% (TRTV: RTV in the treatment group; CRTV: RTV in the negative control group). The relative tumor volume (RTV) was calculated according to the results of tumor measurement, and the formula is RTV=Vt/V0, where V0 is the average tumor volume measured at the time of group administration (i.e. d0), and Vt is the average tumor volume at a certain measurement, and TRTV and CRTV were taken on the same day. After the experiment, the tumor weight would be detected, and the percentage of T/Cweight would be calculated. Tweight and Cweight represent the tumor weight of the administration group and the vehicle control group, respectively.

Statistical analysis: Statistical analysis included the mean and standard error (SEM) of tumor volume at each time point for each group. The treatment group was treated at the end of the trial on the 24th day after administration, so statistical analysis was performed based on this data to evaluate differences between the groups. T-test was used for comparison between two groups, and one-way ANOVA was used for comparison between three or more groups. If there was a significant difference in F value, Games-Howell method was used to test. If there was no significant difference in F value, Dunnet (2-sided) method was used for analysis. All data analyses were performed with SPSS 17.0. $p<0.05$ was considered a significant difference. The weight of experimental animals was used as a reference index for indirect determination of drug toxicity. In this model, all treatment groups showed varying degrees of weight loss during the post-dose period.

Figure 2:
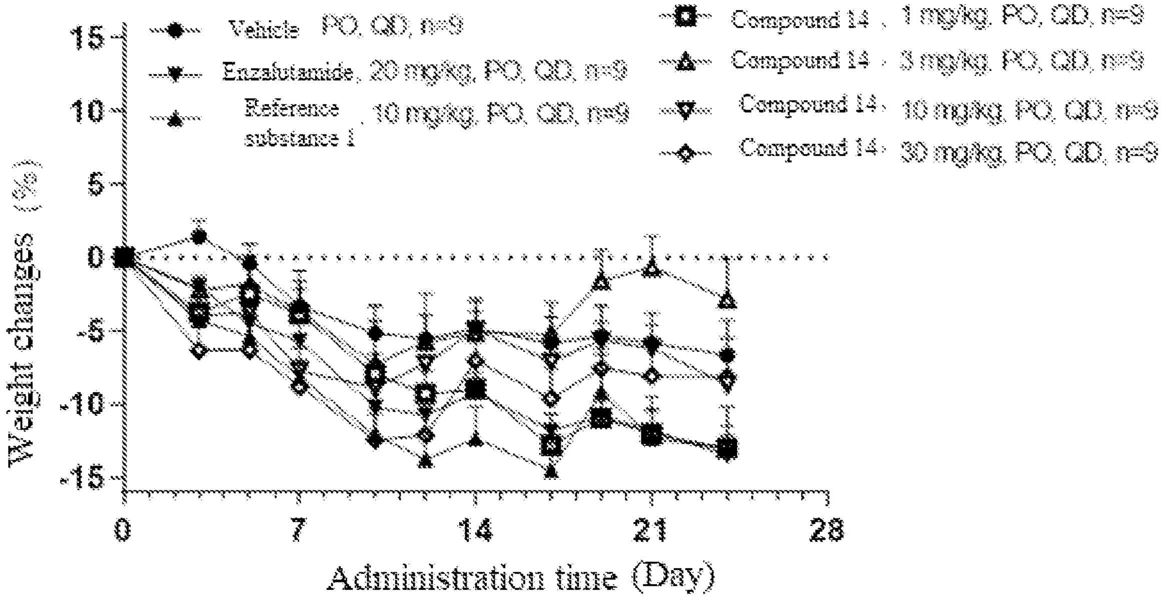
FIG. 2 shows the effect of compound 14 on the body weight in human prostate cancer VCaP cell subcutaneous xenograft tumor CB17 SCID mouse model.

As shown in FIG. 1, compound 14 had a higher tumor growth inhibition rate (TGI: 96%) at doses of 10 mpk and 30 mpk, and was significantly stronger than enzalutamide (20 mpk, TGI: 45%) and Reference substance 1 (10 mpk, TGI: 60%). As shown in FIG. 2, Compound 14 had better tolerance than Reference substance 1 at 10 mpk and 30 mpk.

What is claimed is:

1. A compound represented by formula (I), an optical isomer thereof, or a pharmacologically acceptable salt thereof:

(I)

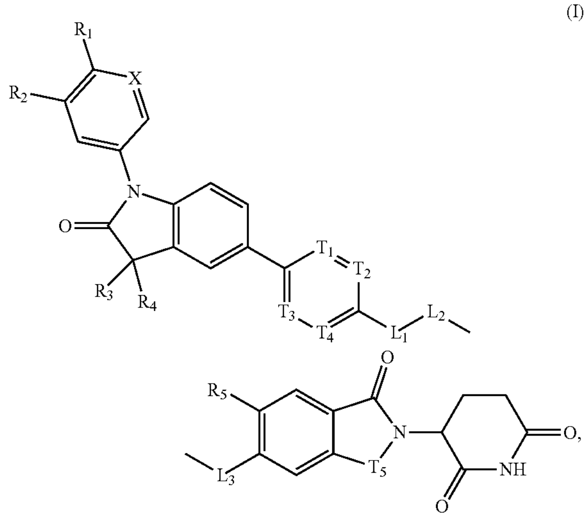

wherein:

X is C(R) or N;

$T_1$, $T_2$, $T_3$ and $T_4$ are each independently C(R) or N;

$T_5$ is —(C═O)— or —$CH_2$—;

$R_1$, $R_2$, $R_3$ and $R_4$ are each independently selected from the group consisting of CN, halogen, $C_{1-6}$ alkyl and $C_{1-6}$ alkoxy, wherein the $C_{1-6}$ alkyl and $C_{1-6}$ alkoxy are optionally substituted by 1, 2 or 3 R;

$L_1$, $L_2$ and $L_3$ are each independently selected from the group consisting of single bond, O, S, NH, C(═O), S(═O), S(═O)$_2$, $C_{1-6}$ alkyl, —$C_{1-6}$ alkyl-O—, —$C_{1-6}$ alkyl-NH—, —O—$C_{1-6}$ alkyl-O—, —O—$C_{1-6}$ alkyl-O—$C_{1-6}$ alkyl-, —O—$C_{2-3}$ alkenyl, $C_{2-3}$ alkynyl, $C_{3-10}$ cycloalkyl, 3- to 10-membered heterocycloalkyl, phenyl, and 5- to 9-membered heteroaryl; wherein the $C_{1-6}$ alkyl, —$C_{1-6}$ alkyl-O—, —$C_{1-6}$ alkyl-NH—, —O—$C_{1-6}$ alkyl-O—, —O—$C_{1-6}$ alkyl-O—$C_{1-6}$ alkyl-, $C_{2-3}$ alkenyl, $C_{2-3}$ alkynyl, $C_{3-10}$ cycloalkyl, 3- to 10-membered heterocycloalkyl, phenyl, and 5- to 9-membered heteroaryl are optionally substituted by 1, 2 or 3 $R_L$;

$R_L$ are each independently selected from the group consisting of H, halogen, OH, $NH_2$, CN,

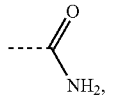

$C_{1-6}$ alkyl, $C_{3-6}$ cycloalkyl, $C_{1-6}$ alkyl-C(═O)—, $C_{1-6}$ alkoxy, $C_{1-6}$ alkylthio and $C_{1-6}$ alkylamino; wherein the $C_{1-6}$ alkyl, $C_{3-6}$ cycloalkyl, $C_{1-6}$ alkoxy, $C_{1-6}$ alkylthio, and $C_{1-6}$ alkylamino are optionally substituted by 1, 2 or 3 R';

R' is F, Cl, Br, I, OH, $NH_2$,

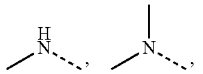

$CH_3$, $CH_2CH_3$, $CH_2F$, $CHF_2$, or $CF_3$;

R is H, F, Cl, Br, I, OH, or $C_{1-6}$ alkyl;

$CH_3$, $CH_2CH_3$, $CH_2F$, $CHF_2$, or $CF_3$;

$R_5$ is H, halogen, or $C_{1-6}$ alkyl;

the 3- to 10-membered heterocycloalkyl or 5- to 9-membered heteroaryl contains 1, 2 or 3 heteroatoms or heteroatomic groups independently selected from the group consisting of —O—, —NH—, —S—, —C(═O)—, —C(═O)O—, —S(═O)—, —S(═O)$_2$—, and N.

2. The compound of claim 1, an optical isomer thereof, or a pharmacologically acceptable salt thereof, wherein the compound of formula (I) is represented by the compound of formula (II):

(II)

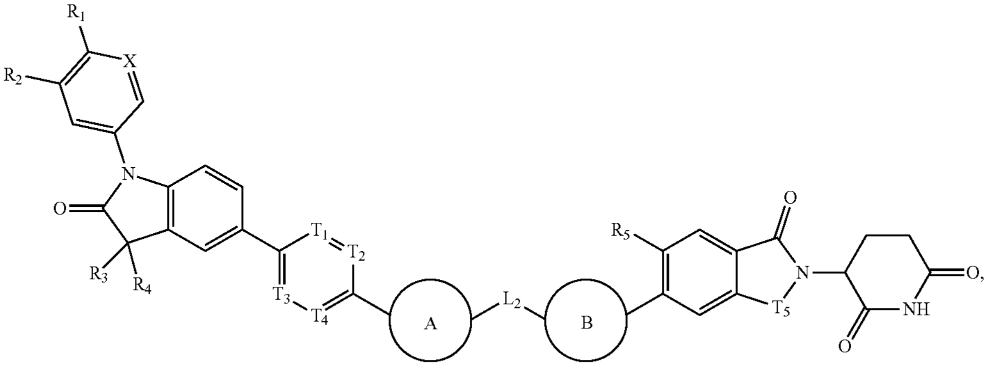

wherein:

ring A and ring B are independently selected from the group consisting of 3- to 8-membered heterocycloalkyl, 5- to 6-membered heteroaryl, or absent; wherein the 3- to 8-membered heterocycloalkyl and 5- to 6-membered heteroaryl are optionally substituted by 1, 2 or 3 R;

$R_1$, $R_2$, $R_3$ and $R_4$ are each independently selected from the group consisting of CN, halogen, $C_{1-6}$ alkyl and $C_{1-6}$ alkoxy; wherein the $C_{1-6}$ alkyl and $C_{1-6}$ alkoxy are optionally substituted by 1, 2 or 3 R;

X is C(R) or N;

$T_1$, $T_2$, $T_3$ and $T_4$ are each independently C(R) or N;

$T_5$ is —(C═O)— or —$CH_2$—;

$L_2$ is single bond, O, S, NH, C(═O), S(═O), S(═O)$_2$, $C_{1-6}$ alkyl, —$C_{1-6}$ alkyl-O—, —$C_{1-3}$ alkyl-NH—, —O—$C_{1-6}$ alkyl-O—, —O—$C_{1-6}$ alkyl-O—$C_{1-6}$ alkyl-, —O—$C_{2-3}$ alkenyl, $C_{2-3}$ alkynyl, $C_{3-10}$ cycloalkyl, 3- to 10-membered heterocycloalkyl, phenyl, or 5- to 9-membered heteroaryl; wherein the $C_{1-6}$ alkyl, —$C_{1-6}$ alkyl-O—, —$C_{1-3}$ alkyl-NH—, —O—$C_{1-6}$ alkyl-O—, —O—$C_{1-6}$ alkyl-O—$C_{1-6}$ alkyl-, $C_{2-3}$ alkenyl, $C_{2-3}$ alkynyl, $C_{3-10}$ cycloalkyl, 3- to 10-membered heterocycloalkyl, phenyl, and 5- to 9-membered heteroaryl are optionally substituted by 1, 2 or 3 $R_L$;

$R_L$ are each independently H, halogen, OH, $NH_2$, CN,

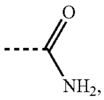, $C_{1-6}$ alkyl, $C_{3-6}$ cycloalkyl, $C_{1-6}$ alkyl-C(═O)—, $C_{1-6}$ alkoxy, $C_{1-6}$ alkylthio, or $C_{1-6}$ alkylamino; wherein the $C_{1-6}$ alkyl, $C_{3-6}$ cycloalkyl, $C_{1-6}$ alkoxy, $C_{1-6}$ alkylthio, and $C_{1-6}$ alkylamino are optionally substituted by 1, 2 or 3 R';

R' is F, Cl, Br, I, OH, $NH_2$,

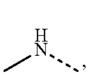, 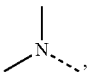, $CH_3$, $CH_2CH_3$, $CH_2F$, $CHF_2$, or $CF_3$;

R is H, F, Cl, Br, I, OH, or $C_{1-6}$ alkyl;

$R_5$ is H, halogen, or $C_{1-6}$ alkyl;

the 3- to 8-membered heterocycloalkyl, 3- to 10-membered heterocycloalkyl, 5- to 6-membered heteroaryl or 5- to 9-membered heteroaryl contains 1, 2 or 3 heteroatoms or heteroatomic groups independently selected from —O—, —NH—, —S—, —C(═O)—, —C(═O)O—, —S(═O)—, —S(═O)$_2$— and N.

3. The compound of claim 1, the optical isomer thereof, or the pharmacologically acceptable salt thereof, wherein the moiety

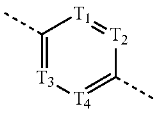

is

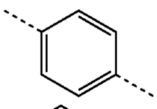, 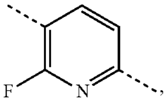, 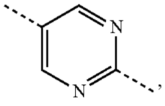, 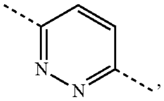, 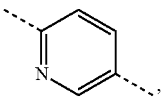, 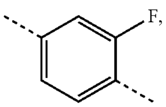, or 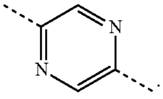.

4. The compound of claim 1, the optical isomer thereof, or the pharmacologically acceptable salt thereof, wherein R is H, halogen, OH, methyl, ethyl, n-propyl, or isopropyl.

5. The compound of claim 1, the optical isomer thereof, or the pharmacologically acceptable salt thereof, wherein $R_1$ and $R_2$ are each independently CN, halogen, $CH_3O$—, or —$CF_3$.

6. The compound of claim 1, the optical isomer thereof, or the pharmacologically acceptable salt thereof, wherein $R_3$ and $R_4$ are each independently methyl, ethyl, n-propyl, or isopropyl.

7. The compound of claim 1, the optical isomer thereof, or the pharmacologically acceptable salt thereof, wherein the moiety

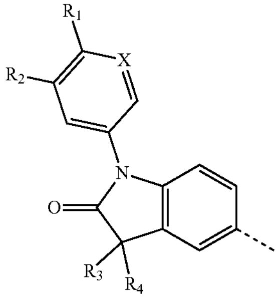

is

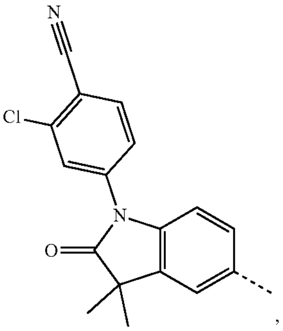,

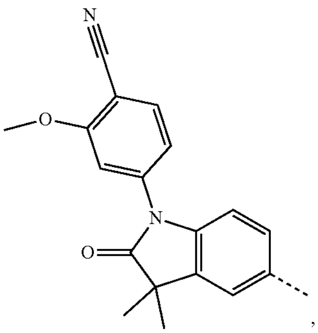,

-continued

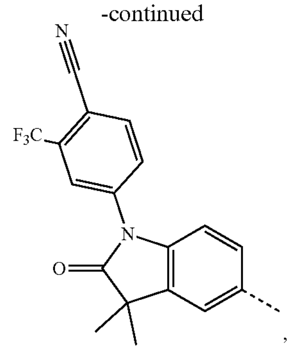

,

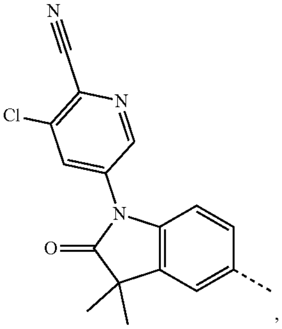

,

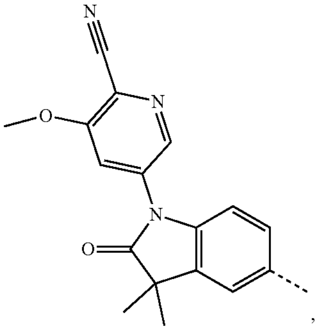

, or

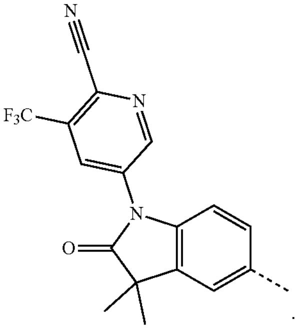

.

8. The compound of claim 1, the optical isomer thereof, or the pharmacologically acceptable salt thereof, wherein $L_1$, $L_2$ and $L_3$ are each independently O, S, NH, C(=O), S(=O), $S(=O)_2$, $C_{1-3}$ alkyl, —$C_{1-4}$ alkyl-O—, —$C_{1-3}$ alkyl-NH—, —O—$C_{1-4}$ alkyl-O—, —O—$C_{1-3}$ alkyl-O—$C_{1-3}$ alkyl-, —O—$C_{2-3}$ alkenyl, $C_{2-3}$ alkynyl, $C_{3-8}$ cycloalkyl, 3- to 8-membered heterocycloalkyl, phenyl, or 5- to 6-membered heteroaryl; wherein the $C_{1-3}$ alkyl, —$C_{1-4}$ alkyl-O—, —O—$C_{1-4}$ alkyl-O—, —$C_{1-3}$ alkyl-NH—, —O—$C_{1-3}$ alkyl-O—$C_{1-3}$ alkyl-, $C_{2-3}$ alkenyl, $C_{2-3}$ alkynyl, $C_{3-8}$ cycloalkyl, 3- to 8-membered heterocycloalkyl, phenyl, and 5- to 6-membered heteroaryl are optionally substituted by 1, 2 or 3 $R_L$.

9. The compound of claim 1, the optical isomer thereof, or the pharmacologically acceptable salt thereof, wherein $R_L$ are each independently H, halogen, OH, $NH_2$, CN,

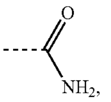

$C_{1-3}$ alkyl, $C_{3-6}$ cycloalkyl, $C_{1-3}$ alkyl-C(=O)—, $C_{1-3}$ alkoxy, $C_{1-3}$ alkylthio, or $C_{1-3}$ alkylamino; wherein the $C_{1-3}$ alkyl, $C_{3-6}$ cycloalkyl, $C_{1-3}$ alkoxy, $C_{1-3}$ alkylthio, and $C_{1-3}$ alkylamino are optionally substituted by 1, 2 or 3 R'.

10. The compound of claim 1, the optical isomer thereof, or the pharmacologically acceptable salt thereof, wherein $L_1$, $L_2$, $L_3$ are each independently single bond, O, S, NH, C(=O), S(=O), $S(=O)_2$, $CH_2$, —$CH(CH_3)$—, $CH_2CH_2$—, —$CH_2CH_2CH_2$—,

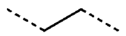 , 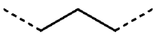 , 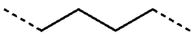 ,

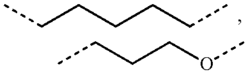 , 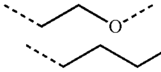 , 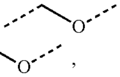 ,

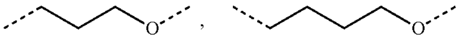 ,

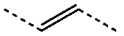 , 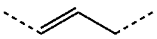 , 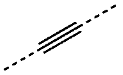 ,

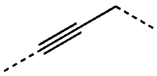 , 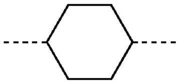 , 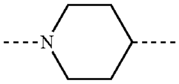 ,

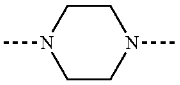 , 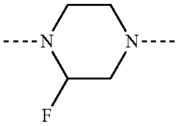 , 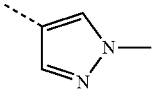 ,

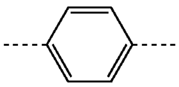 , 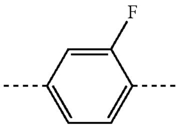 ,

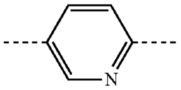 , 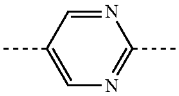 , 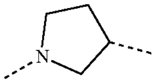 ,

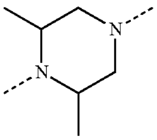 , 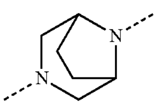 , 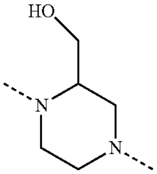 ,

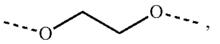 , 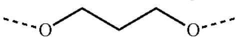 ,

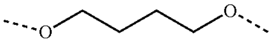 ,

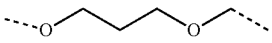 , 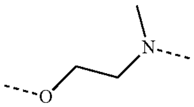 ,

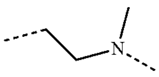 , 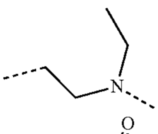 ,

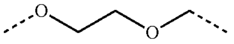 , 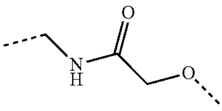 ,

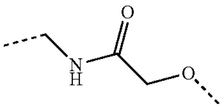 , 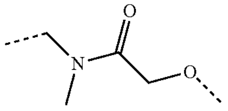 ,

-continued

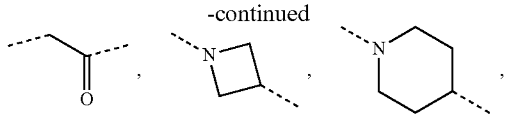
,

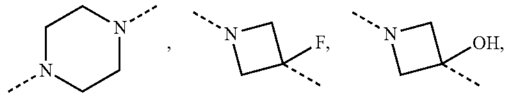
,

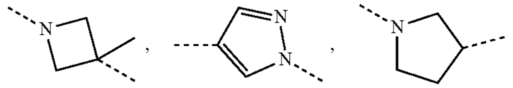
,

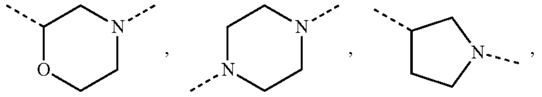
,

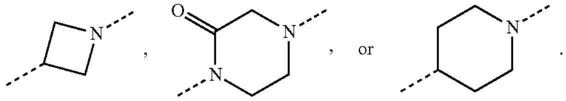
, or .

11. The compound of claim 2, the optical isomer thereof, or the pharmacologically acceptable salt thereof, wherein $L_2$ is O, $C_{1-3}$ alkyl-, —O—$C_{1-4}$ alkyl-, —$C_{1-3}$ alkyl-NH—, —O—$C_{1-4}$ alkyl-O—, —O—$C_{1-3}$ alkyl-O—$C_{1-3}$ alkyl-,

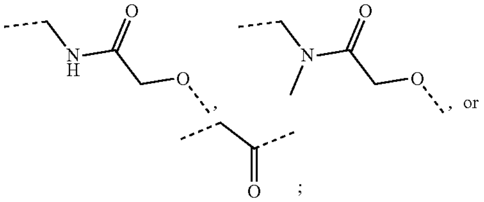
, or ;

wherein the $C_{1-3}$ alkyl, —O—$C_{1-4}$ alkyl-, —$C_{1-3}$ alkyl-NH—, —O—$C_{1-4}$ alkyl-O—, and —O—$C_{1-3}$ alkyl-O—$C_{1-3}$ alkyl- are optionally substituted by 1, 2 or 3 $R_L$.

12. The compound of claim 2, the optical isomer thereof, or the pharmacologically acceptable salt thereof, wherein $L_2$ is —O—, —$CH_2$—, —$CH_2CH_2$—, —$CH_2CH_2CH_2$—, —$CH(CH_3)$—,

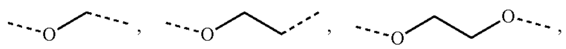
,

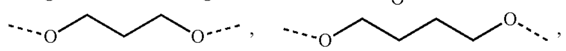
,

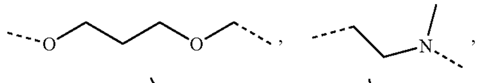
,

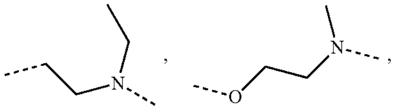
,

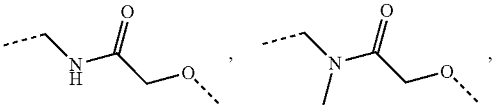
,

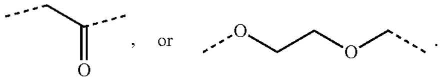
, or .

13. The compound of claim 1, the optical isomer thereof, or the pharmacologically acceptable salt thereof, wherein the moiety

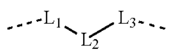

is

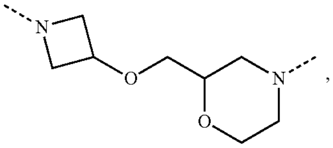
,

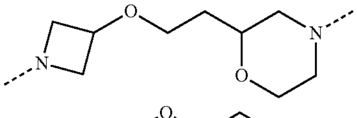
,

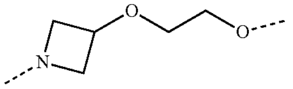
,

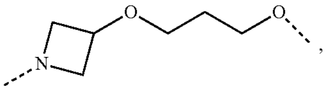
,

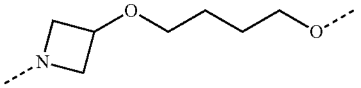
,

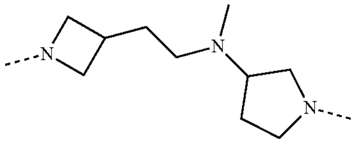
,

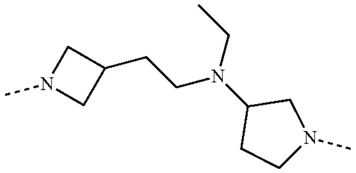
,

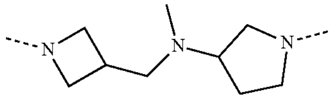
,

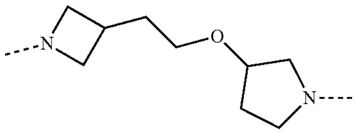
,

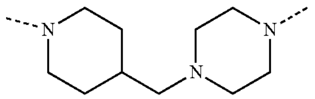
,

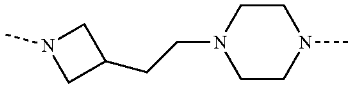
,

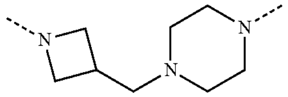
,

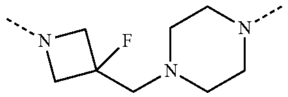
,

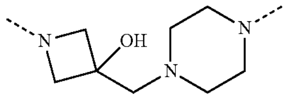
,

-continued
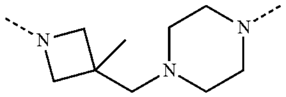
,
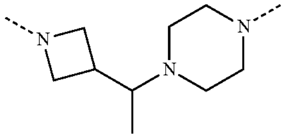
,
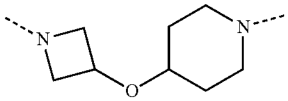
,
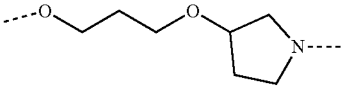
,
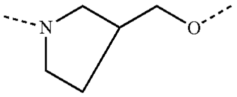
,
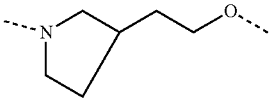
,
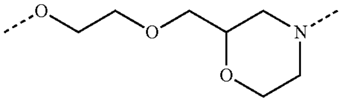
,
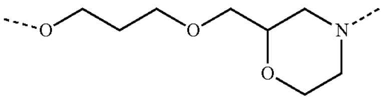
,
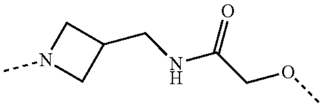
,
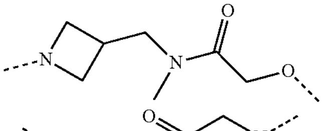
,
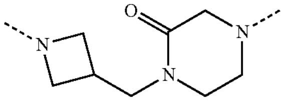
,
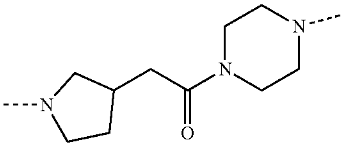
,
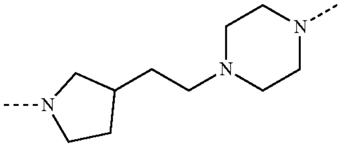
,
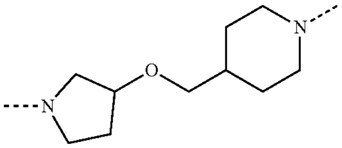
,
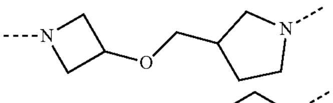
,
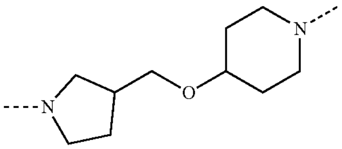
,
-continued
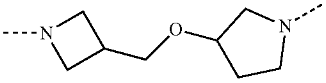
,
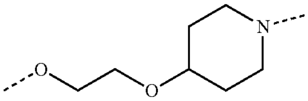
,
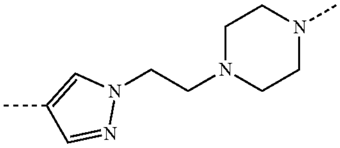
,
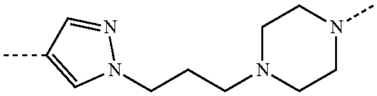
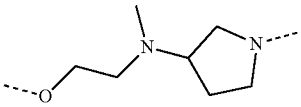
,
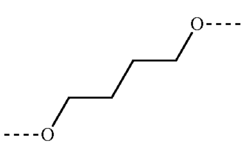
,
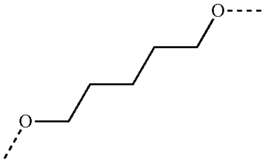
,
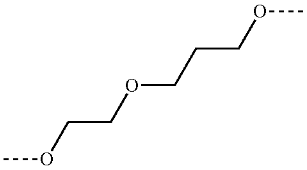
,
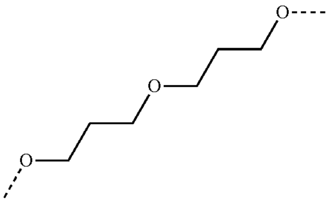
,
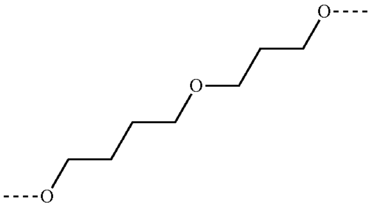
,
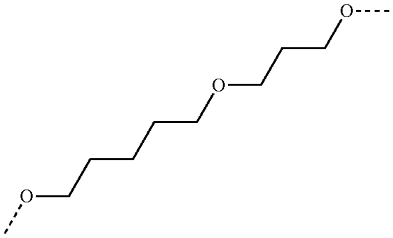
,
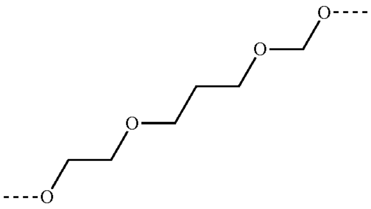
, -continued

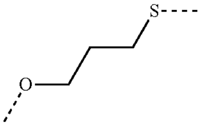,
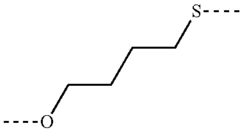,
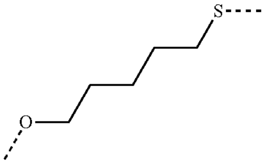,
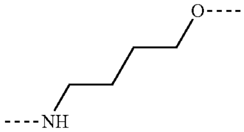,
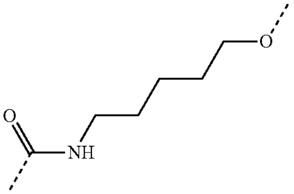,
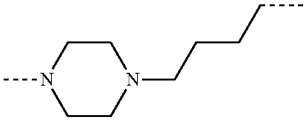,
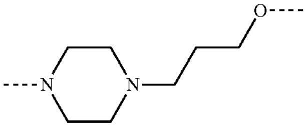,
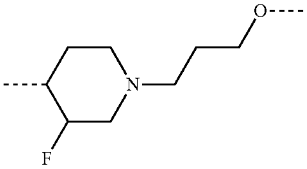,
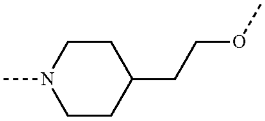,
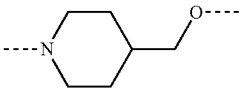,
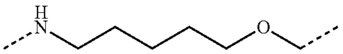,
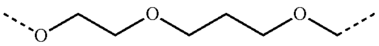,
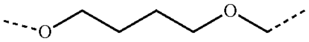,
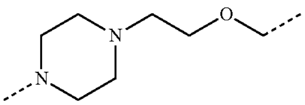,
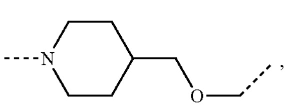,
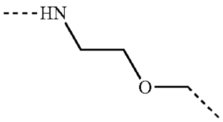,
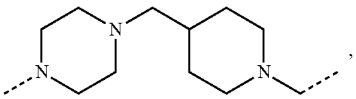,
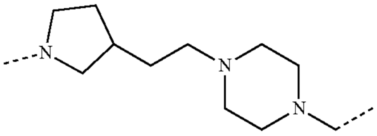, -continued

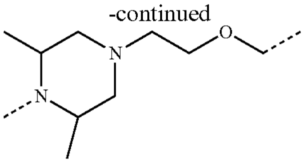,
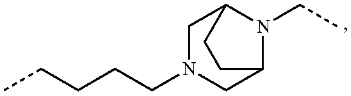, or
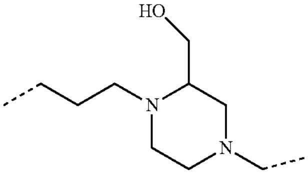.

14. The compound of claim 2, the optical isomer thereof, or the pharmacologically acceptable salt thereof, wherein ring A and ring B are independently 4- to 6-membered heterocycloalkyl or 5- to 6-membered heteroaryl; wherein the 4- to 6-membered heterocycloalkyl and 5- to 6-membered heteroaryl are optionally substituted by 1, 2 or 3 R.

15. The compound of claim 2, the optical isomer thereof, or the pharmacologically acceptable salt thereof, wherein ring A is azetidinyl, piperidinyl, piperazinyl, pyrazolyl, or tetrahydropyrrolyl; wherein the azetidinyl, piperidinyl, piperazinyl, pyrazolyl, and tetrahydropyrrolyl are optionally substituted by 1, 2 or 3 R.

16. The compound of claim 2, the optical isomer thereof, or the pharmacologically acceptable salt thereof, wherein ring A is:

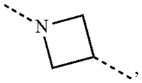, 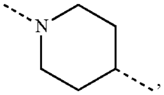, 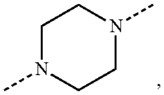,
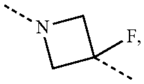 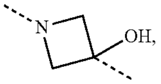 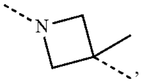,
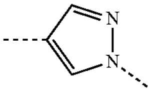, or 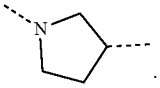.

17. The compound of claim 2, the optical isomer thereof, or the pharmacologically acceptable salt thereof, wherein ring B is morpholinyl, piperazinyl, tetrahydropyrrolyl, piperidinyl, azetidinyl, or piperazine-2-ketonyl; wherein the morpholinyl, piperazinyl, tetrahydropyrrolyl, piperidinyl, azetidinyl, and piperazine-2-ketonyl are optionally substituted by 1, 2 or 3 R.

18. The compound of claim 2, the optical isomer thereof, or the pharmacologically acceptable salt thereof, wherein ring B is:

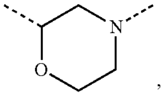, 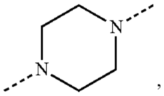, 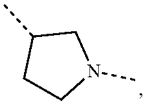,

-continued
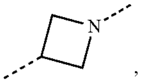 , 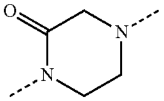 , or 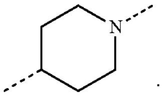 .
19. The compound of claim 2, the optical isomer thereof, or the pharmacologically acceptable salt thereof, wherein the moiety
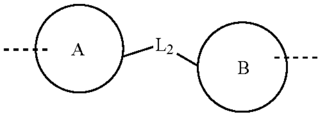
is
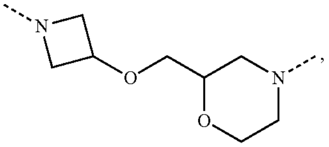,
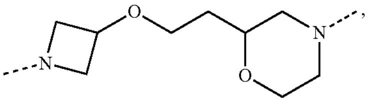,
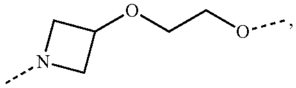,
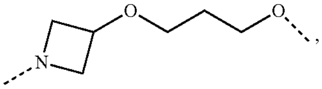,
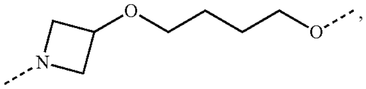,
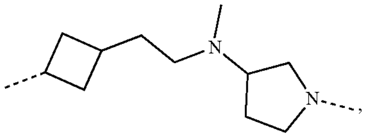,
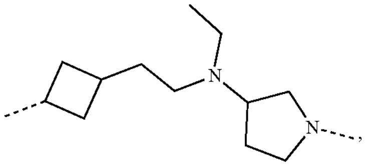,
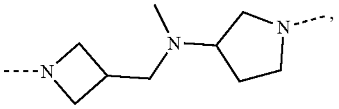,
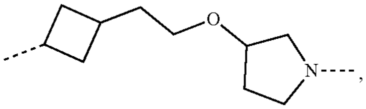,
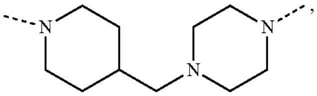,
-continued
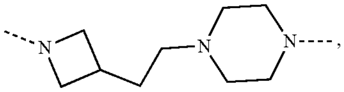,
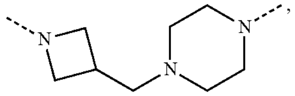,
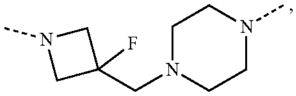,
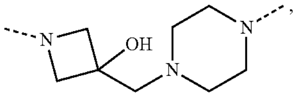,
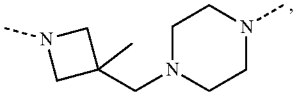,
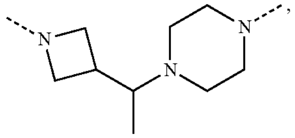,
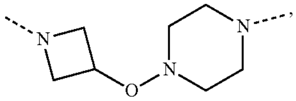,
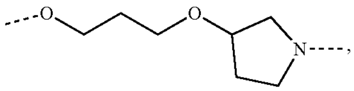,
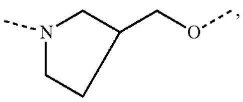, 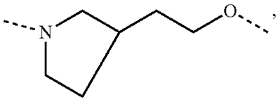,
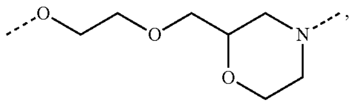,
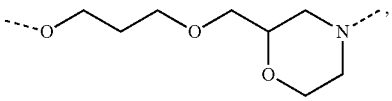,
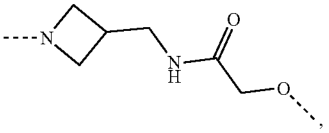,
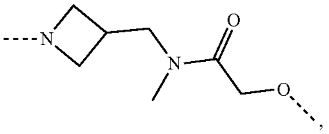,
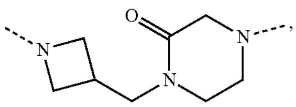,
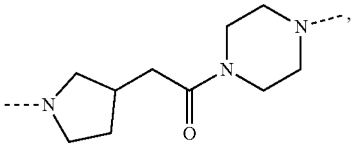, -continued
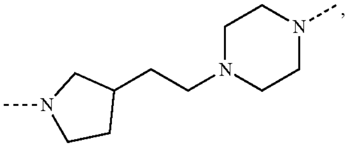
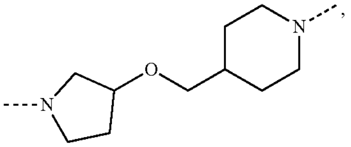
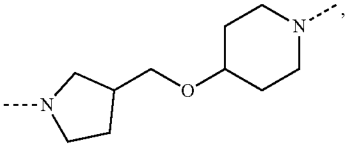
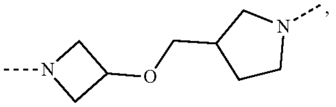
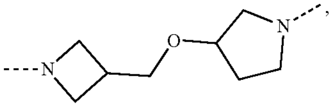
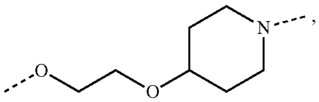
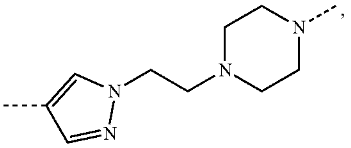
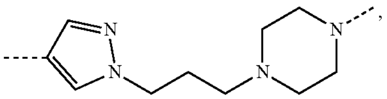
or
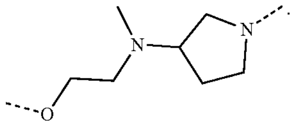
20. The compound of claim 1, the optical isomer thereof, or the pharmacologically acceptable salt thereof, wherein the moiety
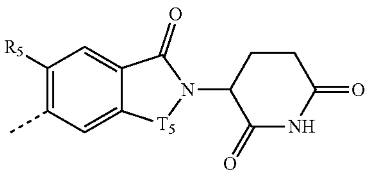
is
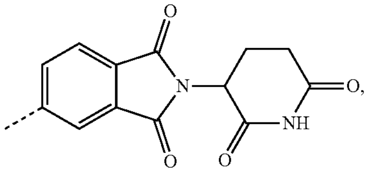
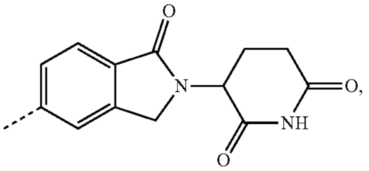
or
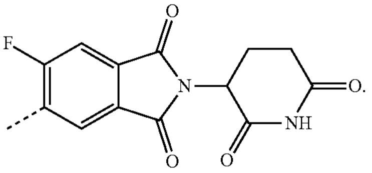
21. The compound of claim 1, the optical isomer thereof, or the pharmacologically acceptable salt thereof, wherein the compound is:
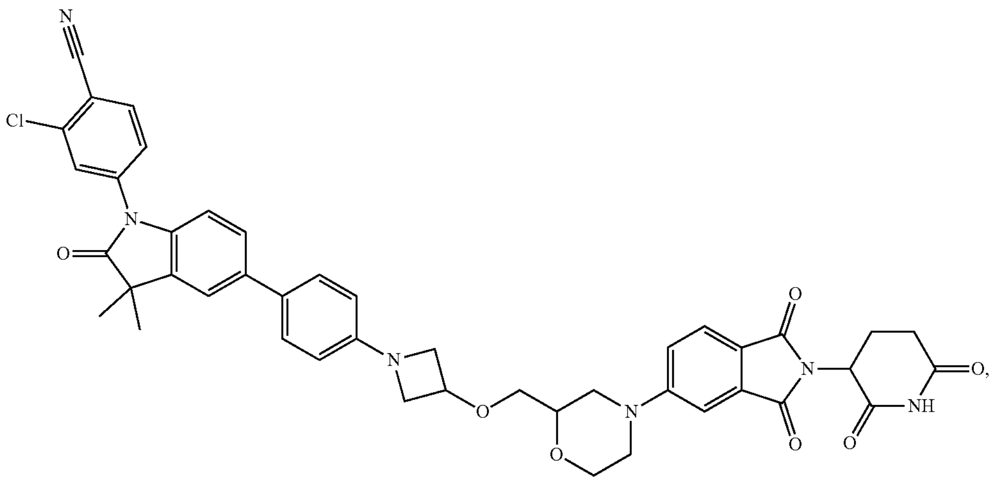

-continued
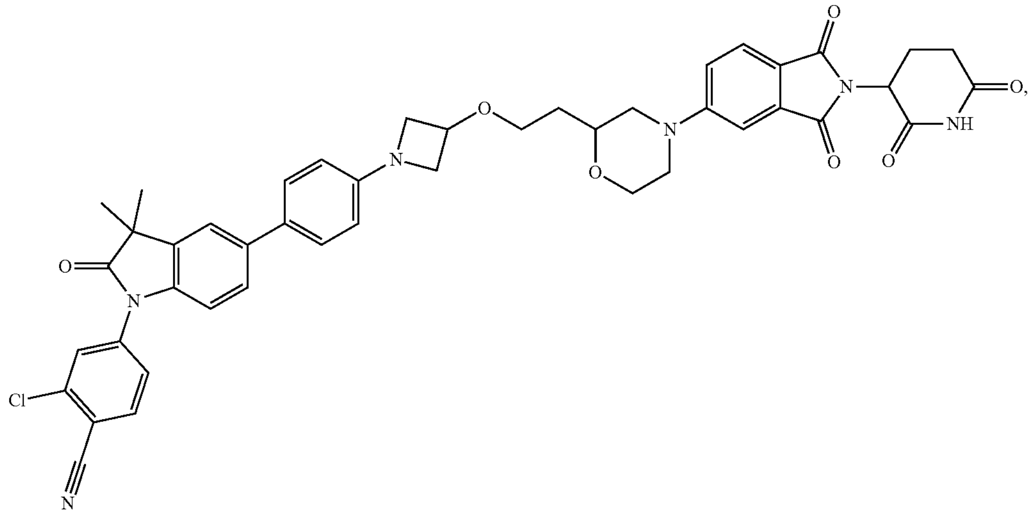
,
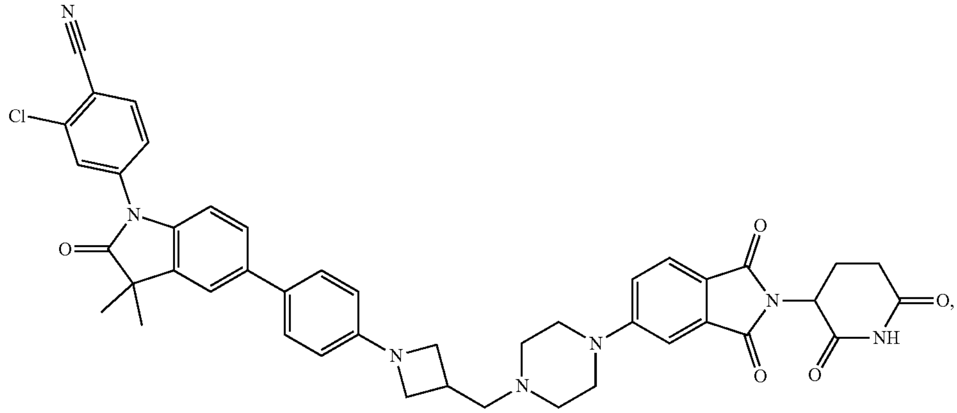
,
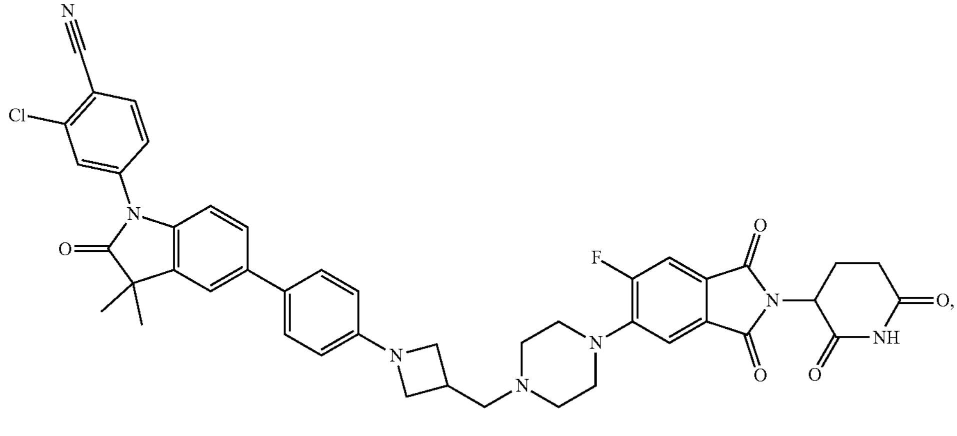
,

-continued
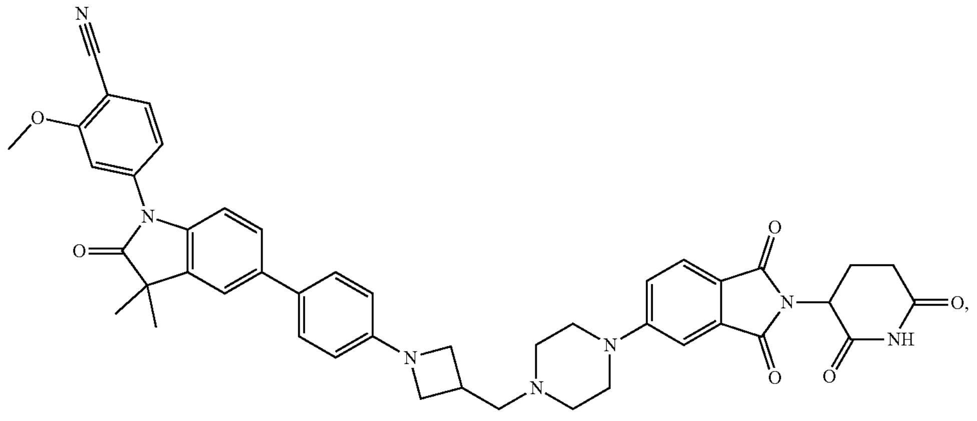
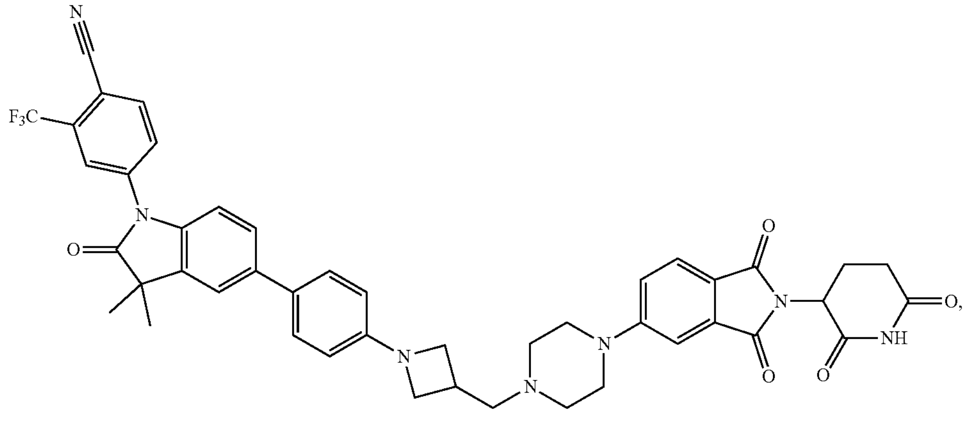
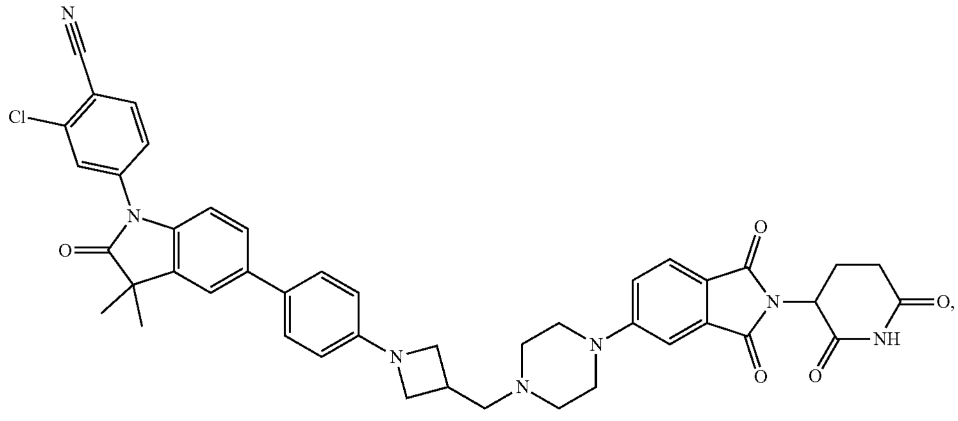

-continued
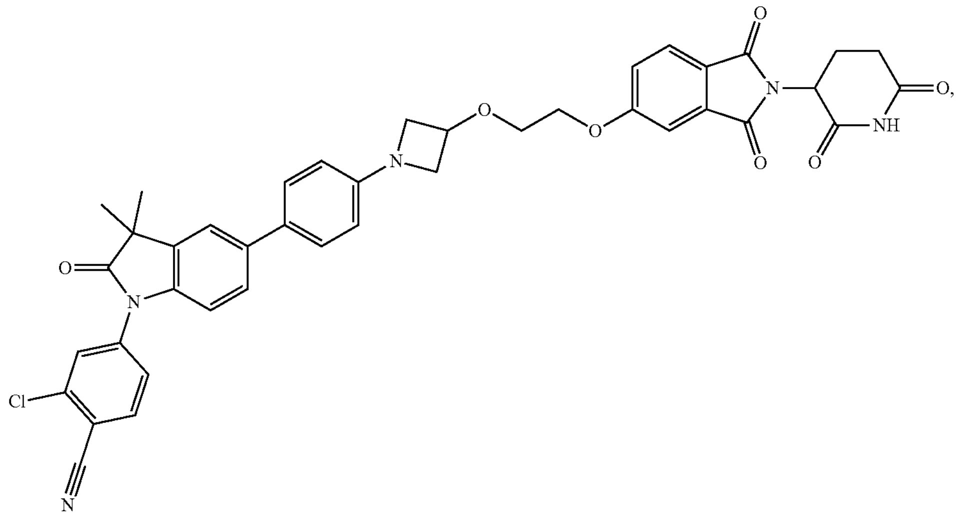
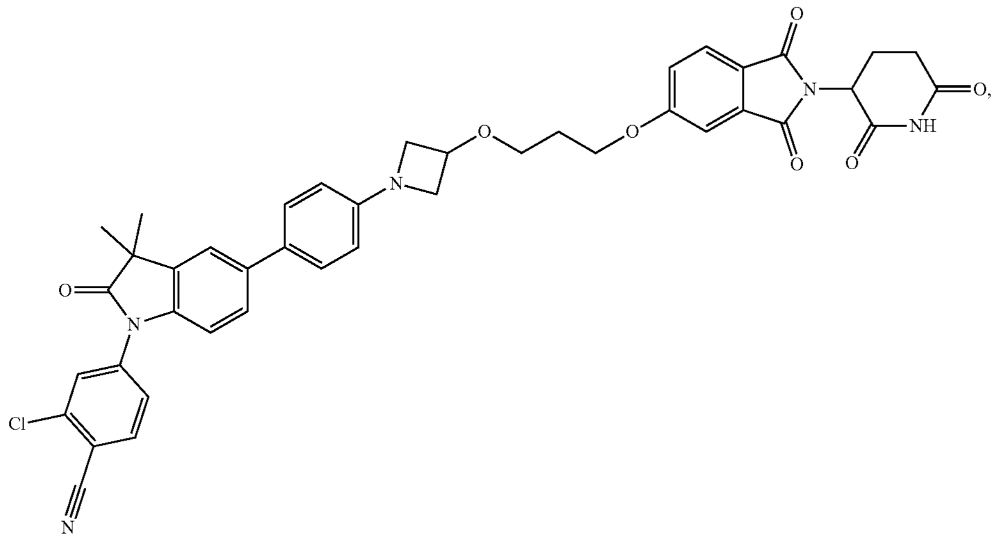
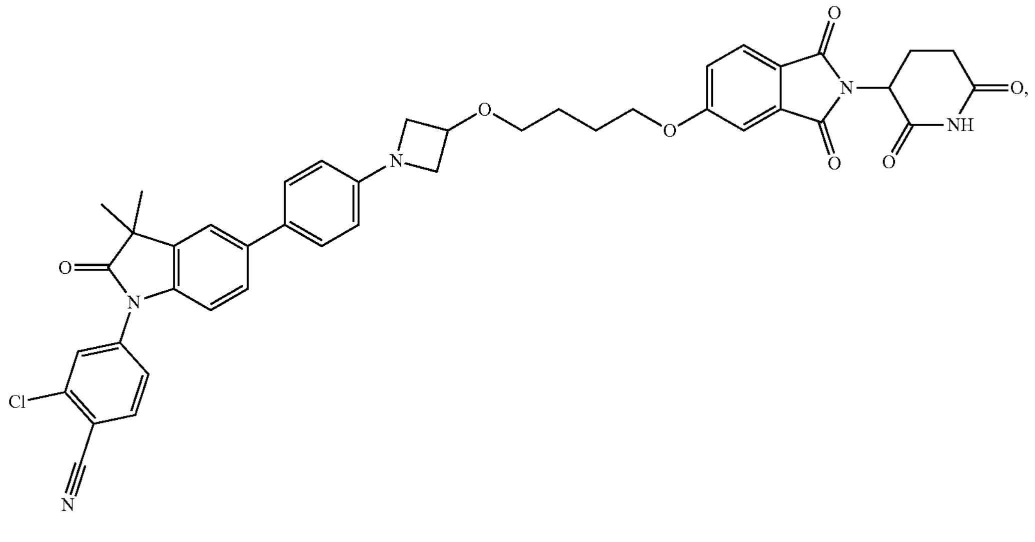

-continued
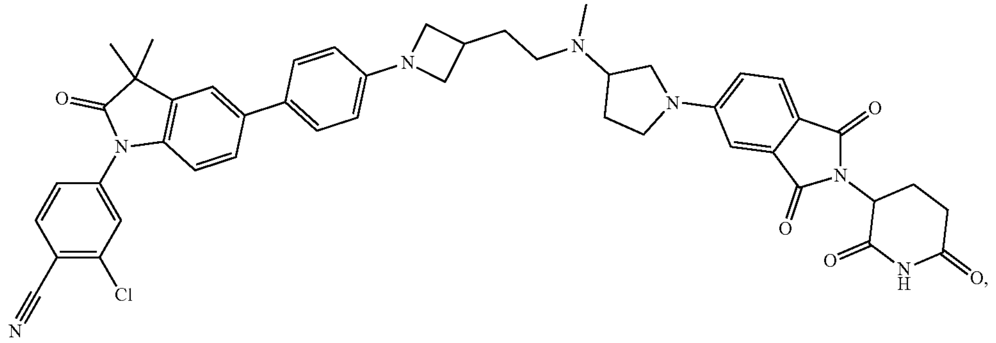
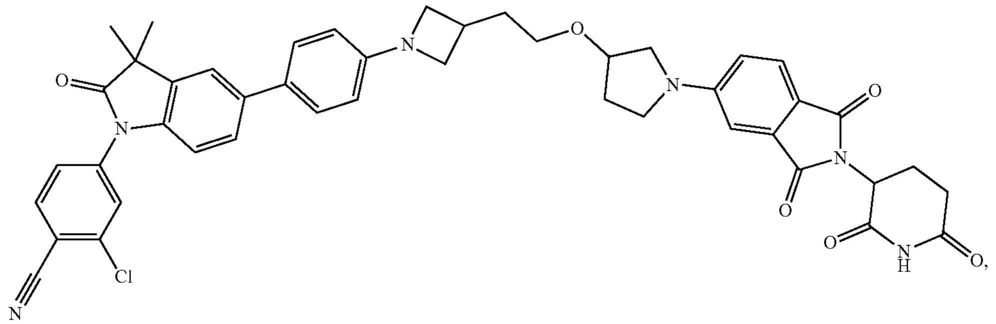
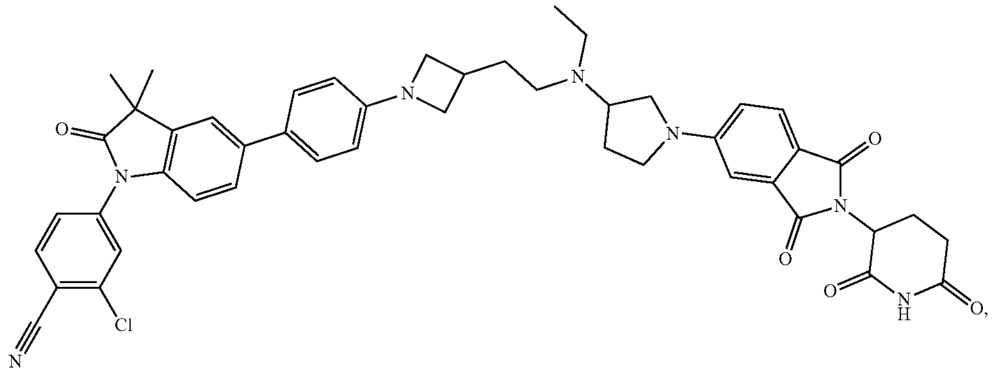
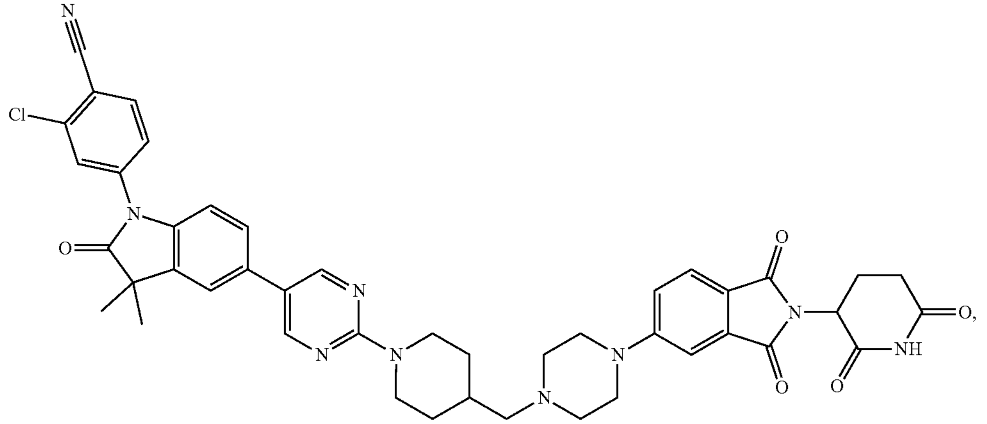

-continued
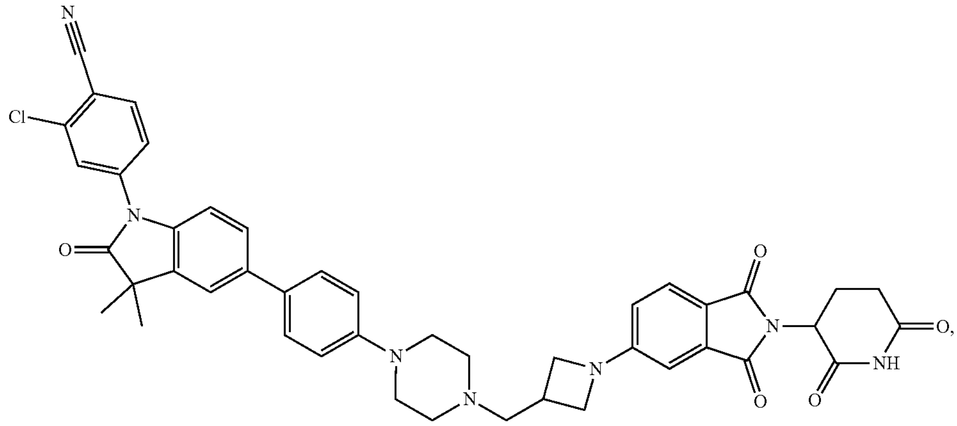
,
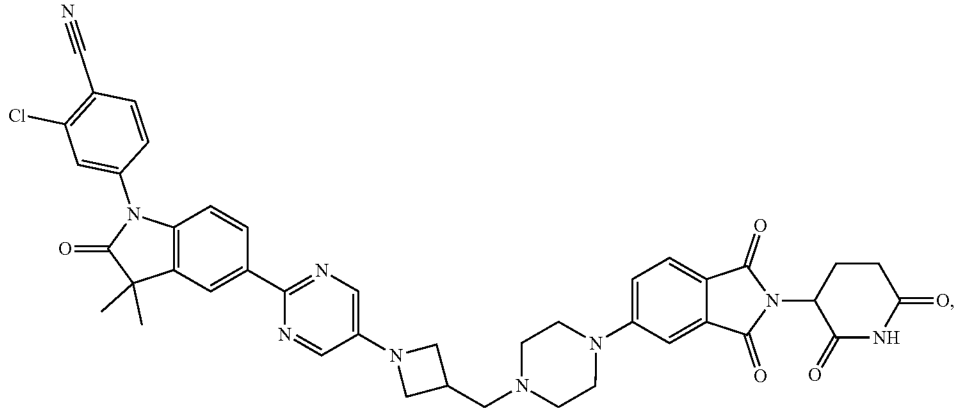 [SMILES: CC1(C)C(=O)N(c2ccc(C#N)c(Cl)c2)c2ccc(-c3ncc(N4CC(CN5CCN(c6ccc7c(c6)C(=O)N(C6CCC(=O)NC6=O)C7=O)CC5)C4)cn3)cc21]
,
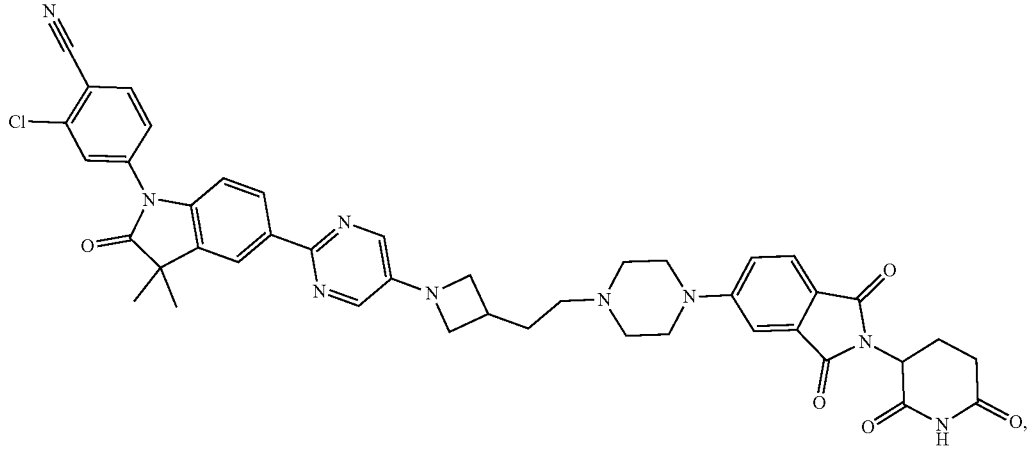
,
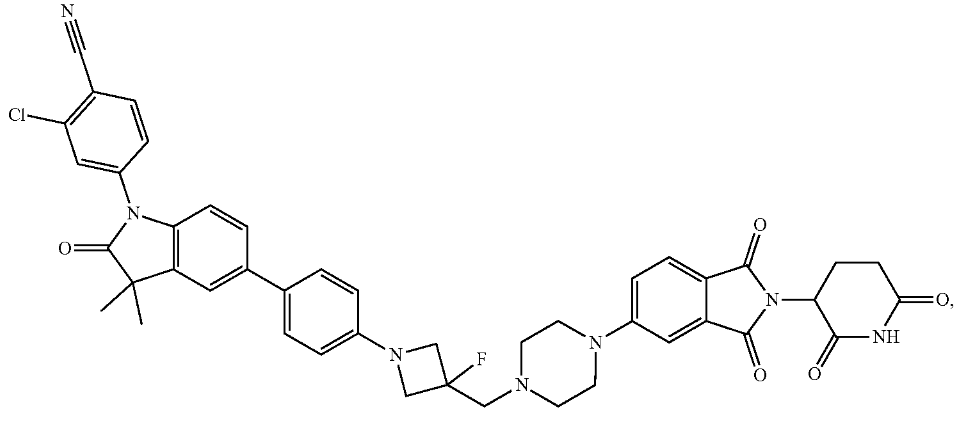
,

-continued
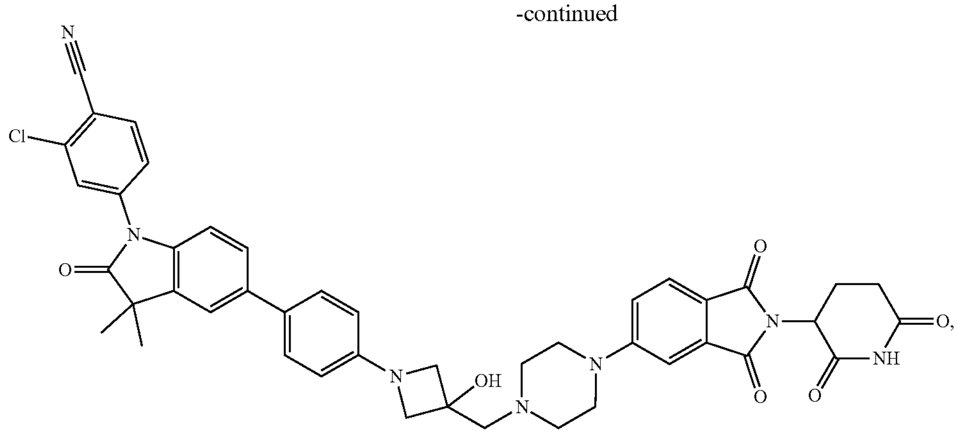
,
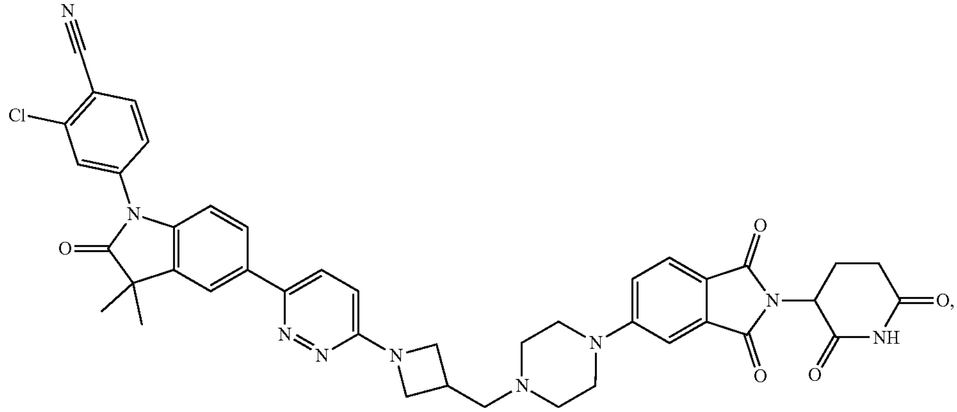
,
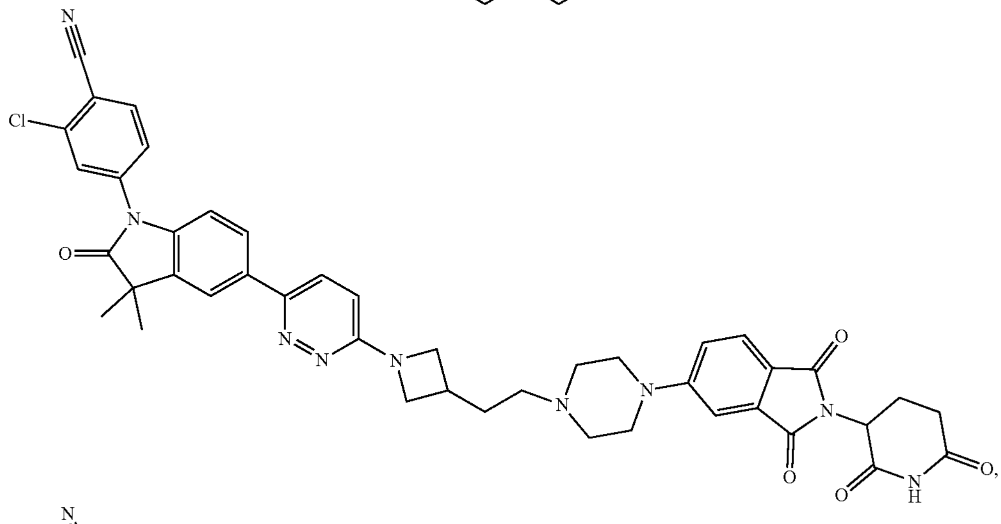
,
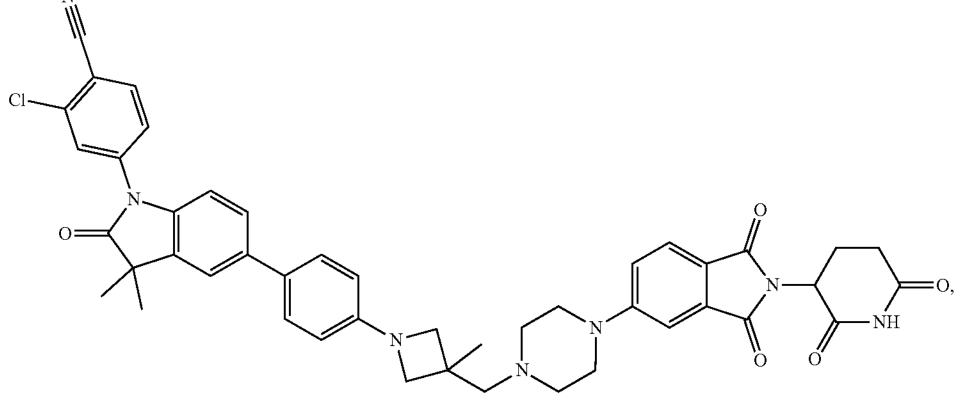
,

-continued
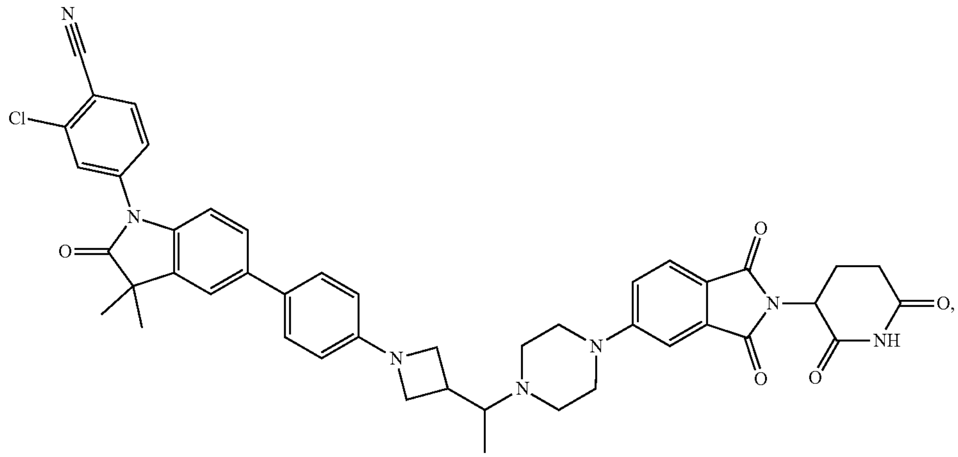
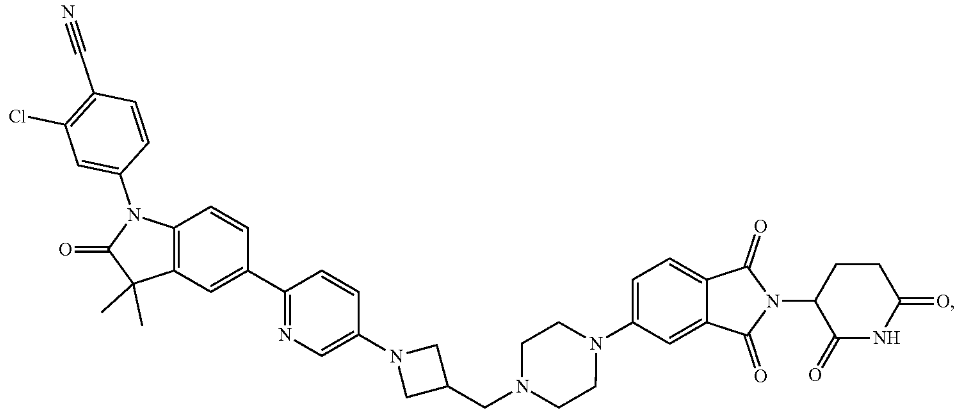
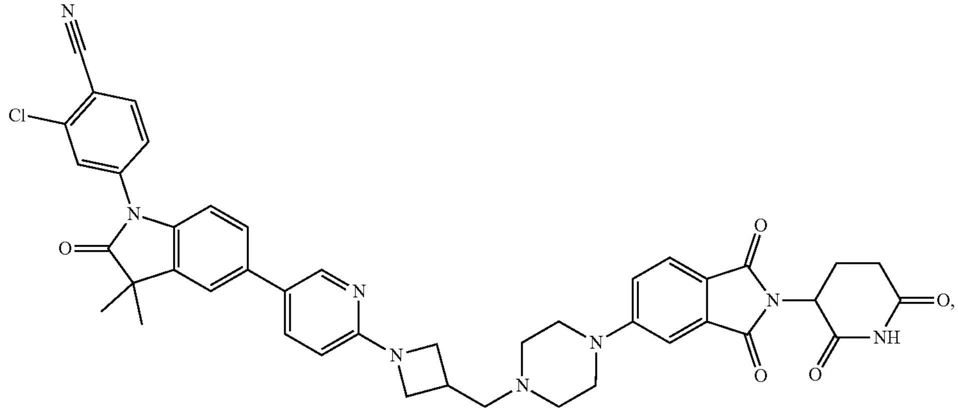
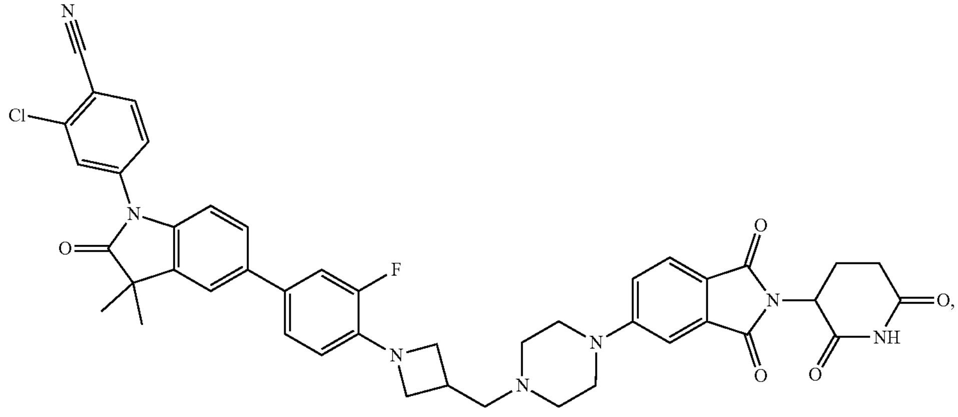

-continued
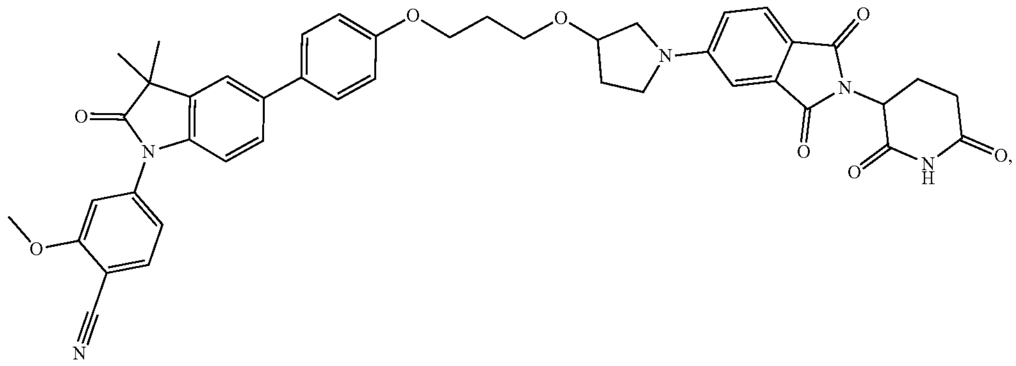
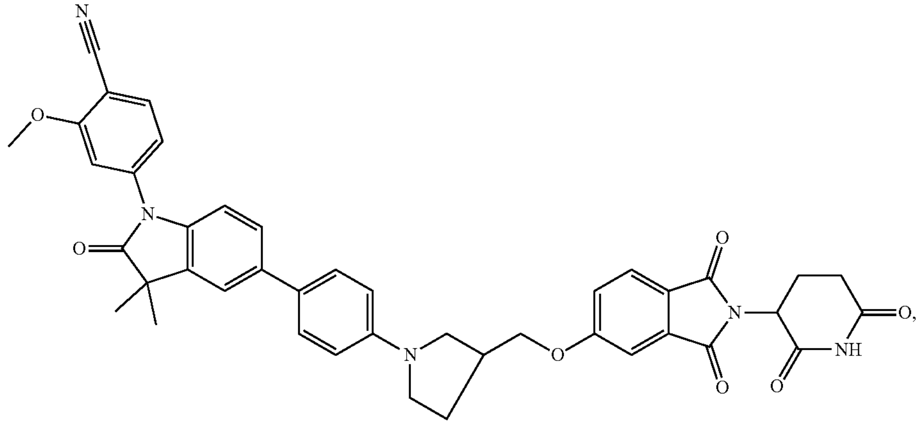
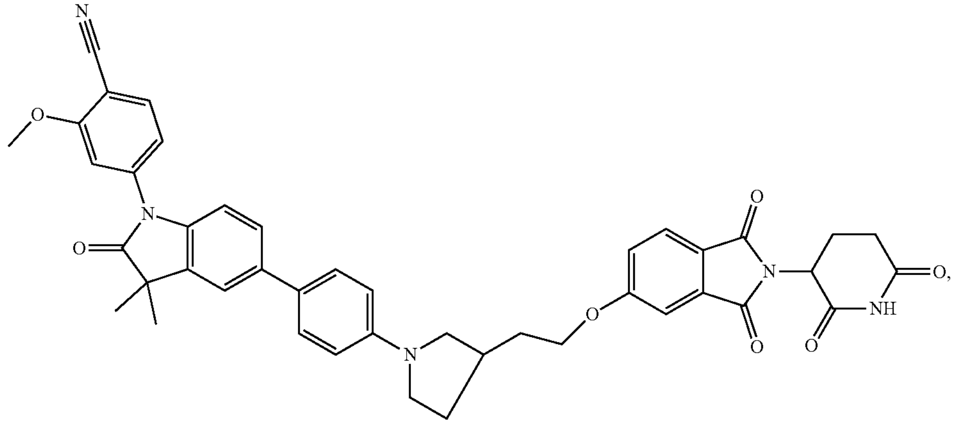
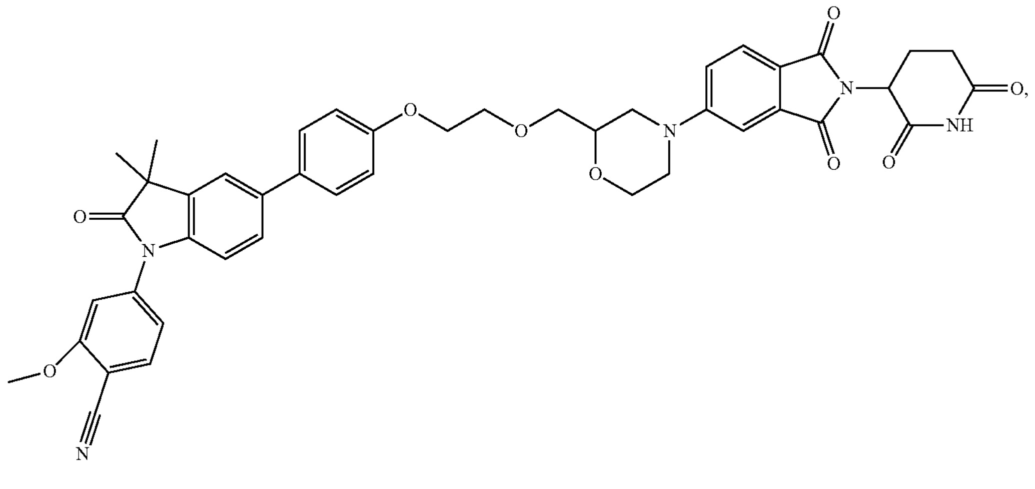

-continued
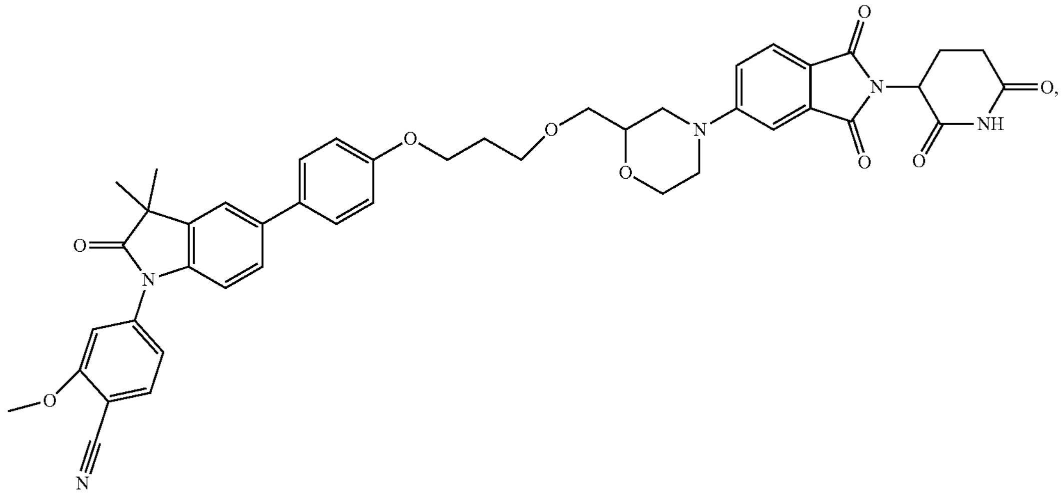
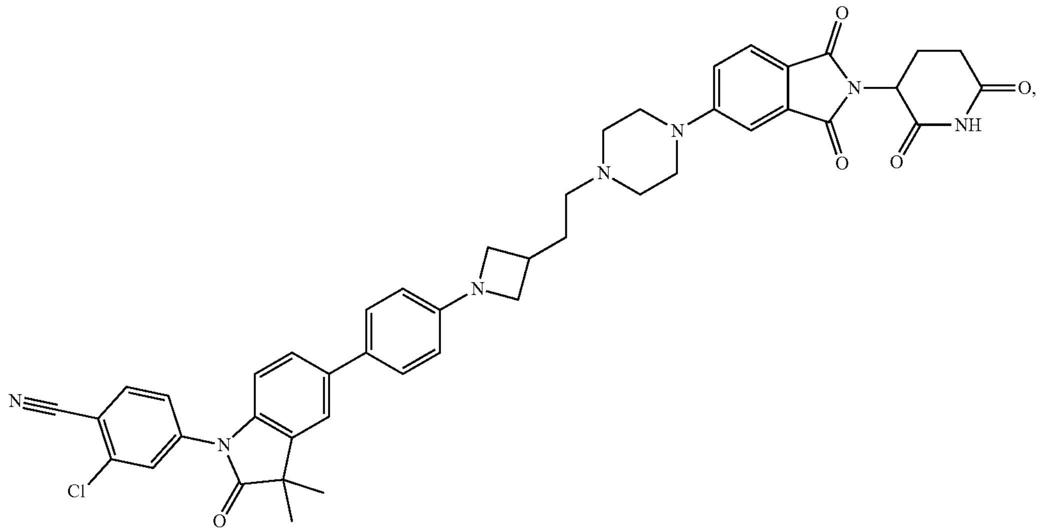
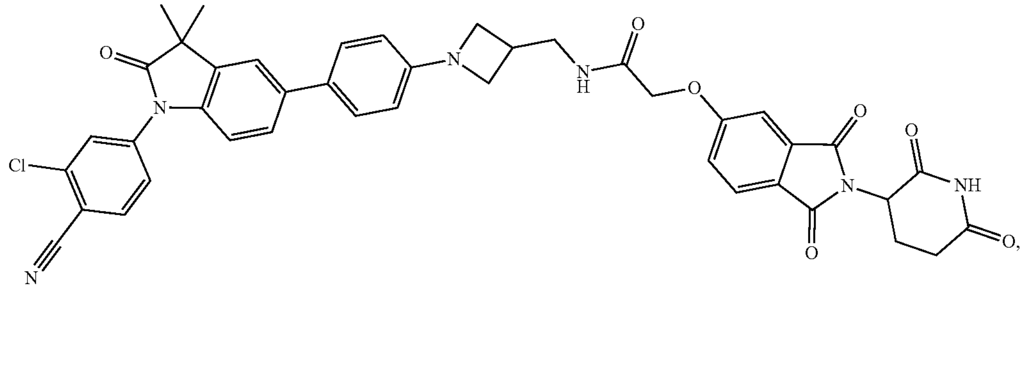
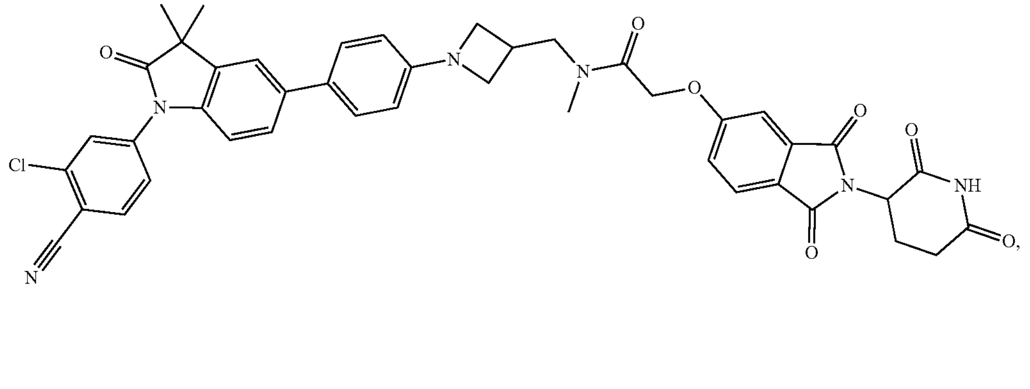

-continued
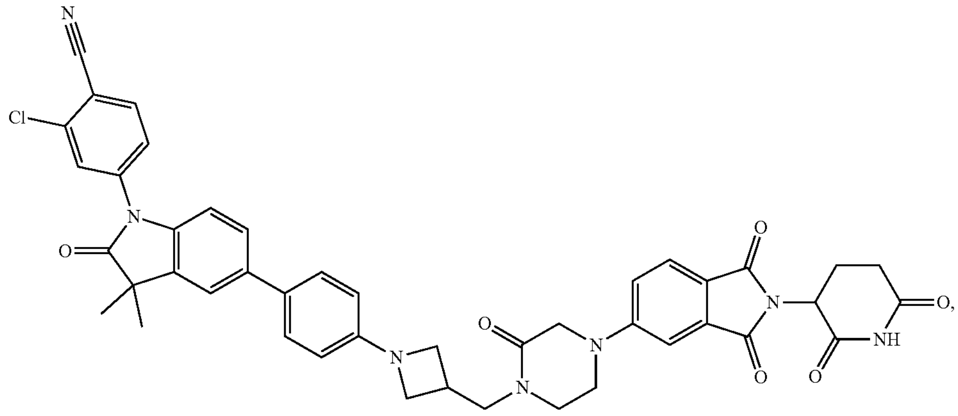
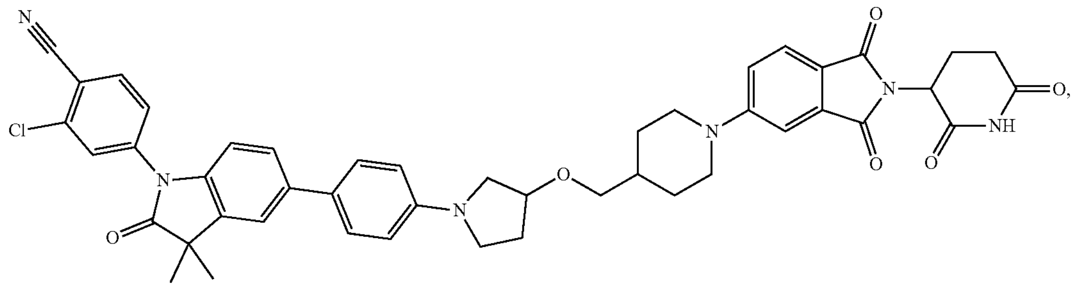
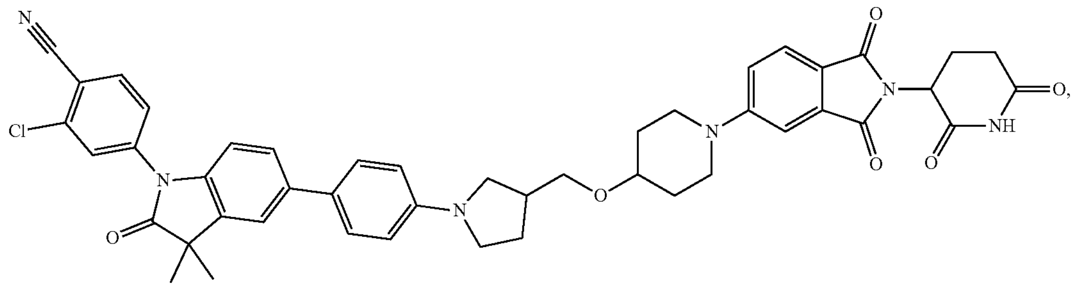
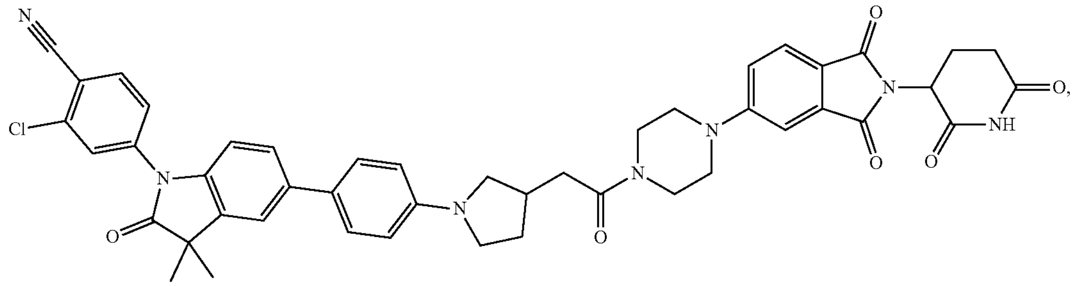
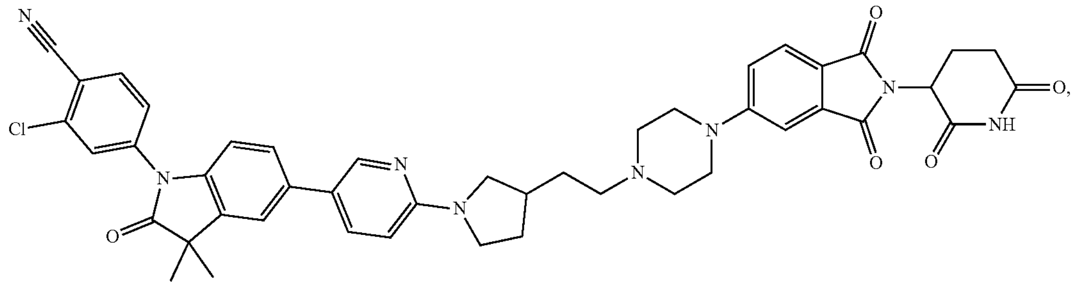

-continued
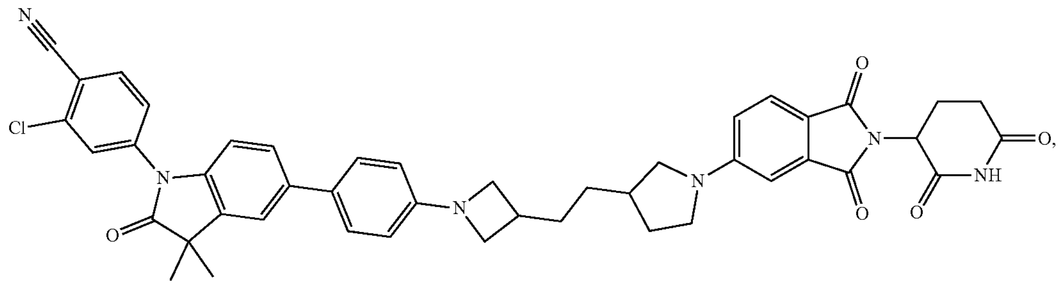
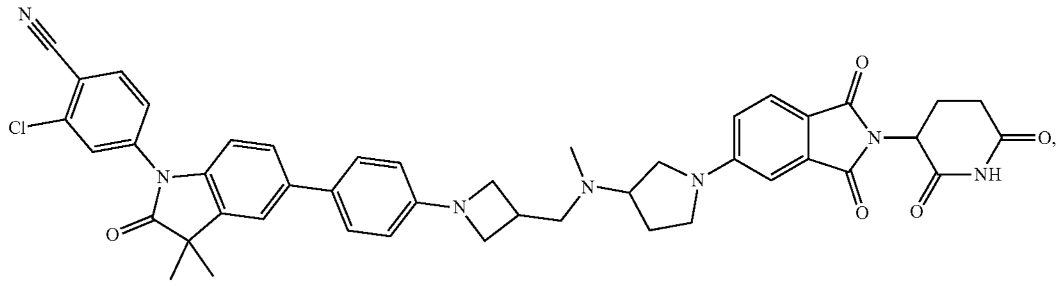
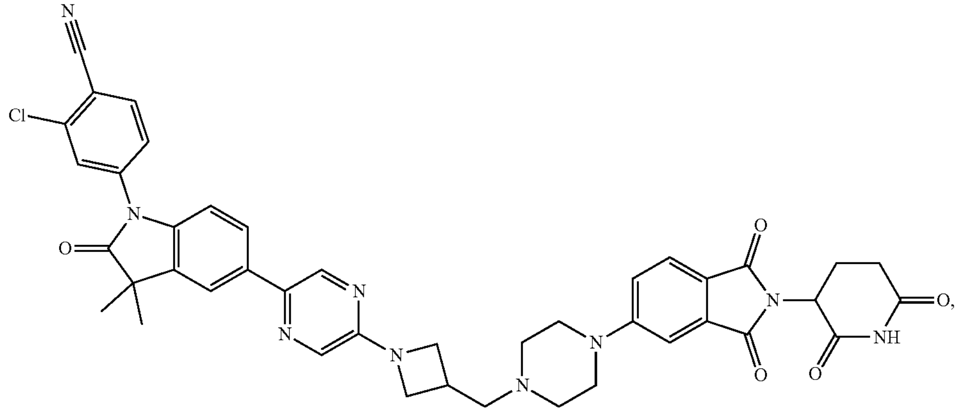
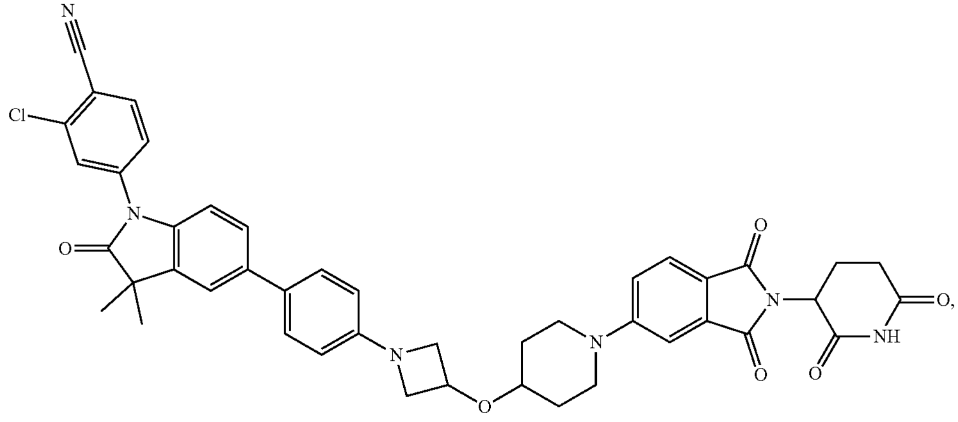
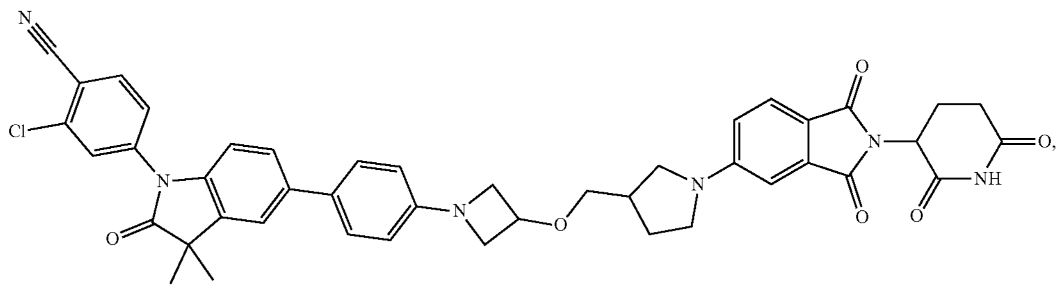

-continued
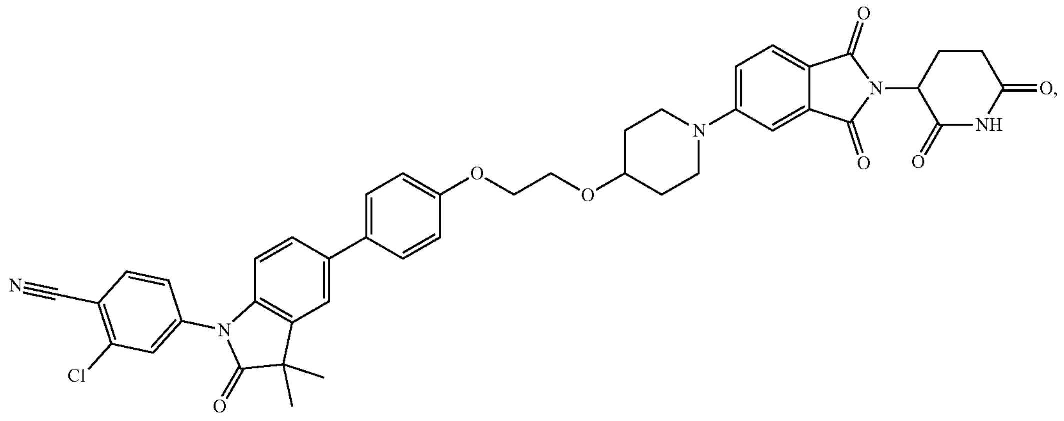
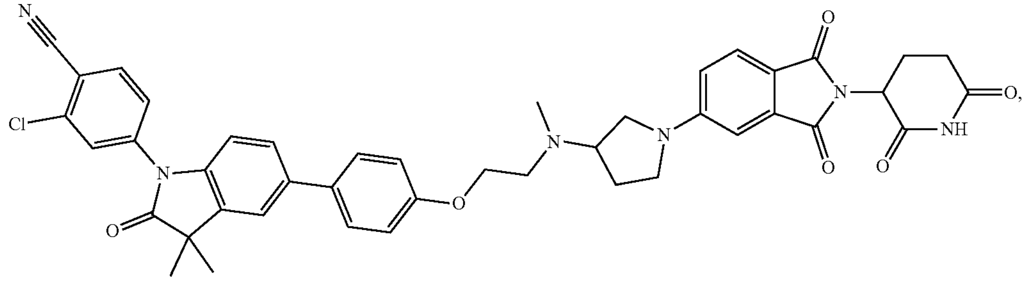
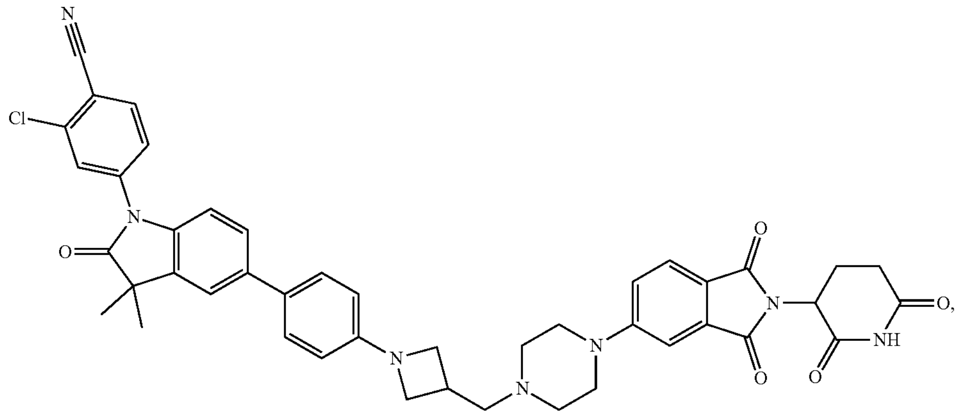
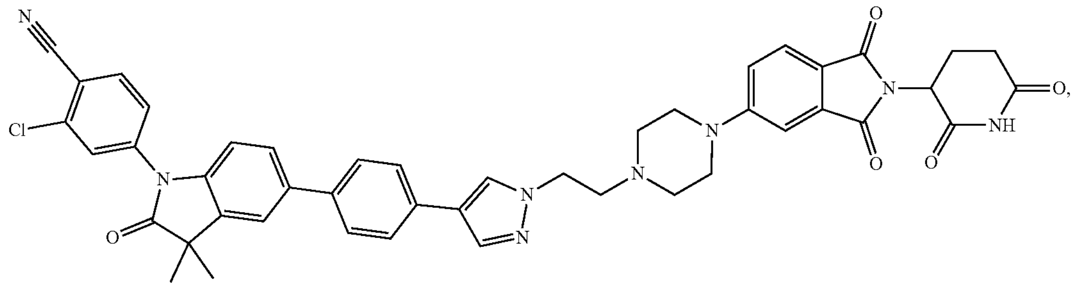

-continued
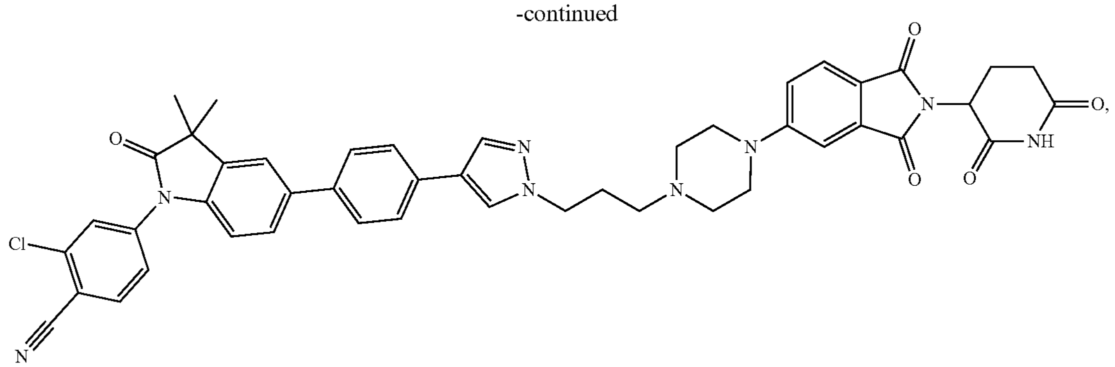
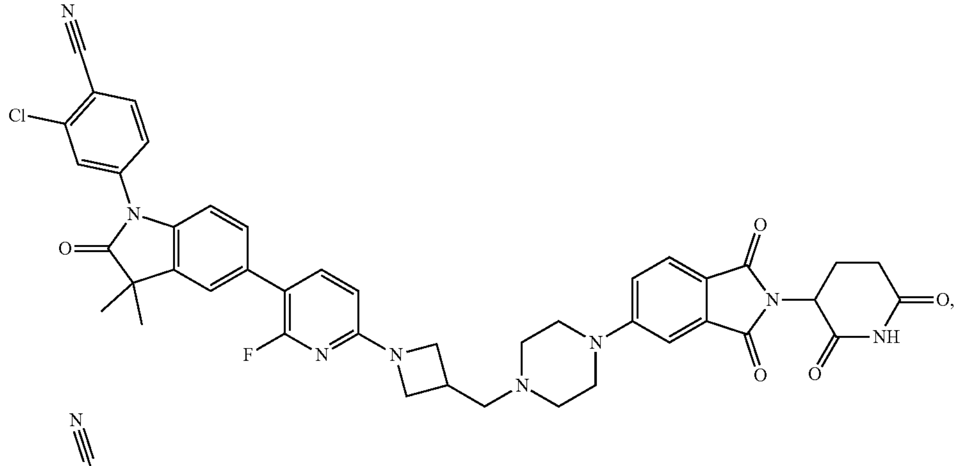
or
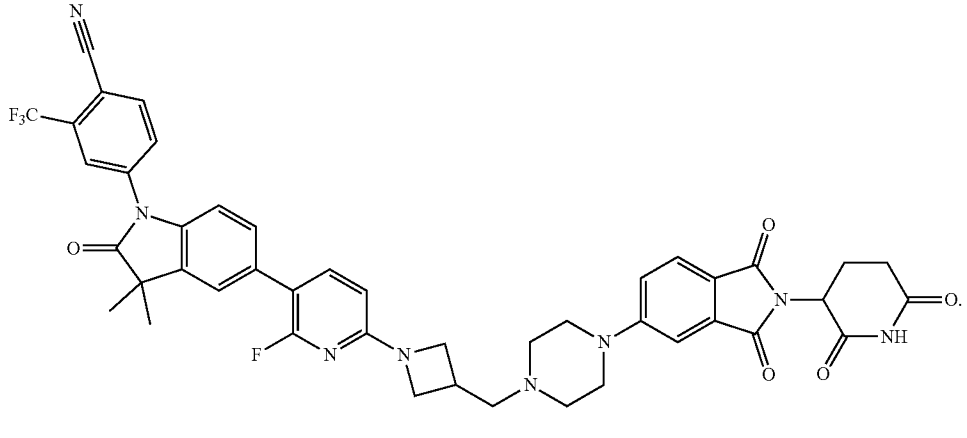
22. The compound of claim 2, the optical isomer thereof, or the pharmacologically acceptable salt thereof, wherein the compound has the formula:
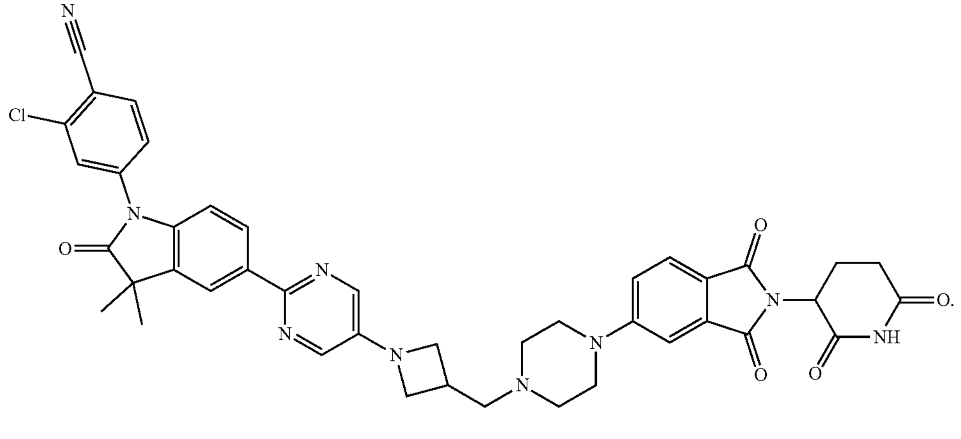

23. The compound of claim 2 or the pharmacologically acceptable salt thereof, wherein the compound has the formula:
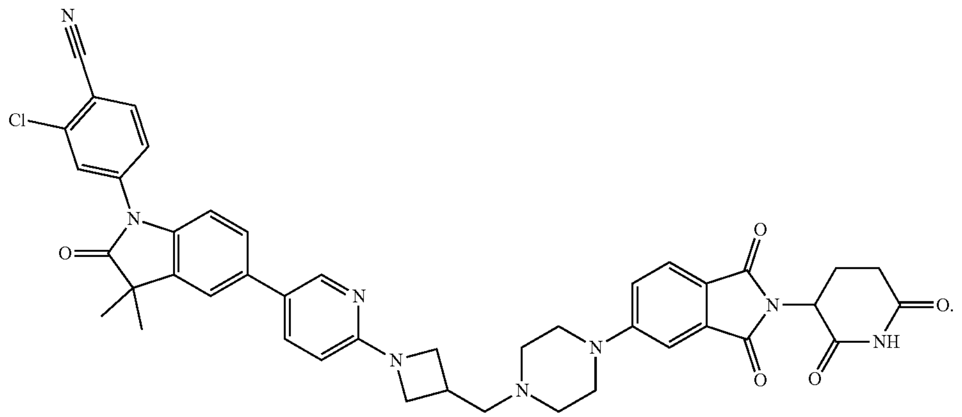 [SMILES: CC1(C)C(=O)N(c2ccc(C#N)c(Cl)c2)c2ccc(-c3ccc(N4CC(CN5CCN(c6ccc7c(c6)C(=O)N(C6CCC(=O)NC6=O)C7=O)CC5)C4)nc3)cc21]
24. The compound of claim 2, or the pharmacologically acceptable salt thereof, wherein the compound has the formula:
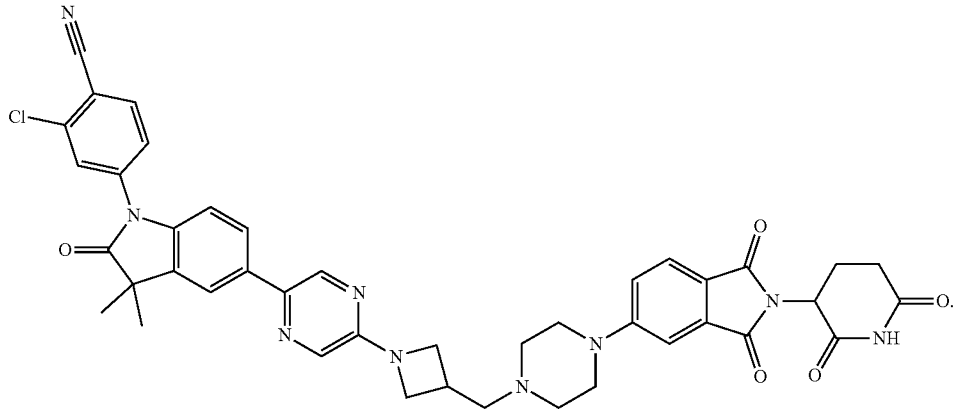 [SMILES: CC1(C)C(=O)N(c2ccc(C#N)c(Cl)c2)c2ccc(-c3cnc(N4CC(CN5CCN(c6ccc7c(c6)C(=O)N(C6CCC(=O)NC6=O)C7=O)CC5)C4)cn3)cc21]
25. The compound of claim 2 or the pharmacologically acceptable salt thereof, wherein the compound has the formula:
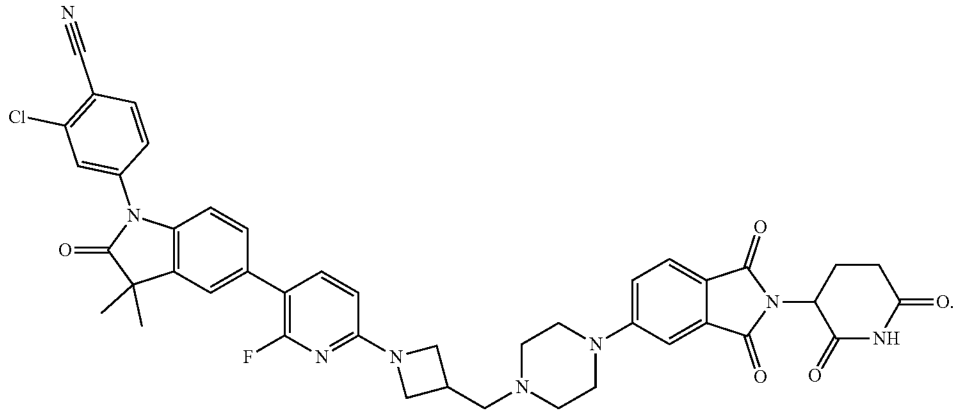 [SMILES: CC1(C)C(=O)N(c2ccc(C#N)c(Cl)c2)c2ccc(-c3ccc(N4CC(CN5CCN(c6ccc7c(c6)C(=O)N(C6CCC(=O)NC6=O)C7=O)CC5)C4)nc3F)cc21]

26. The compound of claim 2 or the pharmacologically acceptable salt thereof, wherein the compound has the formula:

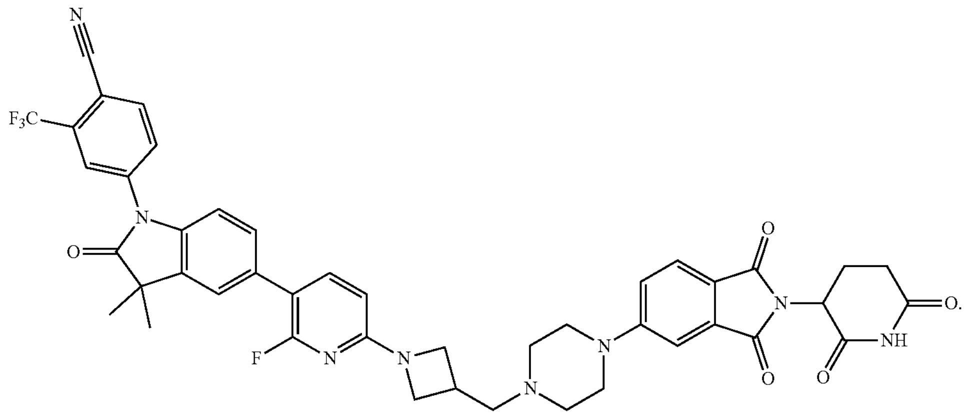 [SMILES: CC1(C)C(=O)N(c2ccc(C#N)c(C(F)(F)F)c2)c2ccc(-c3ccc(N4CC(CN5CCN(c6ccc7c(c6)C(=O)N(C6CCC(=O)NC6=O)C7=O)CC5)C4)nc3F)cc21]

27. A method for treating cancer in a subject in need thereof, the method comprising administering to the subject an effective amount of a compound represented by formula (I), an optical isomer thereof, or a pharmacologically acceptable salt thereof; thereby treating cancer in the subject; wherein the compound represented by formula (I) is:

(I)

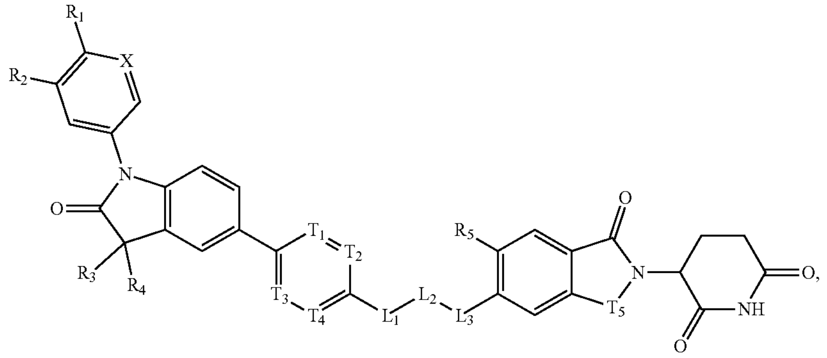

wherein:

X is C(R) or N;

$T_1$, $T_2$, $T_3$ and $T_4$ are each independently C(R) or N;

$T_5$ is —(C═O)— or —$CH_2$—;

$R_1$, $R_2$, $R_3$ and $R_4$ are each independently selected from the group consisting of CN, halogen, $C_{1-6}$ alkyl and $C_{1-6}$ alkoxy, wherein the $C_{1-6}$ alkyl and $C_{1-6}$ alkoxy are optionally substituted by 1, 2 or 3 R;

$L_1$, $L_2$ and $L_3$ are each independently selected from the group consisting of single bond, O, S, NH, C(═O), S(═O), S(═O)$_2$, $C_{1-6}$ alkyl, —$C_{1-6}$ alkyl-O—, —$C_{1-6}$ alkyl-NH—, —O—$C_{1-6}$ alkyl-O—, —O—$C_{1-6}$ alkyl-O—$C_{1-6}$ alkyl-, —O—$C_{2-3}$ alkenyl, $C_{2-3}$ alkynyl, $C_{3-10}$ cycloalkyl, 3- to 10-membered heterocycloalkyl, phenyl, and 5- to 9-membered heteroaryl; wherein the $C_{1-6}$alkyl, —$C_{1-6}$ alkyl-O—, —$C_{1-3}$ alkyl-NH—, —O—$C_{1-6}$ alkyl-O—, —O—$C_{1-6}$ alkyl-O—$C_{1-6}$ alkyl-, $C_{2-3}$ alkenyl, $C_{2-3}$ alkynyl, $C_{3-10}$ cycloalkyl, 3- to 10-membered heterocycloalkyl, phenyl, and 5- to 9-membered heteroaryl are optionally substituted by 1, 2 or 3 $R_L$;

$R_L$ are each independently selected from the group consisting of H, halogen, OH, $NH_2$, CN,

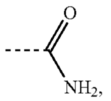

$C_{1-6}$ alkyl, $C_{3-6}$ cycloalkyl, $C_{1-6}$ alkyl-C(═O)—, $C_{1-6}$ alkoxy, $C_{1-6}$ alkylthio and $C_{1-6}$ alkylamino; wherein the $C_{1-6}$ alkyl, $C_{3-6}$ cycloalkyl, $C_{1-6}$ alkoxy, $C_{1-6}$ alkylthio, and $C_{1-6}$ alkylamino are optionally substituted by 1, 2 or 3 R';

R' is F, Cl, Br, I, OH, $NH_2$,

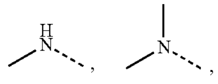

$CH_3$, $CH_2CH_3$, $CH_2F$, $CHF_2$, or $CF_3$;

R is H, F, Cl, Br, I, OH, or $C_{1-6}$ alkyl;

$R_5$ is H, halogen, or $C_{1-6}$ alkyl;

the 3- to 10-membered heterocycloalkyl or 5- to 9-membered heteroaryl contains 1, 2 or 3 heteroatoms or heteroatomic groups independently selected from the group consisting of —O—, —NH—, —S—, —C(═O)—, —C(═O)O—, —S(═O)—, —S(═O)$_2$—, and N.

28. The method of claim 27, wherein the cancer is prostate cancer.

29. A method for treating or preventing Kennedy's disease in a subject in need thereof, the method comprising administering to the subject an effective amount of a compound represented by formula (II), an optical isomer thereof, or a pharmacologically acceptable salt thereof; thereby treating or preventing Kennedy's disease in the subject; wherein the compound represented by formula (II) is:

(II)

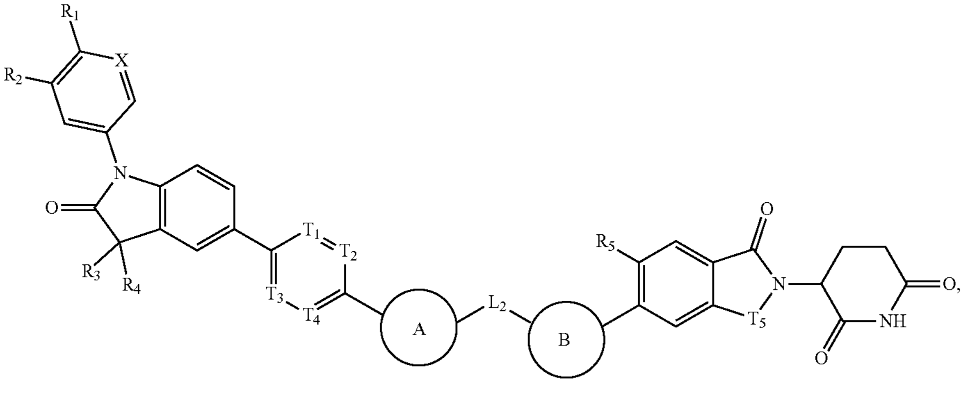

wherein:

ring A and ring B are independently selected from the group consisting of 3- to 8-membered heterocycloalkyl, 5- to 6-membered heteroaryl, or absent; wherein the 3- to 8-membered heterocycloalkyl and 5- to 6-membered heteroaryl are optionally substituted by 1, 2 or 3 R;

$R_1$, $R_2$, $R_3$ and $R_4$ are each independently selected from the group consisting of CN, halogen, $C_{1-6}$ alkyl and $C_{1-6}$ alkoxy; wherein the $C_{1-6}$ alkyl and $C_{1-6}$ alkoxy are optionally substituted by 1, 2 or 3 R;

X is C(R) or N;

$T_1$, $T_2$, $T_3$ and $T_4$ are each independently C(R) or N;

$T_5$ is —(C═O)— or —$CH_2$—;

$L_2$ is single bond, O, S, NH, C(═O), S(═O), S(═O)$_2$, $C_{1-6}$ alkyl, —$C_{1-6}$ alkyl-O—, —$C_{1-3}$ alkyl-NH—, —O—$C_{1-6}$ alkyl-O—, —O—$C_{1-6}$ alkyl-O—$C_{1-6}$ alkyl-, —O—$C_{2-3}$ alkenyl, $C_{2-3}$ alkynyl, $C_{3-10}$ cycloalkyl, 3- to 10-membered heterocycloalkyl, phenyl, or 5- to 9-membered heteroaryl; wherein the $C_{1-6}$ alkyl, —$C_{1-6}$ alkyl-O—, —$C_{1-3}$ alkyl-NH—, —O—$C_{1-6}$ alkyl-O—, —O—$C_{1-6}$ alkyl-O—$C_{1-6}$ alkyl-, $C_{2-3}$ alkenyl, $C_{2-3}$ alkynyl, $C_{3-10}$ cycloalkyl, 3- to 10-membered heterocycloalkyl, phenyl, and 5- to 9-membered heteroaryl are optionally substituted by 1, 2 or 3 $R_L$;

$R_L$ are each independently H, halogen, OH, $NH_2$, CN,

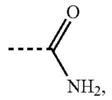

$C_{1-6}$ alkyl, $C_{3-6}$ cycloalkyl, $C_{1-6}$ alkyl-C(═O)—, $C_{1-6}$ alkoxy, $C_{1-6}$ alkylthio, or $C_{1-6}$ alkylamino; wherein the $C_{1-6}$ alkyl, $C_{3-6}$ cycloalkyl, $C_{1-6}$ alkoxy, $C_{1-6}$ alkylthio, and $C_{1-6}$ alkylamino are optionally substituted by 1, 2 or 3 R';

R' is F, Cl, Br, I, OH, $NH_2$,

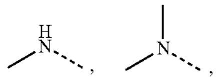

$CH_3$, $CH_2CH_3$, $CH_2F$, $CHF_2$, or $CF_3$;

R is H, F, Cl, Br, I, OH, or $C_{1-6}$ alkyl;

$R_5$ is H, halogen, or $C_{1-6}$ alkyl;

the 3- to 8-membered heterocycloalkyl, 3- to 10-membered heterocycloalkyl, 5- to 6-membered heteroaryl or 5- to 9-membered heteroaryl contains 1, 2 or 3 heteroatoms or heteroatomic groups independently selected from —O—, —NH—, —S—, —C(═O)—, —C(═O)O—, —S(═O)—, —S(═O)$_2$— and N.

30. The method of claim 27, wherein the cancer is breast cancer.

31. The method of claim 27, wherein the compound of formula (I) is represented by the compound of formula (II):

(II)

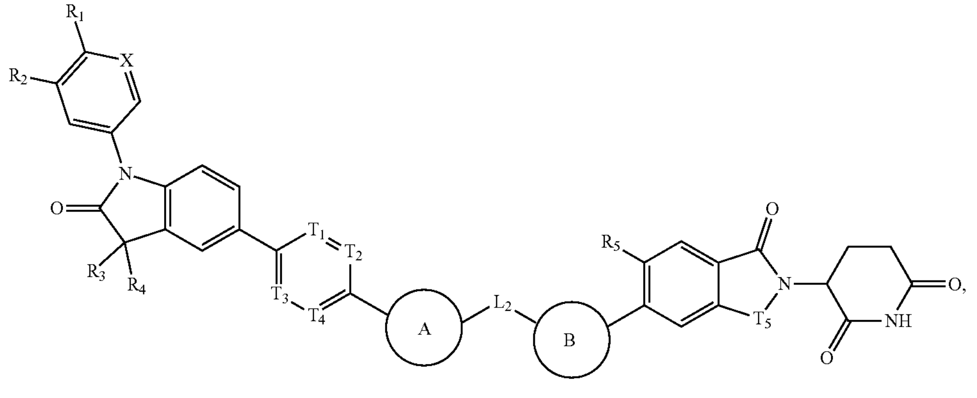

wherein:

ring A and ring B are independently selected from the group consisting of 3-to 8-membered heterocycloalkyl, 5- to 6-membered heteroaryl, or absent; wherein the 3- to 8-membered heterocycloalkyl and 5- to 6-membered heteroaryl are optionally substituted by 1, 2 or 3 R;

$R_1$, $R_2$, $R_3$ and $R_4$ are each independently selected from the group consisting of CN, halogen, $C_{1-6}$ alkyl and $C_{1-6}$ alkoxy; wherein the $C_{1-6}$ alkyl and $C_{1-6}$ alkoxy are optionally substituted by 1, 2 or 3 R;

X is C(R) or N;

$T_1$, $T_2$, $T_3$ and $T_4$ are each independently C(R) or N;

$T_5$ is -(C═O)- or —$CH_2$-;

$L_2$ is single bond, O, S, NH, C(═O), S(═O), $S(═O)_2$, $C_{1-6}$ alkyl, —$C_{1-6}$ alkyl-O—, —$C_{1-3}$ alkyl-NH—, —O-$C_{1-6}$ alkyl-O—, —O—$C_{1-6}$ alkyl-O—$C_{1-6}$ alkyl-, —O—$C_{2-3}$ alkenyl, $C_{2-3}$ alkynyl, $C_{3-10}$ cycloalkyl, 3- to 10-membered heterocycloalkyl, phenyl, or 5- to 9-membered heteroaryl; wherein the $C_{1-6}$ alkyl, —$C_{1-6}$ alkyl-O—, —$C_{1-3}$ alkyl-NH—, —O—$C_{1-6}$ alkyl-O—, —O—$C_{1-6}$ alkyl-O—$C_{1-6}$ alkyl-, $C_{2-3}$ alkenyl, $C_{2-3}$ alkynyl, $C_{3-10}$ cycloalkyl, 3- to 10-membered heterocycloalkyl, phenyl, and 5- to 9-membered heteroaryl are optionally substituted by 1, 2 or 3 $R_L$;

$R_L$ are each independently H, halogen, OH, $NH_2$, CN,

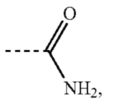

$C_{1-6}$ alkyl, $C_{3-6}$ cycloalkyl, $C_{1-6}$ alkyl-C(═O)-, $C_{1-6}$ alkoxy, $C_{1-6}$ alkylthio, or $C_{1-6}$ alkylamino; wherein the $C_{1-6}$ alkyl, $C_{3-6}$ cycloalkyl, $C_{1-6}$ alkoxy, $C_{1-6}$ alkylthio, and $C_{1-6}$ alkylamino are optionally substituted by 1, 2 or 3 R';

R' is F, Cl, Br, I, OH, $NH_2$,

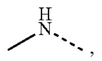

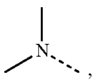

$CH_3$, $CH_2CH_3$, $CH_2F$, $CHF_2$, or $CF_3$;

R is H, F, Cl, Br, I, OH, or $C_{1-6}$ alkyl;

$R_5$ is H, halogen, or $C_{1-6}$ alkyl;

the 3- to 8-membered heterocycloalkyl, 3- to 10-membered heterocycloalkyl, 5- to 6- membered heteroaryl or 5- to 9-membered heteroaryl contains 1, 2 or 3 heteroatoms or heteroatomic groups independently selected from —O—, —NH—, —S—, —C(═O)-, —C(═O)O—, —S(═O)-, —$S(═O)_2$- and N.

* * * * *